US012551209B2

(12) United States Patent
Stone et al.

(10) Patent No.: US 12,551,209 B2
(45) Date of Patent: *Feb. 17, 2026

(54) METHOD AND APPARATUS FOR COUPLING SOFT TISSUE TO A BONE

(71) Applicant: Biomet Sports Medicine, LLC, Warsaw, IN (US)

(72) Inventors: Kevin T. Stone, Winona Lake, IN (US); Gregory J. Denham, Warsaw, IN (US); Ryan Harper, Warsaw, IN (US); Ryan A. Kaiser, Leesburg, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 150 days.

This patent is subject to a terminal disclaimer.

(21) Appl. No.: 18/514,936

(22) Filed: Nov. 20, 2023

(65) Prior Publication Data

US 2024/0081807 A1 Mar. 14, 2024

Related U.S. Application Data

(60) Continuation of application No. 17/190,686, filed on Mar. 3, 2021, now Pat. No. 11,896,210, which is a
(Continued)

(51) Int. Cl.

*A61B 17/04* (2006.01)
*A61F 2/08* (2006.01)

(52) U.S. Cl.

CPC ........ *A61B 17/0401* (2013.01); *A61F 2/0811* (2013.01); *A61B 2017/0409* (2013.01);
(Continued)

(58) Field of Classification Search

CPC .......... A61B 17/06166; A61B 17/0401; A61B 17/0057; A61B 2017/0458;
(Continued)

(56) References Cited

U.S. PATENT DOCUMENTS 26,501 A 12/1859 Kendrick et al.
64,499 A 5/1867 Daubert
(Continued)

FOREIGN PATENT DOCUMENTS

AU 4957264 A 3/1966
AU 440266 A1 10/1967
(Continued)

OTHER PUBLICATIONS

US 6,238,418 B1, 05/2001, Schwartz (withdrawn)
(Continued)

*Primary Examiner* — Dianne Dornbusch
(74) *Attorney, Agent, or Firm* — SCHWEGMAN LUNDBERG & WOESSNER, P.A.

(57) ABSTRACT

A method and apparatus for surgically repairing a tear in soft tissue is disclosed. A plurality of collapsible tubes are positioned about the suture. The collapsible tubes are pushed through soft tissue and orthopedic mesh on opposite sides of a tear in soft tissue. When tension is applied to the suture, the tubes are compressed to fix the suture to the soft tissue and draw the soft tissue portions together.

18 Claims, 31 Drawing Sheets

Related U.S. Application Data continuation of application No. 15/941,481, filed on Mar. 30, 2018, now Pat. No. 10,973,507, which is a continuation of application No. 14/983,747, filed on Dec. 30, 2015, now Pat. No. 10,154,837, which is a continuation of application No. 13/751,846, filed on Jan. 28, 2013, now Pat. No. 9,492,158, which is a division of application No. 12/489,168, filed on Jun. 22, 2009, now Pat. No. 8,361,113.

(52) U.S. Cl.
CPC ................ *A61B 2017/0445* (2013.01); *A61B 2017/0458* (2013.01)

(58) Field of Classification Search
CPC ...... A61B 2017/0445; A61B 2017/044; A61B 2017/0409; A61B 2017/0459; A61B 2017/0414; A61B 2017/06185; A61F 2/0811
See application file for complete search history.

(56) References Cited

U.S. PATENT DOCUMENTS

| | | | |
|---|---|---|---|
| 65,499 | A | 6/1867 | Miller |
| 126,366 | A | 4/1872 | Wills |
| 233,475 | A | 10/1880 | Cook et al. |
| 261,501 | A | 7/1882 | Vandermark |
| 268,407 | A | 12/1882 | Hughes |
| 330,087 | A | 11/1885 | Binns |
| 394,739 | A | 12/1888 | Toulmin |
| 401,677 | A | 4/1889 | Autenrieth |
| 417,805 | A | 12/1889 | Beaman |
| 445,875 | A | 2/1891 | Brickell |
| 487,304 | A | 12/1892 | Todd |
| 687,221 | A | 11/1901 | Gaff et al. |
| 762,710 | A | 6/1904 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,505,470 | A | 8/1924 | Kelm |
| 1,635,066 | A | 7/1927 | Wells |
| 1,950,799 | A | 3/1934 | Jones |
| 2,042,403 | A | 5/1936 | Hrivnak |
| 2,065,659 | A | 12/1936 | Cullen |
| 2,108,206 | A | 2/1938 | Meeker |
| 2,121,193 | A | 6/1938 | Hanicke |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| 2,379,629 | A | 7/1945 | Eweson |
| 2,397,216 | A | 3/1946 | Stellin |
| RE22,857 | E | 3/1947 | Ogburn |
| 2,526,959 | A | 10/1950 | Lorenzo |
| 2,528,456 | A | 10/1950 | Thomas |
| 2,549,382 | A | 4/1951 | Mitterway |
| 2,562,419 | A | 7/1951 | Ferris |
| 2,581,564 | A | 1/1952 | Villegas |
| 2,600,395 | A | 6/1952 | Domoj et al. |
| 2,610,631 | A | 9/1952 | Calicchio |
| 2,665,597 | A | 1/1954 | Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Markman |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Dawson |
| 2,913,042 | A | 11/1959 | Taylor |
| 2,947,504 | A | 8/1960 | Ruhlman |
| 3,000,009 | A | 9/1961 | Selstad |
| 3,003,155 | A | 10/1961 | Mielzynski |
| 3,013,559 | A | 12/1961 | Thomas |
| 3,037,619 | A | 6/1962 | Stevans |
| 3,039,460 | A | 6/1962 | Chandler |
| 3,081,781 | A | 3/1963 | Stermer |
| 3,090,386 | A | 5/1963 | Babcock |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Dritz |
| 3,223,083 | A | 12/1965 | Cobey |
| 3,234,938 | A | 2/1966 | Robinson |
| 3,240,379 | A | 3/1966 | Bremer et al. |
| 3,250,271 | A | 5/1966 | Lippes |
| 3,399,432 | A | 9/1968 | Merser |
| 3,409,014 | A | 11/1968 | Grant |
| RE26,501 | E | 12/1968 | Himmelstein et al. |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |
| 3,515,132 | A | 6/1970 | Mcknight |
| 3,522,803 | A | 8/1970 | Majzlin |
| 3,527,223 | A | 9/1970 | Shein |
| 3,533,406 | A | 10/1970 | Tatum |
| 3,541,591 | A | 11/1970 | Hoegerman |
| 3,545,008 | A | 12/1970 | Bader, Jr. |
| 3,547,389 | A | 12/1970 | Mitchell |
| 3,579,831 | A | 5/1971 | Stevens et al. |
| 3,590,616 | A | 7/1971 | Schussler |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,650,274 | A | 3/1972 | Edwards et al. |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,786,801 | A | 1/1974 | Sartorius |
| 3,802,438 | A | 4/1974 | Wolvek |
| 3,807,407 | A | 4/1974 | Schweizer |
| 3,810,456 | A | 5/1974 | Karman |
| 3,825,010 | A | 7/1974 | McDonald |
| 3,840,017 | A | 10/1974 | Violante |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |

(56) References Cited

U.S. PATENT DOCUMENTS 3,896,810 A 7/1975 Akiyama
3,907,442 A 9/1975 Reid
3,910,281 A 10/1975 Kletschka
3,918,444 A 11/1975 Hoff et al.
3,918,455 A 11/1975 Coplan
3,927,666 A 12/1975 Hoff
3,931,667 A 1/1976 Merser et al.
3,933,153 A 1/1976 Csatary et al.
3,937,217 A 2/1976 Kosonen
3,943,932 A 3/1976 Woo
3,946,446 A 3/1976 Schofield
3,946,728 A 3/1976 Bettex
3,946,740 A 3/1976 Bassett
3,949,755 A 4/1976 Vauquois
3,953,896 A 5/1976 Treace
3,954,103 A 5/1976 Garcia-roel et al.
3,961,632 A 6/1976 Moossun
3,973,560 A 8/1976 Emmett
3,976,079 A 8/1976 Samuels et al.
3,977,050 A 8/1976 Perez
3,979,799 A 9/1976 Merser et al.
3,985,138 A 10/1976 Jarvik
3,990,619 A 11/1976 Russell
4,005,707 A 2/1977 Moulding, Jr.
4,006,747 A 2/1977 Kronenthal et al.
4,007,743 A 2/1977 Blake
4,013,071 A 3/1977 Rosenberg
4,026,281 A 5/1977 Mayberry et al.
4,036,101 A 7/1977 Burnett
4,050,100 A 9/1977 Barry
4,054,954 A 10/1977 Nakayama et al.
4,084,478 A 4/1978 Simmons
4,085,466 A 4/1978 Goodfellow et al.
4,094,313 A 6/1978 Komamura et al.
4,099,750 A 7/1978 Mcgrew
4,103,690 A 8/1978 Harris
RE29,819 E 10/1978 Bone
4,121,487 A 10/1978 Bone
4,143,656 A 3/1979 Holmes
4,144,876 A 3/1979 Deleo
4,146,022 A 3/1979 Johnson et al.
4,149,277 A 4/1979 Bokros
4,157,714 A 6/1979 Foltz et al.
4,158,250 A 6/1979 Ringwald
4,160,453 A 7/1979 Miller
4,164,225 A 8/1979 Johnson et al.
4,172,458 A 10/1979 Pereyra
4,175,555 A 11/1979 Herbert
4,185,636 A 1/1980 Gabbay et al.
4,196,883 A 4/1980 Einhorn et al.
4,207,627 A 6/1980 Cloutier
4,210,148 A 7/1980 Stivala
4,235,161 A 11/1980 Kunreuther
4,235,238 A 11/1980 Ogiu et al.
4,237,779 A 12/1980 Kunreuther
4,243,037 A 1/1981 Smith
4,249,525 A 2/1981 Krzeminski
4,263,913 A 4/1981 Malmin
4,265,246 A 5/1981 Barry
4,273,117 A 6/1981 Neuhauser
4,275,490 A 6/1981 Bivins
4,275,717 A 6/1981 Bolesky
4,287,807 A 9/1981 Pacharis et al.
4,291,698 A 9/1981 Fuchs et al.
4,301,551 A 11/1981 Dore et al.
4,302,397 A 11/1981 Frainier et al.
4,307,723 A 12/1981 Finney
4,312,337 A 1/1982 Donohue
4,316,469 A 2/1982 Kapitanov
4,319,428 A 3/1982 Fox
4,326,531 A 4/1982 Shimonaka
4,344,193 A 8/1982 Kenny
4,345,601 A 8/1982 Fukuda
4,349,027 A 9/1982 Difrancesco
4,388,921 A 6/1983 Sutter et al.
4,400,833 A 8/1983 Kurland
4,402,445 A 9/1983 Green
4,409,974 A 10/1983 Freedland et al.
4,438,769 A 3/1984 Pratt et al.
4,441,489 A 4/1984 Evans et al.
4,454,875 A 6/1984 Pratt et al.
4,462,395 A 7/1984 Johnson
4,463,753 A 8/1984 Gustilo
4,473,102 A 9/1984 Ohman et al.
4,484,570 A 11/1984 Sutter et al.
4,489,446 A 12/1984 Reed
4,489,464 A 12/1984 Massari et al.
4,493,323 A 1/1985 Albright et al.
4,496,468 A 1/1985 House et al.
4,505,274 A 3/1985 Speelman
4,509,516 A 4/1985 Richmond
4,531,522 A 7/1985 Bedi et al.
4,532,926 A 8/1985 O'holla
4,534,350 A 8/1985 Golden et al.
4,535,764 A 8/1985 Ebert
4,537,185 A 8/1985 Stednitz
4,549,545 A 10/1985 Levy
4,549,652 A 10/1985 Free
4,561,432 A 12/1985 Mazor
4,564,007 A 1/1986 Coombs
4,570,623 A 2/1986 Ellison et al.
4,573,844 A 3/1986 Smith
4,576,608 A 3/1986 Homsy
4,584,722 A 4/1986 Levy et al.
4,587,963 A 5/1986 Leibinger et al.
4,590,928 A 5/1986 Hunt et al.
4,595,007 A 6/1986 Mericle
4,596,249 A 6/1986 Freda et al.
4,597,766 A 7/1986 Hilal et al.
4,602,635 A 7/1986 Mulhollan et al.
4,602,636 A 7/1986 Noiles
4,604,997 A 8/1986 De Bastiani et al.
4,605,414 A 8/1986 Czajka
4,616,650 A 10/1986 Green et al.
4,621,640 A 11/1986 Mulhollan et al.
4,624,254 A 11/1986 Mcgarry et al.
4,632,100 A 12/1986 Somers et al.
4,635,637 A 1/1987 Schreiber
4,636,121 A 1/1987 Miller
4,640,271 A 2/1987 Lower
4,641,652 A 2/1987 Hutterer et al.
4,649,916 A 3/1987 Frimberger
4,649,952 A 3/1987 Jobe
4,653,486 A 3/1987 Coker
4,653,487 A 3/1987 Maale
4,653,489 A 3/1987 Tronzo
4,655,771 A 4/1987 Wallsten
4,655,777 A 4/1987 Dunn
4,662,068 A 5/1987 Polonsky
4,667,662 A 5/1987 Titone et al.
4,667,675 A 5/1987 Davis
4,669,473 A 6/1987 Richards et al.
4,683,895 A 8/1987 Pohndorf
4,688,561 A 8/1987 Reese
4,690,169 A 9/1987 Jobe
4,696,300 A 9/1987 Anderson
4,705,040 A 11/1987 Mueller et al.
4,708,132 A 11/1987 Silvestrini
4,711,639 A 12/1987 Grundei
4,714,474 A 12/1987 Brooks, Jr. et al.
4,714,475 A 12/1987 Grundei et al.
4,716,893 A 1/1988 Fischer et al.
4,719,671 A 1/1988 Ito et al.
4,719,917 A 1/1988 Barrows et al.
4,723,540 A 2/1988 Gilmer, Jr.
4,724,839 A 2/1988 Bedi et al.
4,728,329 A 3/1988 Mansat
4,728,332 A 3/1988 Albrektsson
4,730,615 A 3/1988 Sutherland et al.
4,736,746 A 4/1988 Anderson
4,738,255 A 4/1988 Goble et al.
4,739,751 A 4/1988 Sapega et al.
4,741,330 A 5/1988 Hayhurst
4,741,336 A 5/1988 Failla et al.

(56) References Cited

U.S. PATENT DOCUMENTS 4,744,353 A 5/1988 Mcfarland
4,744,793 A 5/1988 Parr et al.
4,750,492 A 6/1988 Jacobs
4,751,922 A 6/1988 Dipietropolo
4,754,685 A 7/1988 Kite et al.
4,760,843 A 8/1988 Fischer et al.
4,760,844 A 8/1988 Kyle
4,760,848 A 8/1988 Hasson
4,770,663 A 9/1988 Hanslik et al.
4,772,261 A 9/1988 Von Hoff et al.
4,772,286 A 9/1988 Goble et al.
4,773,910 A 9/1988 Chen et al.
4,775,380 A 10/1988 Seedhom et al.
4,776,328 A 10/1988 Frey et al.
4,779,372 A 10/1988 Pozo Obeso
4,781,190 A 11/1988 Lee
4,784,126 A 11/1988 Hourahane
4,787,882 A 11/1988 Claren
4,790,297 A 12/1988 Luque
4,790,850 A 12/1988 Dunn et al.
4,793,363 A 12/1988 Ausherman et al.
4,795,468 A 1/1989 Hodorek et al.
4,809,695 A 3/1989 Gwathmey et al.
4,813,406 A 3/1989 Ogle, II
4,813,416 A 3/1989 Pollak et al.
4,823,780 A 4/1989 Odensten et al.
4,823,794 A 4/1989 Pierce
4,828,562 A 5/1989 Kenna
4,832,026 A 5/1989 Jones
4,834,098 A 5/1989 Jones
4,836,080 A 6/1989 Kite, III et al.
4,838,282 A 6/1989 Strasser et al.
4,841,960 A 6/1989 Garner
4,846,835 A 7/1989 Grande
4,851,005 A 7/1989 Hunt et al.
4,858,601 A 8/1989 Glisson
4,858,603 A 8/1989 Clemow et al.
4,858,608 A 8/1989 Mcquilkin
4,860,513 A 8/1989 Whitman
4,863,383 A 9/1989 Grafelmann
4,863,471 A 9/1989 Mansat
4,870,957 A 10/1989 Goble et al.
4,872,450 A 10/1989 Austad
4,873,976 A 10/1989 Schreiber
4,884,572 A 12/1989 Bays et al.
4,887,601 A 12/1989 Richards
4,889,110 A 12/1989 Galline et al.
4,890,615 A 1/1990 Caspari et al.
4,893,619 A 1/1990 Dale et al.
4,893,974 A 1/1990 Fischer et al.
4,895,148 A 1/1990 Bays et al.
4,896,668 A 1/1990 Popoff et al.
4,898,156 A 2/1990 Gatturna et al.
4,899,743 A 2/1990 Nicholson et al.
4,901,721 A 2/1990 Hakki
4,917,700 A 4/1990 Aikins
4,919,667 A 4/1990 Richmond
4,922,897 A 5/1990 Sapega et al.
4,923,461 A 5/1990 Caspari et al.
4,927,421 A 5/1990 Goble et al.
4,946,377 A 8/1990 Kovach
4,946,467 A 8/1990 Ohi et al.
4,946,468 A 8/1990 Li
4,950,270 A 8/1990 Bowman et al.
4,950,285 A 8/1990 Wilk
4,959,069 A 9/1990 Brennan et al.
4,960,381 A 10/1990 Niznick
4,961,741 A 10/1990 Hayhurst
4,962,929 A 10/1990 Melton, Jr.
4,968,315 A 11/1990 Gatturna
4,968,317 A 11/1990 Tormala et al.
4,969,886 A 11/1990 Cziffer et al.
4,974,488 A 12/1990 Spralja
4,974,656 A 12/1990 Judkins
4,976,736 A 12/1990 White et al.
4,978,350 A 12/1990 Wagenknecht
4,979,956 A 12/1990 Silvestrini
4,983,176 A 1/1991 Cushman et al.
4,983,184 A 1/1991 Steinemann
4,983,240 A 1/1991 Orkin et al.
4,988,351 A 1/1991 Paulos et al.
4,994,074 A 2/1991 Bezwada et al.
4,997,433 A 3/1991 Goble et al.
5,002,545 A 3/1991 Whiteside et al.
5,002,550 A 3/1991 Li
5,002,562 A 3/1991 Oberlander
5,002,574 A 3/1991 May et al.
5,007,921 A 4/1991 Brown
5,019,093 A 5/1991 Kaplan et al.
5,020,713 A 6/1991 Kunreuther
5,026,398 A 6/1991 May et al.
5,028,569 A 7/1991 Cihon
5,030,224 A 7/1991 Wright
5,030,235 A 7/1991 Campbell, Jr.
5,035,701 A 7/1991 Kabbara
5,037,422 A 8/1991 Hayhurst et al.
5,037,426 A 8/1991 Goble et al.
5,041,129 A 8/1991 Hayhurst et al.
5,046,513 A 9/1991 Gatturna et al.
5,047,030 A 9/1991 Draenert
5,053,046 A 10/1991 Janese
5,053,047 A 10/1991 Yoon
5,059,201 A 10/1991 Asnis
5,059,206 A 10/1991 Winters
5,061,277 A 10/1991 Carpentier et al.
5,062,344 A 11/1991 Gerker
5,062,843 A 11/1991 Mahony, III
5,064,431 A 11/1991 Gilbertson et al.
5,067,962 A 11/1991 Campbell et al.
5,071,420 A 12/1991 Paulos et al.
5,074,874 A 12/1991 Yoon, Inbae et al.
5,078,731 A 1/1992 Hayhurst
5,078,843 A 1/1992 Pratt
5,080,050 A 1/1992 Dale
5,080,675 A 1/1992 Lawes et al.
5,084,050 A 1/1992 Draenert
5,084,058 A 1/1992 Li
5,085,661 A 2/1992 Moss
5,087,263 A 2/1992 Li
5,087,309 A 2/1992 Melton, Jr.
5,089,012 A 2/1992 Prou
5,092,727 A 3/1992 Moghe
5,092,866 A 3/1992 Breard et al.
5,098,433 A 3/1992 Freedland
5,098,435 A 3/1992 Stednitz et al.
5,100,415 A 3/1992 Hayhurst
5,100,417 A 3/1992 Cerier
5,108,433 A 4/1992 May et al.
5,112,335 A 5/1992 Laboureau et al.
5,116,337 A 5/1992 Johnson
5,116,373 A 5/1992 Jakob et al.
5,116,375 A 5/1992 Hofmann
5,123,913 A 6/1992 Wilk et al.
5,123,914 A 6/1992 Cope
5,127,783 A 7/1992 Moghe et al.
5,127,785 A 7/1992 Faucher
5,129,901 A 7/1992 Decoste
5,129,902 A 7/1992 Goble et al.
5,129,904 A 7/1992 Illi
5,129,906 A 7/1992 Ross et al.
5,139,498 A 8/1992 Astudillo Ley
5,139,499 A 8/1992 Small et al.
5,139,520 A 8/1992 Rosenberg
5,143,498 A 9/1992 Whitman
5,147,362 A 9/1992 Goble
5,149,329 A 9/1992 Richardson
5,151,104 A 9/1992 Kenna
5,152,790 A 10/1992 Rosenberg et al.
5,154,189 A 10/1992 Oberlander
5,156,616 A 10/1992 Meadows et al.
5,163,960 A 11/1992 Bonutti
D331,626 S 12/1992 Hayhurst et al.
5,169,400 A 12/1992 Muhling et al.
5,171,274 A 12/1992 Fluckiger et al.

(56) References Cited

U.S. PATENT DOCUMENTS

| | | | |
|---|---|---|---|
| 5,176,682 | A | 1/1993 | Chow |
| 5,178,629 | A | 1/1993 | Kammerer |
| 5,183,458 | A | 2/1993 | Marx |
| 5,190,545 | A | 3/1993 | Corsi et al. |
| 5,192,282 | A | 3/1993 | Draenert |
| 5,197,987 | A | 3/1993 | Koch et al. |
| 5,199,135 | A | 4/1993 | Gold |
| 5,203,784 | A | 4/1993 | Ross et al. |
| 5,203,787 | A | 4/1993 | Noblitt et al. |
| 5,207,679 | A | 5/1993 | Li |
| 5,209,753 | A | 5/1993 | Biedermann et al. |
| 5,209,805 | A | 5/1993 | Spraggins |
| 5,211,647 | A | 5/1993 | Schmieding |
| 5,211,650 | A | 5/1993 | Noda |
| 5,214,987 | A | 6/1993 | Fenton, Sr. |
| 5,217,495 | A | 6/1993 | Kaplan et al. |
| 5,219,359 | A | 6/1993 | McQuilkin et al. |
| 5,222,976 | A | 6/1993 | Yoon |
| 5,224,940 | A | 7/1993 | Dann et al. |
| 5,224,946 | A | 7/1993 | Hayhurst et al. |
| 5,226,914 | A | 7/1993 | Caplan et al. |
| 5,230,699 | A | 7/1993 | Grasinger |
| 5,232,436 | A | 8/1993 | Janevski |
| 5,234,435 | A | 8/1993 | Seagrave, Jr. |
| 5,235,238 | A | 8/1993 | Nomura et al. |
| 5,236,445 | A | 8/1993 | Hayhurst et al. |
| 5,236,461 | A | 8/1993 | Forte |
| 5,242,447 | A | 9/1993 | Borzone |
| 5,246,441 | A | 9/1993 | Ross et al. |
| 5,249,899 | A | 10/1993 | Wilson |
| 5,250,053 | A | 10/1993 | Snyder |
| 5,258,015 | A | 11/1993 | Li et al. |
| 5,258,016 | A | 11/1993 | Dipoto et al. |
| 5,258,040 | A | 11/1993 | Bruchman et al. |
| 5,261,908 | A | 11/1993 | Campbell, Jr. |
| 5,268,001 | A | 12/1993 | Nicholson et al. |
| 5,269,160 | A | 12/1993 | Wood |
| 5,269,783 | A | 12/1993 | Sander |
| 5,269,806 | A | 12/1993 | Sardelis et al. |
| 5,269,809 | A | 12/1993 | Hayhurst et al. |
| 5,279,311 | A | 1/1994 | Snyder |
| 5,281,422 | A | 1/1994 | Badylak et al. |
| 5,282,809 | A | 2/1994 | Kammerer et al. |
| 5,282,832 | A | 2/1994 | Toso et al. |
| 5,282,867 | A | 2/1994 | Mikhail |
| 5,282,868 | A | 2/1994 | Bahler |
| 5,285,040 | A | 2/1994 | Brandberg et al. |
| 5,290,217 | A | 3/1994 | Campos |
| 5,290,243 | A | 3/1994 | Chodorow et al. |
| 5,306,301 | A | 4/1994 | Graf et al. |
| 5,312,410 | A | 5/1994 | Miller et al. |
| 5,312,422 | A | 5/1994 | Trott |
| 5,312,438 | A | 5/1994 | Johnson |
| 5,314,429 | A | 5/1994 | Goble |
| 5,318,566 | A | 6/1994 | Miller |
| 5,318,575 | A | 6/1994 | Chesterfield et al. |
| 5,318,577 | A | 6/1994 | Li |
| 5,318,578 | A | 6/1994 | Hasson |
| 5,320,115 | A | 6/1994 | Kenna |
| 5,320,626 | A | 6/1994 | Schmieding |
| 5,320,633 | A | 6/1994 | Allen et al. |
| 5,324,308 | A | 6/1994 | Pierce |
| 5,330,489 | A | 7/1994 | Green et al. |
| 5,330,534 | A | 7/1994 | Herrington et al. |
| 5,333,625 | A | 8/1994 | Klein |
| 5,334,204 | A | 8/1994 | Clewett et al. |
| 5,336,229 | A | 8/1994 | Noda |
| 5,336,231 | A | 8/1994 | Adair |
| 5,336,240 | A | 8/1994 | Metzler et al. |
| 5,339,870 | A | 8/1994 | Green et al. |
| 5,342,369 | A | 8/1994 | Harryman, II |
| 5,344,460 | A | 9/1994 | Turanyi et al. |
| 5,346,462 | A | 9/1994 | Barber |
| 5,350,380 | A | 9/1994 | Goble et al. |
| RE34,762 | E | 10/1994 | Goble et al. |
| 5,354,292 | A | 10/1994 | Braeuer et al. |
| 5,354,298 | A | 10/1994 | Lee et al. |
| 5,354,299 | A | 10/1994 | Coleman |
| 5,356,412 | A | 10/1994 | Golds et al. |
| 5,356,413 | A | 10/1994 | Martins et al. |
| 5,356,417 | A | 10/1994 | Golds |
| 5,358,511 | A | 10/1994 | Gatturna et al. |
| 5,358,530 | A | 10/1994 | Hodorek |
| 5,358,531 | A | 10/1994 | Goodfellow et al. |
| 5,360,431 | A | 11/1994 | Puno et al. |
| 5,362,294 | A | 11/1994 | Seitzinger |
| 5,362,911 | A | 11/1994 | Cevasco et al. |
| 5,364,400 | A | 11/1994 | Rego, Jr. et al. |
| 5,366,461 | A | 11/1994 | Blasnik |
| 5,368,599 | A | 11/1994 | Hirsch et al. |
| 5,370,646 | A | 12/1994 | Reese et al. |
| 5,370,661 | A | 12/1994 | Branch |
| 5,370,662 | A | 12/1994 | Stone et al. |
| 5,372,146 | A | 12/1994 | Branch |
| 5,372,604 | A | 12/1994 | Trott |
| 5,372,821 | A | 12/1994 | Badylak et al. |
| 5,374,268 | A | 12/1994 | Sander |
| 5,374,269 | A | 12/1994 | Rosenberg |
| 5,376,118 | A | 12/1994 | Kaplan et al. |
| 5,379,492 | A | 1/1995 | Glesser |
| 5,383,878 | A | 1/1995 | Roger et al. |
| 5,383,904 | A | 1/1995 | Totakura et al. |
| 5,385,567 | A | 1/1995 | Goble |
| 5,391,171 | A | 2/1995 | Schmieding |
| 5,391,176 | A | 2/1995 | De La Torre |
| 5,391,182 | A | 2/1995 | Chin |
| 5,393,302 | A | 2/1995 | Clark et al. |
| RE34,871 | E | 3/1995 | Mcguire et al. |
| 5,395,374 | A | 3/1995 | Miller et al. |
| 5,395,401 | A | 3/1995 | Bahler |
| 5,397,356 | A | 3/1995 | Goble et al. |
| 5,403,328 | A | 4/1995 | Shallman |
| 5,403,329 | A | 4/1995 | Hinchcliffe |
| 5,403,348 | A | 4/1995 | Bonutti |
| 5,405,359 | A | 4/1995 | Pierce |
| 5,411,550 | A | 5/1995 | Herweck et al. |
| 5,415,658 | A | 5/1995 | Kilpela et al. |
| 5,417,690 | A | 5/1995 | Sennett et al. |
| 5,417,691 | A | 5/1995 | Hayhurst |
| 5,417,698 | A | 5/1995 | Green et al. |
| 5,417,712 | A | 5/1995 | Whittaker et al. |
| 5,423,819 | A | 6/1995 | Small et al. |
| 5,423,821 | A | 6/1995 | Pasque |
| 5,423,823 | A | 6/1995 | Schmieding |
| 5,423,824 | A | 6/1995 | Akerfeldt et al. |
| 5,423,860 | A | 6/1995 | Lizardi et al. |
| 5,425,733 | A | 6/1995 | Schmieding |
| 5,425,766 | A | 6/1995 | Bowald |
| 5,433,751 | A | 7/1995 | Christel et al. |
| 5,437,680 | A | 8/1995 | Yoon |
| 5,437,685 | A | 8/1995 | Blasnik |
| 5,439,684 | A | 8/1995 | Prewett et al. |
| 5,441,508 | A | 8/1995 | Gazielly et al. |
| 5,443,468 | A | 8/1995 | Johnson |
| 5,443,482 | A | 8/1995 | Stone et al. |
| 5,443,483 | A | 8/1995 | Kirsch |
| 5,443,509 | A | 8/1995 | Boucher et al. |
| 5,445,833 | A | 8/1995 | Badylak et al. |
| 5,447,512 | A | 9/1995 | Wilson et al. |
| 5,449,361 | A | 9/1995 | Preissman |
| 5,451,203 | A | 9/1995 | Lamb |
| 5,454,811 | A | 10/1995 | Huebner |
| 5,454,821 | A | 10/1995 | Harm et al. |
| 5,456,685 | A | 10/1995 | Huebner |
| 5,456,721 | A | 10/1995 | Legrand |
| 5,456,722 | A | 10/1995 | Mcleod et al. |
| 5,458,601 | A | 10/1995 | Young, Jr. et al. |
| 5,458,604 | A | 10/1995 | Schmieding |
| 5,462,542 | A | 10/1995 | Alesi, Jr. |
| 5,462,560 | A | 10/1995 | Stevens |
| 5,464,426 | A | 11/1995 | Bonutti |
| 5,464,427 | A | 11/1995 | Curtis et al. |
| 5,464,440 | A | 11/1995 | Johansson |
| 5,466,237 | A | 11/1995 | Byrd, III et al. |

(56) References Cited

U.S. PATENT DOCUMENTS

| | | | |
|---|---|---|---|
| 5,467,786 | A | 11/1995 | Allen et al. |
| 5,470,334 | A | 11/1995 | Ross et al. |
| 5,470,337 | A | 11/1995 | Moss |
| 5,470,338 | A | 11/1995 | Whitfield et al. |
| 5,470,354 | A | 11/1995 | Hershberger et al. |
| 5,472,452 | A | 12/1995 | Trott |
| 5,474,565 | A | 12/1995 | Trott |
| 5,474,568 | A | 12/1995 | Scott et al. |
| 5,474,572 | A | 12/1995 | Hayhurst |
| 5,476,465 | A | 12/1995 | Preissman |
| 5,478,344 | A | 12/1995 | Stone et al. |
| 5,478,345 | A | 12/1995 | Stone et al. |
| 5,480,403 | A | 1/1996 | Lee et al. |
| 5,480,406 | A | 1/1996 | Nolan et al. |
| 5,480,446 | A | 1/1996 | Goodfellow et al. |
| 5,484,442 | A | 1/1996 | Melker et al. |
| 5,486,197 | A | 1/1996 | Le et al. |
| 5,486,359 | A | 1/1996 | Caplan et al. |
| 5,489,210 | A | 2/1996 | Hanosh |
| 5,490,750 | A | 2/1996 | Gundy |
| 5,495,974 | A | 3/1996 | Deschenes et al. |
| 5,496,290 | A | 3/1996 | Ackerman |
| 5,496,331 | A | 3/1996 | Xu et al. |
| 5,496,348 | A | 3/1996 | Bonutti |
| 5,498,302 | A | 3/1996 | Davidson |
| 5,500,000 | A | 3/1996 | Feagin et al. |
| 5,505,735 | A | 4/1996 | Li |
| 5,505,736 | A | 4/1996 | Reimels et al. |
| 5,507,754 | A | 4/1996 | Green et al. |
| 5,514,059 | A | 5/1996 | Romney |
| 5,520,691 | A | 5/1996 | Branch |
| 5,520,694 | A | 5/1996 | Dance et al. |
| 5,520,700 | A | 5/1996 | Beyar et al. |
| 5,520,702 | A | 5/1996 | Sauer et al. |
| 5,522,817 | A | 6/1996 | Sander et al. |
| 5,522,820 | A | 6/1996 | Caspari et al. |
| 5,522,843 | A | 6/1996 | Zang |
| 5,522,844 | A | 6/1996 | Johnson |
| 5,522,845 | A | 6/1996 | Wenstrom, Jr. |
| 5,522,846 | A | 6/1996 | Bonutti |
| 5,524,946 | A | 6/1996 | Thompson |
| 5,527,321 | A | 6/1996 | Hinchliffe |
| 5,527,342 | A | 6/1996 | Pietrzak et al. |
| 5,527,343 | A | 6/1996 | Bonutti |
| 5,531,759 | A | 7/1996 | Kensey et al. |
| 5,534,011 | A | 7/1996 | Greene, Jr. et al. |
| 5,534,012 | A | 7/1996 | Bonutti |
| 5,534,033 | A | 7/1996 | Simpson |
| 5,536,270 | A | 7/1996 | Songer et al. |
| 5,540,698 | A | 7/1996 | Preissman |
| 5,540,703 | A | 7/1996 | Barker, Jr. et al. |
| 5,540,718 | A | 7/1996 | Bartlett |
| 5,545,168 | A | 8/1996 | Burke |
| 5,545,178 | A | 8/1996 | Kensey et al. |
| 5,545,180 | A | 8/1996 | Le et al. |
| 5,545,228 | A | 8/1996 | Kambin |
| 5,549,613 | A | 8/1996 | Goble et al. |
| 5,549,617 | A | 8/1996 | Green et al. |
| 5,549,619 | A | 8/1996 | Peters et al. |
| 5,549,630 | A | 8/1996 | Bonutti |
| 5,549,631 | A | 8/1996 | Bonutti |
| 5,562,664 | A | 10/1996 | Durlacher et al. |
| 5,562,668 | A | 10/1996 | Johnson |
| 5,562,669 | A | 10/1996 | Mcguire |
| 5,562,683 | A | 10/1996 | Chan |
| 5,562,685 | A | 10/1996 | Mollenauer et al. |
| 5,562,686 | A | 10/1996 | Sauer et al. |
| 5,569,252 | A | 10/1996 | Justin et al. |
| 5,569,269 | A | 10/1996 | Hart et al. |
| 5,569,305 | A | 10/1996 | Bonutti |
| 5,569,306 | A | 10/1996 | Thal |
| 5,570,706 | A | 11/1996 | Howell |
| 5,571,090 | A | 11/1996 | Sherts |
| 5,571,104 | A | 11/1996 | Li |
| 5,571,139 | A | 11/1996 | Jenkins, Jr. |
| 5,572,655 | A | 11/1996 | Tuljapurkar et al. |
| 5,573,286 | A | 11/1996 | Rogozinski |
| 5,573,542 | A | 11/1996 | Stevens |
| 5,573,547 | A | 11/1996 | LeVeen et al. |
| 5,573,548 | A | 11/1996 | Nazre et al. |
| 5,577,299 | A | 11/1996 | Thompson et al. |
| 5,578,057 | A | 11/1996 | Wenstrom, Jr. |
| 5,584,695 | A | 12/1996 | Sachdeva et al. |
| 5,584,835 | A | 12/1996 | Greenfield |
| 5,584,836 | A | 12/1996 | Ballintyn et al. |
| 5,584,862 | A | 12/1996 | Bonutti |
| 5,586,986 | A | 12/1996 | Hinchliffe |
| 5,588,575 | A | 12/1996 | Davignon |
| 5,591,180 | A | 1/1997 | Hinchliffe |
| 5,591,181 | A | 1/1997 | Stone et al. |
| 5,591,207 | A | 1/1997 | Coleman |
| 5,593,407 | A | 1/1997 | Reis |
| 5,593,425 | A | 1/1997 | Bonutti et al. |
| 5,601,557 | A | 2/1997 | Hayhurst |
| 5,601,559 | A | 2/1997 | Melker et al. |
| 5,601,571 | A | 2/1997 | Moss |
| 5,603,716 | A | 2/1997 | Morgan et al. |
| 5,607,429 | A | 3/1997 | Hayano et al. |
| 5,607,430 | A | 3/1997 | Bailey |
| 5,613,971 | A | 3/1997 | Lower et al. |
| 5,618,290 | A | 4/1997 | Toy et al. |
| 5,626,611 | A | 5/1997 | Liu et al. |
| 5,626,614 | A | 5/1997 | Hart |
| 5,628,756 | A | 5/1997 | Barker, Jr. et al. |
| 5,628,766 | A | 5/1997 | Johnson |
| 5,630,824 | A | 5/1997 | Hart |
| 5,632,745 | A | 5/1997 | Schwartz |
| 5,632,748 | A | 5/1997 | Beck, Jr. et al. |
| 5,641,256 | A | 6/1997 | Gundy |
| 5,643,266 | A | 7/1997 | Li |
| 5,643,269 | A | 7/1997 | Harle |
| 5,643,273 | A | 7/1997 | Clark |
| 5,643,295 | A | 7/1997 | Yoon |
| 5,643,319 | A | 7/1997 | Green et al. |
| 5,643,320 | A | 7/1997 | Lower et al. |
| 5,643,321 | A | 7/1997 | Mcdevitt |
| 5,645,546 | A | 7/1997 | Fard |
| 5,645,547 | A | 7/1997 | Coleman |
| 5,645,568 | A | 7/1997 | Chervitz et al. |
| 5,645,588 | A | 7/1997 | Graf et al. |
| 5,647,874 | A | 7/1997 | Hayhurst |
| 5,649,959 | A | 7/1997 | Hannam et al. |
| 5,649,960 | A | 7/1997 | Pavletic |
| 5,649,963 | A | 7/1997 | Mcdevitt |
| 5,658,289 | A | 8/1997 | Boucher et al. |
| 5,658,299 | A | 8/1997 | Hart |
| 5,658,313 | A | 8/1997 | Thal |
| 5,662,658 | A | 9/1997 | Wenstrom, Jr. |
| 5,662,663 | A | 9/1997 | Shallman |
| 5,662,677 | A | 9/1997 | Wimmer |
| 5,662,681 | A | 9/1997 | Nash et al. |
| 5,665,112 | A | 9/1997 | Thal |
| 5,667,513 | A | 9/1997 | Torrie et al. |
| 5,671,695 | A | 9/1997 | Schroeder |
| 5,673,546 | A | 10/1997 | Abraham et al. |
| 5,674,224 | A | 10/1997 | Howell et al. |
| 5,679,723 | A | 10/1997 | Cooper |
| 5,681,334 | A | 10/1997 | Evans et al. |
| 5,681,352 | A | 10/1997 | Clancy, III et al. |
| 5,683,404 | A | 11/1997 | Johnson |
| 5,683,419 | A | 11/1997 | Thal |
| 5,688,284 | A | 11/1997 | Chervitz et al. |
| 5,688,285 | A | 11/1997 | Yamada |
| 5,690,655 | A | 11/1997 | Hart et al. |
| 5,690,676 | A | 11/1997 | Dipoto et al. |
| 5,690,678 | A | 11/1997 | Johnson |
| 5,693,046 | A | 12/1997 | Songer et al. |
| 5,695,497 | A | 12/1997 | Stahelin |
| 5,697,929 | A | 12/1997 | Mellinger |
| 5,697,969 | A | 12/1997 | Schmitt et al. |
| 5,699,657 | A | 12/1997 | Paulson |
| 5,700,277 | A | 12/1997 | Nash et al. |
| 5,702,397 | A | 12/1997 | Goble et al. |
| 5,702,422 | A | 12/1997 | Stone |

(56) References Cited

U.S. PATENT DOCUMENTS 5,702,462 A 12/1997 Oberlander
5,702,464 A 12/1997 Lackey et al.
5,707,373 A 1/1998 Sevrain et al.
5,709,708 A 1/1998 Thal et al.
5,711,969 A 1/1998 Patel et al.
5,713,005 A 1/1998 Proebsting
5,713,897 A 2/1998 Goble et al.
5,713,904 A 2/1998 Errico et al.
5,713,905 A 2/1998 Goble et al.
5,713,921 A 2/1998 Bonutti
5,715,578 A 2/1998 Knudson
5,716,359 A 2/1998 Ojima et al.
5,716,397 A 2/1998 Myers
5,716,616 A 2/1998 Prockop et al.
5,718,717 A 2/1998 Bonutti
5,720,747 A 2/1998 Burke
5,720,765 A 2/1998 Thal
5,720,766 A 2/1998 Zang et al.
5,722,976 A 3/1998 Brown
5,723,331 A 3/1998 Tubo et al.
5,725,529 A 3/1998 Nicholson et al.
5,725,549 A 3/1998 Lam
5,725,556 A 3/1998 Moser et al.
5,725,557 A 3/1998 Gatturna et al.
5,725,581 A 3/1998 Branemark
5,725,582 A 3/1998 Bevan et al.
5,726,722 A 3/1998 Uehara et al.
5,728,107 A 3/1998 Zlock et al.
5,728,109 A 3/1998 Schulze et al.
5,728,136 A 3/1998 Thal
5,733,293 A 3/1998 Scirica et al.
5,733,306 A 3/1998 Bonutti
5,733,307 A 3/1998 Dinsdale
5,735,875 A 4/1998 Bonutti et al.
5,741,259 A 4/1998 Chan
5,741,260 A 4/1998 Songer et al.
5,741,281 A 4/1998 Martin
5,743,912 A 4/1998 Lahille et al.
5,746,751 A 5/1998 Sherts
5,746,752 A 5/1998 Burkhart
5,746,754 A 5/1998 Chan
5,749,898 A 5/1998 Schulze et al.
5,755,729 A 5/1998 De La Torre et al.
5,755,791 A 5/1998 Whitson et al.
5,766,176 A 6/1998 Duncan
5,766,218 A 6/1998 Arnott
5,766,250 A 6/1998 Chervitz et al.
5,769,894 A 6/1998 Ferragamo
5,769,899 A 6/1998 Schwartz et al.
5,772,673 A 6/1998 Cuny et al.
5,776,196 A 7/1998 Matsuzaki et al.
5,776,200 A 7/1998 Johnson et al.
5,782,845 A 7/1998 Shewchuk
5,782,862 A 7/1998 Bonutti
5,782,864 A 7/1998 Lizardi
5,782,866 A 7/1998 Wenstrom, Jr.
5,782,925 A 7/1998 Collazo et al.
5,785,714 A 7/1998 Morgan et al.
5,786,217 A 7/1998 Tubo et al.
5,792,142 A 8/1998 Galitzer
5,792,149 A 8/1998 Sherts et al.
5,796,127 A 8/1998 Hayafuji et al.
5,797,913 A 8/1998 Dambreville et al.
5,797,915 A 8/1998 Pierson, III et al.
5,797,916 A 8/1998 McDowell
5,797,928 A 8/1998 Kogasaka
5,800,407 A 9/1998 Eldor
5,800,447 A 9/1998 Wenstrom, Jr.
5,800,543 A 9/1998 Mcleod et al.
5,810,824 A 9/1998 Chan
5,810,848 A 9/1998 Hayhurst
5,811,094 A 9/1998 Caplan et al.
5,814,056 A 9/1998 Prosst et al.
5,814,069 A 9/1998 Schulze et al.
5,814,070 A 9/1998 Borzone et al.
5,814,071 A 9/1998 Mcdevitt et al.
5,814,072 A 9/1998 Bonutti
5,814,073 A 9/1998 Bonutti
5,817,095 A 10/1998 Smith
5,823,980 A 10/1998 Kopfer
5,824,011 A 10/1998 Stone et al.
5,824,066 A 10/1998 Gross
5,827,285 A 10/1998 Bramlet
5,830,234 A 11/1998 Wojciechowicz et al.
5,836,955 A 11/1998 Buelna et al.
5,843,084 A 12/1998 Hart et al.
5,845,645 A 12/1998 Bonutti
5,846,254 A 12/1998 Schulze et al.
5,848,983 A 12/1998 Basaj et al.
5,849,012 A 12/1998 Abboudi
5,860,947 A 1/1999 Stamler
5,860,973 A 1/1999 Michelson
5,860,978 A 1/1999 Mcdevitt et al.
5,868,740 A 2/1999 LaVeen et al.
5,868,748 A 2/1999 Burke
5,868,789 A 2/1999 Huebner
5,871,456 A 2/1999 Armstrong et al.
5,871,484 A 2/1999 Spievack et al.
5,871,486 A 2/1999 Huebner
5,871,490 A 2/1999 Schulze et al.
5,871,542 A 2/1999 Goodfellow et al.
5,871,543 A 2/1999 Hofmann
5,885,294 A 3/1999 Pedlick et al.
5,891,168 A 4/1999 Thal
5,893,592 A 4/1999 Schulze et al.
5,895,395 A 4/1999 Yeung
5,897,564 A 4/1999 Schulze et al.
5,897,574 A 4/1999 Bonutti
5,899,902 A 5/1999 Brown et al.
5,899,920 A 5/1999 Desatnick et al.
5,899,938 A 5/1999 Sklar et al.
5,906,934 A 5/1999 Grande et al.
5,908,421 A 6/1999 Beger
5,908,436 A 6/1999 Cuschieri et al.
5,910,148 A 6/1999 Reimels et al.
5,911,721 A 6/1999 Nicholson et al.
5,916,557 A 6/1999 Berlowitz-tarrant et al.
5,918,604 A 7/1999 Whelan
5,919,232 A 7/1999 Chaffringeon et al.
5,921,986 A 7/1999 Bonutti
5,925,008 A 7/1999 Douglas
5,928,231 A 7/1999 Klein et al.
5,928,267 A 7/1999 Bonutti et al.
5,928,286 A 7/1999 Ashby et al.
RE36,289 E 8/1999 Le et al.
5,931,838 A 8/1999 Vito
5,931,844 A 8/1999 Thompson et al.
5,931,869 A 8/1999 Boucher et al.
5,935,119 A 8/1999 Guy et al.
5,935,129 A 8/1999 Mcdevitt et al.
5,935,133 A 8/1999 Wagner et al.
5,935,134 A 8/1999 Pedlick et al.
5,935,149 A 8/1999 Ek
5,938,668 A 8/1999 Scirica et al.
5,941,439 A 8/1999 Kammerer et al.
5,941,900 A 8/1999 Bonutti
5,944,739 A 8/1999 Zlock et al.
5,946,783 A 9/1999 Plociennik et al.
5,947,915 A 9/1999 Thibodo, Jr.
5,947,982 A 9/1999 Duran
5,947,999 A 9/1999 Groiso
5,948,002 A 9/1999 Bonutti
5,951,559 A 9/1999 Burkhart
5,951,560 A 9/1999 Simon et al.
5,954,747 A 9/1999 Clark
5,957,953 A 9/1999 Dipoto et al.
5,961,520 A 10/1999 Beck, Jr. et al.
5,961,521 A 10/1999 Roger
5,961,524 A 10/1999 Crombie
5,963,869 A 10/1999 Fehnel
5,964,764 A 10/1999 West, Jr. et al.
5,964,767 A 10/1999 Tapia et al.
5,964,769 A 10/1999 Wagner et al.
5,964,783 A 10/1999 Grafton et al.

(56) References Cited

U.S. PATENT DOCUMENTS

| | | | |
|---|---|---|---|
| 5,964,808 | A | 10/1999 | Blaha et al. |
| 5,968,045 | A | 10/1999 | Frazier |
| 5,968,047 | A | 10/1999 | Reed |
| 5,968,077 | A | 10/1999 | Wojciechowicz et al. |
| 5,968,078 | A | 10/1999 | Grotz |
| 5,968,099 | A | 10/1999 | Badorf et al. |
| 5,970,697 | A | 10/1999 | Jacobs et al. |
| 5,972,006 | A | 10/1999 | Sciaino, Jr. |
| 5,976,125 | A | 11/1999 | Graham |
| 5,976,127 | A | 11/1999 | Lax |
| 5,980,473 | A | 11/1999 | Korakianitis et al. |
| 5,980,524 | A | 11/1999 | Justin et al. |
| 5,980,539 | A | 11/1999 | Kontos |
| 5,980,548 | A | 11/1999 | Evans et al. |
| 5,980,558 | A | 11/1999 | Wiley |
| 5,980,559 | A | 11/1999 | Bonutti |
| 5,989,252 | A | 11/1999 | Fumex |
| 5,989,256 | A | 11/1999 | Kuslich et al. |
| 5,989,282 | A | 11/1999 | Bonutti |
| 5,989,294 | A | 11/1999 | Marlow |
| 5,993,452 | A | 11/1999 | Vandewalle |
| 5,993,476 | A | 11/1999 | Groiso |
| 5,997,542 | A | 12/1999 | Burke |
| 5,997,552 | A | 12/1999 | Person et al. |
| 5,997,575 | A | 12/1999 | Whitson et al. |
| 6,001,100 | A | 12/1999 | Sherman et al. |
| 6,001,106 | A | 12/1999 | Ryan et al. |
| 6,004,351 | A | 12/1999 | Tomita et al. |
| 6,004,352 | A | 12/1999 | Buni |
| 6,007,538 | A | 12/1999 | Levin |
| 6,007,567 | A | 12/1999 | Bonutti |
| 6,010,525 | A | 1/2000 | Bonutti et al. |
| 6,013,103 | A | 1/2000 | Kaufman et al. |
| 6,016,727 | A | 1/2000 | Morgan |
| 6,019,767 | A | 2/2000 | Howell |
| 6,022,352 | A | 2/2000 | Vandewalle |
| 6,022,373 | A | 2/2000 | Li |
| 6,023,661 | A | 2/2000 | Sottery |
| 6,024,758 | A | 2/2000 | Thal |
| 6,027,523 | A | 2/2000 | Schmieding |
| 6,030,410 | A | 2/2000 | Zurbrugg |
| 6,033,429 | A | 3/2000 | Magovern |
| 6,033,430 | A | 3/2000 | Bonutti |
| 6,036,695 | A | 3/2000 | Smith |
| 6,039,753 | A | 3/2000 | Meislin |
| 6,041,485 | A | 3/2000 | Pedlick et al. |
| 6,042,601 | A | 3/2000 | Smith |
| 6,042,609 | A | 3/2000 | Giordano et al. |
| 6,045,551 | A | 4/2000 | Bonutti |
| 6,045,571 | A | 4/2000 | Hill et al. |
| 6,045,572 | A | 4/2000 | Johnson et al. |
| 6,045,573 | A | 4/2000 | Wenstrom, Jr. et al. |
| 6,045,574 | A | 4/2000 | Thal |
| 6,047,826 | A | 4/2000 | Kalinski et al. |
| 6,048,343 | A | 4/2000 | Mathis et al. |
| 6,051,006 | A | 4/2000 | Shluzas et al. |
| 6,051,007 | A | 4/2000 | Hogendijk et al. |
| 6,053,916 | A | 4/2000 | Moore |
| 6,053,921 | A | 4/2000 | Wagner et al. |
| 6,056,752 | A | 5/2000 | Roger |
| 6,056,772 | A | 5/2000 | Bonutti |
| 6,056,773 | A | 5/2000 | Bonutti |
| 6,059,817 | A | 5/2000 | Bonutti et al. |
| 6,059,818 | A | 5/2000 | Johnson et al. |
| 6,062,344 | A | 5/2000 | Okabe et al. |
| 6,066,146 | A | 5/2000 | Carroll et al. |
| 6,066,173 | A | 5/2000 | Mckernan et al. |
| 6,068,648 | A | 5/2000 | Cole et al. |
| 6,071,305 | A | 6/2000 | Brown et al. |
| 6,074,403 | A | 6/2000 | Nord |
| 6,077,277 | A | 6/2000 | Mollenauer et al. |
| 6,077,292 | A | 6/2000 | Bonutti |
| 6,080,185 | A | 6/2000 | Johnson et al. |
| 6,083,257 | A | 7/2000 | Taylor et al. |
| 6,086,591 | A | 7/2000 | Bojarski |
| 6,086,592 | A | 7/2000 | Rosenberg et al. |
| 6,086,608 | A | 7/2000 | Ek et al. |
| 6,093,200 | A | 7/2000 | Liu et al. |
| 6,096,060 | A | 8/2000 | Fitts et al. |
| 6,099,527 | A | 8/2000 | Hochschuler et al. |
| 6,099,530 | A | 8/2000 | Simonian et al. |
| 6,099,568 | A | 8/2000 | Simonian et al. |
| 6,102,934 | A | 8/2000 | Li |
| 6,106,545 | A | 8/2000 | Egan et al. |
| 6,110,128 | A | 8/2000 | Andelin et al. |
| 6,110,207 | A | 8/2000 | Eichhorn et al. |
| 6,113,604 | A | 9/2000 | Whittaker et al. |
| 6,117,160 | A | 9/2000 | Bonutti |
| 6,117,162 | A | 9/2000 | Schmieding et al. |
| 6,123,710 | A | 9/2000 | Pinczewski et al. |
| 6,127,596 | A | 10/2000 | Brown et al. |
| 6,132,433 | A | 10/2000 | Whelan |
| 6,132,437 | A | 10/2000 | Omurtag |
| 6,136,010 | A | 10/2000 | Modesitt et al. |
| 6,139,565 | A | 10/2000 | Stone et al. |
| RE36,974 | E | 11/2000 | Bonutti |
| 6,143,017 | A | 11/2000 | Thal |
| 6,146,406 | A | 11/2000 | Shluzas et al. |
| 6,146,408 | A | 11/2000 | Bartlett |
| 6,149,653 | A | 11/2000 | Deslauriers |
| 6,149,669 | A | 11/2000 | Li |
| 6,150,163 | A | 11/2000 | McPherson et al. |
| 6,152,928 | A | 11/2000 | Wenstrom, Jr. |
| 6,152,934 | A | 11/2000 | Harper et al. |
| 6,152,936 | A | 11/2000 | Christy et al. |
| 6,152,949 | A | 11/2000 | Bonutti |
| 6,156,039 | A | 12/2000 | Thal |
| 6,156,056 | A | 12/2000 | Kearns et al. |
| 6,159,234 | A | 12/2000 | Bonutti et al. |
| 6,165,203 | A | 12/2000 | Krebs |
| 6,168,598 | B1 | 1/2001 | Martello |
| 6,168,628 | B1 | 1/2001 | Huebner |
| 6,171,310 | B1 | 1/2001 | Giordano et al. |
| 6,174,324 | B1 | 1/2001 | Egan et al. |
| 6,179,840 | B1 | 1/2001 | Bowman |
| 6,183,461 | B1 | 2/2001 | Matsuura et al. |
| 6,183,737 | B1 | 2/2001 | Zaleske et al. |
| 6,187,025 | B1 | 2/2001 | Machek |
| 6,190,348 | B1 | 2/2001 | Tiemann |
| 6,190,401 | B1 | 2/2001 | Green et al. |
| 6,190,411 | B1 | 2/2001 | Lo |
| 6,190,415 | B1 | 2/2001 | Cooke et al. |
| 6,193,754 | B1 | 2/2001 | Seedhom |
| 6,200,318 | B1 | 3/2001 | Har-shai et al. |
| 6,200,329 | B1 | 3/2001 | Fung et al. |
| 6,200,330 | B1 | 3/2001 | Benderev et al. |
| 6,200,606 | B1 | 3/2001 | Peterson et al. |
| 6,200,685 | B1 | 3/2001 | Davidson |
| 6,203,556 | B1 | 3/2001 | Evans et al. |
| 6,203,563 | B1 | 3/2001 | Fernandez |
| 6,203,565 | B1 | 3/2001 | Bonutti et al. |
| 6,203,572 | B1 | 3/2001 | Johnson et al. |
| 6,203,576 | B1 | 3/2001 | Afriat et al. |
| 6,206,883 | B1 | 3/2001 | Tunc |
| 6,210,376 | B1 | 4/2001 | Grayson |
| 6,210,381 | B1 | 4/2001 | Morse |
| 6,210,445 | B1 | 4/2001 | Zawadzki |
| 6,214,007 | B1 | 4/2001 | Anderson |
| 6,214,012 | B1 | 4/2001 | Karpman et al. |
| 6,217,580 | B1 | 4/2001 | Levin |
| 6,221,107 | B1 | 4/2001 | Steiner |
| 6,228,096 | B1 | 5/2001 | Marchand |
| 6,231,592 | B1 | 5/2001 | Bonutti et al. |
| 6,234,980 | B1 | 5/2001 | Bell |
| 6,235,057 | B1 | 5/2001 | Roger et al. |
| 6,235,058 | B1 | 5/2001 | Huene |
| 6,238,395 | B1 | 5/2001 | Bonutti |
| 6,241,734 | B1 | 6/2001 | Scribner et al. |
| 6,241,747 | B1 | 6/2001 | Ruff |
| 6,241,771 | B1 | 6/2001 | Gresser et al. |
| 6,245,024 | B1 | 6/2001 | Montagnino et al. |
| 6,245,081 | B1 | 6/2001 | Bowman |
| 6,254,604 | B1 | 7/2001 | Howell |
| 6,258,091 | B1 | 7/2001 | Sevrain et al. |

(56) References Cited

U.S. PATENT DOCUMENTS

| | | | |
|---|---|---|---|
| 6,267,766 | B1 | 7/2001 | Burkhart |
| 6,269,716 | B1 | 8/2001 | Amis |
| 6,270,518 | B1 | 8/2001 | Pedlick et al. |
| 6,273,890 | B1 | 8/2001 | Frazier |
| 6,280,474 | B1 | 8/2001 | Cassidy et al. |
| 6,283,973 | B1 | 9/2001 | Hubbard et al. |
| 6,283,996 | B1 | 9/2001 | Chervitz et al. |
| 6,287,307 | B1 | 9/2001 | Abboudi |
| 6,287,325 | B1 | 9/2001 | Bonutti |
| 6,293,929 | B1 | 9/2001 | Smith et al. |
| 6,293,961 | B2 | 9/2001 | Schwartz et al. |
| 6,296,659 | B1 | 10/2001 | Foerster |
| 6,299,615 | B1 | 10/2001 | Huebner |
| 6,302,888 | B1 | 10/2001 | Mellinger et al. |
| 6,302,899 | B1 | 10/2001 | Johnson et al. |
| 6,302,915 | B1 | 10/2001 | Cooney, III et al. |
| 6,303,158 | B1 | 10/2001 | Odgaard et al. |
| 6,306,156 | B1 | 10/2001 | Clark |
| 6,306,158 | B1 | 10/2001 | Bartlett |
| 6,306,159 | B1 | 10/2001 | Schwartz et al. |
| 6,309,124 | B1 | 10/2001 | Gueret |
| 6,309,405 | B1 | 10/2001 | Bonutti |
| 6,312,448 | B1 | 11/2001 | Bonutti |
| 6,315,788 | B1 | 11/2001 | Roby |
| 6,319,224 | B1 | 11/2001 | Stout et al. |
| 6,319,271 | B1 | 11/2001 | Schwartz et al. |
| 6,328,758 | B1 | 12/2001 | Tornier et al. |
| 6,334,064 | B1 | 12/2001 | Fiddian-green |
| 6,342,060 | B1 | 1/2002 | Adams |
| 6,343,531 | B2 | 2/2002 | Amis |
| 6,355,066 | B1 | 3/2002 | Kim et al. |
| 6,358,270 | B1 | 3/2002 | Lemer |
| 6,364,897 | B1 | 4/2002 | Bonutti |
| 6,368,322 | B1 | 4/2002 | Luks et al. |
| 6,368,326 | B1 | 4/2002 | Dakin et al. |
| 6,368,343 | B1 | 4/2002 | Bonutti et al. |
| 6,371,124 | B1 | 4/2002 | Whelan |
| 6,379,361 | B1 | 4/2002 | Beck, Jr. et al. |
| 6,383,190 | B1 | 5/2002 | Preissman |
| 6,383,199 | B2 | 5/2002 | Carter et al. |
| 6,387,111 | B1 | 5/2002 | Barber |
| 6,387,113 | B1 | 5/2002 | Hawkins et al. |
| 6,387,129 | B2 | 5/2002 | Rieser et al. |
| 6,391,030 | B1 | 5/2002 | Wagner et al. |
| 6,398,785 | B2 | 6/2002 | Carchidi et al. |
| 6,406,456 | B1 | 6/2002 | Slate et al. |
| 6,406,479 | B1 | 6/2002 | Justin et al. |
| 6,409,743 | B1 | 6/2002 | Fenton, Jr. |
| 6,413,260 | B1 | 7/2002 | Berrevoets et al. |
| 6,423,073 | B2 | 7/2002 | Bowman |
| 6,423,088 | B1 | 7/2002 | Fenton, Jr. |
| 6,425,924 | B1 | 7/2002 | Rousseau |
| 6,428,562 | B2 | 8/2002 | Bonutti |
| 6,432,123 | B2 | 8/2002 | Schwartz et al. |
| 6,436,123 | B1 | 8/2002 | Magovern |
| 6,436,124 | B1 | 8/2002 | Anderson et al. |
| 6,440,134 | B1 | 8/2002 | Zaccherotti et al. |
| 6,440,136 | B1 | 8/2002 | Gambale et al. |
| 6,447,516 | B1 | 9/2002 | Bonutti |
| 6,451,030 | B2 | 9/2002 | Li et al. |
| 6,454,768 | B1 | 9/2002 | Jackson |
| 6,458,134 | B1 | 10/2002 | Songer et al. |
| 6,458,161 | B1 | 10/2002 | Gibbs et al. |
| 6,461,373 | B2 | 10/2002 | Wyman et al. |
| 6,464,690 | B1 | 10/2002 | Castaneda et al. |
| 6,464,713 | B2 | 10/2002 | Bonutti |
| 6,468,293 | B2 | 10/2002 | Bonutti et al. |
| 6,471,707 | B1 | 10/2002 | Miller et al. |
| 6,475,230 | B1 | 11/2002 | Bonutti et al. |
| 6,478,753 | B2 | 11/2002 | Reay-young |
| 6,482,210 | B1 | 11/2002 | Skiba et al. |
| 6,485,504 | B1 | 11/2002 | Johnson et al. |
| 6,491,714 | B1 | 12/2002 | Bennett |
| 6,497,901 | B1 | 12/2002 | Royer |
| 6,500,184 | B1 | 12/2002 | Chan et al. |
| 6,500,195 | B2 | 12/2002 | Bonutti |
| 6,500,208 | B1 | 12/2002 | Metzger et al. |
| RE37,963 | E | 1/2003 | Thal |
| 6,503,267 | B2 | 1/2003 | Bonutti et al. |
| 6,506,190 | B1 | 1/2003 | Walshe |
| 6,508,820 | B2 | 1/2003 | Bales |
| 6,508,821 | B1 | 1/2003 | Schwartz et al. |
| 6,508,830 | B2 | 1/2003 | Steiner |
| 6,511,498 | B1 | 1/2003 | Fumex |
| 6,511,499 | B2 | 1/2003 | Schmieding et al. |
| 6,514,274 | B1 | 2/2003 | Boucher et al. |
| 6,517,542 | B1 | 2/2003 | Papay et al. |
| 6,517,552 | B1 | 2/2003 | Nord et al. |
| 6,517,564 | B1 | 2/2003 | Grafton et al. |
| 6,517,578 | B2 | 2/2003 | Hein |
| 6,517,579 | B1 | 2/2003 | Paulos et al. |
| 6,520,964 | B2 | 2/2003 | Tallarida et al. |
| 6,520,980 | B1 | 2/2003 | Foerster |
| 6,524,317 | B1 | 2/2003 | Ritchart et al. |
| 6,527,777 | B2 | 3/2003 | Justin |
| 6,527,794 | B1 | 3/2003 | Mcdevitt et al. |
| 6,527,795 | B1 | 3/2003 | Lizardi |
| 6,533,795 | B1 | 3/2003 | Tran et al. |
| 6,533,802 | B2 | 3/2003 | Bojarski et al. |
| 6,537,319 | B2 | 3/2003 | Whelan |
| 6,540,750 | B2 | 4/2003 | Burkhart |
| 6,540,769 | B1 | 4/2003 | Miller, III |
| 6,540,770 | B1 | 4/2003 | Tornier et al. |
| 6,540,783 | B1 | 4/2003 | Whittaker et al. |
| 6,543,094 | B2 | 4/2003 | D'addario |
| 6,544,281 | B2 | 4/2003 | Elattrache et al. |
| 6,547,564 | B1 | 4/2003 | Hansson |
| 6,547,778 | B1 | 4/2003 | Sklar et al. |
| 6,547,800 | B2 | 4/2003 | Foerster et al. |
| 6,551,330 | B1 | 4/2003 | Bain et al. |
| 6,551,343 | B1 | 4/2003 | Tormala et al. |
| 6,551,353 | B1 | 4/2003 | Baker et al. |
| 6,553,802 | B1 | 4/2003 | Jacob |
| 6,554,830 | B1 | 4/2003 | Chappius |
| 6,554,852 | B1 | 4/2003 | Oberlander |
| 6,554,862 | B2 | 4/2003 | Hays et al. |
| 6,558,389 | B2 | 5/2003 | Clark et al. |
| 6,562,071 | B2 | 5/2003 | Järvinen |
| 6,565,572 | B2 | 5/2003 | Chappius |
| 6,565,573 | B1 | 5/2003 | Ferrante |
| 6,569,167 | B1 | 5/2003 | Bobechko et al. |
| 6,569,186 | B1 | 5/2003 | Winters et al. |
| 6,569,187 | B1 | 5/2003 | Bonutti et al. |
| 6,572,635 | B1 | 6/2003 | Bonutti |
| 6,572,655 | B1 | 6/2003 | Johnson |
| 6,575,925 | B1 | 6/2003 | Noble |
| 6,579,295 | B1 | 6/2003 | Supinski |
| 6,582,453 | B1 | 6/2003 | Tran et al. |
| 6,585,730 | B1 | 7/2003 | Foerster |
| 6,585,740 | B2 | 7/2003 | Schlapfer et al. |
| 6,585,750 | B2 | 7/2003 | Bonutti et al. |
| 6,589,245 | B1 | 7/2003 | Weiler et al. |
| 6,589,246 | B1 | 7/2003 | Hack et al. |
| 6,592,609 | B1 | 7/2003 | Bonutti |
| 6,592,622 | B1 | 7/2003 | Ferguson |
| 6,595,911 | B2 | 7/2003 | Lovuolo |
| 6,599,289 | B1 | 7/2003 | Bojarski et al. |
| 6,599,319 | B2 | 7/2003 | Knudsen et al. |
| 6,605,096 | B1 | 8/2003 | Ritchart |
| 6,607,548 | B2 | 8/2003 | Pohjonen et al. |
| 6,610,064 | B1 | 8/2003 | Goble et al. |
| 6,610,079 | B1 | 8/2003 | Li et al. |
| 6,613,018 | B2 | 9/2003 | Bagga et al. |
| 6,616,694 | B1 | 9/2003 | Hart |
| 6,620,166 | B1 | 9/2003 | Wenstrom, Jr. et al. |
| 6,620,185 | B1 | 9/2003 | Harvie et al. |
| 6,620,195 | B2 | 9/2003 | Goble et al. |
| 6,620,329 | B2 | 9/2003 | Rosen et al. |
| 6,620,349 | B1 | 9/2003 | Lopez |
| 6,623,492 | B1 | 9/2003 | Berube et al. |
| 6,623,524 | B2 | 9/2003 | Schmieding |
| 6,626,910 | B1 | 9/2003 | Hugues |
| 6,626,919 | B1 | 9/2003 | Swanstrom |
| 6,626,930 | B1 | 9/2003 | Allen et al. |

(56) References Cited

U.S. PATENT DOCUMENTS

| | | | |
|---|---|---|---|
| 6,629,977 | B1 | 10/2003 | Wolf |
| 6,629,997 | B2 | 10/2003 | Mansmann |
| 6,632,245 | B2 | 10/2003 | Kim |
| 6,635,073 | B2 | 10/2003 | Bonutti |
| 6,638,279 | B2 | 10/2003 | Bonutti |
| 6,638,286 | B1 | 10/2003 | Burbank et al. |
| 6,638,312 | B2 | 10/2003 | Plouhar et al. |
| 6,641,596 | B1 | 11/2003 | Lizardi |
| 6,641,597 | B2 | 11/2003 | Burkhart et al. |
| 6,645,169 | B1 | 11/2003 | Slate et al. |
| 6,645,211 | B2 | 11/2003 | Magana |
| 6,645,227 | B2 | 11/2003 | Fallin et al. |
| 6,648,903 | B1 | 11/2003 | Pierson, III |
| 6,648,921 | B2 | 11/2003 | Anderson et al. |
| 6,652,450 | B2 | 11/2003 | Neisz et al. |
| 6,652,533 | B2 | 11/2003 | O'neil |
| 6,652,560 | B1 | 11/2003 | Gerke et al. |
| 6,652,562 | B2 | 11/2003 | Collier et al. |
| 6,652,563 | B2 | 11/2003 | Dreyfuss |
| 6,656,182 | B1 | 12/2003 | Hayhurst |
| 6,656,183 | B2 | 12/2003 | Colleran et al. |
| 6,658,182 | B1 | 12/2003 | Gonthier |
| 6,660,008 | B1 | 12/2003 | Foerster et al. |
| 6,660,022 | B1 | 12/2003 | Li et al. |
| 6,663,634 | B2 | 12/2003 | Ahrens et al. |
| 6,663,656 | B2 | 12/2003 | Schmieding et al. |
| 6,666,868 | B2 | 12/2003 | Fallin |
| 6,666,877 | B2 | 12/2003 | Morgan et al. |
| 6,669,707 | B1 | 12/2003 | Swanstrom et al. |
| 6,679,889 | B1 | 1/2004 | West, Jr. et al. |
| 6,682,533 | B1 | 1/2004 | Dinsdale et al. |
| 6,682,549 | B2 | 1/2004 | Bartlett |
| 6,685,728 | B2 | 2/2004 | Sinnott et al. |
| 6,689,137 | B2 | 2/2004 | Reed |
| 6,689,153 | B1 | 2/2004 | Skiba |
| 6,689,154 | B2 | 2/2004 | Bartlett |
| 6,692,499 | B2 | 2/2004 | Tormala et al. |
| 6,692,516 | B2 | 2/2004 | West, Jr. et al. |
| 6,695,852 | B2 | 2/2004 | Gleason |
| 6,712,849 | B2 | 3/2004 | Re et al. |
| 6,712,859 | B2 | 3/2004 | Rousseau |
| 6,716,190 | B1 | 4/2004 | Glines et al. |
| 6,716,224 | B2 | 4/2004 | Singhatat |
| 6,716,234 | B2 | 4/2004 | Grafton et al. |
| 6,716,957 | B2 | 4/2004 | Tunc |
| 6,730,092 | B2 | 5/2004 | Songer |
| 6,730,124 | B2 | 5/2004 | Steiner |
| 6,736,799 | B1 | 5/2004 | Erbe et al. |
| 6,737,053 | B1 | 5/2004 | Goh et al. |
| 6,746,483 | B1 | 6/2004 | Bojarski et al. |
| 6,752,780 | B2 | 6/2004 | Stout et al. |
| 6,752,810 | B1 | 6/2004 | Gao et al. |
| 6,752,831 | B2 | 6/2004 | Sybert et al. |
| 6,755,836 | B1 | 6/2004 | Lewis |
| 6,755,868 | B2 | 6/2004 | Rousseau |
| 6,761,722 | B2 | 7/2004 | Cole et al. |
| 6,761,739 | B2 | 7/2004 | Shepard |
| 6,767,037 | B2 | 7/2004 | Wenstrom, Jr. |
| 6,770,076 | B2 | 8/2004 | Foerster |
| 6,770,084 | B1 | 8/2004 | Bain et al. |
| 6,773,450 | B2 | 8/2004 | Leung et al. |
| 6,779,701 | B2 | 8/2004 | Bailly et al. |
| 6,780,190 | B2 | 8/2004 | Maroney |
| 6,780,198 | B1 | 8/2004 | Gregoire et al. |
| 6,790,210 | B1 | 9/2004 | Cragg et al. |
| 6,793,595 | B1 | 9/2004 | Monnet |
| 6,802,862 | B1 | 10/2004 | Roger et al. |
| 6,808,502 | B2 | 10/2004 | Nguyen |
| 6,808,526 | B1 | 10/2004 | Magerl et al. |
| 6,814,741 | B2 | 11/2004 | Bowman et al. |
| 6,830,572 | B2 | 12/2004 | Mcdevitt et al. |
| 6,833,005 | B1 | 12/2004 | Mantas |
| 6,835,377 | B2 | 12/2004 | Goldberg et al. |
| 6,840,953 | B2 | 1/2005 | Martinek |
| 6,860,885 | B2 | 3/2005 | Bonutti |
| 6,860,895 | B1 | 3/2005 | Akerfeldt et al. |
| 6,863,671 | B1 | 3/2005 | Strobel et al. |
| 6,872,040 | B2 | 3/2005 | Deeg et al. |
| 6,872,210 | B2 | 3/2005 | Hearn |
| 6,875,216 | B2 | 4/2005 | Wolf |
| 6,884,249 | B2 | 4/2005 | May et al. |
| 6,887,243 | B2 | 5/2005 | Culbert |
| 6,887,259 | B2 | 5/2005 | Lizardi |
| 6,887,271 | B2 | 5/2005 | Justin et al. |
| 6,890,354 | B2 | 5/2005 | Steiner et al. |
| 6,893,448 | B2 | 5/2005 | O'quinn et al. |
| 6,896,686 | B2 | 5/2005 | Weber |
| 6,899,722 | B2 | 5/2005 | Bonutti |
| 6,902,573 | B2 | 6/2005 | Strobel et al. |
| 6,905,513 | B1 | 6/2005 | Metzger |
| 6,908,466 | B1 | 6/2005 | Bonutti et al. |
| 6,911,202 | B2 | 6/2005 | Amir et al. |
| 6,916,292 | B2 | 7/2005 | Morawski et al. |
| 6,916,321 | B2 | 7/2005 | Tenhuisen et al. |
| 6,921,402 | B2 | 7/2005 | Contiliano et al. |
| 6,923,823 | B1 | 8/2005 | Bartlett et al. |
| 6,923,824 | B2 | 8/2005 | Morgan et al. |
| 6,923,832 | B1 | 8/2005 | Sharkey et al. |
| 6,939,379 | B2 | 9/2005 | Sklar |
| 6,946,001 | B2 | 9/2005 | Sanford et al. |
| 6,949,102 | B2 | 9/2005 | Andrews |
| 6,951,565 | B2 | 10/2005 | Keane et al. |
| 6,960,214 | B2 | 11/2005 | Burkinshaw |
| 6,966,887 | B1 | 11/2005 | Chin |
| 6,966,916 | B2 | 11/2005 | Kumar |
| 6,969,391 | B1 | 11/2005 | Gazzani |
| 6,969,398 | B2 | 11/2005 | Stevens et al. |
| 6,972,027 | B2 | 12/2005 | Fallin et al. |
| 6,980,903 | B2 | 12/2005 | Daniels et al. |
| 6,984,237 | B2 | 1/2006 | Hatch et al. |
| 6,986,781 | B2 | 1/2006 | Smith |
| 6,989,034 | B2 | 1/2006 | Hammer et al. |
| 6,994,719 | B2 | 2/2006 | Grafton |
| 6,994,725 | B1 | 2/2006 | Goble |
| 7,001,429 | B2 | 2/2006 | Ferguson |
| 7,004,959 | B2 | 2/2006 | Bonutti |
| 7,008,451 | B2 | 3/2006 | Justin et al. |
| 7,011,682 | B2 | 3/2006 | Lashinski et al. |
| 7,033,397 | B2 | 4/2006 | Webster et al. |
| 7,048,754 | B2 | 5/2006 | Martin et al. |
| 7,052,499 | B2 | 5/2006 | Steger et al. |
| 7,060,101 | B2 | 6/2006 | O'Connor et al. |
| 7,066,942 | B2 | 6/2006 | Treace |
| 7,066,944 | B2 | 6/2006 | Laufer et al. |
| 7,081,126 | B2 | 7/2006 | Mcdevitt et al. |
| 7,083,638 | B2 | 8/2006 | Foerster |
| 7,087,064 | B1 | 8/2006 | Hyde |
| 7,087,073 | B2 | 8/2006 | Bonutti |
| 7,090,690 | B2 | 8/2006 | Foerster et al. |
| 7,097,654 | B1 | 8/2006 | Freedland |
| 7,101,395 | B2 | 9/2006 | Tremulis et al. |
| 7,105,010 | B2 | 9/2006 | Hart et al. |
| 7,105,026 | B2 | 9/2006 | Johnson et al. |
| 7,112,221 | B2 | 9/2006 | Harris |
| 7,118,578 | B2 | 10/2006 | West, Jr. et al. |
| 7,118,583 | B2 | 10/2006 | O'quinn et al. |
| 7,125,421 | B2 | 10/2006 | Tremulis et al. |
| 7,131,467 | B2 | 11/2006 | Gao et al. |
| 7,137,996 | B2 | 11/2006 | Steiner et al. |
| 7,141,066 | B2 | 11/2006 | Steiner et al. |
| 7,144,414 | B2 | 12/2006 | Harvie et al. |
| 7,148,209 | B2 | 12/2006 | Hoemann et al. |
| 7,153,127 | B2 | 12/2006 | Struble et al. |
| 7,153,307 | B2 | 12/2006 | Scribner |
| 7,153,312 | B1 | 12/2006 | Torrie et al. |
| 7,153,327 | B1 | 12/2006 | Metzger |
| 7,160,285 | B2 | 1/2007 | Sklar et al. |
| 7,160,333 | B2 | 1/2007 | Plouhar et al. |
| 7,172,626 | B1 | 2/2007 | Andrews |
| 7,179,259 | B1 | 2/2007 | Gibbs |
| 7,201,722 | B2 | 4/2007 | Krueger |
| 7,207,993 | B1 | 4/2007 | Baldwin et al. |
| 7,229,441 | B2 | 6/2007 | Trieu et al. |
| 7,235,091 | B2 | 6/2007 | Thornes |

(56) References Cited

U.S. PATENT DOCUMENTS

| | | | |
|---|---|---|---|
| 7,255,675 | B2 | 8/2007 | Gertner et al. |
| 7,255,700 | B2 | 8/2007 | Kaiser et al. |
| 7,255,715 | B2 | 8/2007 | Metzger |
| 7,261,716 | B2 | 8/2007 | Strobel et al. |
| 7,264,634 | B2 | 9/2007 | Schmieding |
| 7,279,008 | B2 | 10/2007 | Brown et al. |
| 7,285,124 | B2 | 10/2007 | Foerster |
| 7,291,177 | B2 | 11/2007 | Gibbs |
| 7,303,577 | B1 | 12/2007 | Dean |
| 7,306,417 | B2 | 12/2007 | Dorstewitz |
| 7,309,355 | B2 | 12/2007 | Donnelly et al. |
| 7,326,222 | B2 | 2/2008 | Dreyfuss et al. |
| 7,329,272 | B2 | 2/2008 | Burkhart et al. |
| 7,354,354 | B2 | 4/2008 | Palumbo et al. |
| 7,361,179 | B2 | 4/2008 | Rousseau et al. |
| 7,377,845 | B2 | 5/2008 | Stewart et al. |
| 7,390,329 | B2 | 6/2008 | Westra et al. |
| 7,390,332 | B2 | 6/2008 | Selvitelli et al. |
| 7,399,018 | B1 | 7/2008 | Khachaturian |
| 7,442,210 | B2 | 10/2008 | Segal et al. |
| 7,462,198 | B2 | 12/2008 | Webster et al. |
| 7,463,198 | B2 | 12/2008 | Deaett et al. |
| 7,465,308 | B2 | 12/2008 | Sikora et al. |
| 7,468,074 | B2 | 12/2008 | Caborn |
| 7,481,814 | B1 | 1/2009 | Metzger |
| 7,484,539 | B1 | 2/2009 | Huang |
| 7,485,149 | B1 | 2/2009 | White |
| 7,494,496 | B2 | 2/2009 | Swain et al. |
| 7,494,506 | B2 | 2/2009 | Brulez et al. |
| D587,807 | S | 3/2009 | Wolf et al. |
| 7,500,983 | B1 | 3/2009 | Kaiser et al. |
| 7,513,910 | B2 | 4/2009 | Buskirk et al. |
| 7,517,357 | B2 | 4/2009 | Abrams et al. |
| 7,572,275 | B2 | 8/2009 | Fallin et al. |
| 7,572,298 | B2 | 8/2009 | Roller et al. |
| 7,578,825 | B2 | 8/2009 | Huebner |
| 7,585,311 | B2 | 9/2009 | Green et al. |
| 7,588,587 | B2 | 9/2009 | Barbieri et al. |
| 7,591,823 | B2 | 9/2009 | Tipirneni |
| 7,597,705 | B2 | 10/2009 | Forsberg et al. |
| 7,601,165 | B2 | 10/2009 | Stone |
| 7,604,636 | B1 | 10/2009 | Walters et al. |
| 7,608,092 | B1 | 10/2009 | Schaffhasen |
| 7,608,098 | B1 | 10/2009 | Stone et al. |
| 7,615,076 | B2 | 11/2009 | Cauthen, III et al. |
| 7,621,937 | B2 | 11/2009 | Pipenhagen et al. |
| 7,632,287 | B2 | 12/2009 | Baker et al. |
| 7,651,509 | B2 | 1/2010 | Bojarski et al. |
| 7,658,750 | B2 | 2/2010 | Li |
| 7,658,751 | B2 | 2/2010 | Stone et al. |
| 7,670,279 | B2 | 3/2010 | Gertner |
| 7,678,123 | B2 | 3/2010 | Chanduszko |
| 7,686,810 | B2 | 3/2010 | West, Jr. et al. |
| 7,691,112 | B2 | 4/2010 | Chanduszko et al. |
| 7,695,493 | B2 | 4/2010 | Saadat et al. |
| 7,695,503 | B1 | 4/2010 | Kaiser |
| 7,703,372 | B1 | 4/2010 | Shakespeare |
| 7,713,188 | B2 | 5/2010 | Bouffier |
| 7,713,285 | B1 | 5/2010 | Stone et al. |
| 7,717,929 | B2 | 5/2010 | Fallman |
| 7,731,732 | B2 | 6/2010 | Ken |
| 7,736,364 | B2 | 6/2010 | Stone |
| 7,736,379 | B2 | 6/2010 | Ewers et al. |
| 7,749,250 | B2 | 7/2010 | Stone et al. |
| 7,758,594 | B2 | 7/2010 | Lamson et al. |
| 7,758,611 | B2 | 7/2010 | Kato |
| 7,762,942 | B2 | 7/2010 | Neisz et al. |
| 7,771,482 | B1 | 8/2010 | Karmon |
| 7,776,041 | B1 | 8/2010 | Walters |
| 7,780,701 | B1 | 8/2010 | Meridew et al. |
| 7,790,945 | B1 | 9/2010 | Watson, Jr. |
| 7,803,173 | B2 | 9/2010 | Burkhart et al. |
| 7,819,895 | B2 | 10/2010 | Ginn et al. |
| 7,828,820 | B2 | 11/2010 | Stone et al. |
| 7,828,850 | B2 | 11/2010 | Cauthen, III et al. |
| 7,856,698 | B2 | 12/2010 | Hays |
| 7,857,830 | B2 | 12/2010 | Stone et al. |
| 7,867,252 | B2 | 1/2011 | Criscuolo et al. |
| 7,867,264 | B2 | 1/2011 | Mcdevitt et al. |
| 7,875,058 | B2 | 1/2011 | Holmes, Jr. |
| 7,878,058 | B2 | 2/2011 | Blendinger et al. |
| 7,887,586 | B2 | 2/2011 | Linares |
| 7,896,907 | B2 | 3/2011 | Mcdevitt et al. |
| 7,905,903 | B2 | 3/2011 | Stone et al. |
| 7,905,904 | B2 | 3/2011 | Stone et al. |
| 7,909,851 | B2 | 3/2011 | Stone et al. |
| 7,914,539 | B2 | 3/2011 | Stone et al. |
| 7,938,847 | B2 | 5/2011 | Fanton et al. |
| 7,951,198 | B2 | 5/2011 | Sucec et al. |
| 7,955,388 | B2 | 6/2011 | Jensen et al. |
| 7,959,650 | B2 * | 6/2011 | Kaiser .............. A61B 17/06166 606/232 |
| 7,976,565 | B1 | 7/2011 | Meridew |
| 7,981,140 | B2 | 7/2011 | Burkhart |
| 7,998,203 | B2 | 8/2011 | Blum |
| 8,034,090 | B2 | 10/2011 | Stone et al. |
| 8,062,334 | B2 | 11/2011 | Green et al. |
| 8,066,776 | B2 | 11/2011 | O'Connor et al. |
| 8,075,574 | B2 | 12/2011 | May et al. |
| 8,075,626 | B2 | 12/2011 | Dun |
| 8,088,108 | B2 | 1/2012 | Kraft |
| 8,088,130 | B2 | 1/2012 | Kaiser et al. |
| 8,109,867 | B2 | 2/2012 | Rosenblatt |
| 8,114,127 | B2 | 2/2012 | West, Jr. |
| 8,114,128 | B2 | 2/2012 | Cauldwell et al. |
| 8,118,835 | B2 | 2/2012 | Weisel et al. |
| 8,118,836 | B2 | 2/2012 | Denham et al. |
| 8,118,868 | B2 | 2/2012 | May et al. |
| 8,128,658 | B2 | 3/2012 | Kaiser et al. |
| 8,137,354 | B2 | 3/2012 | Stone |
| 8,137,382 | B2 | 3/2012 | Denham et al. |
| 8,137,407 | B2 | 3/2012 | Todd et al. |
| 8,142,510 | B2 | 3/2012 | Lee et al. |
| 8,147,557 | B2 | 4/2012 | Lee et al. |
| 8,147,558 | B2 | 4/2012 | Lee et al. |
| 8,162,997 | B2 | 4/2012 | Struhl |
| 8,167,906 | B2 | 5/2012 | Cauldwell et al. |
| 8,177,810 | B2 | 5/2012 | Ferree |
| 8,202,295 | B2 | 6/2012 | Kaplan |
| 8,202,318 | B2 | 6/2012 | Willobee |
| 8,221,454 | B2 | 7/2012 | Schaffhasen |
| 8,231,654 | B2 | 7/2012 | Kaiser et al. |
| 8,251,998 | B2 | 8/2012 | Hoeppner et al. |
| 8,252,022 | B2 | 8/2012 | Holman et al. |
| 8,273,106 | B2 | 9/2012 | Stone et al. |
| 8,292,921 | B2 | 10/2012 | Stone et al. |
| 8,298,262 | B2 | 10/2012 | Stone et al. |
| 8,298,284 | B2 | 10/2012 | Cassani |
| 8,303,589 | B2 | 11/2012 | Tyber et al. |
| 8,303,604 | B2 | 11/2012 | Stone et al. |
| 8,317,825 | B2 | 11/2012 | Stone |
| 8,328,806 | B2 | 12/2012 | Tyber et al. |
| 8,333,788 | B2 | 12/2012 | Maiorino |
| 8,337,525 | B2 | 12/2012 | Stone et al. |
| 8,343,155 | B2 | 1/2013 | Fisher et al. |
| 8,343,227 | B2 | 1/2013 | Metzger et al. |
| 8,361,054 | B2 | 1/2013 | Ducharme et al. |
| 8,361,113 | B2 | 1/2013 | Stone et al. |
| 8,409,253 | B2 | 4/2013 | Stone et al. |
| 8,454,635 | B2 | 6/2013 | Paolitto et al. |
| 8,486,114 | B2 | 7/2013 | Gillard et al. |
| 8,500,818 | B2 | 8/2013 | Metzger et al. |
| 8,506,597 | B2 | 8/2013 | Kaiser et al. |
| 8,545,535 | B2 | 10/2013 | Hirotsuka et al. |
| 8,551,140 | B2 | 10/2013 | Denham et al. |
| 8,562,645 | B2 | 10/2013 | Stone et al. |
| 8,562,647 | B2 | 10/2013 | Kaiser et al. |
| 8,574,235 | B2 | 11/2013 | Stone |
| 8,579,901 | B1 | 11/2013 | Foerster |
| 8,579,944 | B2 | 11/2013 | Holloway et al. |
| 8,591,544 | B2 | 11/2013 | Jolly et al. |
| 8,597,327 | B2 | 12/2013 | Stone et al. |
| 8,608,777 | B2 | 12/2013 | Kaiser et al. |
| 8,632,566 | B2 | 1/2014 | Olson |

(56) References Cited

U.S. PATENT DOCUMENTS

| | | | |
|---|---|---|---|
| 8,632,569 | B2 | 1/2014 | Stone et al. |
| 8,652,171 | B2 | 2/2014 | Stone et al. |
| 8,652,172 | B2 | 2/2014 | Denham et al. |
| 8,672,904 | B1 | 3/2014 | Schultz |
| 8,672,968 | B2 | 3/2014 | Stone et al. |
| 8,672,969 | B2 | 3/2014 | Stone et al. |
| 8,702,718 | B2 | 4/2014 | Bhatnagar et al. |
| 8,715,297 | B1 | 5/2014 | Foerster et al. |
| 8,721,650 | B2 | 5/2014 | Fanton et al. |
| 8,721,684 | B2 | 5/2014 | Denham et al. |
| 8,771,316 | B2 | 7/2014 | Denham et al. |
| 8,771,352 | B2 | 7/2014 | Conner et al. |
| 8,777,956 | B2 | 7/2014 | Hoeppner et al. |
| 8,801,783 | B2 | 8/2014 | Stone et al. |
| 8,808,374 | B2 | 8/2014 | Eggli |
| 8,814,903 | B2 | 8/2014 | Sengun et al. |
| 8,828,067 | B2 | 9/2014 | Tipirneni et al. |
| 8,840,645 | B2 | 9/2014 | Denham et al. |
| 8,858,642 | B2 | 10/2014 | Metzger et al. |
| 8,894,715 | B2 | 11/2014 | Metzger et al. |
| 8,900,314 | B2 | 12/2014 | Metzger et al. |
| 8,926,613 | B2 | 1/2015 | Kaiser et al. |
| 8,932,331 | B2 | 1/2015 | Kaiser et al. |
| 8,936,621 | B2 | 1/2015 | Denham et al. |
| 8,961,548 | B2 | 2/2015 | Buser |
| 8,968,364 | B2 | 3/2015 | Berelsman |
| 8,998,949 | B2 | 4/2015 | Stone et al. |
| 9,005,287 | B2 | 4/2015 | Stone |
| 9,017,381 | B2 | 4/2015 | Kaiser et al. |
| 9,023,058 | B2 | 5/2015 | Jaramillo et al. |
| 9,028,509 | B2 | 5/2015 | Chu et al. |
| 9,078,644 | B2 | 7/2015 | Stone |
| 9,149,267 | B2 | 10/2015 | Norton et al. |
| 9,173,651 | B2 | 11/2015 | Stone et al. |
| 9,179,950 | B2 | 11/2015 | Zajac et al. |
| 9,198,673 | B2 | 12/2015 | Stone |
| 9,216,078 | B2 | 12/2015 | Conner et al. |
| 9,271,713 | B2 | 3/2016 | Denham et al. |
| 9,271,826 | B2 | 3/2016 | Eggli et al. |
| 9,289,285 | B2 | 3/2016 | Eggli |
| 9,314,235 | B2 | 4/2016 | Bojarski et al. |
| 9,314,241 | B2 | 4/2016 | Stone et al. |
| 9,357,991 | B2 | 6/2016 | Denham et al. |
| 9,357,992 | B2 | 6/2016 | Stone et al. |
| 9,370,350 | B2 | 6/2016 | Norton |
| 9,381,013 | B2 | 7/2016 | Norton |
| 9,402,621 | B2 | 8/2016 | Stone et al. |
| 9,408,599 | B2 | 8/2016 | Kaiser et al. |
| 9,414,833 | B2 | 8/2016 | Stone et al. |
| 9,414,925 | B2 | 8/2016 | Metzger et al. |
| 9,468,433 | B2 | 10/2016 | Denham et al. |
| 9,486,211 | B2 | 11/2016 | Stone et al. |
| 9,492,158 | B2 | 11/2016 | Stone et al. |
| 9,498,204 | B2 | 11/2016 | Denham et al. |
| 9,504,460 | B2 | 11/2016 | Stone et al. |
| 9,510,819 | B2 | 12/2016 | Stone et al. |
| 9,510,821 | B2 | 12/2016 | Denham et al. |
| 9,532,777 | B2 | 1/2017 | Kaiser et al. |
| 9,538,998 | B2 | 1/2017 | Stone et al. |
| 9,539,003 | B2 | 1/2017 | Stone et al. |
| 9,561,025 | B2 | 2/2017 | Stone et al. |
| 9,572,655 | B2 | 2/2017 | Denham |
| 9,585,651 | B2 | 3/2017 | Lam et al. |
| 9,603,591 | B2 | 3/2017 | Denham et al. |
| 9,622,736 | B2 | 4/2017 | Stone et al. |
| 9,642,661 | B2 | 5/2017 | Stone et al. |
| 9,681,940 | B2 | 6/2017 | Stone et al. |
| 9,724,090 | B2 | 8/2017 | Kaiser et al. |
| 9,743,919 | B2 | 8/2017 | Manos et al. |
| 9,757,119 | B2 | 9/2017 | Norton et al. |
| 9,763,656 | B2 | 9/2017 | Stone et al. |
| 9,782,245 | B2 | 10/2017 | Mujwid et al. |
| 9,788,876 | B2 | 10/2017 | Stone |
| 9,801,620 | B2 | 10/2017 | Kaiser et al. |
| 9,801,708 | B2 | 10/2017 | Denham et al. |
| 9,833,230 | B2 | 12/2017 | Stone |
| 9,861,351 | B2 | 1/2018 | Kaiser et al. |
| 9,918,826 | B2 | 3/2018 | Berelsman et al. |
| 9,918,827 | B2 | 3/2018 | Berelsman et al. |
| 9,993,241 | B2 | 6/2018 | Denham et al. |
| 10,004,489 | B2 | 6/2018 | Kaiser et al. |
| 10,004,493 | B2 | 6/2018 | Stone et al. |
| 10,004,588 | B2 | 6/2018 | Berelsman et al. |
| 10,022,118 | B2 | 7/2018 | Norton et al. |
| 10,092,288 | B2 | 10/2018 | Denham et al. |
| 10,098,629 | B2 | 10/2018 | Kaiser et al. |
| 10,154,837 | B2 | 12/2018 | Stone et al. |
| 10,167,582 | B1 | 1/2019 | Pilgeram et al. |
| 10,251,637 | B2 | 4/2019 | Stone et al. |
| 10,265,064 | B2 | 4/2019 | Stone et al. |
| 10,265,159 | B2 | 4/2019 | Denham et al. |
| 10,321,906 | B2 | 6/2019 | Stone et al. |
| 10,349,931 | B2 | 7/2019 | Stone |
| 10,363,028 | B2 | 7/2019 | Norton |
| 10,368,856 | B2 | 8/2019 | Stone et al. |
| 10,398,428 | B2 | 9/2019 | Denham et al. |
| 10,398,430 | B2 | 9/2019 | Stone et al. |
| 10,441,264 | B2 | 10/2019 | Stone et al. |
| 10,517,587 | B2 | 12/2019 | Denham et al. |
| 10,517,714 | B2 | 12/2019 | Stone et al. |
| 10,542,967 | B2 | 1/2020 | Kaiser et al. |
| 10,595,851 | B2 | 3/2020 | Kaiser et al. |
| 10,603,029 | B2 | 3/2020 | Kaiser et al. |
| 10,610,217 | B2 | 4/2020 | Stone et al. |
| 10,675,073 | B2 | 6/2020 | Stone et al. |
| 10,687,803 | B2 | 6/2020 | Denham et al. |
| 10,695,045 | B2 | 6/2020 | Kaiser et al. |
| 10,695,052 | B2 | 6/2020 | Denham et al. |
| 10,702,259 | B2 | 7/2020 | Stone et al. |
| 10,716,557 | B2 | 7/2020 | Denham et al. |
| 10,729,421 | B2 | 8/2020 | Stone et al. |
| 10,729,423 | B2 | 8/2020 | Kaiser et al. |
| 10,729,430 | B2 | 8/2020 | Denham et al. |
| 10,743,925 | B2 | 8/2020 | Stone et al. |
| 10,758,221 | B2 | 9/2020 | Berelsman et al. |
| 10,835,232 | B2 | 11/2020 | Stone et al. |
| 10,932,770 | B2 | 3/2021 | Stone et al. |
| 10,973,507 | B2 | 4/2021 | Stone et al. |
| 10,987,099 | B2 | 4/2021 | Stone et al. |
| 11,039,826 | B2 | 6/2021 | Denham et al. |
| 11,065,103 | B2 | 7/2021 | Berelsman et al. |
| 11,096,684 | B2 | 8/2021 | Stone et al. |
| 11,109,857 | B2 | 9/2021 | Stone et al. |
| 11,116,495 | B2 | 9/2021 | Stone et al. |
| 11,185,320 | B2 | 11/2021 | Kaiser et al. |
| 11,241,305 | B2 | 2/2022 | Denham et al. |
| 11,259,792 | B2 | 3/2022 | Denham et al. |
| 11,259,794 | B2 | 3/2022 | Stone et al. |
| 11,284,884 | B2 | 3/2022 | Denham et al. |
| 11,311,287 | B2 | 4/2022 | Stone et al. |
| 11,317,907 | B2 | 5/2022 | Denham et al. |
| 11,376,115 | B2 | 7/2022 | Stone et al. |
| 11,446,019 | B2 | 9/2022 | Stone et al. |
| 11,471,147 | B2 | 10/2022 | Kaiser et al. |
| 11,534,157 | B2 | 12/2022 | Norton |
| 11,534,159 | B2 | 12/2022 | Denham et al. |
| 11,589,859 | B2 | 2/2023 | Kaiser et al. |
| 11,612,391 | B2 | 3/2023 | Stone et al. |
| 11,617,572 | B2 | 4/2023 | Stone et al. |
| 11,672,527 | B2 | 6/2023 | Stone et al. |
| 11,723,648 | B2 | 8/2023 | Stone et al. |
| 11,730,464 | B2 | 8/2023 | Stone et al. |
| 11,786,236 | B2 | 10/2023 | Denham et al. |
| 11,819,205 | B2 | 11/2023 | Stone et al. |
| 11,896,210 | B2 | 2/2024 | Stone et al. |
| 11,998,185 | B2 | 6/2024 | Kaiser et al. |
| 12,064,101 | B2 | 8/2024 | Denham et al. |
| 12,096,928 | B2 | 9/2024 | Kaiser et al. |
| 12,096,931 | B2 | 9/2024 | Denham et al. |
| 12,245,759 | B2 | 3/2025 | Kaiser et al. |
| 12,251,093 | B2 | 3/2025 | Kaiser et al. |
| 12,251,100 | B2 | 3/2025 | Norton et al. |
| 12,303,122 | B2 | 5/2025 | Kaiser et al. |
| 12,329,373 | B2 | 6/2025 | Stone et al. |

(56) References Cited

U.S. PATENT DOCUMENTS

| | | | |
|---|---|---|---|
| 12,336,701 | B2 | 6/2025 | Stone et al. |
| 2001/0002439 | A1 | 5/2001 | Bonutti et al. |
| 2001/0010005 | A1 | 7/2001 | Kammerer et al. |
| 2001/0014825 | A1 | 8/2001 | Burke et al. |
| 2001/0019649 | A1 | 9/2001 | Field et al. |
| 2001/0027341 | A1 | 10/2001 | Gianotti |
| 2001/0029387 | A1 | 10/2001 | Wolf et al. |
| 2001/0037131 | A1 | 11/2001 | Schmieding et al. |
| 2001/0037153 | A1 | 11/2001 | Charles, Jr. et al. |
| 2001/0041916 | A1 | 11/2001 | Bonutti |
| 2001/0041937 | A1 | 11/2001 | Rieser et al. |
| 2001/0041938 | A1 | 11/2001 | Hein |
| 2001/0044627 | A1 | 11/2001 | Justin |
| 2001/0044639 | A1 | 11/2001 | Levinson |
| 2001/0047206 | A1 | 11/2001 | Sklar et al. |
| 2001/0051815 | A1 | 12/2001 | Esplin |
| 2001/0051816 | A1 | 12/2001 | Enzerink et al. |
| 2001/0053934 | A1 | 12/2001 | Schmieding |
| 2001/0056299 | A1 | 12/2001 | Thompson |
| 2002/0001964 | A1 | 1/2002 | Choi |
| 2002/0004669 | A1 | 1/2002 | Bartlett |
| 2002/0007182 | A1 | 1/2002 | Kim |
| 2002/0010513 | A1 | 1/2002 | Schmieding |
| 2002/0013607 | A1 | 1/2002 | Lemer |
| 2002/0013608 | A1 | 1/2002 | Elattrache et al. |
| 2002/0019649 | A1 | 2/2002 | Sikora et al. |
| 2002/0029048 | A1 | 3/2002 | Miller |
| 2002/0029066 | A1 | 3/2002 | Foerster |
| 2002/0032465 | A1 | 3/2002 | Lemer |
| 2002/0045902 | A1 | 4/2002 | Bonutti |
| 2002/0052628 | A1 | 5/2002 | Bowman |
| 2002/0055780 | A1 | 5/2002 | Sklar |
| 2002/0058966 | A1 | 5/2002 | Tormala et al. |
| 2002/0068254 | A1 | 6/2002 | Campbell |
| 2002/0077629 | A1 | 6/2002 | Hoffman et al. |
| 2002/0077659 | A1 | 6/2002 | Johnson et al. |
| 2002/0082220 | A1 | 6/2002 | Hoemann et al. |
| 2002/0091391 | A1 | 7/2002 | Cole et al. |
| 2002/0099411 | A1 | 7/2002 | Bartlett |
| 2002/0111591 | A1 | 8/2002 | Mckinnon et al. |
| 2002/0111653 | A1 | 8/2002 | Foerster |
| 2002/0120270 | A1 | 8/2002 | Trieu et al. |
| 2002/0120292 | A1 | 8/2002 | Morgan |
| 2002/0123752 | A1 | 9/2002 | Schultheiss et al. |
| 2002/0128654 | A1 | 9/2002 | Steger et al. |
| 2002/0128684 | A1 | 9/2002 | Foerster |
| 2002/0129820 | A1 | 9/2002 | Ryan et al. |
| 2002/0143336 | A1 | 10/2002 | Hearn |
| 2002/0147463 | A1 | 10/2002 | Martinek |
| 2002/0156475 | A1 | 10/2002 | Lerch et al. |
| 2002/0161401 | A1 | 10/2002 | Steiner |
| 2002/0161439 | A1 | 10/2002 | Strobel et al. |
| 2002/0165548 | A1 | 11/2002 | Jutley |
| 2002/0165611 | A1 | 11/2002 | Enzerink et al. |
| 2002/0169452 | A1 | 11/2002 | Tormala et al. |
| 2002/0169477 | A1 | 11/2002 | Demopulos et al. |
| 2002/0169478 | A1 | 11/2002 | Schwartz et al. |
| 2002/0173788 | A1 | 11/2002 | Bojarski et al. |
| 2002/0177853 | A1 | 11/2002 | Chervitz et al. |
| 2002/0188298 | A1 | 12/2002 | Chan |
| 2002/0193830 | A1 | 12/2002 | Bonutti |
| 2003/0004545 | A1 | 1/2003 | Burkhart et al. |
| 2003/0009235 | A1 | 1/2003 | Manrique et al. |
| 2003/0023268 | A1 | 1/2003 | Lizardi |
| 2003/0032961 | A1 | 2/2003 | Pelo et al. |
| 2003/0033021 | A1 | 2/2003 | Plouhar et al. |
| 2003/0033022 | A1 | 2/2003 | Plouhar et al. |
| 2003/0036797 | A1 | 2/2003 | Malaviya et al. |
| 2003/0036801 | A1 | 2/2003 | Schwartz et al. |
| 2003/0050667 | A1 | 3/2003 | Grafton et al. |
| 2003/0065361 | A1 | 4/2003 | Dreyfuss |
| 2003/0065391 | A1 | 4/2003 | Re et al. |
| 2003/0065402 | A1 | 4/2003 | Anderson et al. |
| 2003/0078585 | A1 | 4/2003 | Johnson et al. |
| 2003/0078603 | A1 | 4/2003 | Schaller et al. |
| 2003/0078617 | A1 | 4/2003 | Schwartz et al. |
| 2003/0083662 | A1 | 5/2003 | Middleton |
| 2003/0083694 | A1 | 5/2003 | Archibald, III |
| 2003/0088251 | A1 | 5/2003 | Braun et al. |
| 2003/0088272 | A1 | 5/2003 | Smith |
| 2003/0093156 | A1 | 5/2003 | Metzger et al. |
| 2003/0105477 | A1 | 6/2003 | Schwartz et al. |
| 2003/0105489 | A1 | 6/2003 | Eichhorn et al. |
| 2003/0114929 | A1 | 6/2003 | Knudsen |
| 2003/0120309 | A1 | 6/2003 | Colleran et al. |
| 2003/0130670 | A1 | 7/2003 | Anderson et al. |
| 2003/0130694 | A1 | 7/2003 | Bojarski et al. |
| 2003/0130695 | A1 | 7/2003 | Mcdevitt et al. |
| 2003/0135214 | A1 | 7/2003 | Fetto |
| 2003/0135239 | A1 | 7/2003 | Gabriel et al. |
| 2003/0135265 | A1 | 7/2003 | Stinson |
| 2003/0135963 | A1 | 7/2003 | Holbrook et al. |
| 2003/0139752 | A1 | 7/2003 | Pasricha et al. |
| 2003/0139775 | A1 | 7/2003 | Grafton |
| 2003/0144696 | A1 | 7/2003 | Sinnott et al. |
| 2003/0149448 | A1 | 8/2003 | Foerster et al. |
| 2003/0152522 | A1 | 8/2003 | Miller et al. |
| 2003/0153947 | A1 | 8/2003 | Koseki |
| 2003/0167072 | A1 | 9/2003 | Oberlander |
| 2003/0167090 | A1 | 9/2003 | Chervitz et al. |
| 2003/0171811 | A1 | 9/2003 | Steiner et al. |
| 2003/0176865 | A1 | 9/2003 | Supinski |
| 2003/0176919 | A1 | 9/2003 | Schmieding |
| 2003/0176920 | A1 | 9/2003 | Sklar et al. |
| 2003/0181925 | A1 | 9/2003 | Bain et al. |
| 2003/0187510 | A1 | 10/2003 | Hyde |
| 2003/0195528 | A1 | 10/2003 | Ritchart |
| 2003/0195564 | A1 | 10/2003 | Tran et al. |
| 2003/0195565 | A1 | 10/2003 | Bonutti |
| 2003/0208209 | A1 | 11/2003 | Gambale et al. |
| 2003/0208210 | A1 | 11/2003 | Dreyfuss et al. |
| 2003/0212456 | A1 | 11/2003 | Lipchitz et al. |
| 2003/0216809 | A1 | 11/2003 | Ferguson |
| 2003/0220646 | A1 | 11/2003 | Thelen et al. |
| 2003/0220660 | A1 | 11/2003 | Kortenbach et al. |
| 2003/0225459 | A1 | 12/2003 | Hammer et al. |
| 2003/0229361 | A1 | 12/2003 | Jackson |
| 2003/0229396 | A1 | 12/2003 | Andrews |
| 2003/0236555 | A1 | 12/2003 | Thornes |
| 2004/0002734 | A1 | 1/2004 | Fallin et al. |
| 2004/0006345 | A1 | 1/2004 | Vlahos et al. |
| 2004/0006346 | A1 | 1/2004 | Holmen et al. |
| 2004/0013380 | A1 | 1/2004 | Jimenez |
| 2004/0015171 | A1 | 1/2004 | Bojarski et al. |
| 2004/0015172 | A1 | 1/2004 | Biedermann et al. |
| 2004/0024456 | A1 | 2/2004 | Charles, Jr. et al. |
| 2004/0024457 | A1 | 2/2004 | Boyce et al. |
| 2004/0039389 | A1 | 2/2004 | Hugh, Jr. et al. |
| 2004/0044351 | A1 | 3/2004 | Searle |
| 2004/0044391 | A1 | 3/2004 | Porter |
| 2004/0059357 | A1 | 3/2004 | Koseki |
| 2004/0073176 | A1 | 4/2004 | Utterberg |
| 2004/0087981 | A1 | 5/2004 | Berube et al. |
| 2004/0092936 | A1 | 5/2004 | Miller et al. |
| 2004/0093031 | A1 | 5/2004 | Burkhart et al. |
| 2004/0093032 | A1 | 5/2004 | Sinnott et al. |
| 2004/0098051 | A1 | 5/2004 | Fallin et al. |
| 2004/0098053 | A1 | 5/2004 | Tran |
| 2004/0098099 | A1 | 5/2004 | McCullagh et al. |
| 2004/0111117 | A1 | 6/2004 | Colleran et al. |
| 2004/0122431 | A1 | 6/2004 | Biedermann et al. |
| 2004/0122454 | A1 | 6/2004 | Wang et al. |
| 2004/0122456 | A1 | 6/2004 | Saadat et al. |
| 2004/0127907 | A1 | 7/2004 | Dakin et al. |
| 2004/0133206 | A1 | 7/2004 | Stevens et al. |
| 2004/0133211 | A1 | 7/2004 | Raskin et al. |
| 2004/0133238 | A1 | 7/2004 | Cerier |
| 2004/0133239 | A1 | 7/2004 | Singhatat |
| 2004/0138664 | A1 | 7/2004 | Bowman |
| 2004/0138683 | A1 | 7/2004 | Shelton et al. |
| 2004/0138704 | A1 | 7/2004 | Gambale et al. |
| 2004/0138706 | A1 | 7/2004 | Abrams et al. |
| 2004/0138747 | A1 | 7/2004 | Kaladelfos |
| 2004/0138755 | A1 | 7/2004 | O'connor et al. |

(56) References Cited

U.S. PATENT DOCUMENTS

| | | | |
|---|---|---|---|
| 2004/0143344 | A1 | 7/2004 | Malaviya et al. |
| 2004/0144535 | A1 | 7/2004 | Kalman et al. |
| 2004/0147932 | A1 | 7/2004 | Burkinshaw et al. |
| 2004/0147958 | A1 | 7/2004 | Lam et al. |
| 2004/0148030 | A1 | 7/2004 | Ek |
| 2004/0153103 | A1 | 8/2004 | Schwartz et al. |
| 2004/0153153 | A1 | 8/2004 | Elson et al. |
| 2004/0162579 | A1 | 8/2004 | Foerster |
| 2004/0166169 | A1 | 8/2004 | Malaviya et al. |
| 2004/0181234 | A1 | 9/2004 | Mcdevitt et al. |
| 2004/0182968 | A1 | 9/2004 | Gentry |
| 2004/0187314 | A1 | 9/2004 | Johnson |
| 2004/0193185 | A1 | 9/2004 | Mcbrayer |
| 2004/0199169 | A1 | 10/2004 | Koons et al. |
| 2004/0204722 | A1 | 10/2004 | Sikora et al. |
| 2004/0220574 | A1 | 11/2004 | Pelo et al. |
| 2004/0225183 | A1 | 11/2004 | Michlitsch et al. |
| 2004/0225292 | A1 | 11/2004 | Sasso et al. |
| 2004/0225305 | A1 | 11/2004 | Ewers et al. |
| 2004/0230302 | A1 | 11/2004 | May et al. |
| 2004/0236353 | A1 | 11/2004 | Bain et al. |
| 2004/0236373 | A1 | 11/2004 | William, III |
| 2004/0243139 | A1 | 12/2004 | Lewis et al. |
| 2004/0243178 | A1 | 12/2004 | Haut et al. |
| 2004/0243180 | A1 | 12/2004 | Donnelly et al. |
| 2004/0243235 | A1 | 12/2004 | Goh et al. |
| 2004/0249394 | A1 | 12/2004 | Morris et al. |
| 2004/0260296 | A1 | 12/2004 | Kaiser et al. |
| 2004/0260298 | A1 | 12/2004 | Kaiser et al. |
| 2004/0267164 | A1 | 12/2004 | Rhodes et al. |
| 2004/0267265 | A1 | 12/2004 | Kyle |
| 2004/0267270 | A1 | 12/2004 | Jacobs et al. |
| 2004/0267276 | A1 | 12/2004 | Camino et al. |
| 2004/0267277 | A1 | 12/2004 | Zannis et al. |
| 2004/0267286 | A1 | 12/2004 | Gao et al. |
| 2004/0267304 | A1 | 12/2004 | Zannis et al. |
| 2004/0267309 | A1 | 12/2004 | Garvin |
| 2004/0267317 | A1 | 12/2004 | Higgins et al. |
| 2004/0267361 | A1 | 12/2004 | Donnelly et al. |
| 2004/0267362 | A1 | 12/2004 | Hwang et al. |
| 2005/0004670 | A1 | 1/2005 | Gebhardt et al. |
| 2005/0021087 | A1 | 1/2005 | Koseki |
| 2005/0021148 | A1 | 1/2005 | Gibbs |
| 2005/0027307 | A1 | 2/2005 | Schwartz et al. |
| 2005/0033289 | A1 | 2/2005 | Warren et al. |
| 2005/0033362 | A1 | 2/2005 | Grafton |
| 2005/0033363 | A1 | 2/2005 | Bojarski et al. |
| 2005/0038426 | A1 | 2/2005 | Chan |
| 2005/0049598 | A1 | 3/2005 | West, Jr. et al. |
| 2005/0055027 | A1 | 3/2005 | Yeung et al. |
| 2005/0055037 | A1 | 3/2005 | Fathauer, Jr. |
| 2005/0064042 | A1 | 3/2005 | Vunjak-novakovic et al. |
| 2005/0065521 | A1 | 3/2005 | Steger et al. |
| 2005/0065526 | A1 | 3/2005 | Drew et al. |
| 2005/0070906 | A1 | 3/2005 | Clark et al. |
| 2005/0070928 | A1 | 3/2005 | Heino et al. |
| 2005/0074495 | A1 | 4/2005 | Schwartz et al. |
| 2005/0076478 | A1 | 4/2005 | Miyazaki et al. |
| 2005/0085819 | A1 | 4/2005 | Ellis et al. |
| 2005/0090827 | A1 | 4/2005 | Gedebou |
| 2005/0090828 | A1 | 4/2005 | Alford |
| 2005/0090862 | A1 | 4/2005 | Mcdevitt et al. |
| 2005/0096696 | A1 | 5/2005 | Forsberg |
| 2005/0096697 | A1 | 5/2005 | Forsberg et al. |
| 2005/0096743 | A1 | 5/2005 | Schmieding et al. |
| 2005/0101957 | A1 | 5/2005 | Buskirk et al. |
| 2005/0107795 | A1 | 5/2005 | Morris et al. |
| 2005/0107828 | A1 | 5/2005 | Reese |
| 2005/0107882 | A1 | 5/2005 | Stone et al. |
| 2005/0119531 | A1 | 6/2005 | Sharratt |
| 2005/0119696 | A1 | 6/2005 | Walters et al. |
| 2005/0124996 | A1 | 6/2005 | Hearn |
| 2005/0125031 | A1 | 6/2005 | Pipenhagen et al. |
| 2005/0125036 | A1 | 6/2005 | Roby |
| 2005/0125073 | A1 | 6/2005 | Orban et al. |
| 2005/0130301 | A1 | 6/2005 | Mckay et al. |
| 2005/0131413 | A1 | 6/2005 | O'driscoll et al. |
| 2005/0137600 | A1 | 6/2005 | Jacobs et al. |
| 2005/0137624 | A1 | 6/2005 | Fallman |
| 2005/0143734 | A1 | 6/2005 | Cachia et al. |
| 2005/0149033 | A1 | 7/2005 | Mcguire et al. |
| 2005/0149118 | A1 | 7/2005 | Koyfman et al. |
| 2005/0149119 | A1 | 7/2005 | Koyfman et al. |
| 2005/0149122 | A1 | 7/2005 | Mcdevitt et al. |
| 2005/0149187 | A1 | 7/2005 | Clark et al. |
| 2005/0154471 | A1 | 7/2005 | Aram et al. |
| 2005/0159812 | A1 | 7/2005 | Dinger, III et al. |
| 2005/0160656 | A1 | 7/2005 | Safwat et al. |
| 2005/0165416 | A1 | 7/2005 | Bojarski et al. |
| 2005/0165482 | A1 | 7/2005 | Goldhahn et al. |
| 2005/0171547 | A1 | 8/2005 | Aram |
| 2005/0171603 | A1 | 8/2005 | Justin et al. |
| 2005/0171604 | A1 | 8/2005 | Michalow |
| 2005/0177237 | A1 | 8/2005 | Shappley et al. |
| 2005/0187565 | A1 | 8/2005 | Baker et al. |
| 2005/0187577 | A1 | 8/2005 | Selvitelli et al. |
| 2005/0187635 | A1 | 8/2005 | Metzger |
| 2005/0192581 | A1 | 9/2005 | Molz et al. |
| 2005/0192632 | A1 | 9/2005 | Geissler et al. |
| 2005/0197711 | A1 | 9/2005 | Cachia |
| 2005/0203620 | A1 | 9/2005 | Steiner et al. |
| 2005/0209703 | A1 | 9/2005 | Fell |
| 2005/0222618 | A1 | 10/2005 | Dreyfuss et al. |
| 2005/0222619 | A1 | 10/2005 | Dreyfuss et al. |
| 2005/0228448 | A1 | 10/2005 | Li |
| 2005/0229433 | A1 | 10/2005 | Cachia |
| 2005/0234472 | A1 | 10/2005 | Huebner |
| 2005/0234549 | A1 | 10/2005 | Kladakis et al. |
| 2005/0240198 | A1 | 10/2005 | Albertson et al. |
| 2005/0251153 | A1 | 11/2005 | Sakamoto et al. |
| 2005/0251159 | A1 | 11/2005 | Ewers et al. |
| 2005/0251177 | A1 | 11/2005 | Saadat et al. |
| 2005/0251207 | A1 | 11/2005 | Flores et al. |
| 2005/0251208 | A1 | 11/2005 | Elmer et al. |
| 2005/0251209 | A1 | 11/2005 | Saadat et al. |
| 2005/0251210 | A1 | 11/2005 | Westra et al. |
| 2005/0261642 | A1 | 11/2005 | Weston |
| 2005/0267479 | A1 | 12/2005 | Morgan et al. |
| 2005/0267533 | A1 | 12/2005 | Gertner |
| 2005/0277088 | A1 | 12/2005 | Fischer et al. |
| 2005/0277939 | A1 | 12/2005 | Miller, III |
| 2005/0277961 | A1 | 12/2005 | Stone et al. |
| 2005/0277985 | A1 | 12/2005 | Wert et al. |
| 2005/0283040 | A1 | 12/2005 | Greenhalgh |
| 2005/0283156 | A1 | 12/2005 | Schmieding et al. |
| 2005/0283158 | A1 | 12/2005 | West, Jr. |
| 2005/0283192 | A1 | 12/2005 | Torrie et al. |
| 2005/0283220 | A1 | 12/2005 | Gobran et al. |
| 2005/0288710 | A1 | 12/2005 | Fallin et al. |
| 2006/0004364 | A1 | 1/2006 | Green et al. |
| 2006/0004410 | A1 | 1/2006 | Nobis et al. |
| 2006/0004460 | A1 | 1/2006 | Engh et al. |
| 2006/0015103 | A1 | 1/2006 | Burke |
| 2006/0015106 | A1 | 1/2006 | Lerch et al. |
| 2006/0015107 | A1 | 1/2006 | Sklar |
| 2006/0030884 | A1 | 2/2006 | Yeung et al. |
| 2006/0030948 | A1 | 2/2006 | Manrique et al. |
| 2006/0036265 | A1 | 2/2006 | Dant et al. |
| 2006/0052787 | A1 | 3/2006 | Re et al. |
| 2006/0052818 | A1 | 3/2006 | Drake et al. |
| 2006/0064125 | A1 | 3/2006 | Henderson et al. |
| 2006/0064126 | A1 | 3/2006 | Fallin et al. |
| 2006/0069334 | A1 | 3/2006 | Moskowitz |
| 2006/0079904 | A1 | 4/2006 | Thal |
| 2006/0084943 | A1 | 4/2006 | Rosenman et al. |
| 2006/0085000 | A1 | 4/2006 | Mohr et al. |
| 2006/0089525 | A1 | 4/2006 | Mamo et al. |
| 2006/0089672 | A1 | 4/2006 | Martinek |
| 2006/0095130 | A1 | 5/2006 | Caborn et al. |
| 2006/0095131 | A1 | 5/2006 | Justin et al. |
| 2006/0100627 | A1 | 5/2006 | Stone et al. |
| 2006/0100637 | A1 | 5/2006 | Rathbun et al. |
| 2006/0106423 | A1 | 5/2006 | Weisel et al. |
| 2006/0111721 | A1 | 5/2006 | Puricelli |

(56) References Cited

U.S. PATENT DOCUMENTS

| | | | |
|---|---|---|---|
| 2006/0116685 | A1 | 6/2006 | Urbanski et al. |
| 2006/0121084 | A1 | 6/2006 | Borden et al. |
| 2006/0122608 | A1 | 6/2006 | Fallin et al. |
| 2006/0122611 | A1 | 6/2006 | Morales et al. |
| 2006/0135958 | A1 | 6/2006 | Marissen et al. |
| 2006/0149258 | A1 | 7/2006 | Sousa |
| 2006/0149266 | A1 | 7/2006 | Cordasco |
| 2006/0155287 | A1 | 7/2006 | Montgomery et al. |
| 2006/0155328 | A1 | 7/2006 | Foerster |
| 2006/0161161 | A1 | 7/2006 | Shifrin et al. |
| 2006/0167458 | A1 | 7/2006 | Gabele |
| 2006/0167481 | A1 | 7/2006 | Baker et al. |
| 2006/0167482 | A1 | 7/2006 | Swain et al. |
| 2006/0173492 | A1 | 8/2006 | Akerfeldt et al. |
| 2006/0178680 | A1 | 8/2006 | Nelson et al. |
| 2006/0178701 | A1 | 8/2006 | Schmieding |
| 2006/0178743 | A1 | 8/2006 | Carter |
| 2006/0189993 | A1 | 8/2006 | Stone |
| 2006/0190041 | A1 | 8/2006 | Fallin et al. |
| 2006/0190042 | A1 | 8/2006 | Stone et al. |
| 2006/0195101 | A1 | 8/2006 | Stevens |
| 2006/0195106 | A1 | 8/2006 | Jones et al. |
| 2006/0200235 | A1 | 9/2006 | Bianchi et al. |
| 2006/0212055 | A1 | 9/2006 | Karabey et al. |
| 2006/0229623 | A1 | 10/2006 | Bonutti et al. |
| 2006/0229671 | A1 | 10/2006 | Steiner et al. |
| 2006/0229676 | A1 | 10/2006 | Doll et al. |
| 2006/0235407 | A1 | 10/2006 | Wang et al. |
| 2006/0235413 | A1 | 10/2006 | Denham et al. |
| 2006/0241624 | A1 | 10/2006 | Kizuka et al. |
| 2006/0241776 | A1 | 10/2006 | Brown et al. |
| 2006/0241781 | A1 | 10/2006 | Brown et al. |
| 2006/0247642 | A1 | 11/2006 | Stone et al. |
| 2006/0253130 | A1 | 11/2006 | Wolniewicz |
| 2006/0259048 | A1 | 11/2006 | Koseki |
| 2006/0259076 | A1 | 11/2006 | Burkhart |
| 2006/0264944 | A1 | 11/2006 | Cole |
| 2006/0271192 | A1 | 11/2006 | Olsen et al. |
| 2006/0276793 | A1 | 12/2006 | Berry |
| 2006/0276809 | A1 | 12/2006 | Oliveira |
| 2006/0276818 | A1 | 12/2006 | Buser et al. |
| 2006/0276841 | A1 | 12/2006 | Barbieri et al. |
| 2006/0276896 | A1 | 12/2006 | Fallin et al. |
| 2006/0280768 | A1 | 12/2006 | Hwang et al. |
| 2006/0280803 | A1 | 12/2006 | Kumar et al. |
| 2006/0282082 | A1 | 12/2006 | Fanton et al. |
| 2006/0282083 | A1 | 12/2006 | Fanton et al. |
| 2006/0282085 | A1 | 12/2006 | Stone |
| 2006/0293709 | A1 | 12/2006 | Bojarski et al. |
| 2007/0005068 | A1 | 1/2007 | Sklar |
| 2007/0005080 | A1 | 1/2007 | Wolniewicz, III et al. |
| 2007/0010857 | A1 | 1/2007 | Sugimoto et al. |
| 2007/0016305 | A1 | 1/2007 | Chudik |
| 2007/0021779 | A1 | 1/2007 | Garvin et al. |
| 2007/0027476 | A1 | 2/2007 | Harris et al. |
| 2007/0032800 | A1 | 2/2007 | Ortiz et al. |
| 2007/0032823 | A1 | 2/2007 | Tegg |
| 2007/0038218 | A1 | 2/2007 | Grevious |
| 2007/0043371 | A1 | 2/2007 | Teague |
| 2007/0055249 | A1 | 3/2007 | Jensen et al. |
| 2007/0055251 | A1 | 3/2007 | Huebner et al. |
| 2007/0055255 | A1 | 3/2007 | Siegel |
| 2007/0060922 | A1 | 3/2007 | Dreyfuss |
| 2007/0067025 | A1 | 3/2007 | Schwartz |
| 2007/0071568 | A1 | 3/2007 | Dorstewitz |
| 2007/0073307 | A1 | 3/2007 | Scribner et al. |
| 2007/0073319 | A1 | 3/2007 | Mikkaichi et al. |
| 2007/0073322 | A1 | 3/2007 | Mikkaichi et al. |
| 2007/0078435 | A1 | 4/2007 | Stone et al. |
| 2007/0078517 | A1 | 4/2007 | Engh et al. |
| 2007/0083236 | A1 | 4/2007 | Sikora et al. |
| 2007/0088362 | A1 | 4/2007 | Bonutti et al. |
| 2007/0093847 | A1 | 4/2007 | Scribner et al. |
| 2007/0100350 | A1 | 5/2007 | Deffenbaugh et al. |
| 2007/0112384 | A1 | 5/2007 | Conlon et al. |
| 2007/0118217 | A1 | 5/2007 | Brulez et al. |
| 2007/0123883 | A1 | 5/2007 | Ellis et al. |
| 2007/0123984 | A1 | 5/2007 | Hodorek |
| 2007/0129809 | A1 | 6/2007 | Meridew et al. |
| 2007/0135843 | A1 | 6/2007 | Burkhart |
| 2007/0142838 | A1 | 6/2007 | Jordan |
| 2007/0156174 | A1 | 7/2007 | Kaiser et al. |
| 2007/0162018 | A1 | 7/2007 | Jensen et al. |
| 2007/0162120 | A1 | 7/2007 | Bouffier |
| 2007/0167926 | A1 | 7/2007 | Blott et al. |
| 2007/0167950 | A1 | 7/2007 | Tauro et al. |
| 2007/0173948 | A1 | 7/2007 | Meridew et al. |
| 2007/0185488 | A1 | 8/2007 | Pohjonen et al. |
| 2007/0185532 | A1 | 8/2007 | Stone et al. |
| 2007/0185568 | A1 | 8/2007 | Schwartz |
| 2007/0191849 | A1 | 8/2007 | Elattrache et al. |
| 2007/0191853 | A1 | 8/2007 | Stone |
| 2007/0198022 | A1 | 8/2007 | Lang et al. |
| 2007/0198036 | A1 | 8/2007 | Sklar et al. |
| 2007/0219558 | A1 | 9/2007 | Deutsch |
| 2007/0225715 | A1 | 9/2007 | Deffenbaugh et al. |
| 2007/0225719 | A1 | 9/2007 | Stone et al. |
| 2007/0225763 | A1 | 9/2007 | Zwolinski et al. |
| 2007/0225805 | A1 | 9/2007 | Schmieding |
| 2007/0233241 | A1 | 10/2007 | Graf et al. |
| 2007/0239209 | A1 | 10/2007 | Fallman |
| 2007/0239275 | A1 | 10/2007 | Willobee |
| 2007/0244565 | A1 | 10/2007 | Stchur |
| 2007/0250059 | A1 | 10/2007 | Weisshaupt et al. |
| 2007/0250163 | A1 | 10/2007 | Cassani |
| 2007/0250175 | A1 | 10/2007 | Meridew et al. |
| 2007/0255282 | A1 | 11/2007 | Simonton et al. |
| 2007/0260251 | A1 | 11/2007 | Weier et al. |
| 2007/0260279 | A1 | 11/2007 | Hotter et al. |
| 2007/0265704 | A1 | 11/2007 | Mayer et al. |
| 2007/0270856 | A1 | 11/2007 | Morales et al. |
| 2007/0270878 | A1 | 11/2007 | Leisinger |
| 2007/0276387 | A1 | 11/2007 | Morales et al. |
| 2007/0288023 | A1 | 12/2007 | Pellegrino et al. |
| 2008/0009904 | A1 | 1/2008 | Bourque et al. |
| 2008/0027430 | A1 | 1/2008 | Montgomery et al. |
| 2008/0027440 | A1 | 1/2008 | Marissen et al. |
| 2008/0027446 | A1 | 1/2008 | Stone et al. |
| 2008/0033549 | A1 | 2/2008 | Marshall et al. |
| 2008/0046009 | A1 | 2/2008 | Albertorio et al. |
| 2008/0051834 | A1 | 2/2008 | Mazzocca et al. |
| 2008/0051836 | A1 | 2/2008 | Foerster et al. |
| 2008/0058787 | A1 | 3/2008 | Gertner |
| 2008/0065114 | A1 | 3/2008 | Stone et al. |
| 2008/0071299 | A1 | 3/2008 | Allinniemi et al. |
| 2008/0082101 | A1 | 4/2008 | Reisberg |
| 2008/0082127 | A1 | 4/2008 | Stone et al. |
| 2008/0082128 | A1 | 4/2008 | Stone |
| 2008/0086138 | A1 | 4/2008 | Stone et al. |
| 2008/0097430 | A1 | 4/2008 | Bernstein et al. |
| 2008/0103528 | A1 | 5/2008 | Zirps et al. |
| 2008/0114460 | A1 | 5/2008 | Willobee et al. |
| 2008/0119892 | A1 | 5/2008 | Brailovski et al. |
| 2008/0132753 | A1 | 6/2008 | Goddard |
| 2008/0132932 | A1 | 6/2008 | Hoeppner et al. |
| 2008/0132948 | A1 | 6/2008 | Surti et al. |
| 2008/0133007 | A1 | 6/2008 | Donnelly et al. |
| 2008/0137624 | A1 | 6/2008 | Silverstrim et al. |
| 2008/0140092 | A1 | 6/2008 | Stone et al. |
| 2008/0140093 | A1 | 6/2008 | Stone et al. |
| 2008/0140128 | A1 | 6/2008 | Smisson et al. |
| 2008/0147127 | A1 | 6/2008 | Tipirneni et al. |
| 2008/0147187 | A1 | 6/2008 | Bollinger et al. |
| 2008/0154260 | A1 | 6/2008 | Hoof |
| 2008/0154314 | A1 | 6/2008 | Mcdevitt |
| 2008/0161806 | A1 | 7/2008 | Donnelly et al. |
| 2008/0161852 | A1 | 7/2008 | Kaiser et al. |
| 2008/0161861 | A1 | 7/2008 | Huebner |
| 2008/0161864 | A1 | 7/2008 | Beck et al. |
| 2008/0166421 | A1 | 7/2008 | Buhr et al. |
| 2008/0172097 | A1 | 7/2008 | Lerch et al. |
| 2008/0177302 | A1 | 7/2008 | Shurnas |
| 2008/0183290 | A1 | 7/2008 | Baird et al. |
| 2008/0188933 | A1 | 8/2008 | Koob et al. |

(56) References Cited

U.S. PATENT DOCUMENTS

| | | | |
|---|---|---|---|
| 2008/0188935 | A1 | 8/2008 | Saylor et al. |
| 2008/0188936 | A1 | 8/2008 | Ball et al. |
| 2008/0208252 | A1 | 8/2008 | Holmes |
| 2008/0217263 | A1 | 9/2008 | Higgins et al. |
| 2008/0221527 | A1 | 9/2008 | Bradley et al. |
| 2008/0221578 | A1 | 9/2008 | Zeitani |
| 2008/0228186 | A1 | 9/2008 | Gall et al. |
| 2008/0228271 | A1 | 9/2008 | Stone et al. |
| 2008/0234730 | A1 | 9/2008 | Cotton et al. |
| 2008/0243260 | A1 | 10/2008 | Lee et al. |
| 2008/0243261 | A1 | 10/2008 | Wyss et al. |
| 2008/0243262 | A1 | 10/2008 | Lee |
| 2008/0255613 | A1 | 10/2008 | Kaiser et al. |
| 2008/0257363 | A1 | 10/2008 | Schoenefeld et al. |
| 2008/0262544 | A1 | 10/2008 | Burkhart |
| 2008/0268064 | A1 | 10/2008 | Woodell-may |
| 2008/0269674 | A1 | 10/2008 | Stone |
| 2008/0275469 | A1 | 11/2008 | Fanton et al. |
| 2008/0275477 | A1 | 11/2008 | Sterrett et al. |
| 2008/0281428 | A1 | 11/2008 | Meyers et al. |
| 2008/0288070 | A1 | 11/2008 | Lo |
| 2008/0300611 | A1 | 12/2008 | Houser et al. |
| 2008/0312689 | A1 | 12/2008 | Denham et al. |
| 2008/0319478 | A1 | 12/2008 | Foerster et al. |
| 2009/0018589 | A1 | 1/2009 | Smisson, III et al. |
| 2009/0018654 | A1 | 1/2009 | Schmieding et al. |
| 2009/0018655 | A1 | 1/2009 | Brunelle et al. |
| 2009/0043342 | A1 | 2/2009 | Freedland |
| 2009/0054928 | A1 | 2/2009 | Denham et al. |
| 2009/0062847 | A1 | 3/2009 | Ken |
| 2009/0062854 | A1 | 3/2009 | Kaiser et al. |
| 2009/0082790 | A1 | 3/2009 | Shad et al. |
| 2009/0082805 | A1* | 3/2009 | Kaiser .............. A61B 17/06166 606/228 |
| 2009/0084491 | A1 | 4/2009 | Uthgenannt et al. |
| 2009/0099598 | A1 | 4/2009 | Mcdevitt et al. |
| 2009/0105717 | A1 | 4/2009 | Bluechel |
| 2009/0105754 | A1 | 4/2009 | Sethi |
| 2009/0118774 | A1 | 5/2009 | Miller, III |
| 2009/0118775 | A1 | 5/2009 | Burke |
| 2009/0125073 | A1 | 5/2009 | Rehm |
| 2009/0138002 | A1 | 5/2009 | Fenton |
| 2009/0138054 | A1 | 5/2009 | Teague et al. |
| 2009/0156997 | A1 | 6/2009 | Trenhaile |
| 2009/0163949 | A1 | 6/2009 | Rolnick et al. |
| 2009/0177233 | A1 | 7/2009 | Malek |
| 2009/0182335 | A1 | 7/2009 | Struhl |
| 2009/0192468 | A1 | 7/2009 | Stone |
| 2009/0198277 | A1 | 8/2009 | Gordon et al. |
| 2009/0204146 | A1 | 8/2009 | Kaiser et al. |
| 2009/0216325 | A1 | 8/2009 | May et al. |
| 2009/0228015 | A1 | 9/2009 | Ellis |
| 2009/0228042 | A1 | 9/2009 | Koogle, Jr. et al. |
| 2009/0234357 | A1 | 9/2009 | Morales et al. |
| 2009/0234358 | A1 | 9/2009 | Morales et al. |
| 2009/0234451 | A1 | 9/2009 | Manderson |
| 2009/0240251 | A1 | 9/2009 | Gabele |
| 2009/0240335 | A1 | 9/2009 | Arcenio et al. |
| 2009/0241497 | A1 | 10/2009 | Imai et al. |
| 2009/0248091 | A1 | 10/2009 | Teague et al. |
| 2009/0254089 | A1 | 10/2009 | Tipirneni et al. |
| 2009/0265014 | A1 | 10/2009 | May et al. |
| 2009/0265015 | A1 | 10/2009 | May et al. |
| 2009/0287215 | A1 | 11/2009 | Fisher et al. |
| 2009/0299409 | A1 | 12/2009 | Coe et al. |
| 2009/0306711 | A1 | 12/2009 | Stone et al. |
| 2009/0312776 | A1* | 12/2009 | Kaiser .............. A61B 17/06166 606/228 |
| 2009/0312793 | A1 | 12/2009 | Huxel et al. |
| 2009/0318960 | A1 | 12/2009 | Burkhart |
| 2009/0318961 | A1 | 12/2009 | Stone et al. |
| 2009/0318965 | A1 | 12/2009 | Burkhart |
| 2010/0016891 | A1 | 1/2010 | Kennedy et al. |
| 2010/0016899 | A1 | 1/2010 | Gelfand |
| 2010/0030321 | A1 | 2/2010 | Mach |
| 2010/0042114 | A1 | 2/2010 | Schaffhausen et al. |
| 2010/0063540 | A1 | 3/2010 | Maiorino |
| 2010/0063541 | A1 | 3/2010 | Brunelle et al. |
| 2010/0087857 | A1 | 4/2010 | Stone et al. |
| 2010/0094341 | A1 | 4/2010 | Raju |
| 2010/0094355 | A1 | 4/2010 | Trenhaile |
| 2010/0106254 | A1 | 4/2010 | Delsignore |
| 2010/0121348 | A1 | 5/2010 | Van Der Burg et al. |
| 2010/0145384 | A1 | 6/2010 | Stone et al. |
| 2010/0152752 | A1 | 6/2010 | Denove et al. |
| 2010/0191319 | A1 | 7/2010 | Lilburn et al. |
| 2010/0191342 | A1 | 7/2010 | Byrd et al. |
| 2010/0204700 | A1 | 8/2010 | Falahee |
| 2010/0211071 | A1 | 8/2010 | Lettmann et al. |
| 2010/0211075 | A1 | 8/2010 | Stone |
| 2010/0256677 | A1 | 10/2010 | Albertorio et al. |
| 2010/0268273 | A1 | 10/2010 | Albertorio et al. |
| 2010/0268275 | A1 | 10/2010 | Stone et al. |
| 2010/0270306 | A1 | 10/2010 | Shiffer |
| 2010/0274282 | A1 | 10/2010 | Olson |
| 2010/0292792 | A1 | 11/2010 | Stone et al. |
| 2010/0298872 | A1 | 11/2010 | Berndt et al. |
| 2010/0298952 | A1 | 11/2010 | Busold et al. |
| 2010/0305698 | A1 | 12/2010 | Metzger et al. |
| 2010/0305709 | A1 | 12/2010 | Metzger et al. |
| 2010/0305710 | A1 | 12/2010 | Metzger |
| 2010/0312245 | A1 | 12/2010 | Tipirneni et al. |
| 2010/0312341 | A1 | 12/2010 | Kaiser et al. |
| 2010/0324676 | A1 | 12/2010 | Albertorio |
| 2010/0331881 | A1 | 12/2010 | Hart |
| 2011/0009885 | A1 | 1/2011 | Graf et al. |
| 2011/0022083 | A1 | 1/2011 | Dimatteo et al. |
| 2011/0026141 | A1 | 2/2011 | Barrows |
| 2011/0040387 | A1 | 2/2011 | Ries et al. |
| 2011/0046733 | A1 | 2/2011 | Eggli |
| 2011/0087225 | A1 | 4/2011 | Fritzinger |
| 2011/0087280 | A1 | 4/2011 | Albertorio |
| 2011/0087284 | A1 | 4/2011 | Stone et al. |
| 2011/0098727 | A1 | 4/2011 | Kaiser et al. |
| 2011/0106153 | A1 | 5/2011 | Stone et al. |
| 2011/0112537 | A1 | 5/2011 | Bernstein et al. |
| 2011/0112538 | A1 | 5/2011 | Dell'oca |
| 2011/0124954 | A1 | 5/2011 | Ogdahl et al. |
| 2011/0125153 | A1 | 5/2011 | Tyber et al. |
| 2011/0160767 | A1 | 6/2011 | Stone et al. |
| 2011/0160768 | A1 | 6/2011 | Stone et al. |
| 2011/0166608 | A1 | 7/2011 | Duggal et al. |
| 2011/0184227 | A1 | 7/2011 | Altman et al. |
| 2011/0208239 | A1 | 8/2011 | Stone et al. |
| 2011/0208240 | A1 | 8/2011 | Stone et al. |
| 2011/0213367 | A1 | 9/2011 | Tyber et al. |
| 2011/0213416 | A1 | 9/2011 | Kaiser |
| 2011/0218625 | A1 | 9/2011 | Berelsman et al. |
| 2011/0224799 | A1 | 9/2011 | Stone |
| 2011/0245868 | A1 | 10/2011 | Teeslink et al. |
| 2011/0264141 | A1 | 10/2011 | Denham et al. |
| 2011/0270278 | A1 | 11/2011 | Overes et al. |
| 2011/0270306 | A1 | 11/2011 | Denham et al. |
| 2011/0295284 | A1 | 12/2011 | Purdue et al. |
| 2011/0319932 | A1 | 12/2011 | Avelar et al. |
| 2012/0004669 | A1 | 1/2012 | Overes et al. |
| 2012/0024134 | A1 | 2/2012 | Dow et al. |
| 2012/0029561 | A1 | 2/2012 | Olson |
| 2012/0041485 | A1 | 2/2012 | Kaiser et al. |
| 2012/0041486 | A1 | 2/2012 | Stone et al. |
| 2012/0041496 | A1 | 2/2012 | Walker |
| 2012/0042768 | A1 | 2/2012 | Chou et al. |
| 2012/0046693 | A1 | 2/2012 | Denham et al. |
| 2012/0053630 | A1 | 3/2012 | Denham et al. |
| 2012/0059417 | A1 | 3/2012 | Norton et al. |
| 2012/0059418 | A1 | 3/2012 | Denham et al. |
| 2012/0059468 | A1 | 3/2012 | Mattern et al. |
| 2012/0060278 | A1 | 3/2012 | Mccurdy |
| 2012/0083837 | A1 | 4/2012 | Ferragamo et al. |
| 2012/0089193 | A1 | 4/2012 | Stone et al. |
| 2012/0095470 | A1 | 4/2012 | Kaiser et al. |
| 2012/0109156 | A1 | 5/2012 | Overes et al. |
| 2012/0116409 | A1 | 5/2012 | Stone |
| 2012/0116450 | A1 | 5/2012 | Mcdevitt et al. |

(56) References Cited

U.S. PATENT DOCUMENTS

2012/0116452 A1 5/2012 Stone et al.
2012/0123447 A1 5/2012 Corrao et al.
2012/0123474 A1 5/2012 Zajac et al.
2012/0123541 A1 5/2012 Albertorio et al.
2012/0130423 A1 5/2012 Sengun et al.
2012/0130492 A1 5/2012 Eggli et al.
2012/0143215 A1 6/2012 Corrao et al.
2012/0150223 A1 6/2012 Manos et al.
2012/0150297 A1 6/2012 Denham et al.
2012/0165864 A1 6/2012 Hernandez et al.
2012/0165866 A1 6/2012 Kaiser et al.
2012/0165867 A1 6/2012 Denham et al.
2012/0165938 A1 6/2012 Denham et al.
2012/0192455 A1 8/2012 Hansen et al.
2012/0197271 A1 8/2012 Astorino et al.
2012/0215257 A1 8/2012 Mcdevitt et al.
2012/0239159 A1 9/2012 Metzger et al.
2012/0245585 A1 9/2012 Kaiser et al.
2012/0265219 A1 10/2012 Rushdy et al.
2012/0265294 A1 10/2012 Nishigishi
2012/0271403 A1 10/2012 Gries
2012/0273085 A1 11/2012 David et al.
2012/0290002 A1 11/2012 Astorino
2012/0290003 A1 11/2012 Dreyfuss
2012/0290004 A1 11/2012 Lombardo et al.
2012/0296427 A1 11/2012 Conner et al.
2012/0310245 A1 12/2012 Hoeppner et al.
2013/0018375 A1 1/2013 Dell'oca
2013/0018416 A1 1/2013 Lombardo et al.
2013/0023928 A1 1/2013 Dreyfuss
2013/0023929 A1 1/2013 Sullivan et al.
2013/0023930 A1 1/2013 Stone et al.
2013/0035698 A1 2/2013 Stone
2013/0035722 A1 2/2013 Mcdevitt et al.
2013/0046341 A1 2/2013 Stone et al.
2013/0060323 A1 3/2013 Mchugo
2013/0090720 A1 4/2013 Mahr et al.
2013/0090731 A1 4/2013 Walker
2013/0103082 A1 4/2013 Kaiser et al.
2013/0110165 A1 5/2013 Burkhart et al.
2013/0110251 A1 5/2013 Metzger et al.
2013/0116730 A1 5/2013 Denham
2013/0123810 A1 5/2013 Brown et al.
2013/0123813 A1 5/2013 Stone et al.
2013/0131722 A1 5/2013 Marchand et al.
2013/0138123 A1 5/2013 Stone et al.
2013/0144337 A1 6/2013 Stone et al.
2013/0144338 A1 6/2013 Stone et al.
2013/0158599 A1 6/2013 Hester et al.
2013/0158601 A1 6/2013 Stone et al.
2013/0172942 A1 7/2013 Lewis et al.
2013/0190818 A1 7/2013 Norton
2013/0190819 A1 7/2013 Norton
2013/0204276 A1 8/2013 Stone et al.
2013/0211452 A1 8/2013 Stone et al.
2013/0231700 A1 9/2013 Gedet et al.
2013/0237997 A1 9/2013 Arai et al.
2013/0245761 A1 9/2013 Conner et al.
2013/0267956 A1 10/2013 Terrill et al.
2013/0274812 A1 10/2013 Dell'oca
2013/0289564 A1 10/2013 Bernstein et al.
2013/0317621 A1 11/2013 Metzger et al.
2013/0331742 A1 12/2013 Aupperle et al.
2013/0331848 A1 12/2013 Kaiser et al.
2014/0005754 A1 1/2014 Finley et al.
2014/0018804 A1 1/2014 Foerster
2014/0046367 A1 2/2014 Stone et al.
2014/0046368 A1 2/2014 Kaiser et al.
2014/0052179 A1 2/2014 Dreyfuss et al.
2014/0058436 A1 2/2014 Rosenbluth et al.
2014/0067081 A1 3/2014 Stone
2014/0081322 A1 3/2014 Sengun et al.
2014/0088655 A1 3/2014 Stone et al.
2014/0094913 A1 4/2014 Berelsman et al.
2014/0128985 A1 5/2014 Sanders et al.
2014/0135835 A1 5/2014 Stone et al.
2014/0163613 A1 6/2014 Stone et al.
2014/0163614 A1 6/2014 Denham et al.
2014/0194927 A1 7/2014 Kaiser et al.
2014/0200583 A1 7/2014 Stone et al.
2014/0257378 A1 9/2014 Norton et al.
2014/0276992 A1 9/2014 Stone et al.
2014/0277447 A1 9/2014 Berelsman et al.
2014/0324101 A1 10/2014 Denham et al.
2014/0330311 A1 11/2014 Denham et al.
2014/0336760 A1 11/2014 Eggli
2014/0350674 A1 11/2014 Stone et al.
2015/0012094 A1 1/2015 Denham et al.
2015/0032216 A1 1/2015 Metzger et al.
2015/0057665 A1 2/2015 Neal et al.
2015/0057757 A1 2/2015 Metzger et al.
2015/0066081 A1 3/2015 Martin
2015/0119890 A1 4/2015 Kaiser et al.
2015/0127051 A1 5/2015 Kaiser et al.
2015/0128792 A1 5/2015 Zachariades et al.
2015/0134000 A1 5/2015 Denham et al.
2015/0143981 A1 5/2015 Dunker
2015/0148888 A1 5/2015 Milner et al.
2015/0173753 A1 6/2015 Spivey et al.
2015/0173887 A1 6/2015 Berelsman et al.
2015/0257750 A1 9/2015 Kaiser et al.
2015/0320026 A1 11/2015 Toddes
2016/0000483 A1 1/2016 Stone
2016/0022261 A1 1/2016 Stone et al.
2016/0038187 A1 2/2016 Mcdonnell
2016/0058436 A1 3/2016 Stone et al.
2016/0058484 A1 3/2016 Mccombs-stearnes et al.
2016/0074049 A1 3/2016 Russell et al.
2016/0081789 A1 3/2016 Denham et al.
2016/0106414 A1 4/2016 Stone et al.
2016/0128684 A1 5/2016 Stone et al.
2016/0183935 A1 6/2016 Stone
2016/0199053 A1 7/2016 Norton et al.
2016/0213369 A1 7/2016 Stone et al.
2016/0242760 A1 8/2016 Kaiser et al.
2017/0014225 A1 1/2017 Denham et al.
2017/0020507 A1 1/2017 Denham et al.
2017/0020569 A1 1/2017 Grant
2017/0035411 A1 2/2017 Kaiser et al.
2017/0049557 A1 2/2017 Denham et al.
2017/0065278 A1 3/2017 Stone
2017/0071593 A1 3/2017 Stone
2017/0071595 A1 3/2017 Stone et al.
2017/0086816 A1 3/2017 Norton
2017/0119382 A1 5/2017 Denham et al.
2017/0128061 A1 5/2017 Stone et al.
2017/0181746 A1 6/2017 Denham et al.
2017/0189011 A1 7/2017 Stone et al.
2017/0189197 A1 7/2017 Werber et al.
2017/0202587 A1 7/2017 Stone et al.
2017/0231752 A1 8/2017 Rodriguez et al.
2017/0273686 A1 9/2017 Denham et al.
2017/0311947 A1 11/2017 Kaiser et al.
2017/0319194 A1 11/2017 Mayeski et al.
2017/0319195 A1 11/2017 Denham et al.
2017/0319204 A1 11/2017 Norton et al.
2017/0325808 A1 11/2017 Stone et al.
2017/0333176 A1 11/2017 Stone et al.
2017/0360425 A1 12/2017 Stone et al.
2018/0000477 A1 1/2018 Kaiser et al.
2018/0014864 A1 1/2018 Stone et al.
2018/0020762 A1 1/2018 Jamison
2018/0021036 A1 1/2018 Kaiser et al.
2018/0021125 A1 1/2018 Berelsman et al.
2018/0042609 A1 2/2018 Denham et al.
2018/0098858 A1 4/2018 Valderrabano et al.
2018/0125476 A1 5/2018 Kaiser et al.
2018/0125477 A1 5/2018 Stone
2018/0153538 A1 6/2018 Kaiser et al.
2018/0153558 A1 6/2018 Bake et al.
2018/0161030 A1 6/2018 Stone et al.
2018/0177501 A1 6/2018 Kaiser et al.
2018/0193015 A1 7/2018 Denham et al.
2018/0221017 A1 8/2018 Stone et al.

(56) References Cited

U.S. PATENT DOCUMENTS

| | | | |
|---|---|---|---|
| 2018/0235747 | A1 | 8/2018 | Berelsman et al. |
| 2018/0249997 | A1 | 9/2018 | Stone et al. |
| 2018/0256153 | A1 | 9/2018 | Stone et al. |
| 2019/0083233 | A1 | 3/2019 | Denham et al. |
| 2019/0150909 | A1 | 5/2019 | Stone et al. |
| 2019/0150923 | A1 | 5/2019 | Stone et al. |
| 2019/0231348 | A1 | 8/2019 | Stone et al. |
| 2019/0254652 | A1 | 8/2019 | Stone et al. |
| 2019/0274681 | A1 | 9/2019 | Denham et al. |
| 2019/0282227 | A1 | 9/2019 | Norton |
| 2019/0290258 | A1 | 9/2019 | Denham et al. |
| 2019/0298345 | A1 | 10/2019 | Denham et al. |
| 2019/0328382 | A1 | 10/2019 | Stone et al. |
| 2019/0365376 | A1 | 12/2019 | Stone et al. |
| 2020/0029955 | A1 | 1/2020 | Stone et al. |
| 2020/0085562 | A1 | 3/2020 | Stone et al. |
| 2020/0178959 | A1 | 6/2020 | Denham et al. |
| 2020/0187932 | A1 | 6/2020 | Kaiser et al. |
| 2020/0187933 | A1 | 6/2020 | Kaiser et al. |
| 2020/0197002 | A1 | 6/2020 | Stone et al. |
| 2020/0297338 | A1 | 9/2020 | Stone et al. |
| 2020/0367880 | A1 | 11/2020 | Stone et al. |
| 2021/0177397 | A1 | 6/2021 | Stone et al. |
| 2021/0228203 | A1 | 7/2021 | Denham et al. |
| 2021/0361286 | A1 | 11/2021 | Stone et al. |
| 2022/0015757 | A1 | 1/2022 | Stone et al. |
| 2022/0054123 | A1 | 2/2022 | Kaiser et al. |
| 2022/0096074 | A1 | 3/2022 | Denham et al. |
| 2022/0096081 | A1 | 3/2022 | Denham et al. |
| 2022/0133296 | A1 | 5/2022 | Stone et al. |
| 2023/0000484 | A1 | 1/2023 | Kaiser et al. |
| 2023/0084732 | A1 | 3/2023 | Norton |
| 2023/0146316 | A1 | 5/2023 | Stone et al. |
| 2023/0165580 | A1 | 6/2023 | Kaiser et al. |
| 2023/0172602 | A1 | 6/2023 | Kaiser et al. |
| 2023/0248356 | A1 | 8/2023 | Stone et al. |
| 2023/0293165 | A1 | 9/2023 | Stone et al. |
| 2023/0389916 | A1 | 12/2023 | Denham et al. |
| 2024/0057992 | A1 | 2/2024 | Stone et al. |
| 2024/0081810 | A1 | 3/2024 | Stone et al. |
| 2024/0108328 | A1 | 4/2024 | Stone et al. |
| 2024/0130723 | A1 | 4/2024 | Denham et al. |
| 2024/0130727 | A1 | 4/2024 | Stone et al. |
| 2024/0188952 | A1 | 6/2024 | Kaiser et al. |

FOREIGN PATENT DOCUMENTS

| | | | |
|---|---|---|---|
| AU | 4381268 | A | 4/1970 |
| AU | 5850469 | A | 1/1971 |
| AU | 5963869 | A | 2/1971 |
| AU | 1505470 | A | 11/1971 |
| AU | 2223767 | A | 5/1973 |
| AU | 3615171 | A | 5/1973 |
| AU | 440266 | B2 | 9/1973 |
| AU | 5028569 | A | 9/1973 |
| AU | 7110887 | A | 10/1987 |
| AU | 639410 | A | 11/1989 |
| AU | 1713188 | A | 11/1989 |
| AU | 651929 | B2 | 8/1994 |
| AU | 3877493 | B2 | 8/1994 |
| BE | 1010569 | A6 | 10/1998 |
| CN | 1720872 | A | 1/2006 |
| CN | 1777450 | A | 5/2006 |
| CN | 101083954 | A | 12/2007 |
| CN | 101584592 | A | 11/2009 |
| CN | 105208970 | A | 12/2015 |
| DE | 2529669 | A1 | 3/1976 |
| DE | 2747312 | A1 | 4/1979 |
| DE | 2818254 | A1 | 10/1979 |
| DE | 2919009 | A1 | 11/1979 |
| DE | 3027138 | A1 | 12/1981 |
| DE | 3225620 | A1 | 2/1983 |
| DE | 3136083 | A1 | 3/1983 |
| DE | 233303 | A1 | 2/1986 |
| DE | 4127550 | A1 | 2/1993 |
| DE | 4302397 | A | 7/1993 |
| DE | 29621340 | U1 | 4/1998 |
| DE | 19841252 | A1 | 3/2000 |
| DE | 29922088 | U1 | 4/2000 |
| DE | 20207781 | U1 | 8/2002 |
| EP | 0019062 | A1 | 11/1980 |
| EP | 0108912 | A2 | 5/1984 |
| EP | 0129422 | A2 | 12/1984 |
| EP | 0129442 | A1 | 12/1984 |
| EP | 0172130 | A2 | 2/1986 |
| EP | 0241240 | A2 | 10/1987 |
| EP | 0241792 | A1 | 10/1987 |
| EP | 0260970 | A2 | 3/1988 |
| EP | 0270704 | A1 | 6/1988 |
| EP | 0282789 | A2 | 9/1988 |
| EP | 0315371 | A2 | 5/1989 |
| EP | 0317406 | A1 | 5/1989 |
| EP | 0340159 | A1 | 11/1989 |
| EP | 0346183 | A1 | 12/1989 |
| EP | 0349173 | A1 | 1/1990 |
| EP | 0374088 | A1 | 6/1990 |
| EP | 0409364 | A2 | 1/1991 |
| EP | 0415915 | A1 | 3/1991 |
| EP | 0440991 | A1 | 8/1991 |
| EP | 0441065 | A2 | 8/1991 |
| EP | 0447065 | A2 | 9/1991 |
| EP | 0451932 | A1 | 10/1991 |
| EP | 0464480 | A1 | 1/1992 |
| EP | 0490417 | A1 | 6/1992 |
| EP | 0497079 | A1 | 8/1992 |
| EP | 0502509 | A1 | 9/1992 |
| EP | 0502698 | A1 | 9/1992 |
| EP | 0520177 | A1 | 12/1992 |
| EP | 0546726 | A1 | 6/1993 |
| EP | 0552950 | A1 | 7/1993 |
| EP | 0574707 | A1 | 12/1993 |
| EP | 0582514 | A1 | 2/1994 |
| EP | 0591991 | A2 | 4/1994 |
| EP | 0598219 | A2 | 5/1994 |
| EP | 0611551 | A1 | 8/1994 |
| EP | 0627203 | A2 | 12/1994 |
| EP | 0651979 | A1 | 5/1995 |
| EP | 0669110 | A2 | 8/1995 |
| EP | 0686373 | A1 | 12/1995 |
| EP | 0702933 | A1 | 3/1996 |
| EP | 0775473 | A1 | 5/1997 |
| EP | 0913123 | A1 | 5/1999 |
| EP | 0913131 | A2 | 5/1999 |
| EP | 0995409 | A1 | 4/2000 |
| EP | 1013229 | A2 | 6/2000 |
| EP | 1093773 | A1 | 4/2001 |
| EP | 1093774 | A1 | 4/2001 |
| EP | 1555945 | A2 | 7/2005 |
| EP | 1741412 | A2 | 1/2007 |
| EP | 1864617 | A2 | 12/2007 |
| EP | 2238944 | A2 | 10/2010 |
| EP | 2544607 | A1 | 1/2013 |
| EP | 2709557 | A1 | 3/2014 |
| EP | 2895112 | A1 | 7/2015 |
| EP | 2934379 | A1 | 10/2015 |
| EP | 2434987 | B1 | 6/2016 |
| EP | 2775935 | B1 | 5/2017 |
| FR | 2634373 | A1 | 1/1990 |
| FR | 2655840 | A1 | 6/1991 |
| FR | 2663837 | A1 | 1/1992 |
| FR | 2682867 | A1 | 4/1993 |
| FR | 2687911 | A1 | 9/1993 |
| FR | 2688689 | A1 | 9/1993 |
| FR | 2704140 | A3 | 10/1994 |
| FR | 2717070 | A1 | 9/1995 |
| FR | 2723528 | A1 | 2/1996 |
| FR | 2734709 | A1 | 12/1996 |
| FR | 2744010 | A1 | 8/1997 |
| FR | 2745999 | A1 | 9/1997 |
| FR | 2622790 | A1 | 5/1999 |
| FR | 2770764 | A1 | 5/1999 |
| GB | 401677 | A | 11/1933 |
| GB | 1413477 | A | 11/1975 |
| GB | 1485681 | A | 9/1977 |

(56) References Cited

FOREIGN PATENT DOCUMENTS

| | | | |
|---|---|---|---|
| GB | 2083751 | A | 3/1982 |
| GB | 2118474 | A | 11/1983 |
| GB | 2129306 | A | 5/1984 |
| GB | 2227175 | A | 7/1990 |
| GB | 2253147 | A | 9/1992 |
| GB | 2312376 | A | 10/1997 |
| GB | 2403416 | A | 1/2005 |
| GB | 2454251 | A | 5/2009 |
| JP | 5362911 | U | 5/1978 |
| JP | 5362912 | U | 5/1978 |
| JP | 5374942 | B2 | 6/1978 |
| JP | 5374942 | U | 6/1978 |
| JP | 5378230 | U | 6/1978 |
| JP | 62159647 | U | 10/1978 |
| JP | 54166092 | U | 11/1979 |
| JP | 54166093 | U | 11/1979 |
| JP | 54176284 | U | 12/1979 |
| JP | 54178988 | U | 12/1979 |
| JP | 5362911 | A | 7/1987 |
| JP | 62159647 | A | 7/1987 |
| JP | 62295657 | A | 12/1987 |
| JP | 5269160 | A | 10/1993 |
| JP | 5300917 | A | 11/1993 |
| JP | 751292 | A | 2/1995 |
| JP | 10127672 | A | 5/1998 |
| JP | 10211213 | A | 8/1998 |
| JP | 5362911 | B2 | 12/2013 |
| JP | 5362912 | B2 | 12/2013 |
| JP | 5378230 | B2 | 12/2013 |
| RU | 2051647 | C1 | 1/1996 |
| RU | 207667 | C1 | 4/1997 |
| WO | WO-8300615 | A1 | 3/1983 |
| WO | WO-8603666 | A1 | 7/1986 |
| WO | WO-8701270 | A1 | 3/1987 |
| WO | WO-8909030 | A1 | 10/1989 |
| WO | WO-8910096 | A1 | 11/1989 |
| WO | WO-9008510 | A1 | 8/1990 |
| WO | WO-9203980 | A1 | 3/1992 |
| WO | WO-9314705 | A1 | 8/1993 |
| WO | WO-9315694 | A1 | 8/1993 |
| WO | WO-9502373 | A1 | 1/1995 |
| WO | WO-9503003 | A1 | 2/1995 |
| WO | WO-9529637 | A1 | 11/1995 |
| WO | WO-9532670 | A1 | 12/1995 |
| WO | WO-9609797 | A1 | 4/1996 |
| WO | WO-9629029 | A1 | 9/1996 |
| WO | WO-9737603 | A1 | 10/1997 |
| WO | WO-9812991 | A1 | 4/1998 |
| WO | WO-9812992 | A1 | 4/1998 |
| WO | WO-9822047 | A1 | 5/1998 |
| WO | WO-9822048 | A1 | 5/1998 |
| WO | WO-9901084 | A2 | 1/1999 |
| WO | WO-8901767 | A1 | 3/1999 |
| WO | WO-9912480 | A1 | 3/1999 |
| WO | WO-9937219 | A1 | 7/1999 |
| WO | WO-9944544 | A1 | 9/1999 |
| WO | WO-9952472 | A1 | 10/1999 |
| WO | WO-0004159 | A1 | 1/2000 |
| WO | WO-0040159 | A1 | 7/2000 |
| WO | WO-0139671 | A1 | 6/2001 |
| WO | WO-0236020 | A1 | 5/2002 |
| WO | WO-03005914 | A1 | 1/2003 |
| WO | WO-03071962 | A2 | 9/2003 |
| WO | WO-03077772 | A1 | 9/2003 |
| WO | WO-03092551 | A1 | 11/2003 |
| WO | WO-2004091412 | A1 | 10/2004 |
| WO | WO-05104992 | A1 | 11/2005 |
| WO | WO-2005122954 | A1 | 12/2005 |
| WO | WO-2006011786 | A1 | 2/2006 |
| WO | WO-2006023661 | A2 | 3/2006 |
| WO | WO-2006055823 | A2 | 5/2006 |
| WO | WO-2007045460 | A2 | 4/2007 |
| WO | WO-2007103562 | A2 | 9/2007 |
| WO | WO-2007109280 | A2 | 9/2007 |
| WO | WO-2007119057 | A1 | 10/2007 |
| WO | WO-2008002550 | A2 | 1/2008 |
| WO | WO-2008015171 | A1 | 2/2008 |
| WO | WO-2008073588 | A2 | 6/2008 |
| WO | WO-2009012021 | A1 | 1/2009 |
| WO | WO-2009083047 | A1 | 7/2009 |
| WO | WO-2009131820 | A1 | 10/2009 |
| WO | WO-2010138832 | A1 | 12/2010 |
| WO | WO-2011112371 | A1 | 9/2011 |
| WO | WO-2011150238 | A1 | 12/2011 |
| WO | WO-2012134999 | A1 | 10/2012 |
| WO | WO-2012158583 | A1 | 11/2012 |
| WO | WO-2013066974 | A1 | 5/2013 |
| WO | WO-2013074525 | A1 | 5/2013 |
| WO | WO-2014043078 | A1 | 3/2014 |
| WO | WO-2014100109 | A1 | 6/2014 |
| WO | WO-2014151766 | A1 | 9/2014 |

OTHER PUBLICATIONS

"AperFix® System Surgical Technique Guide. Single Tunnel Double Bundle.®", Cayenne Medical brochure, (Aug. 2008), 8 pgs.

"U.S. Appl. No. 10/984,624, Final Office Action mailed Jan. 5, 2009", 9 pgs.

"U.S. Appl. No. 10/984,624, Non Final Office Action mailed Jul. 10, 2008", 9 pgs.

"U.S. Appl. No. 10/984,624, Notice of Allowance mailed Jun. 12, 2009", 9 pgs.

"U.S. Appl. No. 10/984,624, Response filed Apr. 1, 2009 to Final Office Action mailed Jan. 5, 2009", 16 pgs.

"U.S. Appl. No. 10/984,624, Response filed Apr. 15, 2008 to Restriction Requirement mailed Mar. 24, 2008", 1 pg.

"U.S. Appl. No. 10/984,624, Response filed Oct. 10, 2008 to Non Final Office Action mailed Jul. 10, 2008", 12 pgs.

"U.S. Appl. No. 10/984,624, Restriction Requirement mailed Mar. 24, 2008", 5 pgs.

"U.S. Appl. No. 11/294,694, Final Office Action mailed Sep. 1, 2010", 14 pgs.

"U.S. Appl. No. 11/294,694, Non Final Office Action mailed Mar. 16, 2010", 19 pgs.

"U.S. Appl. No. 11/294,694, Notice of Allowance mailed Nov. 17, 2010", 4 pgs.

"U.S. Appl. No. 11/294,694, Preliminary Amendment filed Jan. 13, 2010", 9 pgs.

"U.S. Appl. No. 11/294,694, Response filed Jun. 16, 2010 to Non Final Office Action mailed Mar. 16, 2010", 16 pgs.

"U.S. Appl. No. 11/294,694, Response filed Nov. 1, 2010 to Final Office Action mailed Sep. 1, 2010", 10 pgs.

"U.S. Appl. No. 11/294,694, Response filed Dec. 22, 2009 to Restriction Requirement mailed Nov. 25, 2009", 1 pg.

"U.S. Appl. No. 11/294,694, Restriction Requirement mailed Nov. 25, 2009", 9 pgs.

"U.S. Appl. No. 11/347,661, Examiner Interview Summary mailed Sep. 11, 2009", 2 pgs.

"U.S. Appl. No. 11/347,661, Final Office Action mailed Mar. 3, 2009", 15 pgs.

"U.S. Appl. No. 11/347,661, Non Final Office Action mailed Aug. 13, 2009", 19 pgs.

"U.S. Appl. No. 11/347,661, Non Final Office Action mailed Aug. 21, 2008", 11 pgs.

"U.S. Appl. No. 11/347,661, Notice of Allowance mailed Feb. 24, 2010", 8 pgs.

"U.S. Appl. No. 11/347,661, Notice of Allowance mailed May 5, 2010", 8 pgs.

"U.S. Appl. No. 11/347,661, Response filed May 29, 2008 to Restriction Requirement mailed Apr. 30, 2008", 1 pg.

"U.S. Appl. No. 11/347,661, Response filed Jun. 3, 2009 to Final Office Action mailed Mar. 3, 2009", 19 pgs.

"U.S. Appl. No. 11/347,661, Response filed Nov. 6, 2009 to Non Final Office Action mailed Aug. 13, 2009", 16 pgs.

"U.S. Appl. No. 11/347,661, Response filed Nov. 19, 2008 to Non Final Office Action mailed Aug. 21, 2008", 12 pgs.

"U.S. Appl. No. 11/347,661, Restriction Requirement mailed Apr. 30, 2008", 6 pgs.

(56) References Cited

OTHER PUBLICATIONS

"U.S. Appl. No. 11/347,662, Examiner Interview Summary mailed Jun. 24, 2010", 3 pgs.
"U.S. Appl. No. 11/347,662, Examiner Interview Summary mailed Nov. 9, 2009", 3 pgs.
"U.S. Appl. No. 11/347,662, Final Office Action mailed Sep. 16, 2009", 13 pgs.
"U.S. Appl. No. 11/347,662, Final Office Action mailed Oct. 26, 2010", 10 pgs.
"U.S. Appl. No. 11/347,662, Non Final Office Action mailed Mar. 9, 2009", 11 pgs.
"U.S. Appl. No. 11/347,662, Non Final Office Action mailed May 21, 2010", 19 pgs.
"U.S. Appl. No. 11/347,662, Non Final Office Action mailed Oct. 28, 2008", 13 pgs.
"U.S. Appl. No. 11/347,662, Response filed Jan. 16, 2009 to Non Final Office Action mailed Oct. 28, 2008", 16 pgs.
"U.S. Appl. No. 11/347,662, Response filed Feb. 12, 2010 to Final Office Action mailed Sep. 16, 2009", 21 pgs.
"U.S. Appl. No. 11/347,662, Response filed Jun. 5, 2009 to Non Final Office Action mailed Mar. 9, 2009", 13 pgs.
"U.S. Appl. No. 11/347,662, Response filed Aug. 20, 2010 to Non Final Office Action mailed May 21, 2010", 13 pgs.
"U.S. Appl. No. 11/386,071, Advisory Action mailed Dec. 23, 2010", 3 pgs.
"U.S. Appl. No. 11/386,071, Examiner Interview Summary mailed Jan. 31, 2011", 3 pgs.
"U.S. Appl. No. 11/386,071, Examiner Interview Summary mailed Jul. 21, 2010", 3 pgs.
"U.S. Appl. No. 11/386,071, Final Office Action mailed Oct. 27, 2010", 10 pgs.
"U.S. Appl. No. 11/386,071, Non Final Office Action mailed May 12, 2010", 13 pgs.
"U.S. Appl. No. 11/386,071, Notice of Allowance mailed Jun. 6, 2011", 6 pgs.
"U.S. Appl. No. 11/386,071, Response filed Jan. 26, 2011 to Advisory Action mailed Dec. 23, 2010", 13 pgs.
"U.S. Appl. No. 11/386,071, Response filed Aug. 12, 2010 to Non Final Office Action mailed May 12, 2010", 14 pgs.
"U.S. Appl. No. 11/386,071, Response filed Dec. 15, 2010 to Final Office Action mailed Oct. 27, 2010", 14 pgs.
"U.S. Appl. No. 11/408,282, Final Office Action mailed Dec. 15, 2008", 8 pgs.
"U.S. Appl. No. 11/408,282, Non Final Office Action mailed May 23, 2008", 12 pgs.
"U.S. Appl. No. 11/408,282, Response filed Aug. 21, 2008 to Non Final Office Action mailed May 23, 2008", 10 pgs.
"U.S. Appl. No. 11/504,882, Examiner Interview Summary mailed Sep. 2, 2010", 3 pgs.
"U.S. Appl. No. 11/504,882, Final Office Action mailed Dec. 21, 2010", 7 pgs.
"U.S. Appl. No. 11/504,882, Non Final Office Action mailed Jun. 19, 2014", 11 pgs.
"U.S. Appl. No. 11/504,882, Non Final Office Action mailed Jun. 23, 2010", 8 pgs.
"U.S. Appl. No. 11/504,882, Non Final Office Action mailed Nov. 13, 2013", 13 pgs.
"U.S. Appl. No. 11/504,882, Notice of Allowance mailed Dec. 1, 2014", 9 pgs.
"U.S. Appl. No. 11/504,882, Response filed Feb. 10, 2014 to Non Final Office Action mailed Nov. 13, 2013", 11 pgs.
"U.S. Appl. No. 11/504,882, Response filed Mar. 18, 2011 to Final Office Action mailed Dec. 21, 2010", 11 pgs.
"U.S. Appl. No. 11/504,882, Response filed Sep. 17, 2014 to Non Final Office Action mailed Jun. 19, 2014", 14 pgs.
"U.S. Appl. No. 11/504,882, Response filed Sep. 23, 2010 to Non Final Office Action mailed Jun. 23, 2010", 12 pgs.
"U.S. Appl. No. 11/504,882, Supplemental Notice of Allowability mailed Mar. 12, 2015", 5 pgs.
"U.S. Appl. No. 11/541,505, Non Final Office Action mailed May 19, 2009", 7 pgs.
"U.S. Appl. No. 11/541,505, Notice of Allowance mailed Sep. 18, 2009", 8 pgs.
"U.S. Appl. No. 11/541,505, Response filed Apr. 9, 2009 to Restriction Requirement mailed Mar. 9, 2009", 1 pg.
"U.S. Appl. No. 11/541,505, Response filed Jun. 18, 2009 to Non Final Office Action mailed May 19, 2009", 5 pgs.
"U.S. Appl. No. 11/541,505, Restriction Requirement mailed Mar. 9, 2009", 9 pgs.
"U.S. Appl. No. 11/541,506, Notice of Allowance mailed Jun. 1, 2009", 10 pgs.
"U.S. Appl. No. 11/541,506, Notice of Allowance mailed Jun. 29, 2009", 8 pgs.
"U.S. Appl. No. 11/541,506, Response filed Apr. 9, 2009 to Restriction Requirement mailed Mar. 9, 2009", 1 pg.
"U.S. Appl. No. 11/541,506, Restriction Requirement mailed Mar. 9, 2009", 6 pgs.
"U.S. Appl. No. 11/739,768, Examiner Interview Summary mailed May 11, 2011", 3 pgs.
"U.S. Appl. No. 11/739,768, Examiner Interview Summary mailed Oct. 4, 2011", 3 pgs.
"U.S. Appl. No. 11/739,768, Final Office Action mailed Aug. 22, 2011", 14 pgs.
"U.S. Appl. No. 11/739,768, Non Final Office Action mailed Mar. 4, 2011", 11 pgs.
"U.S. Appl. No. 11/739,768, Notice of Allowance mailed Nov. 15, 2011", 5 pgs.
"U.S. Appl. No. 11/739,768, Response filed Jun. 6, 2011 to Non Final Office Action mailed Mar. 4, 2011", 15 pgs.
"U.S. Appl. No. 11/739,768, Response filed Oct. 26, 2011 to Final Office Action mailed Aug. 22, 2011", 14 pgs.
"U.S. Appl. No. 11/740,035, Final Office Action mailed Aug. 7, 2008", 9 pgs.
"U.S. Appl. No. 11/740,035, Non Final Office Action mailed Jan. 3, 2008", 9 pgs.
"U.S. Appl. No. 11/740,035, Response filed Apr. 3, 2008 to Non Final Office Action mailed Jan. 3, 2008", 6 pgs.
"U.S. Appl. No. 11/784,821, Corrected Notice of Allowance mailed Dec. 24, 2014", 4 pgs.
"U.S. Appl. No. 11/784,821, Examiner Interview Summary mailed Jun. 26, 2014", 3 pgs.
"U.S. Appl. No. 11/784,821, Examiner Interview Summary mailed Nov. 17, 2009", 3 pgs.
"U.S. Appl. No. 11/784,821, Final Office Action mailed Mar. 10, 2010", 11 pgs.
"U.S. Appl. No. 11/784,821, Non Final Office Action mailed Mar. 28, 2014", 14 pgs.
"U.S. Appl. No. 11/784,821, Non Final Office Action mailed Sep. 4, 2009", 12 pgs.
"U.S. Appl. No. 11/784,821, Notice of Allowance mailed Oct. 21, 2014", 10 pgs.
"U.S. Appl. No. 11/784,821, Response filed Jun. 10, 2010 to Final Office Action mailed Mar. 10, 2010", 20 pgs.
"U.S. Appl. No. 11/784,821, Response filed Jun. 15, 2009 to Restriction Requirement mailed May 13, 2009", 2 pgs.
"U.S. Appl. No. 11/784,821, Response filed Jun. 26, 2014 to Non Final Office Action mailed Mar. 28, 2014", 16 pgs.
"U.S. Appl. No. 11/784,821, Response filed Nov. 23, 2009 to Non Final Office Action mailed Sep. 4, 2009", 17 pgs.
"U.S. Appl. No. 11/784,821, Restriction Requirement mailed May 13, 2009", 6 pgs.
"U.S. Appl. No. 11/869,440, Examiner Interview Summary mailed Mar. 25, 2010", 3 pgs.
"U.S. Appl. No. 11/869,440, Non Final Office Action mailed Mar. 1, 2010", 13 pgs.
"U.S. Appl. No. 11/869,440, Notice of Allowance mailed Aug. 19, 2010", 10 pgs.
"U.S. Appl. No. 11/869,440, Response filed Jun. 1, 2010 to Non Final Office Action mailed Mar. 1, 2010", 14 pgs.
"U.S. Appl. No. 11/935,681, Examiner Interview Summary mailed Jul. 19, 2010", 3 pgs.

(56) References Cited

OTHER PUBLICATIONS

"U.S. Appl. No. 11/935,681, Non Final Office Action mailed May 24, 2010", 12 pgs.
"U.S. Appl. No. 11/935,681, Notice of Allowance mailed Nov. 8, 2010", 10 pgs.
"U.S. Appl. No. 11/935,681, Response filed Apr. 19, 2010 to Restriction Requirement mailed Mar. 17, 2010", 4 pgs.
"U.S. Appl. No. 11/935,681, Response filed Aug. 24, 2010 to Non Final Office Action mailed May 24, 2010", 13 pgs.
"U.S. Appl. No. 11/935,681, Restriction Requirement mailed Mar. 17, 2010", 6 pgs.
"U.S. Appl. No. 12/014,340, Examiner Interview Summary mailed Jun. 22, 2010", 3 pgs.
"U.S. Appl. No. 12/014,340, Non Final Office Action mailed May 25, 2010", 12 pgs.
"U.S. Appl. No. 12/014,340, Notice of Allowance mailed Nov. 8, 2010", 9 pgs.
"U.S. Appl. No. 12/014,340, Preliminary Amendment filed May 21, 2010", 11 pgs.
"U.S. Appl. No. 12/014,340, Response filed Apr. 26, 2010 to Restriction Requirement mailed Mar. 25, 2010", 2 pgs.
"U.S. Appl. No. 12/014,340, Response filed Aug. 25, 2010 to Non Final Office Action mailed May 25, 2010", 16 pgs.
"U.S. Appl. No. 12/014,340, Restriction Requirement mailed Mar. 25, 2010", 9 pgs.
"U.S. Appl. No. 12/014,399, Examiner Interview Summary mailed Jun. 23, 2010", 3 pgs.
"U.S. Appl. No. 12/014,399, Non Final Office Action mailed May 26, 2010", 13 pgs.
"U.S. Appl. No. 12/014,399, Notice of Allowance mailed Nov. 12, 2010", 11 pgs.
"U.S. Appl. No. 12/014,399, Preliminary Amendment filed May 25, 2010", 10 pgs.
"U.S. Appl. No. 12/014,399, Response filed May 5, 2010 to Restriction Requirement mailed Apr. 6, 2010", 2 pgs.
"U.S. Appl. No. 12/014,399, Response filed Aug. 25, 2010 to Non Final Office Action mailed May 26, 2010", 14 pgs.
"U.S. Appl. No. 12/014,399, Restriction Requirement mailed Apr. 6, 2010", 9 pgs.
"U.S. Appl. No. 12/029,861, Examiner Interview Summary mailed Jan. 27, 2012", 3 pgs.
"U.S. Appl. No. 12/029,861, Final Office Action mailed Dec. 8, 2011", 11 pgs.
"U.S. Appl. No. 12/029,861, Non Final Office Action mailed Jul. 26, 2011", 11 pgs.
"U.S. Appl. No. 12/029,861, Notice of Allowance mailed Apr. 26, 2012", 5 pgs.
"U.S. Appl. No. 12/029,861, Response filed Jan. 26, 2012 to Final Office Action mailed Dec. 8, 2011", 15 pgs.
"U.S. Appl. No. 12/029,861, Response filed May 6, 2011 to Restriction Requirement mailed Apr. 7, 2011", 10 pgs.
"U.S. Appl. No. 12/029,861, Response filed Jun. 23, 2011 to Restriction Requirement mailed May 24, 2011", 1 pgs.
"U.S. Appl. No. 12/029,861, Response filed Oct. 14, 2011 to Non Final Office Action mailed Jul. 26, 2011", 11 pgs.
"U.S. Appl. No. 12/029,861, Restriction Requirement mailed Apr. 7, 2011", 8 pgs.
"U.S. Appl. No. 12/029,861, Restriction Requirement mailed May 24, 2011", 6 pgs.
"U.S. Appl. No. 12/107,437, Examiner Interview Summary mailed May 10, 2010", 4 pgs.
"U.S. Appl. No. 12/107,437, Non Final Office Action mailed Mar. 17, 2010", 9 pgs.
"U.S. Appl. No. 12/107,437, Preliminary Amendment filed Feb. 23, 2010", 9 pgs.
"U.S. Appl. No. 12/107,437, Response filed Jan. 29, 2010 to Restriction Requirement mailed Jan. 13, 2010", 1 pgs.
"U.S. Appl. No. 12/107,437, Restriction Requirement mailed Jan. 13, 2010", 7 pgs.
"U.S. Appl. No. 12/196,398, Examiner Interview Summary mailed Nov. 8, 2010", 3 pgs.
"U.S. Appl. No. 12/196,398, Notice of Allowance mailed Feb. 3, 2011", 12 pgs.
"U.S. Appl. No. 12/196,398, Preliminary Amendment filed Nov. 10, 2008", 3 pgs.
"U.S. Appl. No. 12/196,398, Preliminary Amendment filed Dec. 1, 2010", 12 pgs.
"U.S. Appl. No. 12/196,398, Preliminary Amendment filed Dec. 9, 2008", 46 pgs.
"U.S. Appl. No. 12/196,398, Response filed Oct. 29, 2010 to Restriction Requirement mailed Sep. 29, 2010", 2 pgs.
"U.S. Appl. No. 12/196,398, Restriction Requirement mailed Sep. 29, 2010", 6 pgs.
"U.S. Appl. No. 12/196,398, Supplemental Notice of Allowability mailed Mar. 9, 2011", 4 pgs.
"U.S. Appl. No. 12/196,398, Supplemental Notice of Allowability mailed Apr. 15, 2011", 4 pgs.
"U.S. Appl. No. 12/196,405, Examiner Interview Summary mailed Jun. 20, 2011", 3 pgs.
"U.S. Appl. No. 12/196,405, Non Final Office Action mailed Apr. 11, 2011", 13 pgs.
"U.S. Appl. No. 12/196,405, Notice of Allowance mailed Oct. 26, 2011", 11 pgs.
"U.S. Appl. No. 12/196,405, Preliminary Amendment filed Nov. 10, 2008", 3 pgs.
"U.S. Appl. No. 12/196,405, Response filed Mar. 16, 2011 to Restriction Requirement mailed Feb. 14, 2011", 1 pgs.
"U.S. Appl. No. 12/196,405, Response filed Jul. 12, 2011 to Non Final Office Action mailed Apr. 11, 2011", 19 pgs.
"U.S. Appl. No. 12/196,405, Restriction Requirement mailed Feb. 14, 2011", 6 pgs.
"U.S. Appl. No. 12/196,405, Supplemental Amendment filed Oct. 3, 2011", 12 pgs.
"U.S. Appl. No. 12/196,407, Examiner Interview Summary mailed Jul. 14, 2011", 3 pgs.
"U.S. Appl. No. 12/196,407, Non Final Office Action mailed May 4, 2011", 11 pgs.
"U.S. Appl. No. 12/196,407, Notice of Allowance mailed Oct. 26, 2011", 10 pgs.
"U.S. Appl. No. 12/196,407, Preliminary Amendment filed Nov. 10, 2008", 3 pgs.
"U.S. Appl. No. 12/196,407, Response filed Apr. 20, 2011 to Restriction Requirement mailed Mar. 22, 2011", 12 pgs.
"U.S. Appl. No. 12/196,407, Response filed Aug. 2, 2011 to Non Final Office Action mailed May 4, 2011", 27 pgs.
"U.S. Appl. No. 12/196,407, Restriction Requirement mailed Mar. 22, 2011", 6 pgs.
"U.S. Appl. No. 12/196,407, Supplemental Response to Non Final Office Action filed Oct. 3, 2011", 18 pgs.
"U.S. Appl. No. 12/196,410, Examiner Interview Summary mailed Jul. 14, 2011", 3 pgs.
"U.S. Appl. No. 12/196,410, Non Final Office Action mailed May 9, 2011", 9 pgs.
"U.S. Appl. No. 12/196,410, Notice of Allowance mailed Oct. 13, 2011", 8 pgs.
"U.S. Appl. No. 12/196,410, Response filed Apr. 20, 2011 to Restriction Requirement mailed Mar. 22, 2011", 13 pgs.
"U.S. Appl. No. 12/196,410, Response filed Aug. 1, 2011 to Non Final Office Action mailed May 9, 2011", 23 pgs.
"U.S. Appl. No. 12/196,410, Restriction Requirement mailed Mar. 22, 2011", 6 pgs.
"U.S. Appl. No. 12/196,410, Supplemental Amendment filed Oct. 3, 2011", 15 pgs.
"U.S. Appl. No. 12/398,548, Examiner Interview Summary mailed Jul. 12, 2011", 3 pgs.
"U.S. Appl. No. 12/398,548, Non Final Office Action mailed Apr. 12, 2011", 7 pgs.
"U.S. Appl. No. 12/398,548, Notice of Allowance mailed Oct. 18, 2011", 7 pgs.
"U.S. Appl. No. 12/398,548, Response filed Jul. 12, 2011 to Non Final Office Action mailed Apr. 12, 2011", 15 pgs.

(56) References Cited

OTHER PUBLICATIONS

"U.S. Appl. No. 12/398,548, Supplemental Preliminary Amendment filed Sep. 7, 2010", 11 pgs.
"U.S. Appl. No. 12/419,491, Examiner Interview Summary mailed May 30, 2012", 3 pgs.
"U.S. Appl. No. 12/419,491, Examiner Interview Summary mailed Nov. 29, 2011", 3 pgs.
"U.S. Appl. No. 12/419,491, Final Office Action mailed Apr. 12, 2012", 12 pgs.
"U.S. Appl. No. 12/419,491, Non Final Office Action mailed Sep. 22, 2011", 12 pgs.
"U.S. Appl. No. 12/419,491, Notice of Allowance mailed Jul. 13, 2012", 10 pgs.
"U.S. Appl. No. 12/419,491, Response filed May 30, 2012 to Final Office Action mailed Apr. 12, 2012", 12 pgs.
"U.S. Appl. No. 12/419,491, Response filed Dec. 9, 2011 to Non Final Office Action mailed Sep. 22, 2011", 17 pgs.
"U.S. Appl. No. 12/474,802, Notice of Allowance mailed Aug. 31, 2011", 13 pgs.
"U.S. Appl. No. 12/474,802, Notice of Allowance mailed Oct. 26, 2011", 4 pgs.
"U.S. Appl. No. 12/474,802, Response filed Mar. 28, 2011 to Restriction Requirement mailed Feb. 24, 2011", 12 pgs.
"U.S. Appl. No. 12/474,802, Restriction Requirement mailed Feb. 24, 2011", 6 pgs.
"U.S. Appl. No. 12/489,168, Examiner Interview Summary mailed Feb. 21, 2012", 3 pgs.
"U.S. Appl. No. 12/489,168, Non Final Office Action mailed Dec. 7, 2011", 10 pgs.
"U.S. Appl. No. 12/489,168, Notice of Allowance mailed Apr. 26, 2012", 8 pgs.
"U.S. Appl. No. 12/489,168, Notice of Allowance mailed Sep. 5, 2012", 8 pgs.
"U.S. Appl. No. 12/489,168, Preliminary Amendment filed Oct. 22, 2009", 3 pgs.
"U.S. Appl. No. 12/489,168, Response filed Feb. 27, 2012 to Non Final Office Action mailed Dec. 7, 2011", 15 pgs.
"U.S. Appl. No. 12/489,168, Response filed Nov. 11, 2011 to Restriction Requirement mailed Oct. 20, 2011", 1 pg.
"U.S. Appl. No. 12/489,168, Restriction Requirement mailed Oct. 20, 2011", 8 pgs.
"U.S. Appl. No. 12/489,181, Examiner Interview Summary mailed Feb. 13, 2012", 3 pgs.
"U.S. Appl. No. 12/489,181, Non Final Office Action mailed Jan. 3, 2012", 9 pgs.
"U.S. Appl. No. 12/489,181, Notice of Allowance mailed May 23, 2012", 9 pgs.
"U.S. Appl. No. 12/489,181, Preliminary Amendment filed Mar. 31, 2011", 10 pgs.
"U.S. Appl. No. 12/489,181, Preliminary Amendment filed Oct. 22, 2009", 3 pgs.
"U.S. Appl. No. 12/489,181, Response filed Mar. 27, 2012 to Non Final Office Action mailed Jan. 3, 2012", 12 pgs.
"U.S. Appl. No. 12/489,181, Response filed Dec. 5, 2011 to Restriction Requirement mailed Nov. 4, 2011", 1 pg.
"U.S. Appl. No. 12/489,181, Restriction Requirement mailed Nov. 4, 2011", 7 pgs.
"U.S. Appl. No. 12/570,854, Examiner Interview Summary mailed Apr. 16, 2012", 3 pgs.
"U.S. Appl. No. 12/570,854, Non Final Office Action mailed Feb. 10, 2012", 8 pgs.
"U.S. Appl. No. 12/570,854, Notice of Allowance mailed Jun. 29, 2012", 10 pgs.
"U.S. Appl. No. 12/570,854, Notice of Allowance mailed Sep. 19, 2012", 6 pgs.
"U.S. Appl. No. 12/570,854, Response filed May 10, 2012 to Non Final Office Action mailed Feb. 10, 2012", 27 pgs.
"U.S. Appl. No. 12/570,854, Response filed Dec. 20, 2011 to Restriction Requirement mailed Dec. 14, 2011", 1 pg.
"U.S. Appl. No. 12/570,854, Restriction Requirement mailed Dec. 14, 2011", 6 pgs.
"U.S. Appl. No. 12/702,067, Non Final Office Action mailed Mar. 5, 2013", 8 pgs.
"U.S. Appl. No. 12/702,067, Notice of Allowance mailed Oct. 7, 2013", 11 pgs.
"U.S. Appl. No. 12/702,067, Preliminary Amendment filed Jan. 11, 2011", 13 pgs.
"U.S. Appl. No. 12/702,067, Response filed Jun. 5, 2013 to Non Final Office Action mailed Mar. 5, 2013", 17 pgs.
"U.S. Appl. No. 12/702,067, Response filed Oct. 2, 2012 to Restriction Requirement mailed Sep. 4, 2012", 1 pg.
"U.S. Appl. No. 12/702,067, Restriction Requirement mailed Sep. 4, 2012", 9 pgs.
"U.S. Appl. No. 12/719,337, Advisory Action mailed Sep. 30, 2014", 4 pgs.
"U.S. Appl. No. 12/719,337, Examiner Interview Summary mailed Apr. 4, 2014", 4 pgs.
"U.S. Appl. No. 12/719,337, Examiner Interview Summary mailed May 14, 2013", 3 pgs.
"U.S. Appl. No. 12/719,337, Examiner Interview Summary mailed Sep. 18, 2014", 3 pgs.
"U.S. Appl. No. 12/719,337, Final Office Action mailed Mar. 12, 2013", 8 pgs.
"U.S. Appl. No. 12/719,337, Final Office Action mailed Jul. 18, 2014", 15 pgs.
"U.S. Appl. No. 12/719,337, Non Final Office Action mailed Jan. 10, 2014", 14 pgs.
"U.S. Appl. No. 12/719,337, Non Final Office Action mailed Sep. 5, 2012", 7 pgs.
"U.S. Appl. No. 12/719,337, Notice of Allowance mailed Mar. 11, 2015", 10 pgs.
"U.S. Appl. No. 12/719,337, Notice of Non-Compliant Amendment mailed May 2, 2014", 3 pgs.
"U.S. Appl. No. 12/719,337, Response filed Apr. 10, 2014 to Non Final Office Action mailed Jan. 10, 2014", 16 pgs.
"U.S. Appl. No. 12/719,337, Response filed May 25, 2012 to Restriction Requirement mailed Apr. 26, 2012", 9 pgs.
"U.S. Appl. No. 12/719,337, Response filed Jun. 5, 2013 to Final Office Action mailed Mar. 12, 2013", 16 pgs.
"U.S. Appl. No. 12/719,337, Response filed Jun. 25, 2014 to Notice of Non-Compliant Amendment mailed May 2, 2014", 10 pgs.
"U.S. Appl. No. 12/719,337, Response filed Sep. 18, 2014 to Final Office Action mailed Jul. 18, 2014", 13 pgs.
"U.S. Appl. No. 12/719,337, Response filed Nov. 28, 2012 to Non Final Office Action mailed Sep. 5, 2012", 14 pgs.
"U.S. Appl. No. 12/719,337, Restriction Requirement mailed Apr. 26, 2012", 8 pgs.
"U.S. Appl. No. 12/788,966, Examiner Interview Summary mailed Jun. 1, 2012", 3 pgs.
"U.S. Appl. No. 12/788,966, Final Office Action mailed May 4, 2012", 16 pgs.
"U.S. Appl. No. 12/788,966, Non Final Office Action mailed Jan. 4, 2012", 12 pgs.
"U.S. Appl. No. 12/788,966, Notice of Allowance mailed Aug. 16, 2012", 10 pgs.
"U.S. Appl. No. 12/788,966, Notice of Allowance mailed Nov. 23, 2012", 2 pgs.
"U.S. Appl. No. 12/788,966, Response filed Apr. 4, 2012 to Non Final Office Action mailed Jan. 4, 2012", 15 pgs.
"U.S. Appl. No. 12/788,966, Response filed Aug. 6, 2012 to Final Office Action mailed May 4, 2012", 12 pgs.
"U.S. Appl. No. 12/788,966, Response filed Dec. 16, 2011 to Restriction Requirement mailed Dec. 7, 2011", 11 pgs.
"U.S. Appl. No. 12/788,966, Restriction Requirement mailed Dec. 7, 2011", 9 pgs.
"U.S. Appl. No. 12/788,973, Advisory Action mailed Jan. 23, 2013", 3 pgs.
"U.S. Appl. No. 12/788,973, Advisory Action mailed Dec. 27, 2012", 8 pgs.
"U.S. Appl. No. 12/788,973, Final Office Action mailed Sep. 18, 2012", 16 pgs.

(56) References Cited

OTHER PUBLICATIONS

"U.S. Appl. No. 12/788,973, Non Final Office Action mailed May 8, 2012", 12 pgs.
"U.S. Appl. No. 12/788,973, Notice of Allowance mailed Mar. 21, 2013", 6 pgs.
"U.S. Appl. No. 12/788,973, Response filed Jan. 16, 2013 to Advisory Action mailed Dec. 27, 2012", 9 pgs.
"U.S. Appl. No. 12/788,973, Response filed Jul. 19, 2012 to Non Final Office Action mailed May 8, 2012", 21 pgs.
"U.S. Appl. No. 12/788,973, Response filed Dec. 16, 2011 to Restriction Requirement mailed Dec. 6, 2011", 11 pgs.
"U.S. Appl. No. 12/788,973, Response filed Dec. 17, 2012 to Final Office Action mailed Sep. 18, 2012", 15 pgs.
"U.S. Appl. No. 12/788,973, Restriction Requirement mailed Dec. 6, 2011", 9 pgs.
"U.S. Appl. No. 12/788,973, Supplemental Notice of Allowance mailed May 24, 2013", 2 pgs.
"U.S. Appl. No. 12/788,978, Advisory Action mailed Dec. 24, 2013", 4 pgs.
"U.S. Appl. No. 12/788,978, Applicant's Summary of Examiner Interview filed Dec. 12, 2013", 2 pgs.
"U.S. Appl. No. 12/788,978, Corrected Notice of Allowance mailed Apr. 30, 2014", 2 pgs.
"U.S. Appl. No. 12/788,978, Examiner Interview Summary mailed Jan. 28, 2014", 3 pgs.
"U.S. Appl. No. 12/788,978, Examiner Interview Summary mailed Mar. 22, 2013", 3 pgs.
"U.S. Appl. No. 12/788,978, Examiner Interview Summary mailed Sep. 11, 2012", 3 pgs.
"U.S. Appl. No. 12/788,978, Examiner Interview Summary mailed Oct. 29, 2013", 4 pgs.
"U.S. Appl. No. 12/788,978, Examiner Interview Summary mailed Dec. 16, 2013", 3 pgs.
"U.S. Appl. No. 12/788,978, Examiner Interview Summary mailed Dec. 27, 2012", 3 pgs.
"U.S. Appl. No. 12/788,978, Final Office Action mailed Aug. 20, 2013", 17 pgs.
"U.S. Appl. No. 12/788,978, Final Office Action mailed Nov. 2, 2012", 14 pgs.
"U.S. Appl. No. 12/788,978, Non Final Office Action mailed Jan. 11, 2013", 16 pgs.
"U.S. Appl. No. 12/788,978, Non Final Office Action mailed Jul. 13, 2012", 17 pgs.
"U.S. Appl. No. 12/788,978, Notice of Allowance mailed Jan. 24, 2014", 9 pgs.
"U.S. Appl. No. 12/788,978, Notice of Non-Compliant Amendment mailed Jun. 6, 2013", 3 pgs.
"U.S. Appl. No. 12/788,978, Response filed Jan. 2, 2013 to Final Office Action mailed Nov. 2, 2012", 13 pgs.
"U.S. Appl. No. 12/788,978, Response filed Jan. 20, 2014 to Advisory Action mailed Dec. 24, 2013", 4 pgs.
"U.S. Appl. No. 12/788,978, Response filed Apr. 8, 2013 to Non Final Office Action mailed Jan. 11, 2013", 16 pgs.
"U.S. Appl. No. 12/788,978, Response filed May 21, 2012 to Restriction Requirement mailed Apr. 20, 2012", 12 pgs.
"U.S. Appl. No. 12/788,978, Response filed Jul. 3, 2013 to Notice of Non-Compliant Amendment mailed Jun. 6, 2013", 17 pgs.
"U.S. Appl. No. 12/788,978, Response filed Oct. 5, 2012 to Non Final Office Action mailed Jul. 13, 2012", 20 pgs.
"U.S. Appl. No. 12/788,978, Response filed Nov. 20, 2013 to Final Office Action mailed Aug. 20, 2013", 15 pgs.
"U.S. Appl. No. 12/788,978, Restriction Requirement mailed Apr. 20, 2012", 8 pgs.
"U.S. Appl. No. 12/828,977, Examiner Interview Summary mailed Jul. 9, 2012", 3 pgs.
"U.S. Appl. No. 12/828,977, Non Final Office Action mailed May 3, 2012", 9 pgs.
"U.S. Appl. No. 12/828,977, Notice of Allowance mailed Sep. 5, 2012", 9 pgs.
"U.S. Appl. No. 12/828,977, Preliminary Amendment filed Jul. 19, 2011", 10 pgs.
"U.S. Appl. No. 12/828,977, Response filed Mar. 14, 2012 to Restriction Requirement mailed Feb. 13, 2012", 9 pgs.
"U.S. Appl. No. 12/828,977, Response filed Jul. 25, 2012 to Non Final Office Action mailed May 3, 2012", 11 pgs.
"U.S. Appl. No. 12/828,977, Restriction Requirement mailed Feb. 13, 2012", 7 pgs.
"U.S. Appl. No. 12/915,962, Examiner Interview Summary mailed Jul. 25, 2012", 3 pgs.
"U.S. Appl. No. 12/915,962, Non Final Office Action mailed May 7, 2012", 11 pgs.
"U.S. Appl. No. 12/915,962, Non Final Office Action mailed Oct. 15, 2012", 9 pgs.
"U.S. Appl. No. 12/915,962, Notice of Allowance mailed Jun. 10, 2013", 12 pgs.
"U.S. Appl. No. 12/915,962, Response filed Jan. 10, 2013 to Non Final Office Action mailed Oct. 15, 2012", 21 pgs.
"U.S. Appl. No. 12/915,962, Response filed Mar. 16, 2012 to Restriction Requirement mailed Feb. 15, 2012", 15 pgs.
"U.S. Appl. No. 12/915,962, Response filed Aug. 7, 2012 to Non Final Office Action mailed May 7, 2012", 26 pgs.
"U.S. Appl. No. 12/915,962, Restriction Requirement mailed Feb. 15, 2012", 8 pgs.
"U.S. Appl. No. 12/938,902, Examiner Interview Summary mailed Dec. 3, 2012", 3 pgs.
"U.S. Appl. No. 12/938,902, Non Final Office Action mailed Sep. 17, 2012", 11 pgs.
"U.S. Appl. No. 12/938,902, Notice of Allowance mailed Jun. 21, 2013", 13 pgs.
"U.S. Appl. No. 12/938,902, Notice of Allowance mailed Oct. 1, 2013", 9 pgs.
"U.S. Appl. No. 12/938,902, Response filed Aug. 6, 2012 to Restriction Requirement mailed Jul. 6, 2012", 14 pgs.
"U.S. Appl. No. 12/938,902, Response filed Dec. 10, 2012 to Non Final Office Action mailed Sep. 17, 2012", 20 pgs.
"U.S. Appl. No. 12/938,902, Restriction Requirement mailed Jul. 6, 2012", 8 pgs.
"U.S. Appl. No. 12/976,328, Examiner Interview Summary mailed Feb. 13, 2012", 3 pgs.
"U.S. Appl. No. 12/976,328, Non Final Office Action mailed Dec. 15, 2011", 13 pgs.
"U.S. Appl. No. 12/976,328, Notice of Allowance mailed Apr. 30, 2012", 9 pgs.
"U.S. Appl. No. 12/976,328, Response filed Mar. 2, 2012 to Non Final Office Action mailed Dec. 15, 2011", 15 pgs.
"U.S. Appl. No. 13/045,689, Examiner Interview Summary mailed May 14, 2012", 3 pgs.
"U.S. Appl. No. 13/045,689, Non Final Office Action mailed Mar. 20, 2012", 11 pgs.
"U.S. Appl. No. 13/045,689, Notice of Allowance mailed Aug. 10, 2012", 10 pgs.
"U.S. Appl. No. 13/045,689, Notice of Allowance mailed Sep. 24, 2012", 7 pgs.
"U.S. Appl. No. 13/045,689, Response filed Jan. 30, 2012 to Restriction Requirement mailed Dec. 29, 2011", 13 pgs.
"U.S. Appl. No. 13/045,689, Response filed Jun. 8, 2012 to Non Final Office Action mailed Mar. 20, 2012", 15 pgs.
"U.S. Appl. No. 13/045,689, Restriction Requirement mailed Dec. 29, 2011", 6 pgs.
"U.S. Appl. No. 13/045,691, Examiner Interview Summary mailed May 14, 2012", 3 pgs.
"U.S. Appl. No. 13/045,691, Non Final Office Action mailed Mar. 20, 2012", 12 pgs.
"U.S. Appl. No. 13/045,691, Notice of Allowance mailed Jun. 19, 2012", 10 pgs.
"U.S. Appl. No. 13/045,691, Response filed Feb. 9, 2012 to Restriction Requirement mailed Jan. 9, 2012", 1 pg.
"U.S. Appl. No. 13/045,691, Response filed Jun. 8, 2012 to Non Final Office Action mailed Mar. 20, 2012", 17 pgs.
"U.S. Appl. No. 13/045,691, Restriction Requirement mailed Jan. 9, 2012", 6 pgs.

(56) References Cited

OTHER PUBLICATIONS

"U.S. Appl. No. 13/071,563, Final Office Action mailed May 23, 2014", 13 pgs.
"U.S. Appl. No. 13/071,563, Non Final Office Action mailed Oct. 23, 2013", 18 pgs.
"U.S. Appl. No. 13/071,563, Notice of Allowance mailed Aug. 15, 2014", 7 pgs.
"U.S. Appl. No. 13/071,563, Preliminary Amendment filed May 1, 2012", 8 pgs.
"U.S. Appl. No. 13/071,563, Preliminary Amendment filed Dec. 6, 2011", 7 pgs.
"U.S. Appl. No. 13/071,563, Response filed Jan. 21, 2014 to Non Final Office Action mailed Oct. 23, 2013", 13 pgs.
"U.S. Appl. No. 13/071,563, Response filed Jul. 23, 2014 to Final Office Action mailed May 23, 2014", 14 pgs.
"U.S. Appl. No. 13/071,563, Response filed Sep. 19, 2013 to Restriction Requirement mailed Aug. 19, 2013", 11 pgs.
"U.S. Appl. No. 13/071,563, Restriction Requirement mailed Aug. 19, 2013", 7 pgs.
"U.S. Appl. No. 13/098,897, Examiner Interview Summary mailed Nov. 27, 2012", 3 pgs.
"U.S. Appl. No. 13/098,897, Non Final Office Action mailed Sep. 21, 2012", 9 pgs.
"U.S. Appl. No. 13/098,897, Notice of Allowance mailed Jun. 11, 2013", 13 pgs.
"U.S. Appl. No. 13/098,897, Response filed Aug. 30, 2012 to Restriction Requirement mailed Jul. 30, 2012", 16 pgs.
"U.S. Appl. No. 13/098,897, Response filed Dec. 18, 2012 to Non Final Office Action mailed Sep. 21, 2012", 21 pgs.
"U.S. Appl. No. 13/098,897, Restriction Requirement mailed Jul. 30, 2012", 8 pgs.
"U.S. Appl. No. 13/098,927, Advisory Action mailed Aug. 8, 2013", 3 pgs.
"U.S. Appl. No. 13/098,927, Applicant's Summary of Examiner Interview filed Sep. 23, 2013", 12 pgs.
"U.S. Appl. No. 13/098,927, Examiner Interview Summary mailed Jun. 28, 2013", 3 pgs.
"U.S. Appl. No. 13/098,927, Examiner Interview Summary mailed Sep. 20, 2013", 3 pgs.
"U.S. Appl. No. 13/098,927, Final Office Action mailed May 22, 2013", 10 pgs.
"U.S. Appl. No. 13/098,927, Non Final Office Action mailed Sep. 24, 2012", 12 pgs.
"U.S. Appl. No. 13/098,927, Notice of Allowance mailed Jan. 8, 2014", 5 pgs.
"U.S. Appl. No. 13/098,927, Notice of Allowance mailed Sep. 26, 2013", 14 pgs.
"U.S. Appl. No. 13/098,927, Response filed Jul. 22, 2015 to Final Office Action mailed May 22, 2013", 17 pgs.
"U.S. Appl. No. 13/098,927, Response filed Aug. 27, 2012 to Restriction Requirement mailed Jul. 25, 2012", 14 pgs.
"U.S. Appl. No. 13/098,927, Response filed Dec. 21, 2012 to Non Final Office Action mailed Sep. 24, 2012", 21 pgs.
"U.S. Appl. No. 13/098,927, Restriction Requirement mailed Jul. 25, 2012", 8 pgs.
"U.S. Appl. No. 13/102,182, Notice of Allowance mailed Mar. 22, 2012", 10 pgs.
"U.S. Appl. No. 13/109,667, Advisory Action mailed Feb. 4, 2014", 4 pgs.
"U.S. Appl. No. 13/109,667, Examiner Interview Summary mailed Dec. 20, 2013", 3 pgs.
"U.S. Appl. No. 13/109,667, Final Office Action mailed Oct. 11, 2013", 19 pgs.
"U.S. Appl. No. 13/109,667, Non Final Office Action mailed May 21, 2013", 21 pgs.
"U.S. Appl. No. 13/109,667, Notice of Allowance mailed Feb. 18, 2014", 10 pgs.
"U.S. Appl. No. 13/109,667, Response filed Jan. 13, 2014 to Final Office Action mailed Oct. 11, 2013", 20 pgs.
"U.S. Appl. No. 13/109,667, Response filed May 2, 2013 to Restriction Requirement mailed Apr. 2, 2013", 1 pg.
"U.S. Appl. No. 13/109,667, Response filed Aug. 21, 2013 to Non Final Office Action mailed May 21, 2013", 27 pgs.
"U.S. Appl. No. 13/109,667, Restriction Requirement mailed Apr. 2, 2013", 8 pgs.
"U.S. Appl. No. 13/109,667, Supplemental Notice of Allowability mailed Jun. 12, 2014", 3 pgs.
"U.S. Appl. No. 13/109,667, Supplemental Notice of Allowance mailed May 28, 2014", 2 pgs.
"U.S. Appl. No. 13/109,667, Supplemental Preliminary Amendment filed Feb. 4, 2014", 16 pgs.
"U.S. Appl. No. 13/109,672, 312 Amendment filed Jan. 15, 2015", 3 pgs.
"U.S. Appl. No. 13/109,672, Non Final Office Action mailed May 15, 2014", 10 pgs.
"U.S. Appl. No. 13/109,672, Notice of Allowance mailed Feb. 3, 2015", 2 pgs.
"U.S. Appl. No. 13/109,672, Notice of Allowance mailed Sep. 29, 2014", 9 pgs.
"U.S. Appl. No. 13/109,672, PTO Response to Rule 312 Communication mailed Jan. 27, 2015", 2 pgs.
"U.S. Appl. No. 13/109,672, Response filed Apr. 14, 2014 to Restriction Requirement mailed Feb. 14, 2014", 15 pgs.
"U.S. Appl. No. 13/109,672, Response filed Aug. 15, 2014 to Non Final Office Action mailed May 15, 2014", 20 pgs.
"U.S. Appl. No. 13/109,672, Response filed Nov. 4, 2013 to Restriction Requirement mailed Oct. 2, 2013", 10 pgs.
"U.S. Appl. No. 13/109,672, Restriction Requirement mailed Feb. 14, 2014", 7 pgs.
"U.S. Appl. No. 13/109,672, Restriction Requirement mailed Oct. 2, 2013", 7 pgs.
"U.S. Appl. No. 13/111,564, Corrected Notice of Allowance mailed Oct. 9, 2013", 2 pgs.
"U.S. Appl. No. 13/111,564, Examiner Interview Summary mailed Jun. 18, 2013", 3 pgs.
"U.S. Appl. No. 13/111,564, Non Final Office Action mailed Mar. 18, 2013", 8 pgs.
"U.S. Appl. No. 13/111,564, Notice of Allowance mailed Jun. 28, 2013", 12 pgs.
"U.S. Appl. No. 13/111,564, Response filed Feb. 4, 2013 to Restriction Requirement mailed Jan. 3, 2013", 20 pgs.
"U.S. Appl. No. 13/111,564, Response filed Jun. 18, 2013 to Non Final Office Action mailed Mar. 18, 2013", 25 pgs.
"U.S. Appl. No. 13/111,564, Restriction Requirement mailed Jan. 3, 2013", 5 pgs.
"U.S. Appl. No. 13/177,153, Final Office Action mailed May 28, 2013", 11 pgs.
"U.S. Appl. No. 13/177,153, Non Final Office Action mailed Oct. 2, 2012", 11 pgs.
"U.S. Appl. No. 13/177,153, Notice of Allowance mailed Jan. 7, 2014", 4 pgs.
"U.S. Appl. No. 13/177,153, Notice of Allowance mailed Sep. 17, 2013", 13 pgs.
"U.S. Appl. No. 13/177,153, Response filed Aug. 28, 2013 to Final Office Action mailed May 28, 2013", 19 pgs.
"U.S. Appl. No. 13/177,153, Response filed Sep. 4, 2012 to Restriction Requirement mailed Aug. 2, 2012", 15 pgs.
"U.S. Appl. No. 13/177,153, Response filed Dec. 20, 2012 to Non Final Office Action mailed Oct. 2, 2012", 16 pgs.
"U.S. Appl. No. 13/177,153, Restriction Requirement mailed Aug. 2, 2012", 9 pgs.
"U.S. Appl. No. 13/181,729, Examiner Interview Summary mailed May 9, 2013", 3 pgs.
"U.S. Appl. No. 13/181,729, Final Office Action mailed Mar. 13, 2013", 14 pgs.
"U.S. Appl. No. 13/181,729, Non Final Office Action mailed Oct. 2, 2012", 7 pgs.
"U.S. Appl. No. 13/181,729, Notice of Allowance mailed May 23, 2013", 9 pgs.
"U.S. Appl. No. 13/181,729, Response filed May 13, 2013 to Final Office Action mailed Mar. 13, 2013", 13 pgs.

(56) References Cited

OTHER PUBLICATIONS

"U.S. Appl. No. 13/181,729, Response filed Dec. 20, 2012 to Non Final Office Action mailed Oct. 2, 2012", 15 pgs.
"U.S. Appl. No. 13/269,097, Final Office Action mailed Aug. 8, 2013", 7 pgs.
"U.S. Appl. No. 13/269,097, Non Final Office Action mailed Feb. 12, 2013", 10 pgs.
"U.S. Appl. No. 13/269,097, Notice of Allowance mailed Feb. 3, 2014", 5 pgs.
"U.S. Appl. No. 13/269,097, Notice of Allowance mailed Oct. 21, 2013", 9 pgs.
"U.S. Appl. No. 13/269,097, Response filed May 13, 2013 to Non Final Office Action mailed Feb. 12, 2013", 17 pgs.
"U.S. Appl. No. 13/269,097, Response filed Oct. 8, 2013 to Final Office Action mailed Aug. 8, 2013", 12 pgs.
"U.S. Appl. No. 13/269,097, Response filed Nov. 13, 2012 to Restriction Requirement mailed Oct. 17, 2012", 1 pg.
"U.S. Appl. No. 13/269,097, Restriction Requirement mailed Oct. 17, 2012", 8 pgs.
"U.S. Appl. No. 13/278,341, Notice of Allowance mailed Jun. 18, 2013", 10 pgs.
"U.S. Appl. No. 13/278,341, Response filed Mar. 8, 2013 to Restriction Requirement mailed Feb. 11, 2013", 1 pg.
"U.S. Appl. No. 13/278,341, Restriction Requirement mailed Feb. 11, 2013", 6 pgs.
"U.S. Appl. No. 13/281,009, Corrected Notice of Allowance mailed Nov. 18, 2016", 4 pgs.
"U.S. Appl. No. 13/281,009, Corrected Notice of Allowance mailed Dec. 12, 2016", 2 pgs.
"U.S. Appl. No. 13/281,009, Examiner Interview Summary mailed Nov. 18, 2016", 2 pgs.
"U.S. Appl. No. 13/281,009, Non Final Office Action mailed Jun. 2, 2015", 9 pgs.
"U.S. Appl. No. 13/281,009, Notice of Allowance mailed Feb. 24, 2016", 9 pgs.
"U.S. Appl. No. 13/281,009, Notice of Allowance mailed Jun. 23, 2016", 9 pgs.
"U.S. Appl. No. 13/281,009, Notice of Allowance mailed Oct. 29, 2015", 8 pgs.
"U.S. Appl. No. 13/281,009, Response filed Sep. 2, 2015 to Non Final Office Action mailed Jun. 2, 2015", 13 pgs.
"U.S. Appl. No. 13/281,009, Restriction Requirement mailed Feb. 11, 2015", 6 pgs.
"U.S. Appl. No. 13/288,459, Corrected Notice of Allowance mailed Aug. 3, 2016", 4 pgs.
"U.S. Appl. No. 13/288,459, Corrected Notice of Allowance mailed Sep. 9, 2016", 4 pgs.
"U.S. Appl. No. 13/288,459, Corrected Notice of Allowance mailed Sep. 23, 2016", 4 pgs.
"U.S. Appl. No. 13/288,459, Examiner Interview Summary mailed Feb. 6, 2015", 3 pgs.
"U.S. Appl. No. 13/288,459, Examiner Interview Summary mailed Jan. 11, 2016", 1 pg.
"U.S. Appl. No. 13/288,459, Non Final Office Action mailed Jun. 24, 2015", 10 pgs.
"U.S. Appl. No. 13/288,459, Non Final Office Action mailed Nov. 4, 2014", 15 pgs.
"U.S. Appl. No. 13/288,459, Notice of Allowance mailed Jan. 11, 2016", 13 pgs.
"U.S. Appl. No. 13/288,459, Notice of Allowance mailed May 10, 2016", 7 pgs.
"U.S. Appl. No. 13/288,459, Response filed Mar. 3, 2015 to Non Final Office Action mailed Nov. 4, 2014", 16 pgs.
"U.S. Appl. No. 13/288,459, Response filed Oct. 13, 2014 to Restriction Requirement mailed Aug. 11, 2014", 15 pgs.
"U.S. Appl. No. 13/288,459, Response filed Oct. 23, 2015 to Non Final Office Action mailed Jun. 24, 2015", 14 pgs.
"U.S. Appl. No. 13/288,459, Restriction Requirement mailed Aug. 11, 2014", 9 pgs.
"U.S. Appl. No. 13/288,463, Examiner Interview Summary mailed Jun. 3, 2014", 3 pgs.
"U.S. Appl. No. 13/288,463, Non Final Office Action mailed Feb. 24, 2014", 13 pgs.
"U.S. Appl. No. 13/288,463, Notice of Allowance mailed Aug. 27, 2014", 9 pgs.
"U.S. Appl. No. 13/288,463, Response filed May 27, 2014 to Non Final Office Action mailed Feb. 24, 2014", 15 pgs.
"U.S. Appl. No. 13/288,463, Supplemental Notice of Allowability mailed Dec. 8, 2014", 5 pgs.
"U.S. Appl. No. 13/288,463, Supplemental Notice of Allowability mailed Dec. 19, 2014", 5 pgs.
"U.S. Appl. No. 13/293,825, Notice of Allowability mailed Jun. 22, 2015", 7 pgs.
"U.S. Appl. No. 13/293,825, Notice of Allowance mailed May 19, 2015", 9 pgs.
"U.S. Appl. No. 13/293,825, Response filed Apr. 15, 2015 to Restriction Requirement mailed Feb. 12, 2015", 17 pgs.
"U.S. Appl. No. 13/293,825, Restriction Requirement mailed Feb. 12, 2015", 9 pgs.
"U.S. Appl. No. 13/295,126, Non Final Office Action mailed May 19, 2015", 9 pgs.
"U.S. Appl. No. 13/295,126, Notice of Allowance mailed Oct. 22, 2015", 9 pgs.
"U.S. Appl. No. 13/295,126, Response filed Apr. 13, 2015 to Restriction Requirement mailed Feb. 12, 2015", 1 pgs.
"U.S. Appl. No. 13/295,126, Response filed Aug. 17, 2015 to Non Final Office Action mailed May 19, 2015", 21 pgs.
"U.S. Appl. No. 13/295,126, Restriction Requirement mailed Feb. 12, 2015", 9 pgs.
"U.S. Appl. No. 13/311,936, Examiner Interview Summary mailed Feb. 12, 2015", 2 pgs.
"U.S. Appl. No. 13/311,936, Non Final Office Action mailed Feb. 9, 2015", 13 pgs.
"U.S. Appl. No. 13/311,936, Non Final Office Action mailed Oct. 19, 2015", 8 pgs.
"U.S. Appl. No. 13/311,936, Notice of Allowance mailed Mar. 29, 2016", 8 pgs.
"U.S. Appl. No. 13/311,936, PTO Response to Rule 312 Communication mailed May 10, 2016", 2 pgs.
"U.S. Appl. No. 13/311,936, Response filed Jan. 18, 2016 to Non Final Office Action mailed Oct. 19, 2015", 8 pgs.
"U.S. Appl. No. 13/311,936, Response filed Jun. 9, 2015 to Non Final Office Action mailed Feb. 9, 2015", 12 pgs.
"U.S. Appl. No. 13/311,936, Response filed Oct. 3, 2014 to Restriction Requirement mailed Aug. 5, 2014", 10 pgs.
"U.S. Appl. No. 13/311,936, Restriction Requirement mailed Aug. 5, 2014", 7 pgs.
"U.S. Appl. No. 13/350,985, Final Office Action mailed Apr. 16, 2015", 8 pgs.
"U.S. Appl. No. 13/350,985, Non Final Office Action mailed Dec. 15, 2014", 8 pgs.
"U.S. Appl. No. 13/350,985, Notice of Allowance mailed Jul. 27, 2015", 5 pgs.
"U.S. Appl. No. 13/350,985, Response filed Mar. 13, 2015 to Non Final Office Action mailed Dec. 15, 2014", 10 pgs.
"U.S. Appl. No. 13/350,985, Response filed Jul. 9, 2015 to Final Office Action mailed Apr. 16, 2015", 8 pgs.
"U.S. Appl. No. 13/350,985, Response filed Dec. 2, 2014 to Restriction Requirement mailed Oct. 2, 2014", 9 pgs.
"U.S. Appl. No. 13/350,985, Restriction Requirement mailed Oct. 2, 2014", 6 pgs.
"U.S. Appl. No. 13/399,125, Corrected Notice of Allowance mailed Aug. 28, 2014", 2 pgs.
"U.S. Appl. No. 13/399,125, Examiner Interview Summary mailed May 17, 2013", 3 pgs.
"U.S. Appl. No. 13/399,125, Final Office Action mailed Mar. 20, 2013", 12 pgs.
"U.S. Appl. No. 13/399,125, Non Final Office Action mailed Oct. 24, 2012", 12 pgs.
"U.S. Appl. No. 13/399,125, Notice of Allowance mailed May 16, 2014", 8 pgs.

(56) References Cited

OTHER PUBLICATIONS

"U.S. Appl. No. 13/399,125, Response filed Jan. 10, 2013 to Non Final Office Action mailed Oct. 24, 2012", 15 pgs.
"U.S. Appl. No. 13/399,125, Response filed May 20, 2013 to Final Office Action mailed Mar. 20, 2013", 14 pgs.
"U.S. Appl. No. 13/412,105, Advisory Action mailed Feb. 24, 2014", 3 pgs.
"U.S. Appl. No. 13/412,105, Examiner Interview Summary mailed Feb. 6, 2014", 3 pgs.
"U.S. Appl. No. 13/412,105, Examiner Interview Summary mailed Oct. 11, 2013", 3 pgs.
"U.S. Appl. No. 13/412,105, Final Office Action mailed Dec. 13, 2013", 9 pgs.
"U.S. Appl. No. 13/412,105, Non Final Office Action mailed Jul. 15, 2013", 10 pgs.
"U.S. Appl. No. 13/412,105, Notice of Allowance mailed Aug. 18, 2014", 9 pgs.
"U.S. Appl. No. 13/412,105, Response filed Feb. 10, 2014 to Final Office Action mailed Dec. 13, 2013", 14 pgs.
"U.S. Appl. No. 13/412,105, Response filed Mar. 13, 2014 to Advisory Action mailed Feb. 24, 2014", 19 pgs.
"U.S. Appl. No. 13/412,105, Response filed May 6, 2013 to Restriction Requirement mailed Apr. 5, 2013", 9 pgs.
"U.S. Appl. No. 13/412,105, Response filed Oct. 14, 2013 to Non Final Office Action mailed Jul. 15, 2013", 13 pgs.
"U.S. Appl. No. 13/412,105, Restriction Requirement mailed Apr. 5, 2013", 9 pgs.
"U.S. Appl. No. 13/412,116, Corrected Notice of Allowance mailed Jun. 2, 2014", 2 pgs.
"U.S. Appl. No. 13/412,116, Examiner Interview Summary mailed Dec. 13, 2013", 3 pgs.
"U.S. Appl. No. 13/412,116, Non Final Office Action mailed Sep. 11, 2013", 9 pgs.
"U.S. Appl. No. 13/412,116, Notice of Allowance mailed Feb. 19, 2014", 9 pgs.
"U.S. Appl. No. 13/412,116, Response filed Jul. 3, 2013 to Restriction Requirement mailed Jun. 19, 2013", 1 pg.
"U.S. Appl. No. 13/412,116, Response filed Dec. 11, 2013 to Non Final Office Action mailed Sep. 11, 2013", 11 pgs.
"U.S. Appl. No. 13/412,116, Restriction Requirement mailed Jun. 19, 2013", 9 pgs.
"U.S. Appl. No. 13/412,127, Examiner Interview Summary mailed Nov. 5, 2013", 3 pgs.
"U.S. Appl. No. 13/412,127, Non Final Office Action mailed Aug. 7, 2013", 15 pgs.
"U.S. Appl. No. 13/412,127, Notice of Allowance mailed Dec. 24, 2013", 10 pgs.
"U.S. Appl. No. 13/412,127, Response filed May 23, 2013 to Restriction Requirement mailed Apr. 24, 2013", 2 pgs.
"U.S. Appl. No. 13/412,127, Response filed Nov. 5, 2013 to Non Final Office Action mailed Aug. 7, 2013", 16 pgs.
"U.S. Appl. No. 13/412,127, Restriction Requirement mailed Apr. 24, 2013", 10 pgs.
"U.S. Appl. No. 13/587,374, Final Office Action mailed Nov. 6, 2013", 9 pgs.
"U.S. Appl. No. 13/587,374, Non Final Office Action mailed Jul. 17, 2013", 8 pgs.
"U.S. Appl. No. 13/587,374, Notice of Allowance mailed Feb. 28, 2014", 5 pgs.
"U.S. Appl. No. 13/587,374, Preliminary Amendment filed Jun. 21, 2013", 9 pgs.
"U.S. Appl. No. 13/587,374, Response filed Jan. 24, 2014 to Final Office Action mailed Nov. 6, 2013", 15 pgs.
"U.S. Appl. No. 13/587,374, Response filed Oct. 14, 2013 to Non Final Office Action mailed Jul. 17, 2013", 14 pgs.
"U.S. Appl. No. 13/609,389, 312 Amendment filed Sep. 15, 2014", 4 pgs.
"U.S. Appl. No. 13/609,389, Examiner Interview Summary mailed Feb. 4, 2014", 4 pgs.
"U.S. Appl. No. 13/609,389, Final Office Action mailed May 5, 2014", 14 pgs.
"U.S. Appl. No. 13/609,389, Non Final Office Action mailed Nov. 27, 2013", 12 pgs.
"U.S. Appl. No. 13/609,389, Notice of Allowance mailed Jul. 23, 2014", 5 pgs.
"U.S. Appl. No. 13/609,389, PTO Response to Rule 312 Communication mailed Oct. 16, 2014", 2 pgs.
"U.S. Appl. No. 13/609,389, Response filed Feb. 27, 2014 to Non Final Office Action mailed Nov. 27, 2013", 18 pgs.
"U.S. Appl. No. 13/609,389, Response filed Jul. 10, 2014 to Final Office Action mailed May 5, 2014", 12 pgs.
"U.S. Appl. No. 13/625,413, Final Office Action mailed Oct. 30, 2015", 8 pgs.
"U.S. Appl. No. 13/625,413, Non Final Office Action mailed Jun. 8, 2015", 11 pgs.
"U.S. Appl. No. 13/625,413, Notice of Allowance mailed Apr. 1, 2016", 8 pgs.
"U.S. Appl. No. 13/625,413, Notice of Allowance mailed Dec. 11, 2015", 9 pgs.
"U.S. Appl. No. 13/625,413, Response filed May 11, 2015 to Restriction Requirement mailed Mar. 10, 2015", 1 pg.
"U.S. Appl. No. 13/625,413, Response filed Sep. 8, 2015 to Non Final Office Action mailed Jun. 8, 2015", 16 pgs.
"U.S. Appl. No. 13/625,413, Response filed Dec. 1, 2015 to Final Office Action mailed Oct. 30, 2015", 9 pgs.
"U.S. Appl. No. 13/625,413, Restriction Requirement mailed Mar. 10, 2015", 7 pgs.
"U.S. Appl. No. 13/645,964, Advisory Action mailed Feb. 4, 2016", 2 pgs.
"U.S. Appl. No. 13/645,964, Final Office Action mailed Oct. 6, 2015", 17 pgs.
"U.S. Appl. No. 13/645,964, Non Final Office Action mailed Mar. 15, 2016", 15 pgs.
"U.S. Appl. No. 13/645,964, Non Final Office Action mailed Mar. 17, 2015", 15 pgs.
"U.S. Appl. No. 13/645,964, Notice of Allowance mailed Jul. 21, 2016", 9 pgs.
"U.S. Appl. No. 13/645,964, Response filed Jun. 13, 2016 to Non Final Office Action mailed Mar. 15, 2016", 11 pgs.
"U.S. Appl. No. 13/645,964, Response filed Jul. 17, 2015 to Non Final Office Action mailed Mar. 17, 2015", 17 pgs.
"U.S. Appl. No. 13/645,964, Response filed Dec. 4, 2015 to Final Office Action mailed Oct. 6, 2015", 14 pgs.
"U.S. Appl. No. 13/656,821, Notice of Allowance mailed Jun. 18, 2015", 11 pgs.
"U.S. Appl. No. 13/656,821, Response filed May 11, 2015 to Restriction Requirement mailed Mar. 10, 2015", 1 pg.
"U.S. Appl. No. 13/656,821, Restriction Requirement mailed Mar. 10, 2015", 6 pgs.
"U.S. Appl. No. 13/720,631, Final Office Action mailed Jun. 25, 2014", 10 pgs.
"U.S. Appl. No. 13/720,631, Non Final Office Action mailed Mar. 6, 2014", 7 pgs.
"U.S. Appl. No. 13/720,631, Notice of Allowance mailed Jul. 25, 2014", 5 pgs.
"U.S. Appl. No. 13/720,631, Response filed Jun. 6, 2014 to Non Final Office Action mailed Mar. 6, 2014", 11 pgs.
"U.S. Appl. No. 13/720,631, Response filed Jul. 14, 2014 to Final Office Action mailed Jun. 25, 2014", 6 pgs.
"U.S. Appl. No. 13/720,631, Supplemental Notice of Allowance mailed Sep. 8, 2014", 2 pgs.
"U.S. Appl. No. 13/720,648, Final Office Action mailed Nov. 16, 2015", 7 pgs.
"U.S. Appl. No. 13/720,648, Non Final Office Action mailed Jun. 10, 2015", 11 pgs.
"U.S. Appl. No. 13/720,648, Notice of Allowance mailed Feb. 5, 2016", 11 pgs.
"U.S. Appl. No. 13/720,648, Response filed Jan. 13, 2016 to Final Office Action mailed Nov. 16, 2015", 9 pgs.
"U.S. Appl. No. 13/720,648, Response filed May 11, 2015 to Restriction Requirement mailed Mar. 10, 2015", 8 pgs.

(56) References Cited

OTHER PUBLICATIONS

"U.S. Appl. No. 13/720,648, Response filed Oct. 9, 2015 to Non Final Office Action mailed Jun. 10, 2015", 12 pgs.
"U.S. Appl. No. 13/720,648, Restriction Requirement mailed Mar. 10, 2015", 8 pgs.
"U.S. Appl. No. 13/721,970, Notice of Allowance mailed Aug. 12, 2013", 13 pgs.
"U.S. Appl. No. 13/721,970, Preliminary Amendment filed Mar. 15, 2013", 13 pgs.
"U.S. Appl. No. 13/721,970, Response filed May 8, 2013 to Restriction Requirement mailed Apr. 11, 2013", 1 pgs.
"U.S. Appl. No. 13/721,970, Restriction Requirement mailed Apr. 11, 2013", 6 pgs.
"U.S. Appl. No. 13/751,846, Final Office Action mailed Nov. 17, 2015", 9 pgs.
"U.S. Appl. No. 13/751,846, Non Final Office Action mailed Jun. 15, 2015", 10 pgs.
"U.S. Appl. No. 13/751,846, Notice of Allowance mailed Mar. 16, 2016", 11 pgs.
"U.S. Appl. No. 13/751,846, Notice of Allowance mailed Jul. 6, 2016", 9 pgs.
"U.S. Appl. No. 13/751,846, Response filed Feb. 5, 2016 to Final Office Action mailed Nov. 17, 2015", 14 pgs.
"U.S. Appl. No. 13/751,846, Response filed May 11, 2015 to Restriction Requirement mailed Mar. 10, 2015", 15 pgs.
"U.S. Appl. No. 13/751,846, Response filed Oct. 9, 2015 to Non Final Office Action mailed Jun. 15, 2015", 20 pgs.
"U.S. Appl. No. 13/751,846, Restriction Requirement mailed Mar. 10, 2015", 7 pgs.
"U.S. Appl. No. 13/757,003, Non Final Office Action mailed Jun. 25, 2015", 8 pgs.
"U.S. Appl. No. 13/757,003, Notice of Allowance mailed Feb. 8, 2016", 10 pgs.
"U.S. Appl. No. 13/757,003, Response filed May 12, 2015 to Restriction Requirement mailed Mar. 12, 2015", 9 pgs.
"U.S. Appl. No. 13/757,003, Response filed Oct. 26, 2015 to Non Final Office Action mailed Jul. 25, 2015", 8 pgs.
"U.S. Appl. No. 13/757,003, Restriction Requirement mailed Mar. 12, 2015", 6 pgs.
"U.S. Appl. No. 13/757,019, Non Final Office Action mailed Jun. 25, 2015", 11 pgs.
"U.S. Appl. No. 13/757,019, Notice of Allowance mailed Dec. 10, 2015", 10 pgs.
"U.S. Appl. No. 13/757,019, Response filed May 11, 2015 to Restriction Requirement mailed Mar. 11, 2015", 9 pgs.
"U.S. Appl. No. 13/757,019, Response filed Oct. 26, 2015 to Non Final Office Action mailed Jun. 25, 2015", 9 pgs.
"U.S. Appl. No. 13/757,019, Restriction Requirement mailed Mar. 11, 2015", 10 pgs.
"U.S. Appl. No. 13/767,401, Non Final Office Action mailed Aug. 26, 2015", 9 pgs.
"U.S. Appl. No. 13/767,401, Notice of Allowance mailed Apr. 8, 2016", 9 pgs.
"U.S. Appl. No. 13/767,401, Notice of Allowance mailed Dec. 30, 2015", 9 pgs.
"U.S. Appl. No. 13/767,401, Response filed May 18, 2015 to Restriction Requirement mailed Mar. 17, 2015", 15 pgs.
"U.S. Appl. No. 13/767,401, Response filed Nov. 6, 2015 to Non Final Office Action mailed Aug. 26, 2015", 12 pgs.
"U.S. Appl. No. 13/767,401, Restriction Requirement mailed Mar. 17, 2015", 8 pgs.
"U.S. Appl. No. 13/790,982, Examiner Interview Summary mailed Jun. 9, 2015", 3 pgs.
"U.S. Appl. No. 13/790,982, Non Final Office Action mailed Sep. 16, 2015", 11 pgs.
"U.S. Appl. No. 13/790,982, Notice of Allowance mailed Feb. 24, 2016", 10 pgs.
"U.S. Appl. No. 13/790,982, Response filed Jun. 2, 2015 to Restriction Requirement mailed Apr. 2, 2015", 11 pgs.
"U.S. Appl. No. 13/790,982, Response filed Dec. 16, 2015 to Non Final Office Action mailed Sep. 16, 2015", 10 pgs.
"U.S. Appl. No. 13/790,982, Restriction Requirement mailed Apr. 2, 2015", 10 pgs.
"U.S. Appl. No. 13/790,997, Examiner Interview Summary mailed Jun. 8, 2015", 3 pgs.
"U.S. Appl. No. 13/790,997, Non Final Office Action mailed Sep. 21, 2015", 8 pgs.
"U.S. Appl. No. 13/790,997, Notice of Allowance mailed Mar. 2, 2016", 9 pgs.
"U.S. Appl. No. 13/790,997, Response filed Jun. 2, 2015 to Restriction Requirement mailed Apr. 2, 2015", 12 pgs.
"U.S. Appl. No. 13/790,997, Response filed Dec. 18, 2015 to Non Final Office Action mailed Sep. 21, 2015", 9 pgs.
"U.S. Appl. No. 13/790,997, Restriction Requirement mailed Apr. 2, 2015", 8 pgs.
"U.S. Appl. No. 13/791,014, Final Office Action mailed Jan. 8, 2016", 11 pgs.
"U.S. Appl. No. 13/791,014, Non Final Office Action mailed Aug. 14, 2015", 9 pgs.
"U.S. Appl. No. 13/791,014, Notice of Allowability mailed Jul. 27, 2017", 2 pgs.
"U.S. Appl. No. 13/791,014, Notice of Allowance mailed Jan. 10, 2017", 15 pgs.
"U.S. Appl. No. 13/791,014, Notice of Allowance mailed Apr. 27, 2017", 8 pgs.
"U.S. Appl. No. 13/791,014, Response filed Jun. 6, 2016 to Final Office Action mailed Jan. 8, 2016", 13 pgs.
"U.S. Appl. No. 13/791,014, Response filed Aug. 3, 2015 to Restriction Requirement mailed May 1, 2015", 9 pgs.
"U.S. Appl. No. 13/791,014, Response filed Nov. 10, 2015 to Non Final Office Action mailed Aug. 14, 2015", 13 pgs.
"U.S. Appl. No. 13/791,014, Restriction Requirement mailed May 1, 2015", 6 pgs.
"U.S. Appl. No. 13/833,567, Advisory Action mailed Apr. 28, 2016", 3 pgs.
"U.S. Appl. No. 13/833,567, Final Office Action mailed Mar. 9, 2016", 9 pgs.
"U.S. Appl. No. 13/833,567, Non Final Office Action mailed May 27, 2016", 9 pgs.
"U.S. Appl. No. 13/833,567, Non Final Office Action mailed Oct. 23, 2015", 10 pgs.
"U.S. Appl. No. 13/833,567, Notice of Allowance mailed Sep. 27, 2016", 9 pgs.
"U.S. Appl. No. 13/833,567, Response filed Jan. 22, 2016 to Non Final Office Action mailed Oct. 23, 2015", 11 pgs.
"U.S. Appl. No. 13/833,567, Response filed Apr. 20, 2016 to Final Office Action mailed Mar. 9, 2016", 10 pgs.
"U.S. Appl. No. 13/833,567, Response filed Jun. 25, 2015 to Restriction Requirement mailed Apr. 3, 2015", 10 pgs.
"U.S. Appl. No. 13/833,567, Response filed Aug. 4, 2016 to Non Final Office Action mailed May 27, 2016", 11 pgs.
"U.S. Appl. No. 13/833,567, Restriction Requirement mailed Apr. 3, 2015", 6 pgs.
"U.S. Appl. No. 13/838,755, Final Office Action mailed Feb. 22, 2016", 9 pgs.
"U.S. Appl. No. 13/838,755, Non Final Office Action mailed Sep. 17, 2015", 11 pgs.
"U.S. Appl. No. 13/838,755, Notice of Allowance mailed Apr. 27, 2016", 7 pgs.
"U.S. Appl. No. 13/838,755, Notice of Allowance mailed Aug. 3, 2016", 8 pgs.
"U.S. Appl. No. 13/838,755, Response filed Apr. 15, 2016 to Final Office Action mailed Feb. 22, 2016", 11 pgs.
"U.S. Appl. No. 13/838,755, Response filed Jun. 8, 2015 to Restriction Requirement mailed Apr. 6, 2015", 1 pg.
"U.S. Appl. No. 13/838,755, Response filed Dec. 1, 2015 to Non Final Office Action mailed Sep. 17, 2015", 13 pgs.
"U.S. Appl. No. 13/838,755, Restriction Requirement mailed Apr. 6, 2015", 6 pgs.
"U.S. Appl. No. 13/889,851, Non Final Office Action mailed Apr. 6, 2015", 10 pgs.

(56) References Cited

OTHER PUBLICATIONS

"U.S. Appl. No. 13/889,851, Notice of Allowance mailed Aug. 12, 2015", 8 pgs.
"U.S. Appl. No. 13/889,851, Response filed Feb. 26, 2015 to Restriction Requirement mailed Jan. 21, 2015", 12 pgs.
"U.S. Appl. No. 13/889,851, Response filed Jul. 6, 2015 to Non Final Office Action mailed Apr. 6, 2015", 14 pgs.
"U.S. Appl. No. 13/889,851, Restriction Requirement mailed Jan. 21, 2015", 6 pgs.
"U.S. Appl. No. 13/889,851, Supplemental Amendment and Response filed Jul. 6, 2015 to Non Final Office Action mailed Apr. 6, 2015", 8 pgs.
"U.S. Appl. No. 13/959,145, Examiner Interview Summary mailed Sep. 16, 2015", 3 pgs.
"U.S. Appl. No. 13/959,145, Final Office Action mailed Jan. 29, 2016", 16 pgs.
"U.S. Appl. No. 13/959,145, Final Office Action mailed Feb. 5, 2015", 22 pgs.
"U.S. Appl. No. 13/959,145, Non Final Office Action mailed Jul. 31, 2015", 21 pgs.
"U.S. Appl. No. 13/959,145, Non Final Office Action mailed Sep. 15, 2014", 20 pgs.
"U.S. Appl. No. 13/959,145, Notice of Allowability mailed Jun. 14, 2016", 2 pgs.
"U.S. Appl. No. 13/959,145, Notice of Allowance mailed Apr. 13, 2016", 5 pgs.
"U.S. Appl. No. 13/959,145, Response filed Mar. 28, 2016 to Final Office Action mailed Jan. 29, 2016", 10 pgs.
"U.S. Appl. No. 13/959,145, Response filed Jul. 6, 2015 to Final Office Action mailed Feb. 5, 2015", 18 pgs.
"U.S. Appl. No. 13/959,145, Response filed Oct. 30, 2015 to Non Final Office Action mailed Jul. 31, 2015", 14 pgs.
"U.S. Appl. No. 13/959,145, Response filed Dec. 15, 2014 to Non Final Office Action mailed Sep. 15, 2014", 21 pgs.
"U.S. Appl. No. 14/055,172, Final Office Action mailed Dec. 22, 2016", 8 pgs.
"U.S. Appl. No. 14/055,172, Non Final Office Action mailed Jul. 14, 2016", 12 pgs.
"U.S. Appl. No. 14/055,172, Notice of Allowance mailed Mar. 29, 2017", 10 pgs.
"U.S. Appl. No. 14/055,172, Response filed Feb. 22, 2017 to Final Office Action mailed Dec. 22, 2016", 11 pgs.
"U.S. Appl. No. 14/055,172, Response filed May 4, 2016 to Restriction Requirement mailed Mar. 4, 2016", 8 pgs.
"U.S. Appl. No. 14/055,172, Response filed Nov. 14, 2016 to Non Final Office Action mailed Jul. 14, 2016", 19 pgs.
"U.S. Appl. No. 14/055,172, Restriction Requirement mailed Mar. 4, 2016", 6 pgs.
"U.S. Appl. No. 14/055,191, Non Final Office Action mailed May 16, 2016", 8 pgs.
"U.S. Appl. No. 14/055,191, Notice of Allowability mailed Sep. 8, 2016", 7 pgs.
"U.S. Appl. No. 14/055,191, Notice of Allowance mailed Aug. 31, 2016", 13 pgs.
"U.S. Appl. No. 14/055,191, Response filed Apr. 29, 2016 to Restriction Requirement mailed Mar. 7, 2016", 8 pgs.
"U.S. Appl. No. 14/055,191, Response filed Aug. 3, 2016 to Non Final Office Action mailed May 16, 2016", 11 pgs.
"U.S. Appl. No. 14/055,191, Restriction Requirement mailed Mar. 7, 2016", 6 pgs.
"U.S. Appl. No. 14/071,295, Non Final Office Action mailed Aug. 15, 2014", 6 pgs.
"U.S. Appl. No. 14/071,295, Notice of Allowance mailed Dec. 10, 2014", 8 pgs.
"U.S. Appl. No. 14/071,295, Response filed Nov. 17, 2014 to Non Final Office Action mailed Aug. 15, 2014", 14 pgs.
"U.S. Appl. No. 14/071,295, Supplemental Notice of Allowability mailed Jan. 26, 2015", 2 pgs.
"U.S. Appl. No. 14/094,311, Corrected Notice of Allowance mailed Mar. 28, 2017", 5 pgs.
"U.S. Appl. No. 14/094,311, Notice of Allowance mailed Aug. 16, 2016", 12 pgs.
"U.S. Appl. No. 14/094,311, Notice of Allowance mailed Dec. 27, 2016", 8 pgs.
"U.S. Appl. No. 14/094,311, Response filed Jul. 26, 2016 to Restriction Requirement mailed Jun. 22, 2016", 10 pgs.
"U.S. Appl. No. 14/094,311, Restriction Requirement mailed Jun. 22, 2016", 6 pgs.
"U.S. Appl. No. 14/095,614, Non Final Office Action mailed Jan. 19, 2017", 9 pgs.
"U.S. Appl. No. 14/095,614, Notice of Allowance mailed May 8, 2017", 8 pgs.
"U.S. Appl. No. 14/095,614, Notice of Allowance mailed Nov. 6, 2017", 9 pgs.
"U.S. Appl. No. 14/095,614, Preliminary Amendment filed Apr. 15, 2014", 17 pgs.
"U.S. Appl. No. 14/095,614, Response filed Mar. 2, 2017 to Non Final Office Action mailed Jan. 19, 2017", 14 pgs.
"U.S. Appl. No. 14/095,614, Response filed Sep. 12, 2016 to Restriction Requirement mailed Jul. 11, 2016", 11 pgs.
"U.S. Appl. No. 14/095,614, Restriction Requirement mailed Jul. 11, 2016", 8 pgs.
"U.S. Appl. No. 14/095,639, Non Final Office Action mailed Jan. 18, 2017", 10 pgs.
"U.S. Appl. No. 14/095,639, Notice of Allowance mailed Apr. 13, 2017", 9 pgs.
"U.S. Appl. No. 14/095,639, Notice of Allowance mailed Oct. 30, 2017", 9 pgs.
"U.S. Appl. No. 14/095,639, Response filed Mar. 2, 2017 to Non Final Office Action mailed Jan. 18, 2017", 9 pgs.
"U.S. Appl. No. 14/095,639, Response filed Sep. 12, 2016 to Restriction Requirement mailed Jul. 19, 2016", 7 pgs.
"U.S. Appl. No. 14/095,639, Restriction Requirement mailed Jul. 19, 2016", 8 pgs.
"U.S. Appl. No. 14/107,350, Notice of Allowance mailed Feb. 26, 2016", 11 pgs.
"U.S. Appl. No. 14/107,350, Notice of Allowance mailed Jul. 27, 2016", 7 pgs.
"U.S. Appl. No. 14/107,350, Preliminary Amendment filed Feb. 28, 2014", 4 pgs.
"U.S. Appl. No. 14/159,094, Examiner Interview Summary mailed Nov. 29, 2016", 1 pg.
"U.S. Appl. No. 14/159,094, Non Final Office Action mailed Jun. 29, 2016", 15 pgs.
"U.S. Appl. No. 14/159,094, Notice of Allowance mailed Nov. 29, 2016", Examiner Interview Summary from Nov. 29, 2016 included, 11 pgs.
"U.S. Appl. No. 14/159,094, Response filed Jun. 3, 2016 to Restriction Requirement mailed Apr. 20, 2016", 9 pgs.
"U.S. Appl. No. 14/159,094, Response filed Sep. 19, 2016 to Non Final Office Action mailed Jun. 29, 2016", 13 pgs.
"U.S. Appl. No. 14/159,094, Restriction Requirement mailed Apr. 20, 2016", 6 pgs.
"U.S. Appl. No. 14/182,038, Advisory Action mailed Mar. 1, 2017", 3 pgs.
"U.S. Appl. No. 14/182,038, Final Office Action mailed Dec. 19, 2016", 8 pgs.
"U.S. Appl. No. 14/182,038, Non Final Office Action mailed Jul. 19, 2016", 10 pgs.
"U.S. Appl. No. 14/182,038, Notice of Allowance mailed May 24, 2017", 9 pgs.
"U.S. Appl. No. 14/182,038, Response filed Feb. 20, 2017 to Final Office Action mailed Dec. 19, 2016", 11 pgs.
"U.S. Appl. No. 14/182,038, Response filed Jun. 27, 2016 to Restriction Requirement mailed Apr. 26, 2016", 8 pgs.
"U.S. Appl. No. 14/182,038, Response filed Oct. 19, 2016 to Non Final Office Action mailed Jul. 19, 2016", 15 pgs.
"U.S. Appl. No. 14/182,038, Restriction Requirement mailed Apr. 26, 2016", 7 pgs.
"U.S. Appl. No. 14/182,046, Corrected Notice of Allowance mailed Jan. 20, 2017", 6 pgs.
"U.S. Appl. No. 14/182,046, Non Final Office Action mailed Jul. 15, 2016", 9 pgs.

(56) References Cited

OTHER PUBLICATIONS

"U.S. Appl. No. 14/182,046, Notice of Allowance mailed Dec. 8, 2016", 7 pgs.
"U.S. Appl. No. 14/182,046, Response filed Jun. 27, 2016 to Restriction Requirement mailed Apr. 26, 2016", 7 pgs.
"U.S. Appl. No. 14/182,046, Response filed Oct. 17, 2016 to Non Final Office Action mailed Jul. 15, 2016", 11 pgs.
"U.S. Appl. No. 14/182,046, Restriction Requirement mailed Apr. 26, 2016", 6 pgs.
"U.S. Appl. No. 14/211,977, Notice of Allowance mailed Jul. 12, 2016", 9 pgs.
"U.S. Appl. No. 14/211,977, Preliminary Amendment filed Mar. 2, 2016", 7 pgs.
"U.S. Appl. No. 14/211,977, Response filed Apr. 29, 2016 to Restriction Requirement mailed Mar. 11, 2016", 8 pgs.
"U.S. Appl. No. 14/211,977, Restriction Requirement mailed Mar. 11, 2016", 6 pgs.
"U.S. Appl. No. 14/215,550, Corrected Notice of Allowance mailed Jul. 27, 2017", 2 pgs.
"U.S. Appl. No. 14/215,550, Examiner Interview Summary mailed Mar. 9, 2017", 3 pgs.
"U.S. Appl. No. 14/215,550, Final Office Action mailed Feb. 1, 2017", 11 pgs.
"U.S. Appl. No. 14/215,550, Non Final Office Action mailed Jul. 19, 2016", 12 pgs.
"U.S. Appl. No. 14/215,550, Notice of Allowance mailed Jun. 21, 2017", 8 pgs.
"U.S. Appl. No. 14/215,550, Response filed May 1, 2017 to Final Office Action mailed Feb. 1, 2017", 10 pgs.
"U.S. Appl. No. 14/215,550, Response filed Jun. 22, 2016 to Restriction Requirement mailed Apr. 28, 2016", 7 pgs.
"U.S. Appl. No. 14/215,550, Response filed Dec. 5, 2016 to Non Final Office Action mailed Jul. 19, 2016", 13 pgs.
"U.S. Appl. No. 14/215,550, Restriction Requirement mailed Apr. 28, 2016", 6 pgs.
"U.S. Appl. No. 14/275,548, Examiner Interview Summary mailed May 25, 2016", 3 pgs.
"U.S. Appl. No. 14/275,548, Non Final Office Action mailed Feb. 19, 2016", 14 pgs.
"U.S. Appl. No. 14/275,548, Notice of Allowance mailed Jul. 27, 2016", 7 pgs.
"U.S. Appl. No. 14/275,548, Response filed May 19, 2016 to Non Final Office Action mailed Feb. 19, 2016", 19 pgs.
"U.S. Appl. No. 14/324,688, Corrected Notice of Allowance mailed Sep. 22, 2016", 2 pgs.
"U.S. Appl. No. 14/324,688, Non Final Office Action mailed Jan. 8, 2016", 18 pgs.
"U.S. Appl. No. 14/324,688, Notice of Allowance mailed Jun. 9, 2016", 7 pgs.
"U.S. Appl. No. 14/324,688, Response filed Apr. 8, 2016 to Non Final Office Action mailed Jan. 8, 2016", 15 pgs.
"U.S. Appl. No. 14/456,286, Advisory Action mailed Jun. 21, 2016", 3 pgs.
"U.S. Appl. No. 14/456,286, Final Office Action mailed May 27, 2016", 15 pgs.
"U.S. Appl. No. 14/456,286, Non Final Office Action mailed Oct. 17, 2016", 17 pgs.
"U.S. Appl. No. 14/456,286, Non Final Office Action mailed Dec. 30, 2015", 16 pgs.
"U.S. Appl. No. 14/456,286, Notice of Allowance mailed Feb. 15, 2017", 9 pgs.
"U.S. Appl. No. 14/456,286, Response filed Mar. 30, 2016 to Non Final Office Action mailed Dec. 30, 2015", 15 pgs.
"U.S. Appl. No. 14/456,286, Response filed Jun. 13, 2016 to Final Office Action mailed May 27, 2016", 10 pgs.
"U.S. Appl. No. 14/456,286, Response filed Nov. 16, 2016 to Non Final Office Action mailed Oct. 17, 2016", 9 pgs.
"U.S. Appl. No. 14/456,286, Response filed Dec. 11, 2015 to Restriction Requirement mailed Oct. 29, 2015", 6 pgs.
"U.S. Appl. No. 14/456,286, Restriction Requirement mailed Oct. 29, 2015", 9 pgs.
"U.S. Appl. No. 14/492,590, Notice of Allowance mailed Oct. 5, 2016", 10 pgs.
"U.S. Appl. No. 14/492,590, Response filed Sep. 15, 2016 to Restriction Requirement mailed Jul. 25, 2015", 7 pgs.
"U.S. Appl. No. 14/492,590, Restriction Requirement mailed Jul. 25, 2016", 6 pgs.
"U.S. Appl. No. 14/492,590, Supplemental Response filed Sep. 26, 2016 to Restriction Requirement mailed Jul. 25, 2016", 10 pgs.
"U.S. Appl. No. 14/514,453, Final Office Action mailed Mar. 17, 2016", 17 pgs.
"U.S. Appl. No. 14/514,453, Non Final Office Action mailed Sep. 24, 2015", 11 pgs.
"U.S. Appl. No. 14/514,453, Response filed Dec. 16, 2015 to Non Final Office Action mailed Sep. 24, 2015", 14 pgs.
"U.S. Appl. No. 14/532,333, Response filed Apr. 7, 2016 to Restriction Requirement mailed Feb. 8, 2016", 10 pgs.
"U.S. Appl. No. 14/532,333, Restriction Requirement mailed Feb. 8, 2016", 6 pgs.
"U.S. Appl. No. 14/589,101, Advisory Action mailed Feb. 21, 2017", 5 pgs.
"U.S. Appl. No. 14/589,101, Advisory Action mailed May 22, 2018", 3 pgs.
"U.S. Appl. No. 14/589,101, Examiner Interview Summary mailed Jan. 30, 2017", 3 pgs.
"U.S. Appl. No. 14/589,101, Final Office Action mailed Feb. 22, 2018", 15 pgs.
"U.S. Appl. No. 14/589,101, Final Office Action mailed Oct. 2, 2015", 10 pgs.
"U.S. Appl. No. 14/589,101, Final Office Action mailed Nov. 16, 2016", 12 pgs.
"U.S. Appl. No. 14/589,101, Non Final Office Action mailed Feb. 12, 2015", 10 pgs.
"U.S. Appl. No. 14/589,101, Non Final Office Action mailed May 5, 2016", 14 pgs.
"U.S. Appl. No. 14/589,101, Non Final Office Action mailed Sep. 14, 2017", 13 pgs.
"U.S. Appl. No. 14/589,101, Response filed Jan. 23, 2017 to Final Office Action mailed Nov. 16, 2016", 9 pgs.
"U.S. Appl. No. 14/589,101, Response filed Apr. 10, 2018 to Final Office Action mailed Feb. 22, 2018", 10 pgs.
"U.S. Appl. No. 14/589,101, Response filed Jun. 12, 2015 to Non Final Office Action mailed Feb. 12, 2015", 11 pgs.
"U.S. Appl. No. 14/589,101, Response filed Nov. 13, 2017 to Non Final Office Action mailed Sep. 14, 2017", 10 pgs.
"U.S. Appl. No. 14/589,101, Response filed Dec. 29, 2015 to Final Office Action mailed Oct. 2, 2015", 15 pgs.
"U.S. Appl. No. 14/589,191, Response filed Aug. 5, 2016 to Non Final Office Action mailed May 5, 2016", 16 pgs.
"U.S. Appl. No. 14/594,285, Final Office Action mailed May 22, 2017", 12 pgs.
"U.S. Appl. No. 14/594,285, Non Final Office Action mailed Jan. 11, 2017", 15 pgs.
"U.S. Appl. No. 14/594,285, Notice of Allowance mailed Jun. 27, 2017", 10 pgs.
"U.S. Appl. No. 14/594,285, Response filed Apr. 11, 2017 to Non Final Office Action mailed Jan. 11, 2017", 12 pgs.
"U.S. Appl. No. 14/594,285, Response filed Jun. 14, 2017 to Final Office Action mailed May 22, 2017", 9 pgs.
"U.S. Appl. No. 14/594,285, Response filed Dec. 14, 2016 to Restriction Requirement mailed Nov. 7, 2016", 8 pgs.
"U.S. Appl. No. 14/594,285, Restriction Requirement mailed Nov. 7, 2016", 6 pgs.
"U.S. Appl. No. 14/599,909, Non Final Office Action mailed Jul. 27, 2017", 18 pgs.
"U.S. Appl. No. 14/599,909, Notice of Allowance mailed Feb. 13, 2018", 9 pgs.
"U.S. Appl. No. 14/599,909, Response filed Sep. 21, 2017 to Non Final Office Action mailed Jul. 27, 2017", 10 pgs.
"U.S. Appl. No. 14/635,055, Non Final Office Action mailed Aug. 28, 2017", 8 pgs.

(56) References Cited

OTHER PUBLICATIONS

"U.S. Appl. No. 14/635,055, Notice of Allowance mailed Feb. 28, 2018", 11 pgs.
"U.S. Appl. No. 14/635,055, Response filed Jun. 27, 2017 to Restriction Requirement mailed Apr. 27, 2017", 11 pgs.
"U.S. Appl. No. 14/635,055, Response filed Nov. 28, 2017 to Non Final Office Action mailed Aug. 28, 2017", 13 pgs.
"U.S. Appl. No. 14/635,055, Restriction Requirement mailed Apr. 27, 2017", 7 pgs.
"U.S. Appl. No. 14/697,140, Advisory Action mailed Aug. 11, 2017", 3 pgs.
"U.S. Appl. No. 14/697,140, Final Office Action mailed Jun. 30, 2017", 13 pgs.
"U.S. Appl. No. 14/697,140, Final Office Action mailed Sep. 23, 2016", 10 pgs.
"U.S. Appl. No. 14/697,140, Non Final Office Action mailed Jan. 10, 2017", 12 pgs.
"U.S. Appl. No. 14/697,140, Non Final Office Action mailed Apr. 8, 2016", 8 pgs.
"U.S. Appl. No. 14/697,140, Notice of Allowance mailed Sep. 5, 2017", 7 pgs.
"U.S. Appl. No. 14/697,140, Response filed Mar. 1, 2017 to Non Final Office Action mailed Jan. 10, 2017", 11 pgs.
"U.S. Appl. No. 14/697,140, Response filed Jun. 13, 2016 to Non Final Office Action mailed Apr. 8, 2016", 10 pgs.
"U.S. Appl. No. 14/697,140, Response filed Jul. 27, 2017 to Final Office Action mailed Jun. 30, 2017", 10 pgs.
"U.S. Appl. No. 14/697,140, Response filed Nov. 16, 2016 to Final Office Action mailed Sep. 23, 2016", 13 pgs.
"U.S. Appl. No. 14/794,309, Final Office Action mailed Mar. 20, 2017", 18 pgs.
"U.S. Appl. No. 14/794,309, Non Final Office Action mailed Jun. 20, 2017", 16 pgs.
"U.S. Appl. No. 14/794,309, Non Final Office Action mailed Nov. 22, 2016", 13 pgs.
"U.S. Appl. No. 14/794,309, Notice of Allowance mailed Sep. 18, 2017", 5 pgs.
"U.S. Appl. No. 14/794,309, Preliminary Amendment filed Sep. 22, 2015", 6 pgs.
"U.S. Appl. No. 14/794,309, Response filed Feb. 22, 2017 to Non Final Office Action mailed Nov. 22, 2016", 12 pgs.
"U.S. Appl. No. 14/794,309, Response filed May 22, 2017 to Final Office Action mailed Mar. 20, 2017", 13 pgs.
"U.S. Appl. No. 14/794,309, Response filed Aug. 17, 2017 to Non Final Office Action mailed Jun. 20, 2017", 12 pgs.
"U.S. Appl. No. 14/794,309, Supplemental Preliminary Amendment filed Mar. 3, 2016", 8 pgs.
"U.S. Appl. No. 14/854,308, Notice of Allowance mailed Mar. 16, 2018", 11 pgs.
"U.S. Appl. No. 14/854,308, Response filed Dec. 20, 2017 to Restriction Requirement mailed Oct. 20, 2017", 8 pgs.
"U.S. Appl. No. 14/854,308, Restriction Requirement mailed Oct. 20, 2017", 8 pgs.
"U.S. Appl. No. 14/854,308, Supplemental Preliminary Amendment Filed Aug. 31, 2017", 3 pgs.
"U.S. Appl. No. 14/876,167, Final Office Action mailed Jul. 31, 2018", 8 pgs.
"U.S. Appl. No. 14/876,167, Non Final Office Action mailed Mar. 13, 2018", 8 pgs.
"U.S. Appl. No. 14/876,167, Notice of Allowance mailed Dec. 10, 2018", 8 pgs.
"U.S. Appl. No. 14/876,167, Preliminary Amendment filed Oct. 27, 2015", 8 pgs.
"U.S. Appl. No. 14/876,167, Response filed Jan. 9, 2018 to Restriction Requirement mailed Nov. 22, 2017", 6 pgs.
"U.S. Appl. No. 14/876,167, Response filed Jun. 6, 2018 to Non Final Office Action mailed Mar. 13, 2018", 9 pgs.
"U.S. Appl. No. 14/876,167, Response filed Sep. 28, 2018 to Final Office Action mailed Jul. 31, 2018", 10 pgs.
"U.S. Appl. No. 14/876,167, Restriction Requirement mailed Nov. 22, 2017", 9 pgs.
"U.S. Appl. No. 14/936,831, Advisory Action mailed Jan. 29, 2019", 3 pgs.
"U.S. Appl. No. 14/936,831, Final Office Action mailed Nov. 20, 2018", 8 pgs.
"U.S. Appl. No. 14/936,831, Non Final Office Action mailed May 16, 2018", 11 pgs.
"U.S. Appl. No. 14/936,831, Notice of Allowance mailed Jul. 3, 2019", 8 pgs.
"U.S. Appl. No. 14/936,831, Notice of Non-Compliant Amendment mailed Mar. 14, 2018", 2 pgs.
"U.S. Appl. No. 14/936,831, Preliminary Amendment filed Nov. 11, 2015", 6 pgs.
"U.S. Appl. No. 14/936,831, Response filed Jan. 10, 2018 to Restriction Requirement mailed Nov. 22, 2017", 6 pgs.
"U.S. Appl. No. 14/936,831, Response filed Jan. 21, 2019 to Final Office Action mailed Nov. 20, 2018", 9 pgs.
"U.S. Appl. No. 14/936,831, Response filed Mar. 26, 2018 to Notice of Non-Compliant Amendment mailed Mar. 14, 2018", 6 pgs.
"U.S. Appl. No. 14/936,831, Response filed Aug. 16, 2018 to Non Final Office Action mailed May 16, 2018", 9 pgs.
"U.S. Appl. No. 14/936,831, Restriction Requirement mailed Nov. 22, 2017", 8 pgs.
"U.S. Appl. No. 14/956,724, Examiner Interview Summary mailed Jun. 20, 2017", 3 pgs.
"U.S. Appl. No. 14/956,724, Non Final Office Action mailed Mar. 31, 2017", 17 pgs.
"U.S. Appl. No. 14/956,724, Notice of Allowance mailed Aug. 23, 2017", 9 pgs.
"U.S. Appl. No. 14/956,724, Preliminary Amendment filed Dec. 7, 2015", 8 pgs.
"U.S. Appl. No. 14/956,724, Response filed Jun. 16, 2017 to Non Final Office Action mailed Mar. 31, 2017", 12 pgs.
"U.S. Appl. No. 14/956,724, Supplemental Preliminary Amendment filed Feb. 11, 2016", 7 pgs.
"U.S. Appl. No. 14/956,724, Supplemental Preliminary Amendment filed Oct. 3, 2016", 8 pgs.
"U.S. Appl. No. 14/983,108, Final Office Action mailed Aug. 30, 2018", 9 pgs.
"U.S. Appl. No. 14/983,108, Non Final Office Action mailed Apr. 10, 2018", 7 pgs.
"U.S. Appl. No. 14/983,108, Non Final Office Action mailed Nov. 5, 2018", 8 pgs.
"U.S. Appl. No. 14/983,108, Notice of Allowance mailed Mar. 8, 2019", 8 pgs.
"U.S. Appl. No. 14/983,108, Preliminary Amendment filed Dec. 30, 2015", 7 pgs.
"U.S. Appl. No. 14/983,108, Response filed Jan. 24, 2018 to Restriction Requirement mailed Dec. 4, 2017", 6 pgs.
"U.S. Appl. No. 14/983,108, Response filed Feb. 4, 2019 to Non Final Office Action mailed Nov. 5, 2018", 8 pgs.
"U.S. Appl. No. 14/983,108, Response filed Jun. 13, 2018 to Non Final Office Action mailed Apr. 10, 2018", 10 pgs.
"U.S. Appl. No. 14/983,108, Response filed Oct. 22, 2018 to Final Office Action mailed Aug. 30, 2018", 9 pgs.
"U.S. Appl. No. 14/983,108, Restriction Requirement mailed Dec. 4, 2017", 7 pgs.
"U.S. Appl. No. 14/983,747, Non Final Office Action mailed Apr. 9, 2018", 13 pgs.
"U.S. Appl. No. 14/983,747, Notice of Allowance mailed Sep. 24, 2018", 14 pgs.
"U.S. Appl. No. 14/983,747, Preliminary Amendment filed Jan. 4, 2016", 5 pgs.
"U.S. Appl. No. 14/983,747, Response filed Jan. 24, 2018 to Restriction Requirement mailed Dec. 20, 2017", 5 pgs.
"U.S. Appl. No. 14/983,747, Response filed Jun. 13, 2018 to Non Final Office Action mailed Apr. 9, 2018", 9 pgs.
"U.S. Appl. No. 14/983,747, Restriction Requirement mailed Dec. 20, 2017", 7 pgs.
"U.S. Appl. No. 14/983,747, Supplemental Response to Restriction Requirement filed Jan. 24, 2018", 5 pgs.

(56) References Cited

OTHER PUBLICATIONS

"U.S. Appl. No. 15/060,007, Corrected Notice of Allowability mailed May 1, 2019", 2 pgs.
"U.S. Appl. No. 15/060,007, Final Office Action mailed Jan. 3, 2019", 9 pgs.
"U.S. Appl. No. 15/060,007, Non Final Office Action mailed Nov. 9, 2018", 17 pgs.
"U.S. Appl. No. 15/060,007, Notice of Allowance mailed Mar. 6, 2019", 5 pgs.
"U.S. Appl. No. 15/060,007, Preliminary Amendment filed Mar. 9, 2016", 9 pgs.
"U.S. Appl. No. 15/060,007, Response filed Feb. 15, 2019 to Final Office Action mailed Jan. 3, 2019", 9 pgs.
"U.S. Appl. No. 15/060,007, Response filed Nov. 26, 2018 to Non Final Office Action mailed Nov. 9, 2018", 10 pgs.
"U.S. Appl. No. 15/061,352, Corrected Notice of Allowance mailed Feb. 12, 2018", 2 pgs.
"U.S. Appl. No. 15/061,352, Non Final Office Action mailed Nov. 17, 2017", 6 pgs.
"U.S. Appl. No. 15/061,352, Notice of Allowance mailed Jan. 19, 2018", 10 pgs.
"U.S. Appl. No. 15/061,352, Preliminary Amendment filed Mar. 7, 2016", 8 pgs.
"U.S. Appl. No. 15/061,352, Response filed Dec. 12, 2017 to Non Final Office Action mailed Nov. 17, 2017", 9 pgs.
"U.S. Appl. No. 15/074,553, Corrected Notice of Allowance mailed Feb. 12, 2018", 2 pgs.
"U.S. Appl. No. 15/074,553, Non Final Office Action mailed Nov. 17, 2017", 6 pgs.
"U.S. Appl. No. 15/074,553, Notice of Allowance mailed Jan. 19, 2018", 10 pgs.
"U.S. Appl. No. 15/074,553, Preliminary Amendment filed Mar. 21, 2016", 8 pgs.
"U.S. Appl. No. 15/074,553, Response filed Dec. 12, 2017 to Non Final Office Action mailed Nov. 17, 2017", 8 pgs.
"U.S. Appl. No. 15/131,663, Non Final Office Action mailed Oct. 2, 2018", 7 pgs.
"U.S. Appl. No. 15/131,663, Notice of Allowance mailed Mar. 19, 2019", 8 pgs.
"U.S. Appl. No. 15/131,663, Preliminary Amendment filed Dec. 21, 2016", 6 pgs.
"U.S. Appl. No. 15/131,663, Response Filed Jan. 2, 2019 to Non-Final Office Action Mailed Oct. 2, 2018", 9 pgs.
"U.S. Appl. No. 15/131,663, Response filed Jul. 13, 2018 to Restriction Requirement mailed May 18, 2018", 8 pgs.
"U.S. Appl. No. 15/131,663, Restriction Requirement mailed May 18, 2018", 7 pgs.
"U.S. Appl. No. 15/166,480, Notice of Allowance mailed Sep. 20, 2018", 12 pgs.
"U.S. Appl. No. 15/166,480, Response filed Jul. 18, 2018 to Restriction Requirement mailed May 21, 2018", 6 pgs.
"U.S. Appl. No. 15/166,480, Restriction Requirement mailed May 21, 2018", 6 pgs.
"U.S. Appl. No. 15/166,480, Supplemental Preliminary Amendment filed Jul. 18, 2017", 7 pgs.
"U.S. Appl. No. 15/200,546, Non Final Office Action mailed Oct. 15, 2018", 10 pgs.
"U.S. Appl. No. 15/200,546, Notice of Allowance mailed Mar. 19, 2019", 7 pgs.
"U.S. Appl. No. 15/200,546, Preliminary Amendment filed Dec. 21, 2016", 6 pgs.
"U.S. Appl. No. 15/200,546, Response Filed Jan. 15, 2019 to Non-Final Office Action Mailed Oct. 15, 2018", 10 pgs.
"U.S. Appl. No. 15/200,546, Response Filed Sep. 17, 2018 to Restriction Requirement Mailed Jul. 16, 2018", 8 pgs.
"U.S. Appl. No. 15/200,546, Restriction Requirement mailed Jul. 16, 2018", 6 pgs.
"U.S. Appl. No. 15/278,777, Non Final Office Action mailed Feb. 28, 2018", 14 pgs.
"U.S. Appl. No. 15/278,777, Notice of Allowance mailed Jul. 16, 2018", 8 pgs.
"U.S. Appl. No. 15/278,777, Preliminary Amendment filed Oct. 3, 2016", 7 pgs.
"U.S. Appl. No. 15/278,777, Response filed May 29, 2018 to Non Final Office action mailed Feb. 28, 2018", 11 pgs.
"U.S. Appl. No. 15/288,183, Corrected Notice of Allowability mailed Jun. 21, 2019", 7 pgs.
"U.S. Appl. No. 15/288,183, Non Final Office Action mailed Dec. 10, 2018", 13 pgs.
"U.S. Appl. No. 15/288,183, Notice of Allowance mailed May 9, 2019", 11 pgs.
"U.S. Appl. No. 15/288,183, Preliminary Amendment filed Oct. 31, 2016", 7 pgs.
"U.S. Appl. No. 15/288,183, Response filed Feb. 27, 2019 to Non Final Office Action mailed Dec. 10, 2018", 11 pgs.
"U.S. Appl. No. 15/288,183, Response filed Oct. 25, 2018 to Restriction Requirement mailed Sep. 12, 2018", 7 pgs.
"U.S. Appl. No. 15/288,183, Restriction Requirement mailed Sep. 12, 2018", 6 pgs.
"U.S. Appl. No. 15/288,183, Supplemental Preliminary Amendment filed Jul. 27, 2017", 7 pgs.
"U.S. Appl. No. 15/294,994, Examiner Interview Summary mailed Feb. 26, 2019", 3 pgs.
"U.S. Appl. No. 15/294,994, Final Office Action mailed Jan. 25, 2019", 13 pgs.
"U.S. Appl. No. 15/294,994, Non Final Office Action mailed Aug. 9, 2018", 9 pgs.
"U.S. Appl. No. 15/294,994, Notice of Allowance mailed May 22, 2019", 10 pgs.
"U.S. Appl. No. 15/294,994, Preliminary Amendment filed Jan. 25, 2017", 8 pgs.
"U.S. Appl. No. 15/294,994, Response filed Feb. 27, 2019 to Final Office Action mailed Jan. 25, 2019", 9 pgs.
"U.S. Appl. No. 15/294,994, Response filed Oct. 25, 2018 to Non Final Office Action mailed Aug. 9, 2018", 10 pgs.
"U.S. Appl. No. 15/294,994, Supplemental Preliminary Amendment filed May 31, 2017", 6 pgs.
"U.S. Appl. No. 15/297,844, Notice of Allowance mailed Aug. 30, 2018", 10 pgs.
"U.S. Appl. No. 15/297,844, Preliminary Amendment filed Oct. 20, 2016", 7 pgs.
"U.S. Appl. No. 15/297,844, Supplemental Preliminary Amendment filed Jan. 25, 2018", 6 pgs.
"U.S. Appl. No. 15/332,590, Notice of Allowance mailed Dec. 5, 2018", 13 pgs.
"U.S. Appl. No. 15/332,590, Preliminary Amendment filed Nov. 22, 2016", 5 pgs.
"U.S. Appl. No. 15/361,917, Advisory Action mailed Nov. 19, 2019", 3 pgs.
"U.S. Appl. No. 15/361,917, Final Office Action mailed Sep. 3, 2019", 8 pgs.
"U.S. Appl. No. 15/361,917, Non Final Office Action mailed Apr. 19, 2019", 11 pgs.
"U.S. Appl. No. 15/361,917, Notice of Allowance mailed Mar. 4, 2020", 8 pgs.
"U.S. Appl. No. 15/361,917, Preliminary Amendment filed Nov. 30, 2016", 6 pgs.
"U.S. Appl. No. 15/361,917, Response filed Feb. 14, 2019 to Restriction Requirement mailed Jan. 3, 2019", 6 pgs.
"U.S. Appl. No. 15/361,917, Response filed Jun. 19, 2019 to Non Final Office Action mailed Apr. 19, 2019", 9 pgs.
"U.S. Appl. No. 15/361,917, Response filed Nov. 4, 2019 to Final Office Action mailed Sep. 3, 2019", 8 pgs.
"U.S. Appl. No. 15/361,917, Restriction Requirement mailed Jan. 3, 2019", 6 pgs.
"U.S. Appl. No. 15/401,768, Non Final Office Action mailed Jul. 22, 2019", 10 pgs.
"U.S. Appl. No. 15/401,768, Notice of Allowance mailed Nov. 20, 2019", 9 pgs.
"U.S. Appl. No. 15/401,768, Preliminary Amendment filed Mar. 23, 2017", 6 pgs.

(56) References Cited

OTHER PUBLICATIONS

"U.S. Appl. No. 15/401,768, Response filed May 15, 2019 to Restriction Requirement mailed Mar. 15, 2019", 7 pgs.
"U.S. Appl. No. 15/401,768, Response filed Aug. 28, 2019 to Non Final Office Action mailed Jul. 22, 2019", 10 pgs.
"U.S. Appl. No. 15/401,768, Restriction Requirement mailed Mar. 15, 2019", 6 pgs.
"U.S. Appl. No. 15/401,768, Supplemental Preliminary Amendment filed Jun. 22, 2017", 7 pgs.
"U.S. Appl. No. 15/412,676, Non Final Office Action mailed Jul. 23, 2019", 11 pgs.
"U.S. Appl. No. 15/412,676, Notice of Allowance mailed Dec. 30, 2019", 8 pgs.
"U.S. Appl. No. 15/412,676, Preliminary Amendment filed Jul. 3, 2017", 7 pgs.
"U.S. Appl. No. 15/412,676, Response filed May 15, 2019 to Restriction Requirement mailed Mar. 15, 2019", 7 pgs.
"U.S. Appl. No. 15/412,676, Response filed Oct. 23, 2019 to Non Final Office Action mailed Jul. 23, 2019", 12 pgs.
"U.S. Appl. No. 15/412,676, Restriction Requirement mailed Mar. 15, 2019", 6 pgs.
"U.S. Appl. No. 15/455,895, Examiner Interview Summary mailed Nov. 25, 2019", 3 pgs.
"U.S. Appl. No. 15/455,895, Non Final Office Action mailed Sep. 5, 2019", 11 pgs.
"U.S. Appl. No. 15/455,895, Notice of Allowance mailed Feb. 13, 2020", 7 pgs.
"U.S. Appl. No. 15/455,895, Preliminary Amendment filed Mar. 13, 2017", 6 pgs.
"U.S. Appl. No. 15/455,895, Response filed Jan. 28, 2020 to Non Final Office Action mailed Sep. 5, 2019", 14 pgs.
"U.S. Appl. No. 15/455,895, Supplemental Preliminary Amendment filed May 24, 2019", 6 pgs.
"U.S. Appl. No. 15/461,675, Non Final Office Action mailed Aug. 9, 2019", 10 pgs.
"U.S. Appl. No. 15/461,675, Notice of Allowance mailed Jan. 30, 2020", 7 pgs.
"U.S. Appl. No. 15/461,675, Preliminary Amendment filed Jun. 24, 2017", 6 pgs.
"U.S. Appl. No. 15/461,675, Response filed May 24, 2019 to Restriction Requirement mailed Mar. 26, 2019", 6 pgs.
"U.S. Appl. No. 15/461,675, Response filed Nov. 12, 2019 to Non Final Office Action mailed Aug. 9, 2019", 11 pgs.
"U.S. Appl. No. 15/461,675, Restriction Requirement mailed Mar. 26, 2019", 6 pgs.
"U.S. Appl. No. 15/461,675, Supplemental Preliminary Amendment filed Jun. 28, 2018", 7 pgs.
"U.S. Appl. No. 15/622,718, Examiner Interview Summary mailed Nov. 22, 2019", 3 pgs.
"U.S. Appl. No. 15/622,718, Non Final Office Action mailed Aug. 28, 2019", 14 pgs.
"U.S. Appl. No. 15/622,718, Notice of Allowance mailed Feb. 13, 2020", 8 pgs.
"U.S. Appl. No. 15/622,718, Preliminary Amendment filed Jun. 15, 2017", 7 pgs.
"U.S. Appl. No. 15/622,718, Response filed Jan. 28, 2020 to Non Final Office Action mailed Aug. 28, 2019", 11 pgs.
"U.S. Appl. No. 15/622,718, Response filed Jul. 31, 2019 to Restriction Requirement mailed Jun. 7, 2019", 8 pgs.
"U.S. Appl. No. 15/622,718, Restriction Requirement mailed Jun. 7, 2019", 6 pgs.
"U.S. Appl. No. 15/626,384, Non Final Office Action mailed May 3, 2019", 14 pgs.
"U.S. Appl. No. 15/626,384, Notice of Allowability mailed Oct. 18, 2019", 2 pgs.
"U.S. Appl. No. 15/626,384, Notice of Allowance mailed Aug. 21, 2019", 7 pgs.
"U.S. Appl. No. 15/626,384, Preliminary Amendment filed Aug. 10, 2018", 11 pgs.
"U.S. Appl. No. 15/626,384, Response filed Jul. 31, 2019 to Non-Final Office Action mailed May 3, 2019", 13 pgs.
"U.S. Appl. No. 15/654,386, Non Final Office Action mailed Nov. 7, 2019", 10 pgs.
"U.S. Appl. No. 15/654,386, Notice of Allowance mailed Feb. 20, 2020", 8 pgs.
"U.S. Appl. No. 15/654,386, Preliminary Amendment filed Aug. 30, 2017", 11 pgs.
"U.S. Appl. No. 15/654,386, Response filed Feb. 5, 2020 to Non Final Office Action mailed Nov. 7, 2019", 12 pgs.
"U.S. Appl. No. 15/654,386, Response filed Aug. 23, 2019 to Restriction Requirement mailed Jul. 16, 2019", 9 pgs.
"U.S. Appl. No. 15/654,386, Restriction Requirement mailed Jul. 16, 2019", 6 pgs.
"U.S. Appl. No. 15/659,689, Non Final Office Action mailed Oct. 31, 2018", 13 pgs.
"U.S. Appl. No. 15/659,689, Preliminary Amendment filed Jul. 26, 2017", 7 pgs.
"U.S. Appl. No. 15/662,572, Non Final Office Action mailed Oct. 10, 2019", 14 pgs.
"U.S. Appl. No. 15/662,572, Notice of Allowance mailed Mar. 11, 2020", 9 pgs.
"U.S. Appl. No. 15/662,572, Preliminary Amendment filed Jul. 31, 2017", 7 pgs.
"U.S. Appl. No. 15/662,572, Response filed Jan. 8, 2020 to Non Final Office Action mailed Oct. 10, 2019", 10 pgs.
"U.S. Appl. No. 15/662,572, Response filed Aug. 23, 2019 to Restriction Requirement mailed Jul. 1, 2019", 8 pgs.
"U.S. Appl. No. 15/662,572, Restriction Requirement mailed Jul. 1, 2019", 6 pgs.
"U.S. Appl. No. 15/664,572, Non Final Office Action mailed May 15, 2019", 8 pgs.
"U.S. Appl. No. 15/664,572, Notice of Allowance mailed Jun. 12, 2019", 8 pgs.
"U.S. Appl. No. 15/664,572, Preliminary Amendment filed Aug. 3, 2017", 7 pgs.
"U.S. Appl. No. 15/664,572, Response filed May 17, 2019 to Non Final Office Action mailed May 15, 2019", 9 pgs.
"U.S. Appl. No. 15/682,187, Non Final Office Action mailed Dec. 16, 2019", 10 pgs.
"U.S. Appl. No. 15/682,187, Notice of Allowance mailed Mar. 25, 2020", 9 pgs.
"U.S. Appl. No. 15/682,187, Preliminary Amendment filed Sep. 7, 2017", 6 pgs.
"U.S. Appl. No. 15/682,187, Response filed Feb. 27, 2020 to Non Final Office Action mailed Dec. 16, 2019", 11 pgs.
"U.S. Appl. No. 15/682,187, Response filed Sep. 18, 2019 to Restriction Requirement mailed Aug. 9, 2019", 7 pgs.
"U.S. Appl. No. 15/682,187, Restriction Requirement mailed Aug. 9, 2019", 6 pgs.
"U.S. Appl. No. 15/703,727, Non Final Office Action mailed Aug. 1, 2019", 11 pgs.
"U.S. Appl. No. 15/703,727, Notice of Allowance mailed Nov. 20, 2019", 7 pgs.
"U.S. Appl. No. 15/703,727, Preliminary Amendment filed Sep. 14, 2017", 7 pgs.
"U.S. Appl. No. 15/703,727, Response filed Nov. 1, 2019 to Non Final Office Action mailed Aug. 1, 2019", 10 pgs.
"U.S. Appl. No. 15/715,731, Non Final Office Action mailed Jan. 21, 2020", 8 pgs.
"U.S. Appl. No. 15/715,731, Notice of Allowance mailed Apr. 8, 2020", 9 pgs.
"U.S. Appl. No. 15/715,731, Preliminary Amendment Filed Sep. 26, 2017", 9 pgs.
"U.S. Appl. No. 15/715,731, Response filed Feb. 27, 2020 to Non Final Office Action mailed Jan. 21, 2020", 12 pgs.
"U.S. Appl. No. 15/715,731, Response Filed Nov. 4, 2019 to Restriction Requirement Mailed Sep. 4, 2019", 9 pgs.
"U.S. Appl. No. 15/715,731, Restriction Requirement mailed Sep. 4, 2019", 6 pgs.
"U.S. Appl. No. 15/715,731, Supplemental Preliminary Amendment filed Dec. 29, 2017", 8 pgs.

(56) References Cited

OTHER PUBLICATIONS

"U.S. Appl. No. 15/720,997, Advisory Action mailed Jun. 15, 2021", 3 pgs.
"U.S. Appl. No. 15/720,997, Advisory Action mailed Oct. 13, 2020", 2 pgs.
"U.S. Appl. No. 15/720,997, Final Office Action mailed Apr. 7, 2021", 9 pgs.
"U.S. Appl. No. 15/720,997, Final Office Action mailed Aug. 4, 2020", 10 pgs.
"U.S. Appl. No. 15/720,997, Non Final Office Action mailed Jan. 6, 2020", 10 pgs.
"U.S. Appl. No. 15/720,997, Non Final Office Action mailed Jul. 16, 2019", 11 pgs.
"U.S. Appl. No. 15/720,997, Non Final Office Action mailed Nov. 23, 2020", 7 pgs.
"U.S. Appl. No. 15/720,997, Notice of Allowance mailed Jul. 29, 2021", 7 pgs.
"U.S. Appl. No. 15/720,997, Preliminary Amendment filed Oct. 2, 2017", 6 pgs.
"U.S. Appl. No. 15/720,997, Response filed Jan. 25, 2021 to Non Final Office Action mailed Nov. 23, 2020", 9 pgs.
"U.S. Appl. No. 15/720,997, Response filed Mar. 27, 2020 to Non Final Office Action mailed Jan. 6, 2020", 10 pgs.
"U.S. Appl. No. 15/720,997, Response filed Jun. 2, 2021 to Final Office Action mailed Apr. 7, 2021", 9 pgs.
"U.S. Appl. No. 15/720,997, Response filed Jul. 7, 2021 to Advisory Action mailed Jun. 15, 2021", 6 pgs.
"U.S. Appl. No. 15/720,997, Response filed Sep. 30, 2020 to Final Office Action mailed Aug. 4, 2020", 11 pgs.
"U.S. Appl. No. 15/720,997, Response filed Oct. 3, 2019 to Non-Final Office Action mailed Jul. 16, 2019", 9 pgs.
"U.S. Appl. No. 15/722,002, Non Final Office Action mailed Feb. 4, 2020", 8 pgs.
"U.S. Appl. No. 15/722,002, Notice of Allowance mailed Apr. 8, 2020", 7 pgs.
"U.S. Appl. No. 15/722,002, Preliminary Amendment filed Jun. 29, 2018", 5 pgs.
"U.S. Appl. No. 15/722,002, Response filed Mar. 5, 2020 to Non Final Office Action mailed Feb. 4, 2020", 7 pgs.
"U.S. Appl. No. 15/722,002, Response filed Nov. 14, 2019 to Restriction Requirement mailed Sep. 17, 2019", 6 pgs.
"U.S. Appl. No. 15/722,002, Restriction Requirement mailed Sep. 17, 2019", 6 pgs.
"U.S. Appl. No. 15/793,216, Examiner Interview Summary mailed Nov. 4, 2019", 4 pgs.
"U.S. Appl. No. 15/793,216, Non Final Office Action mailed Aug. 1, 2019", 21 pgs.
"U.S. Appl. No. 15/793,216, Notice of Allowance mailed Mar. 23, 2020", 7 pgs.
"U.S. Appl. No. 15/793,216, Preliminary Amendment filed Oct. 26, 2017", 8 pgs.
"U.S. Appl. No. 15/793,216, Response filed Jan. 28, 2020 to Non Final Office Action mailed Aug. 1, 2019", 13 pgs.
"U.S. Appl. No. 15/865,938, Notice of Allowance mailed Sep. 17, 2019", 11 pgs.
"U.S. Appl. No. 15/865,938, Preliminary Amendment filed Jan. 10, 2018", 7 pgs.
"U.S. Appl. No. 15/866,089, Corrected Notice of Allowability mailed Aug. 27, 2020", 2 pgs.
"U.S. Appl. No. 15/866,089, Final Office Action mailed Mar. 25, 2020", 15 pgs.
"U.S. Appl. No. 15/866,089, Non Final Office Action mailed Dec. 4, 2019", 16 pgs.
"U.S. Appl. No. 15/866,089, Notice of Allowance mailed Jul. 15, 2020", 5 pgs.
"U.S. Appl. No. 15/866,089, Preliminary Amendment filed Jan. 10, 2018", 10 pgs.
"U.S. Appl. No. 15/866,089, Response filed Feb. 27, 2020 to Non Final Office Action mailed Dec. 4, 2019", 10 pgs.
"U.S. Appl. No. 15/866,089, Response filed Jun. 18, 2020 to Final Office Action mailed Mar. 25, 2020", 11 pgs.
"U.S. Appl. No. 15/886,712, Non Final Office Action mailed Sep. 27, 2019", 8 pgs.
"U.S. Appl. No. 15/886,712, Notice of Allowance mailed Nov. 14, 2019", 7 pgs.
"U.S. Appl. No. 15/886,712, Preliminary Amendment filed Feb. 2, 2018", 8 pgs.
"U.S. Appl. No. 15/886,712, Response filed Oct. 18, 2019 to Non Final Office Action mailed Sep. 27, 2019", 9 pgs.
"U.S. Appl. No. 15/891,049, Examiner Interview Summary mailed Aug. 10, 2020", 3 pgs.
"U.S. Appl. No. 15/891,049, Examiner Interview Summary mailed Dec. 4, 2020", 2 pgs.
"U.S. Appl. No. 15/891,049, Final Office Action mailed Nov. 10, 2020", 10 pgs.
"U.S. Appl. No. 15/891,049, Non Final Office Action mailed Jul. 14, 2020", 16 pgs.
"U.S. Appl. No. 15/891,049, Notice of Allowance mailed Dec. 22, 2020", 8 pgs.
"U.S. Appl. No. 15/891,049, Preliminary Amendment filed Feb. 8, 2018", 6 pgs.
"U.S. Appl. No. 15/891,049, Response filed May 29, 2020 to Restriction Requirement mailed May 5, 2020", 9 pgs.
"U.S. Appl. No. 15/891,049, Response filed Aug. 17, 2020 to Non Final Office Action mailed Jul. 14, 2020", 18 pgs.
"U.S. Appl. No. 15/891,049, Response filed Dec. 1, 2020 to Final Office Action mailed Nov. 10, 2020", 12 pgs.
"U.S. Appl. No. 15/891,049, Restriction Requirement mailed May 5, 2020", 6 pgs.
"U.S. Appl. No. 15/891,049, Supplemental Preliminary Amendment filed Dec. 20, 2019", 8 pgs.
"U.S. Appl. No. 15/903,261, Notice of Allowance mailed Mar. 26, 2020", 9 pgs.
"U.S. Appl. No. 15/903,261, Preliminary Amendment filed Feb. 28, 2018", 6 pgs.
"U.S. Appl. No. 15/917,143, Non Final Office Action mailed Aug. 7, 2020", 6 pgs.
"U.S. Appl. No. 15/917,143, Notice of Allowance mailed Feb. 24, 2021", 8 pgs.
"U.S. Appl. No. 15/917,143, Preliminary Amendment filed Mar. 14, 2018", 7 pgs.
"U.S. Appl. No. 15/917,143, Response filed Jun. 17, 2020 to Restriction Requirement mailed May 5, 2020", 8 pgs.
"U.S. Appl. No. 15/917,143, Response filed Oct. 29, 2020 to Non Final Office Action mailed Aug. 7, 2020", 11 pgs.
"U.S. Appl. No. 15/917,143, Restriction Requirement mailed May 5, 2020", 6 pgs.
"U.S. Appl. No. 15/941,481, Non Final Office Action mailed Aug. 14, 2020", 21 pgs.
"U.S. Appl. No. 15/941,481, Notice of Allowance mailed Dec. 3, 2020", 8 pgs.
"U.S. Appl. No. 15/941,481, Preliminary Amendment filed Mar. 30, 2018", 7 pgs.
"U.S. Appl. No. 15/941,481, Response filed Jun. 24, 2020 to Restriction Requirement mailed May 19, 2020", 8 pgs.
"U.S. Appl. No. 15/941,481, Response filed Nov. 16, 2020 to Non Final Office Action mailed Aug. 14, 2020", 15 pgs.
"U.S. Appl. No. 15/941,481, Restriction Requirement mailed May 19, 2020", 7 pgs.
"U.S. Appl. No. 15/945,425, Non Final Office Action mailed Aug. 25, 2020", 11 pgs.
"U.S. Appl. No. 15/945,425, Notice of Allowance mailed Dec. 24, 2020", 8 pgs.
"U.S. Appl. No. 15/945,425, Preliminary Amendment filed Apr. 5, 2018", 8 pgs.
"U.S. Appl. No. 15/945,425, Response filed Jun. 24, 2020 to Restriction Requirement mailed May 19, 2020", 7 pgs.
"U.S. Appl. No. 15/945,425, Response filed Nov. 23, 2020 to Non Final Office Action mailed Aug. 25, 2020", 10 pgs.
"U.S. Appl. No. 15/945,425, Restriction Requirement mailed May 19, 2020", 7 pgs.

(56) References Cited

OTHER PUBLICATIONS

"U.S. Appl. No. 15/945,425, Supplemental Preliminary Amendment filed May 10, 2018", 6 pgs.
"U.S. Appl. No. 15/956,444, Non Final Office Action mailed Dec. 7, 2020", 7 pgs.
"U.S. Appl. No. 15/956,444, Notice of Allowance mailed Mar. 11, 2021", 8 pgs.
"U.S. Appl. No. 15/956,444, Preliminary Amendment filed Apr. 19, 2018", 7 pgs.
"U.S. Appl. No. 15/956,444, PTO Response to Rule 312 Communication mailed Jun. 8, 2021", 2 pgs.
"U.S. Appl. No. 15/956,444, Response filed Feb. 23, 2021 to Non Final Office Action mailed Dec. 7, 2020", 11 pgs.
"U.S. Appl. No. 15/956,444, Response filed Sep. 14, 2020 to Restriction Requirement mailed Jul. 14, 2020", 8 pgs.
"U.S. Appl. No. 15/956,444, Restriction Requirement mailed Jul. 14, 2020", 7 pgs.
"U.S. Appl. No. 15/972,646, Non Final Office Action mailed Dec. 7, 2020", 11 pgs.
"U.S. Appl. No. 15/972,646, Notice of Allowance mailed Apr. 21, 2021", 8 pgs.
"U.S. Appl. No. 15/972,646, Preliminary Amendment filed May 9, 2018", 6 pgs.
"U.S. Appl. No. 15/972,646, Response filed Feb. 22, 2021 to Non Final Office Action mailed Dec. 7, 2020", 13 pgs.
"U.S. Appl. No. 15/972,646, Response filed Sep. 21, 2020 to Restriction Requirement mailed Jul. 27, 2020", 7 pgs.
"U.S. Appl. No. 15/972,646, Restriction Requirement mailed Jul. 27, 2020", 6 pgs.
"U.S. Appl. No. 16/160,559, 312 Amendment filed Dec. 9, 2021", 7 pgs.
"U.S. Appl. No. 16/160,559, Non Final Office Action mailed May 14, 2021", 12 pgs.
"U.S. Appl. No. 16/160,559, Notice of Allowance mailed Sep. 16, 2021", 14 pgs.
"U.S. Appl. No. 16/160,559, Preliminary Amendment filed Oct. 17, 2018", 6 pgs.
"U.S. Appl. No. 16/160,559, PTO Response to Rule 312 Communication mailed Dec. 24, 2021", 2 pgs.
"U.S. Appl. No. 16/160,559, Response filed Mar. 2, 2021 to Restriction Requirement mailed Jan. 27, 2021", 7 pgs.
"U.S. Appl. No. 16/160,559, Response filed Aug. 11, 2021 to Non Final Office Action mailed May 14, 2021", 10 pgs.
"U.S. Appl. No. 16/160,559, Restriction Requirement mailed Jan. 27, 2021", 6 pgs.
"U.S. Appl. No. 16/251,342, Notice of Allowance mailed Jul. 26, 2021", 8 pgs.
"U.S. Appl. No. 16/251,342, Preliminary Amendment filed Jan. 21, 2019", 6 pgs.
"U.S. Appl. No. 16/251,342, Response filed May 3, 2021 to Restriction Requirement mailed Apr. 30, 2021", 8 pgs.
"U.S. Appl. No. 16/251,342, Restriction Requirement mailed Apr. 30, 2021", 6 pgs.
"U.S. Appl. No. 16/251,342, Supplemental Preliminary Amendment filed Oct. 28, 2020", 7 pgs.
"U.S. Appl. No. 16/251,342, Supplemental Preliminary Amendment filed Nov. 4, 2020", 7 pgs.
"U.S. Appl. No. 16/255,300 Supplemental Preliminary Amendment Filed Nov. 12, 2020", 8 pgs.
"U.S. Appl. No. 16/255,300, Notice of Allowance mailed Jul. 19, 2021", 10 pgs.
"U.S. Appl. No. 16/255,300, Preliminary Amendment filed Jan. 24, 2019", 6 pgs.
"U.S. Appl. No. 16/380,742, Notice of Allowance mailed Jan. 3, 2022", 13 pgs.
"U.S. Appl. No. 16/380,742, Preliminary Amendment filed Apr. 12, 2019", 6 pgs.
"U.S. Appl. No. 16/380,742, Response filed Oct. 20, 2021 to Restriction Requirement mailed Aug. 20, 2021", 6 pgs.
"U.S. Appl. No. 16/380,742, Restriction Requirement mailed Aug. 20, 2021", 7 pgs.
"U.S. Appl. No. 16/380,742, Supplemental Preliminary Amendment filed Mar. 1, 2021", 5 pgs.
"U.S. Appl. No. 16/400,199, Non Final Office Action mailed Feb. 10, 2022", 8 pgs.
"U.S. Appl. No. 16/400,199, Notice of Allowance mailed May 11, 2022", 8 pgs.
"U.S. Appl. No. 16/400,199, Preliminary Amendment filed May 7, 2019", 7 pgs.
"U.S. Appl. No. 16/400,199, Response filed Apr. 13, 2022 to Non Final Office Action mailed Feb. 10, 2022", 11 pgs.
"U.S. Appl. No. 16/400,199, Response filed Nov. 15, 2021 to Restriction Requirement mailed Oct. 1, 2021", 8 pgs.
"U.S. Appl. No. 16/400,199, Restriction Requirement mailed Oct. 1, 2021", 7 pgs.
"U.S. Appl. No. 16/420,676, Non Final Office Action mailed Jul. 20, 2021", 11 pgs.
"U.S. Appl. No. 16/420,676, Notice of Allowance mailed Nov. 15, 2021", 9 pgs.
"U.S. Appl. No. 16/420,676, Preliminary Amendment filed Jun. 3, 2019", 5 pgs.
"U.S. Appl. No. 16/420,676, Response filed Oct. 20, 2021 to Non Final Office Action mailed Jul. 20, 2021", 14 pgs.
"U.S. Appl. No. 16/428,277, Corrected Notice of Allowability mailed Sep. 16, 2022", 6 pgs.
"U.S. Appl. No. 16/428,277, Non Final Office Action mailed May 24, 2022", 7 pgs.
"U.S. Appl. No. 16/428,277, Notice of Allowance mailed Aug. 25, 2022", 9 pgs.
"U.S. Appl. No. 16/428,277, Preliminary Amendment filed Jun. 3, 2019", 5 pgs.
"U.S. Appl. No. 16/428,277, Response filed Apr. 11, 2022 to Restriction Requirement mailed Feb. 11, 2022", 8 pgs.
"U.S. Appl. No. 16/428,277, Response filed Aug. 3, 2022 to Non Final Office Action mailed May 24, 2022", 8 pgs.
"U.S. Appl. No. 16/428,277, Restriction Requirement mailed Feb. 11, 2022", 6 pgs.
"U.S. Appl. No. 16/436,023, Examiner Interview Summary mailed Aug. 23, 2021", 2 pgs.
"U.S. Appl. No. 16/436,023, Non Final Office Action mailed May 19, 2021", 18 pgs.
"U.S. Appl. No. 16/436,023, Notice of Allowance mailed Oct. 27, 2021", 8 pgs.
"U.S. Appl. No. 16/436,023, Preliminary Amendment filed Jun. 12, 2019", 6 pgs.
"U.S. Appl. No. 16/436,023, Response filed Aug. 19, 2021 to Non Final Office actio mailed May 19, 2021", 9 pgs.
"U.S. Appl. No. 16/443,391, Non Final Office Action mailed Aug. 31, 2021", 11 pgs.
"U.S. Appl. No. 16/443,391, Notice of Allowance mailed Jan. 7, 2022", 5 pgs.
"U.S. Appl. No. 16/443,391, Preliminary Amendment filed Jun. 19, 2019", 6 pgs.
"U.S. Appl. No. 16/443,391, Response filed Nov. 15, 2021 to Non Final Office Action mailed Aug. 31, 2021", 9 pgs.
"U.S. Appl. No. 16/508,764, Notice of Allowance mailed Oct. 20, 2021", 10 pgs.
"U.S. Appl. No. 16/508,764, Preliminary Amendment filed Jul. 12, 2019", 7 pgs.
"U.S. Appl. No. 16/508,764, Supplemental Amendment filed Sep. 30, 2021", 6 pgs.
"U.S. Appl. No. 16/544,293, Corrected Notice of Allowability mailed Mar. 17, 2023", 7 pgs.
"U.S. Appl. No. 16/544,293, Non Final Office Action mailed Sep. 21, 2022", 14 pgs.
"U.S. Appl. No. 16/544,293, Notice of Allowance mailed Mar. 8, 2023", 11 pgs.
"U.S. Appl. No. 16/544,293, Preliminary Amendment filed Aug. 21, 2019", 7 pgs.
"U.S. Appl. No. 16/544,293, Response filed Aug. 15, 2022 to Restriction Requirement mailed Jul. 7, 2022", 7 pgs.

(56) References Cited

OTHER PUBLICATIONS

"U.S. Appl. No. 16/544,293, Response filed Nov. 28, 2022 to Non-Final Office Action mailed Sep. 21, 2022", 10 pgs.
"U.S. Appl. No. 16/544,293, Restriction Requirement mailed Jul. 7, 2022", 6 pgs.
"U.S. Appl. No. 16/544,293, Supplemental Preliminary Amendment filed Oct. 28, 2020", 6 pgs.
"U.S. Appl. No. 16/593,022, Preliminary Amendment filed Oct. 30, 2019", 8 pgs.
"U.S. Appl. No. 16/593,022, Response filed Sep. 9, 2022 to Restriction Requirement mailed Sep. 6, 2022", 8 pgs.
"U.S. Appl. No. 16/593,022, Response filed Nov. 4, 2022 to Restriction Requirement mailed Oct. 31, 2022", 8 pgs.
"U.S. Appl. No. 16/593,022, Restriction Requirement mailed Sep. 6, 2022", 6 pgs.
"U.S. Appl. No. 16/593,022, Restriction Requirement mailed Oct. 31, 2022", 6 pgs.
"U.S. Appl. No. 16/593,022, Supplemental Amendment filed Nov. 7, 2022 to Restriction Requirement mailed Oct. 31, 2022", 9 pgs.
"U.S. Appl. No. 16/593,022, Supplemental Preliminary Amendment filed Oct. 21, 2020", 8 pgs.
"U.S. Appl. No. 16/593,022, Supplemental Preliminary Amendment filed Dec. 5, 2019", 8 pgs.
"U.S. Appl. No. 16/593,022, Supplemental Preliminary Amendment filed Dec. 20, 2019", 5 pgs.
"U.S. Appl. No. 16/690,671, Non Final Office Action mailed Nov. 15, 2021", 8 pgs.
"U.S. Appl. No. 16/690,671, Notice of Allowance mailed Mar. 2, 2022", 7 pgs.
"U.S. Appl. No. 16/690,671, Preliminary Amendment filed Dec. 11, 2019", 7 pgs.
"U.S. Appl. No. 16/690,671, Response filed Feb. 4, 2022 to Non Final Office Action mailed Nov. 15, 2021", 10 pgs.
"U.S. Appl. No. 16/795,181, Examiner Interview Summary mailed Apr. 15, 2022", 2 pgs.
"U.S. Appl. No. 16/795,181, Final Office Action mailed Jun. 7, 2022", 12 pgs.
"U.S. Appl. No. 16/795,181, Non Final Office Action mailed Jan. 24, 2022", 12 pgs.
"U.S. Appl. No. 16/795,181, Notice of Allowance mailed Aug. 25, 2022", 7 pgs.
"U.S. Appl. No. 16/795,181, Preliminary Amendment filed Feb. 20, 2020", 6 pgs.
"U.S. Appl. No. 16/795,181, Response filed Apr. 14, 2022 to Non Final Office Action mailed Jan. 24, 2022", 9 pgs.
"U.S. Appl. No. 16/795,181, Response filed Aug. 3, 2022 to Final Office Action mailed Jun. 7, 2022", 8 pgs.
"U.S. Appl. No. 16/802,228, Notice of Allowance mailed Jun. 15, 2022", 10 pgs.
"U.S. Appl. No. 16/802,228, Preliminary Amendment filed Mar. 4, 2020", 7 pgs.
"U.S. Appl. No. 16/802,248, Non Final Office Action mailed Jun. 17, 2022", 18 pgs.
"U.S. Appl. No. 16/802,248, Notice of Allowance mailed Oct. 28, 2022", 9 pgs.
"U.S. Appl. No. 16/802,248, Preliminary Amendment filed Mar. 5, 2020", 8 pgs.
"U.S. Appl. No. 16/802,248, Response filed Sep. 14, 2022 to Non Final Office Action mailed Jun. 17, 2022", 12 pgs.
"U.S. Appl. No. 16/806,611, Notice of Allowance mailed Feb. 15, 2023", 10 pgs.
"U.S. Appl. No. 16/806,611, Preliminary Amendment filed Mar. 4, 2020", 7 pgs.
"U.S. Appl. No. 16/806,611, Response filed Sep. 9, 2022 to Restriction Requirement mailed Aug. 26, 2022", 9 pgs.
"U.S. Appl. No. 16/806,611, Response filed Nov. 7, 2022 to Restriction Requirement mailed Nov. 1, 2022", 9 pgs.
"U.S. Appl. No. 16/806,611, Restriction Requirement mailed Aug. 26, 2022", 6 pgs.
"U.S. Appl. No. 16/806,611, Restriction Requirement mailed Nov. 1, 2022", 6 pgs.
"U.S. Appl. No. 16/895,246, Non Final Office Action mailed Dec. 13, 2022", 8 pgs.
"U.S. Appl. No. 16/895,246, Notice of Allowance mailed Apr. 5, 2023", 13 pgs.
"U.S. Appl. No. 16/895,246, Preliminary Amendment filed Jun. 9, 2020", 6 pgs.
"U.S. Appl. No. 16/895,246, Response filed Jan. 11, 2023 to Non Final Office Action mailed Dec. 13, 2022", 8 pgs.
"U.S. Appl. No. 16/895,246, Response filed Sep. 28, 2022 to Restriction Requirement mailed Sep. 9, 2022", 7 pgs.
"U.S. Appl. No. 16/895,246, Restriction Requirement mailed Sep. 9, 2022", 6 pgs.
"U.S. Appl. No. 16/987,001, Notice of Allowance mailed Feb. 17, 2023", 15 pgs.
"U.S. Appl. No. 16/989,386, Non Final Office Action mailed Mar. 15, 2023", 13 pgs.
"U.S. Appl. No. 16/989,386, Notice of Allowance mailed Jul. 26, 2023", 9 pgs.
"U.S. Appl. No. 16/989,386, PTO Response to Rule 312 Communication mailed Oct. 19, 2023", 2 pgs.
"U.S. Appl. No. 16/989,386, Response filed May 19, 2023 to Non Final Office Action mailed Mar. 15, 2023", 11 pgs.
"U.S. Appl. No. 16/989,386, Response filed Dec. 5, 2022 to Restriction Requirement mailed Nov. 14, 2022", 9 pgs.
"U.S. Appl. No. 16/989,386, Restriction Requirement mailed Nov. 14, 2022", 6 pgs.
"U.S. Appl. No. 16/989,386, Supplemental Preliminary Amendment filed Oct. 21, 2020", 8 pgs.
"U.S. Appl. No. 17/190,686, Notice of Allowance mailed Oct. 5, 2023", 8 pgs.
"U.S. Appl. No. 17/190,686, Preliminary Amendment filed Mar. 10, 2021", 7 pgs.
"U.S. Appl. No. 17/190,686, Restriction Requirement mailed Jun. 6, 2023", 7 pgs.
"U.S. Appl. No. 17/190,686, Supplemental Amendment filed Apr. 12, 2023", 9 pgs.
"U.S. Appl. No. 17/392,971, Preliminary Amendment filed Aug. 18, 2021", 9 pgs.
"U.S. Appl. No. 17/492,082, Notice of Allowance mailed Apr. 17, 2023", 8 pgs.
"U.S. Appl. No. 17/492,082, Preliminary Amendment filed Oct. 25, 2021", 6 pgs.
"U.S. Appl. No. 17/516,664, Preliminary Amendment filed Nov. 10, 2021", 6 pgs.
"U.S. Appl. No. 17/545,668, Notice of Allowance mailed Jun. 22, 2023", 7 pgs.
"U.S. Appl. No. 17/545,668, Preliminary Amendment filed Dec. 9, 2021", 5 pgs.
"U.S. Appl. No. 17/550,074, Preliminary Amendment filed Dec. 15, 2021", 5 pgs.
"U.S. Appl. No. 17/577,188, Preliminary Amendment filed Jan. 19, 2022", 7 pgs.
"U.S. Appl. No. 17/940,022, Preliminary Amendment filed Sep. 26, 2022", 6 pgs.
"U.S. Appl. No. 17/991,832, Preliminary Amendment filed Dec. 14, 2022", 6 pgs.
"U.S. Appl. No. 17/190,686, Response filed Aug. 3, 2023 to Restriction Requirement mailed Jun. 6, 2023", 9 pgs.
"U.S. Appl. No. 18/093,114, Supplemental Amendment filed Jan. 11, 2023", 6 pgs.
"U.S. Appl. No. 18/101,490, Supplemental Preliminary Amendment filed Jan. 26, 2023", 7 pgs.
"U.S. Appl. No. 18/102,518, Preliminary Amendment filed Jan. 30, 2023", 6 pgs.
"U.S. Appl. No. 18/126,022, Preliminary Amendment filed Apr. 28, 2023", 6 pgs.
"U.S. Appl. No. 18/134,897, Supplemental Amendment filed Nov. 1, 2023", 8 pgs.
"U.S. Appl. No. 18/134,897, Supplemental Preliminary Amendment filed Apr. 17, 2023", 6 pgs.

(56) References Cited

OTHER PUBLICATIONS

"U.S. Appl. No. 18/235,540, Supplemental Preliminary Amendment filed Aug. 30, 2023", 5 pgs.
"U.S. Appl. No. 18/471,089, Supplemental Preliminary Amendment filed Sep. 21, 2023", 7 pgs.
"U.S. Appl. No. 18/497,342, Supplemental Amendment filed Nov. 1, 2023", 7 pgs.
"Arthroscopic Meniscal Repair using the Meniscal Cinch™", Surgical Technique brochure. Arthrex®, 6 sheets, (2008), 6 sheets.
"Australian Application Serial No. 2014236885, First Examination Report mailed Dec. 11, 2017", 2 pgs.
"Australian Application Serial No. 2014236885, Response filed Feb. 14, 2018 to First Examination Report mailed Dec. 11, 2017", 6 pgs.
"Bio-Intrafix Tibial Soft Tissue Fastener, Building on the Legacy of IntraFix", DePuy Mitek brochure, (Feb. 2007), 6 pgs.
"Bio-Intrafix (TCP/PLA) & Intrafix, Tibial Soft Tissue Fasteners", DePuy Mitek, ((date unknown)), 6 pgs.
"Biomechanical Evaluation of the Biomet Sports Medicine JurggerKnot™ Soft Anchor in Porcine Bone", Study completed Jan. 2010. Biomet Sports Medicine Research and Develo ment, Warsaw, Indiana, (Jan. 2010), 2 pgs.
"Canadian Application Serial No. 2906596, Office Action mailed Feb. 26, 2018", 3 pgs.
"Chinese Application Serial No. 201480027708.4, Office Action mailed Feb. 14, 2017", (W/ English Translation), 18 pgs.
"Chinese Application Serial No. 201480027708.4, Office Action mailed May 26, 2016", W/ English Translation, 15 pgs.
"Chinese Application Serial No. 201480027708.4, Office Action mailed Aug. 18, 2017", (W/ English Translation), 8 pgs.
"Chinese Application Serial No. 201480027708.4, Response filed May 2, 2017 to Office Action mailed Feb. 14, 2017", (W/ English Translation), 17 pgs.
"Chinese Application Serial No. 201480027708.4, Response filed Oct. 10, 2016 to Office Action mailed May 26, 2016", (W/ English Translation of Claims), 14 pgs.
"Chinese Application Serial No. 201480027708.4, Response filed Oct. 31, 2017 to Office Action mailed Aug. 18, 2017", (W/ English Claims), 7 pgs.
"Declaration of John White regarding PSCD and Customized Device and Exhibits 1-5".
"Do your next distal tendon repair with . . . The Lubbers Technique", Teno Fix® brochure, Ortheon® Medical, (2003), 2 pgs.
"European Application No. 16168202.6, Extended European Search Report mailed Aug. 16, 2017", 11 pgs.
"European Application No. 16168202.6, Response filed Nov. 3, 2017 to Extended European Search Report mailed Aug. 16, 2017", 9 pgs.
"European Application Serial No. 10727548.9, Examination Notification Art. 94(3) mailed Sep. 18, 2014", 6 pgs.
"European Application Serial No. 10727548.9, Office Action mailed Jan. 11, 2016", 6 pgs.
"European Application Serial No. 10727548.9, Office Action mailed Jan. 19, 2012", 2 pgs.
"European Application Serial No. 10727548.9, Response filed Mar. 19, 2015 to Examination Notification Art. 94(3) mailed Sep. 18, 2014", 23 pgs.
"European Application Serial No. 11707316.3, Examination Notification Art. 94(3) mailed Feb. 4, 2014", 3 pgs.
"European Application Serial No. 11707316.3, Examination Notification Art. 94(3) mailed Dec. 17, 2014", 5 pgs.
"European Application Serial No. 11707316.3, Office Action mailed Nov. 10, 2015", 6 pgs.
"European Application Serial No. 11707316.3, Response filed Jun. 5, 2014 to Examination Notification Art. 94(3) mailed Feb. 4, 2014", 7 pgs.
"European Application Serial No. 11707316.3, Response filed Jun. 29, 2015 to Examination Notification Art. 94(3) mailed Dec. 17, 2014", 25 pgs.
"European Application Serial No. 12721676.0, Communication pursuant to Article 94(3) EPC mailed Sep. 30, 2015", 4 pgs.
"European Application Serial No. 12721676.0, Office Action mailed Jan. 3, 2014", 2 pgs.
"European Application Serial No. 12721676.0, Preliminary Amendment filed Nov. 19, 2013", 9 pgs.
"European Application Serial No. 12721676.0, Response filed Apr. 11, 2016 to Communication pursuant to Article 94(3) EPC mailed Sep. 30, 2015", 38 pgs.
"European Application Serial No. 12721676.0, Response filed Jul. 10, 2014 to Office Action mailed Jan. 3, 2014", 2 pgs.
"European Application Serial No. 12791902.5, Examination Notification Art. 94(3) mailed Aug. 14, 2015", 4 pgs.
"European Application Serial No. 12791902.5, Office Action mailed Jul. 15, 2014", 2 pgs.
"European Application Serial No. 12791902.5, Response filed Feb. 23, 2016 to Examination Notification Art. 94(3) mailed Aug. 14, 2015", 12 pgs.
"European Application Serial No. 12806211.4, Examination Notification Art. 94(3) mailed Aug. 13, 2015", 5 pgs.
"European Application Serial No. 12806211.4, Office Action mailed Jul. 18, 2014", 2 pgs.
"European Application Serial No. 12806211.4, Response filed Feb. 23, 2016 to Communication Pursuant to Article 94(3) EPC mailed Aug. 13, 2015", 11 pgs.
"European Application Serial No. 13818131.8, Office Action mailed Jul. 28, 2015", 2 pgs.
"European Application Serial No. 13818131.8, Response filed Feb. 8, 2016 to Office Action mailed Jul. 28, 2015", 14 pgs.
"European Application Serial No. 14716173.1, Communication Pursuant to Article 94(3) EPC mailed Jul. 13, 2020", 4 pgs.
"European Application Serial No. 14716173.1, Office Action mailed Nov. 5, 2015", 2 pgs.
"European Application Serial No. 14716173.1, Response filed May 16, 2016 to Communication pursuant to Rules 161(1) and 162 EPC mailed Nov. 5, 2015", 10 pgs.
"European Application Serial No. 14716173.1, Response filed Sep. 25, 2017 to Office Action mailed Mar. 14, 2017", 12pgs.
"European Application Serial No. 16168202.6, Communication Pursuant to Article 94(3) EPC mailed Apr. 25, 2018", 5 pgs.
"European Application Serial No. 16168202.6, Communication pursuant to Article 94(3) EPC mailed Dec. 11, 2018", 6 pgs.
"European Application Serial No. 16168202.6, Partial European Search Report mailed May 9, 2017", 12 pgs.
"European Application Serial No. 16168202.6, Response filed Sep. 5, 2018 to Communication Pursuant to Article 94(3) EPC mailed Apr. 25, 2018", 13 pgs.
"European Application Serial No. 17169003.5, Extended European Search Report mailed May 11, 2018", 8 pgs.
"European Application Serial No. 17169003.5, Response Filed Dec. 19, 2018 to Extended European Search Report mailed May 11, 2018", 22 pgs.
"European Application Serial No. 12806211.4, Communication Pursuant to Article 94(3) EPC mailed Jun. 23, 2016", 4 pgs.
"EZ Loc Femoral Fixation Device", copyright 2005 Arthrotek, Inc, (2005), 8 pgs.
"Information of Polydioxanone", Dolphin Sutures, [Online] Retrieved from the internet: <https://www.dolphinsutures.com/resoucres/information-on-polydioxanone>, (2018), 2 pgs.
"International Application Serial No. PCT/US2009/039580, International Preliminary Report on Patentability mailed Nov. 4, 2010", 9 pgs.
"International Application Serial No. PCT/US2009/039580, International Search Report mailed Jul. 30, 2009", 4 pgs.
"International Application Serial No. PCT/US2009/039580, Written Opinion mailed Jul. 30, 2009", 7 pgs.
"International Application Serial No. PCT/US2010/036602, International Preliminary Report on Patentability mailed Dec. 8, 2011", 9 pgs.
"International Application Serial No. PCT/US2010/036602, International Search Report mailed Nov. 8, 2010", 6 pgs.
"International Application Serial No. PCT/US2010/036602, Written Opinion mailed Nov. 8, 2010", 7 pgs.

(56) References Cited

OTHER PUBLICATIONS

"International Application Serial No. PCT/US2011/026349, International Preliminary Report on Patentability mailed Sep. 20, 2012", 11 pgs.
"International Application Serial No. PCT/US2011/026349, International Search Report mailed Jul. 28, 2011", 6 pgs.
"International Application Serial No. PCT/US2011/026349, Invitation to Pay Additional Fees mailed Jun. 9, 2011", 5 pgs.
"International Application Serial No. PCT/US2011/026349, Written Opinion mailed Jul. 28, 2011", 9 pgs.
"International Application Serial No. PCT/US2011/038188, International Preliminary Report on Patentability mailed Dec. 6, 2012", 14 pgs.
"International Application Serial No. PCT/US2011/038188, International Search Report mailed Oct. 14, 2011", 6 pgs.
"International Application Serial No. PCT/US2011/038188, Invitation to Pay Additional Fees mailed Aug. 5, 2011", 5 pgs.
"International Application Serial No. PCT/US2011/038188, Written Opinion mailed Oct. 14, 2011", 12 pgs.
"International Application Serial No. PCT/US2012/030294, International Preliminary Report on Patentability mailed Oct. 10, 2013", 9 pgs.
"International Application Serial No. PCT/US2012/030294, International Search Report mailed May 23, 2012", 6 pgs.
"International Application Serial No. PCT/US2012/030294, Written Opinion mailed May 23, 2012", 7 pgs.
"International Application Serial No. PCT/US2012/037703, International Preliminary Report on Patentability mailed Nov. 28, 2013", 10 pgs.
"International Application Serial No. PCT/US2012/037703, International Search Report mailed Sep. 21, 2012", 6 pgs.
"International Application Serial No. PCT/US2012/037703, Invitation to Pay Additional Fees mailed Jul. 19, 2012", 7 pgs.
"International Application Serial No. PCT/US2012/037703, Written Opinion mailed Sep. 21, 2012", 8 pgs.
"International Application Serial No. PCT/US2012/062738, International Preliminary Report on Patentability mailed May 15, 2014", 9 pgs.
"International Application Serial No. PCT/US2012/062738, International Search Report mailed Mar. 6, 2013", 6 pgs.
"International Application Serial No. PCT/US2012/062738, Written Opinion mailed Mar. 6, 2013", 7 pgs.
"International Application Serial No. PCT/US2012/064832, International Preliminary Report on Patentability mailed May 30, 2014", 9 pgs.
"International Application Serial No. PCT/US2012/064832, International Search Report mailed Feb. 6, 2013", 3 pgs.
"International Application Serial No. PCT/US2012/064832, Written Opinion mailed Feb. 6, 2013", 7 pgs.
"International Application Serial No. PCT/US2013/058921, International Preliminary Report on Patentability mailed Mar. 26, 2015", 9 pgs.
"International Application Serial No. PCT/US2013/058921, International Search Report mailed Oct. 21, 2013", 5 pgs.
"International Application Serial No. PCT/US2013/058921, Written Opinion mailed Oct. 21, 2013", 6 pgs.
"International Application Serial No. PCT/US2013/075989, International Preliminary Report on Patentability mailed Jul. 2, 2015", 10 pgs.
"International Application Serial No. PCT/US2013/075989, International Search Report mailed Mar. 6, 2014", 4 pgs.
"International Application Serial No. PCT/US2013/075989, Written Opinion mailed Mar. 6, 2014", 7 pgs.
"International Application Serial No. PCT/US2014/026413, International Preliminary Report on Patentability mailed Sep. 24, 2015", 10 pgs.
"International Application Serial No. PCT/US2014/026413, International Search Report mailed Jun. 6, 2014", 5 pgs.
"International Application Serial No. PCT/US2014/026413, Written Opinion mailed Jun. 6, 2014", 8 pgs.
"JuggerKnot™ Soft Anchor Midfoot Repair", brochure. Biomet Sports Medicine, (Jul. 2011), 12 pgs.
"JuggerKnot™ Soft Anchor. It's Small. It's strong. And it's all suture . . . ", Ordering Information brochure. Biomet Sports Medicine, (Jun. 2011), 2 pgs.
"JuggerKnot™ Soft Anchor. Labral Repair", brochure. Biomet Sports Medicine, (Apr. 2011), 12 pgs.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique", brochure, Biomet® Sports Medicine, (2013), 16 pgs.
"Make your next tendon repair an open-and-shut case. The Teno Fix® Tendon Repair System", Teno Fix® brochure, Ortheon® Medical, (2003), 2 pgs.
"Mallory-Head Modular Calcar Revision System", Biomet Orthopedics, Inc., (2006), 20 pgs.
"Next Generation in Knee Ligament Reconstruction & Repair Technology", Suture Tensioner w/Tensiometer, Arthrex®, Inc. catalog, (2009).
"Panalok Anchor with PDS II and Ethibond Suture", Mitek Products Ethicon, (1997), 2 pgs.
"Rapid Sternal Closure", KLS Martin L.P., [Online] retrieved from the internet: U.S. Appl. No. 13/645,964 , (2006).
"Rotator Cuff Fixation", Acufex Fastenator System: Shoulder Arthroscopy; H-2-H-22, 22 pgs.
"SE Graft Tensioning System Surgical Technique", Linvatec Corporation copyright 2003, (2004), 12 pgs.
"SportMesh™ Soft Tissue Reinforcment, Made from . . . Artelon® optimal tissue repair", Biomet® Sports Medicine, Inc., (2007), 8 pgs.
"Sternal Cable System", Pioneer®, [Online] retrieved from the internet: U.S. Appl. No. 13/645,964 , (2010).
"The AutoCuff System", Opus Medical, [Online]. Retrieved from the Internet: <www.opusmedical.com>, (2003), 4 pgs.
"Toggleloc™ Femoral Fixation Device", Arthrotek, (Mar. 31, 2006), 8 pgs.
"TriTis ™ Tibial Fixation System and Implant", brochure. Scandius Biomedical, (2006).
Albritton, Mark J, et al., "Toggleloc Fixation Device with Ziploop Technology: Biceps Tendon Reattachment", Biomet Sports Medicine, a Biomet Company Brochure 2099, (2011), 1-12.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Andrews, James R, "Toggleloc™ Fixation Device with Ziploop™ Technology: ACL Reconstruction Bone-Tendon-Bone", Biomet Sports Medicine, a Biomet Company Brochure, (2013), 1-20.
Anitua, Eduardo, et al., "Autologous platelets as a source of proteins for healing and tissue regeneration", Thromb Haemost, vol. 91, (2004), 4-15.
Arthrotek, "A Biomet Company; Sure fire Hybrid Meniscal Device", Fall AANA, (2004), 37 pgs.
Barber, Alan F, "Uses and Abuses of Sutures and Anchors", Shoulder Scope, San Diego Shoulder Arthroscopy Library, (Jul. 1999), 6 pgs.
Barber, Alan F, "Using Sutures and Anchors", San Diego Shoulder Arthroscopy Course, 17th Annual Meetina, (Jun. 14, 2000), 9 pgs.
Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Flavia, Namie Azato, "Traction endurance biomechanical study of metallic suture anchors at different insertion angles", Acta Ortop. Bras., vol. 11, No. 1, Sao Paulo, (Jan./Mar. 2003), pp. 25-31.
Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.

(56) References Cited

OTHER PUBLICATIONS

Fromm, Stuart M.D. E, "", Rapidloc, Meniscal Repair System, Mitek Products, Ethicon, (2001), 6 pgs.
Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Hecker, AT, et al., "Pull-out strength of suture anchors for rotator cuff and Bankart lesion repairs", The American Journal of Sports Medicine 21(6), (1993), 874-879.
Hunt, Patrick, et al., "Development of a Perforated Biodegradable Interference Screw; Arthroscopy:", The Journal of Arthroscopic and Related Surgery, vol. 21, No. 3;, (Mar. 2005), 258-265.
Lawhorn, M D, et al., "MaxFire™ Meniscal Repair Device with Zip Loop™ Technology", Biomet Sports Medicine, (Feb. 29, 2008), 12 pgs.
Majors, MD, Roy Alan, "Meniscal repairs: proven techniques and current trends", Lippincott Williams & Wilkins, Inc.;, (2002), 30-36.
Miller, Mark D, et al., "Pitfalls Associated with FasT-Fix Meniscal Repair", Arthroscopy: The Journal of Arthroscopic and Related Surgery, vol. 18 No. 8 :, (Oct. 2002), 939-943.
Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.
Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.
Roseberg, MD, Thomas D, "ACL Reconstruction with Acufex Director Drill Guide and Endobutton CL Fixation System", Smith & Nephew: Knee Series, Technique Guide, (2005), 12 pgs.
Saxena, Pankaj, et al., "Use of Double Wires in Sternal Closure, A Useful Technique", Texas Heart® Institute. Journal List> Tex Heart Inst J > v.33(4), (2006).
Smith, et al., "Endoscopic Meniscal Repair Using the T-Fix", (1996), 16 pgs.
Smith, et al., "Fast-Fix", Meniscal Repair System;, (2001), 3 pgs.
Steadman, et al., "Microfracture: Surgical Technique and Rehabilitation to Treat Chondral Defects", Clinical Orthopaedics and Related Research 391, (2001), S362-S369.
Thomas, Roseberg D, "Technique for ACL Reconstruction with Acufex Director Drill Guide and Endobutton CL", Smith & Nephew, Technique Guide, (1999), 18 pgs.
Weiler, A, et al., "Biodegradierbare Interferenzschrauben in der Kreuzbandchirurgie", OPJournal 14, (1998), 278-284.
Zeitani, Jacob M.D, "A New Sternal Reinforcement Device to Prevent and Treat Sternal Dehiscence", CTSNet, [Online]. Retrieved from the Internet: <URL: http://www.ctsnet.org/print/article/new-sternal-reinforcement-device-prevent-and-treat-sternal-dehiscence>, (Jun. 30, 2008), 6 pgs.
U.S. Appl. No. 11/541,506 U.S. Pat. No. 7,601,165, filed Sep. 29, 2006, Method and Apparatus for Forming a Self-Locking Adjustable Suture Loop.
U.S. Appl. No. 11/784,821 U.S. Pat. No. 9,017,381, filed Apr. 10, 2007, Adjustable Knotless Loops.
U.S. Appl. No. 14/697,140 U.S. Pat. No. 9,861,351, filed Apr. 27, 2015, Adjustable Knotless Loops.
U.S. Appl. No. 15/720,997 U.S. Pat. No. 11,185,320, filed Sep. 29, 2017, Adjustable Knotless Loops.
U.S. Appl. No. 15/903,261 U.S. Pat. No. 10,729,423, filed Feb. 23, 2018, Adjustable Knotless Loops.
U.S. Appl. No. 17/516,664, filed Nov. 1, 2021, Adjustable Knotless Loops.
U.S. Appl. No. 12/828,977 U.S. Pat. No. 8,409,253, filed Jul. 1, 2010, Soft Tissue Repair Assembly and Associated Method.
U.S. Appl. No. 11/347,661 U.S. Pat. No. 7,749,250, filed Feb. 3, 2006, Soft Tissue Repair Assembly and Associated Method.
U.S. Appl. No. 13/767,401 U.S. Pat. No. 9,414,833, filed Feb. 14, 2013, Soft Tissue Repair Assembly and Associated Method.
U.S. Appl. No. 14/936,831 U.S. Pat. No. 10,441,264, filed Nov. 10, 2015, Soft Tissue Repair Assembly and Associated Method.
U.S. Appl. No. 15/361,917 U.S. Pat. No. 10,702,259, filed Nov. 28, 2016, Soft Tissue Repair Assembly and Associated Method.
U.S. Appl. No. 16/251,342 U.S. Pat. No. 11,116,495, filed Jan. 18, 2019, Soft Tissue Repair Assembly and Associated Method.
U.S. Appl. No. 16/544,293 U.S. Pat. No. 11,730,464, filed Aug. 19, 2019, Soft Tissue Repair Assembly and Associated Method.
U.S. Appl. No. 11/541,505 U.S. Pat. No. 7,658,751, filed Sep. 29, 2006, Method for Implanting Soft Tissue.
U.S. Appl. No. 12/702,067 U.S. Pat. No. 8,672,968, filed Feb. 8, 2010, Method for Implanting Soft Tissue.
U.S. Appl. No. 14/211,977 U.S. Pat. No. 9,486,211, filed Mar. 14, 2014, Method for Implanting Soft Tissue.
U.S. Appl. No. 15/061,352 U.S. Pat. No. 10,004,493, filed Mar. 4, 2016, Method for Implanting Soft Tissue.
U.S. Appl. No. 15/664,572 U.S. Pat. No. 10,398,430, filed Jul. 31, 2017, Method for Implanting Soft Tissue.
U.S. Appl. No. 16/508,764 U.S. Pat. No. 11,259,794, filed Jul. 11, 2019, Method for Implanting Soft Tissue.
U.S. Appl. No. 17/492,082 U.S. Pat. No. 11,672,527, filed Oct. 1, 2021, Method for Implanting Soft Tissue.
U.S. Appl. No. 11/935,681 U.S. Pat. No. 7,905,903, filed Nov. 6, 2007, Method for Tissue Fixation.
U.S. Appl. No. 12/196,398 U.S. Pat. No. 7,959,650, filed Aug. 22, 2008, Adjustable Knotless Loops.
U.S. Appl. No. 13/102,182 U.S. Pat. No. 8,231,654, filed May 6, 2011, Adjustable Knotless Loops.
U.S. Appl. No. 10/984,624 U.S. Pat. No. 7,608,098, filed Nov. 9, 2004, Bone Fixation Device.
U.S. Appl. No. 11/294,694 U.S. Pat. No. 7,914,539, filed Dec. 5, 2005, Tissue Fixation Device.
U.S. Appl. No. 11/408,282, filed Apr. 20, 2006, Soft Tissue Conduit Device.
U.S. Appl. No. 12/419,491 U.S. Pat. No. 8,317,825, filed Apr. 7, 2009, Soft Tissue Conduit Device and Method.
U.S. Appl. No. 11/869,440 U.S. Pat. No. 7,857,830, filed Oct. 9, 2007, Soft Tissue Repair and Conduit Device.
U.S. Appl. No. 12/976,328 U.S. Pat. No. 8,273,106, filed Dec. 22, 2010, Soft Tissue Repair and Conduit Device.
U.S. Appl. No. 12/489,168 U.S. Pat. No. 8,361,113, filed Jun. 22, 2009, Method and Apparatus for Coupling Soft Tissue to a Bone.
U.S. Appl. No. 13/751,846 U.S. Pat. No. 9,492,158, filed Jan. 28, 2013, Method and Apparatus for Coupling Soft Tissue to a Bone.
U.S. Appl. No. 14/983,747 U.S. Pat. No. 10,154,837, filed Dec. 30, 2015, Method and Apparatus for Coupling Soft Tissue to a Bone.
U.S. Appl. No. 15/941,481 U.S. Pat. No. 10,973,507, filed Mar. 30, 2018, Method and Apparatus for Coupling Soft Tissue to a Bone.
U.S. Appl. No. 16/400,199 U.S. Pat. No. 11,446,019, filed May 1, 2019, Method and Apparatus for Coupling Soft Tissue to a Bone.
U.S. Appl. No. 17/190,686, filed Mar. 3, 2021, Method and Apparatus for Coupling Soft Tissue to a Bone.
U.S. Appl. No. 12/014,399 U.S. Pat. No. 7,909,851, filed Jan. 15, 2008, Soft Tissue Repair Assembly and Associated Method.
U.S. Appl. No. 13/045,691 U.S. Pat. No. 8,292,921, filed Mar. 11, 2011, Soft Tissue Repair Assembly and Associated Method.
U.S. Appl. No. 13/656,821 U.S. Pat. No. 9,173,651, filed Oct. 22, 2012, Soft Tissue Repair Device and Associated Methods.
U.S. Appl. No. 14/876,167 U.S. Pat. No. 10,251,637, filed Oct. 6, 2015, Soft Tissue Repair Device and Associated Methods.
U.S. Appl. No. 15/891,049 U.S. Pat. No. 10,932,770, filed Feb. 7, 2018, Soft Tissue Repair Device and Associated Methods.
U.S. Appl. No. 16/593,022 U.S. Pat. No. 11,617,572, filed Oct. 4, 2019, Soft Tissue Repair Device and Associated Methods.
U.S. Appl. No. 16/989,386 U.S. Pat. No. 11,819,205, filed Aug. 10, 2020, Soft Tissue Repair Device and Associated Methods.
U.S. Appl. No. 18/471,089, filed Sep. 20, 2023, Soft Tissue Repair Device and Associated Methods.
U.S. Appl. No. 12/014,340 U.S. Pat. No. 7,905,904, filed Jan. 15, 2008, Soft Tissue Repair Assembly and Associated Method.

(56) References Cited

OTHER PUBLICATIONS

U.S. Appl. No. 13/045,689 U.S. Pat. No. 8,337,525, filed Mar. 11, 2011, Soft Tissue Repair Assembly and Associated Method.
U.S. Appl. No. 13/721,970 U.S. Pat. No. 8,632,569, filed Dec. 20, 2012, Soft Tissue Repair Assembly and Associated Method.
U.S. Appl. No. 13/838,755 U.S. Pat. No. 9,510,819, filed Mar. 15, 2013, Soft Tissue Repair Device and Associated Methods.
U.S. Appl. No. 13/833,567 U.S. Pat. No. 9,561,025, filed Mar. 15, 2013, Soft Tissue Repair Device and Associated Methods.
U.S. Appl. No. 14/159,094 U.S. Pat. No. 9,622,736, filed Jan. 20, 2014, Soft Tissue Repair Device and Associated Methods.
U.S. Appl. No. 15/412,676, filed Jan. 23, 2017, Soft Tissue Repair Device and Associated Methods.
U.S. Appl. No. 16/806,611 U.S. Pat. No. 11,612,391, filed Mar. 2, 2020, Soft Tissue Repair Device and Associated Methods.
U.S. Appl. No. 18/126,022, filed Mar. 24, 2023, Soft Tissue Repair Device and Associated Methods.
U.S. Appl. No. 12/489,181 U.S. Pat. No. 8,298,262, filed Jun. 22, 2009, Method for Tissue Fixation.
U.S. Appl. No. 13/625,413 U.S. Pat. No. 9,402,621, filed Sep. 24, 2012, Method for Tissue Fixation.
U.S. Appl. No. 14/983,108 U.S. Pat. No. 10,321,906, filed Dec. 29, 2015, Method for Tissue Fixation.
U.S. Appl. No. 15/945,425 U.S. Pat. No. 10,987,099, filed Apr. 4, 2018, Method for Tissue Fixation.
U.S. Appl. No. 16/380,742 U.S. Pat. No. 11,311,287, filed Apr. 10, 2019, Method for Tissue Fixation.
U.S. Appl. No. 17/577,188, filed Jan. 17, 2022, Method for Tissue Fixation.
U.S. Appl. No. 10/983,236, filed Nov. 5, 2004, Tissue Repair Assembly.
U.S. Appl. No. 11/347,662, filed Feb. 3, 2006, Tissue Repair Assembly.
U.S. Appl. No. 16/795,181 U.S. Pat. No. 11,534,159, filed Feb. 19, 2020, Method and Apparatus for Coupling Soft Tissue to a Bone.
U.S. Appl. No. 17/550,074, filed Dec. 14, 2021, Method and Apparatus for Coupling Soft Tissue to a Bone.
U.S. Appl. No. 12/196,410 U.S. Pat. No. 8,118,836, filed Aug. 22, 2008, Method and Apparatus for Coupling Soft Tissue to a Bone.
U.S. Appl. No. 13/399,125 U.S. Pat. No. 8,840,645, filed Feb. 17, 2012, Method and Apparatus for Coupling Soft Tissue to a Bone.
U.S. Appl. No. 14/492,590 U.S. Pat. No. 9,572,655, filed Sep. 22, 2014, Method and Apparatus for Coupling Soft Tissue to a Bone.
U.S. Appl. No. 14/956,724 U.S. Pat. No. 9,801,708, filed Dec. 2, 2015, Method and Apparatus for Coupling Soft Tissue to a Bone.
U.S. Appl. No. 15/278,777 U.S. Pat. No. 10,092,288, filed Sep. 28, 2016, Method and Apparatus for Coupling Soft Tissue to a Bone.
U.S. Appl. No. 15/455,895 U.S. Pat. No. 10,695,052, filed Mar. 10, 2017, Method and Apparatus for Coupling Soft Tissue to a Bone.
U.S. Appl. No. 15/622,718 U.S. Pat. No. 10,687,803, filed Jun. 14, 2017, Method and Apparatus for Coupling Soft Tissue to a Bone.
U.S. Appl. No. 15/793,216 U.S. Pat. No. 10,729,430, filed Oct. 25, 2017, Method and Apparatus for Coupling Soft Tissue to a Bone.
U.S. Appl. No. 16/420,676 U.S. Pat. No. 11,284,884, filed May 23, 2019, Method and Apparatus for Coupling Soft Tissue to Bone.
U.S. Appl. No. 18/235,540, filed Aug. 18, 2023, Method and Apparatus for Coupling Anatomical Features.
U.S. Appl. No. 12/196,407 U.S. Pat. No. 8,137,382, filed Aug. 22, 2008, Method and Apparatus for Forming a Self-Locking Adjustable Suture Loop.
U.S. Appl. No. 13/412,116 U.S. Pat. No. 8,771,316, filed Mar. 5, 2012, Method and Apparatus for Coupling Anatomical Features.
U.S. Appl. No. 14/324,688 U.S. Pat. No. 9,498,204, filed Jul. 7, 2014, Method and Apparatus for Coupling Anatomical Features.
U.S. Appl. No. 13/412,127 U.S. Pat. No. 8,721,684, filed Mar. 5, 2012, Method and Apparatus for Coupling Anatomical Features.
U.S. Appl. No. 14/275,548 U.S. Pat. No. 9,510,821, filed May 12, 2014, Method and Apparatus for Coupling Anatomical Features.
U.S. Appl. No. 15/288,183 U.S. Pat. No. 10,398,428, filed Oct. 7, 2016, Method and Apparatus for Coupling Anatomical Features.
U.S. Appl. No. 15/662,572 U.S. Pat. No. 10,716,557, filed Jul. 28, 2017, Method and Apparatus for Coupling Anatomical Features.
U.S. Appl. No. 16/436,023 U.S. Pat. No. 11,259,792, filed Jun. 10, 2019, Method and Apparatus for Coupling Anatomical Features.
U.S. Appl. No. 17/545,668 U.S. Pat. No. 11,786,236, filed Dec. 8, 2021, Method and Apparatus for Coupling Anatomical Features.
U.S. Appl. No. 12/196,405 U.S. Pat. No. 8,128,658, filed Aug. 22, 2008, Method and Apparatus for Coupling Soft Tissue to Bone.
U.S. Appl. No. 13/181,729 U.S. Pat. No. 8,551,140, filed Jul. 13, 2011, Method and Apparatus for Coupling Soft Tissue to Bone.
U.S. Appl. No. 13/412,105 U.S. Pat. No. 8,932,331, filed Mar. 5, 2012, Method and Apparatus for Coupling Soft Tissue to Bone.
U.S. Appl. No. 14/594,285 U.S. Pat. No. 9,801,620, filed Jan. 12, 2015, Method and Apparatus for Coupling Soft Tissue to Bone.
U.S. Appl. No. 15/703,727 U.S. Pat. No. 10,603,029, filed Sep. 13, 2017, Method and Apparatus for Coupling Soft Tissue to Bone.
U.S. Appl. No. 16/802,248 U.S. Pat. No. 11,589,859, filed Feb. 26, 2020, Method and Apparatus for Coupling Soft Tissue to Bone.
U.S. Appl. No. 18/101,490, filed Jan. 25, 2023, Method and Apparatus for Coupling Soft Tissue to Bone.
U.S. Appl. No. 18/102,518, filed Jan. 27, 2023, Method and Apparatus for Coupling Soft Tissue to a Bone.
U.S. Appl. No. 12/474,802 U.S. Pat. No. 8,088,130, filed May 29, 2009, Method and Apparatus for Coupling Soft Tissue to a Bone.
U.S. Appl. No. 13/278,341 U.S. Pat. No. 8,608,777, filed Oct. 21, 2011, Method and Apparatus for Coupling Soft Tissue to a Bone.
U.S. Appl. No. 14/107,350 U.S. Pat. No. 9,532,777, filed Dec. 16, 2013, Method and Apparatus for Coupling Soft Tissue to a Bone.
U.S. Appl. No. 15/074,553 U.S. Pat. No. 10,004,489, filed Mar. 18, 2016, Method and Apparatus for Coupling Soft Tissue to a Bone.
U.S. Appl. No. 15/297,844 U.S. Pat. No. 10,098,629, filed Oct. 19, 2016, Method and Apparatus for Coupling Soft Tissue to a Bone.
U.S. Appl. No. 15/865,938 U.S. Pat. No. 10,542,967, filed Jan. 9, 2018, Method and Apparatus for Coupling Soft Tissue to a Bone.
U.S. Appl. No. 15/886,712 U.S. Pat. No. 10,595,851, filed Feb. 1, 2018, Method and Apparatus for Coupling Soft Tissue to a Bone.
U.S. Appl. No. 16/802,228 U.S. Pat. No. 11,471,147, filed Feb. 26, 2020, Method and Apparatus for Coupling Soft Tissue to a Bone.
U.S. Appl. No. 17/940,022, filed Sep. 8, 2022, Method and Apparatus for Coupling Soft Tissue to a Bone.
U.S. Appl. No. 12/570,854 U.S. Pat. No. 8,303,604, filed Sep. 30, 2009, Soft Tissue Repair Device and Method.
U.S. Appl. No. 13/645,964 U.S. Pat. No. 9,504,460, filed Oct. 5, 2012, Soft Tissue Repair Device and Method.
U.S. Appl. No. 15/332,590 U.S. Pat. No. 10,265,064, filed Oct. 24, 2016, Soft Tissue Repair Device and Method.
U.S. Appl. No. 16/255,300 U.S. Pat. No. 11,109,857, filed Jan. 23, 2019, Soft Tissue Repair Device and Method.
U.S. Appl. No. 17/392,971, filed Aug. 3, 2021, Soft Tissue Repair Device and Method.
U.S. Appl. No. 12/719,337 U.S. Pat. No. 9,078,644, filed Mar. 8, 2010, Fracture Fixation Device.
U.S. Appl. No. 14/794,309 U.S. Pat. No. 9,833,230, filed Jul. 8, 2015, Fracture Fixation Device.
U.S. Appl. No. 15/060,007 U.S. Pat. No. 10,349,931, filed Mar. 3, 2016, Fracture Fixation Device.
U.S. Appl. No. 15/866,089 U.S. Pat. No. 10,835,232, filed Jan. 9, 2018, Fracture Fixation Device.
U.S. Appl. No. 12/915,962 U.S. Pat. No. 8,562,647, filed Oct. 29, 2010, Method and Apparatus for Securing Soft Tissue to Bone.
U.S. Appl. No. 14/055,172 U.S. Pat. No. 9,724,090, filed Oct. 16, 2013, Method and Apparatus for Attaching Soft Tissue to Bone.
U.S. Appl. No. 15/654,386 U.S. Pat. No. 10,695,045, filed Jul. 19, 2017, Method and Apparatus for Attaching Soft Tissue to Bone.
U.S. Appl. No. 12/938,902 U.S. Pat. No. 8,597,327, filed Nov. 3, 2010, Method and Apparatus for Securing Soft Tissue to Bone.
U.S. Appl. No. 14/094,311 U.S. Pat. No. 9,642,661, filed Dec. 2, 2013, Method and Apparatus for Sternal Closure.
U.S. Appl. No. 15/461,675 U.S. Pat. No. 10,675,073, filed Mar. 17, 2017, Method and Apparatus for Sternal Closure.
U.S. Appl. No. 11/504,882 U.S. Pat. No. 8,998,949, filed Aug. 16, 2006, Soft Tissue Conduit Device.

(56) References Cited

OTHER PUBLICATIONS

U.S. Appl. No. 12/029,861 U.S. Pat. No. 8,251,998, filed Feb. 12, 2008, Chondral Defect Repair.
U.S. Appl. No. 13/587,374 U.S. Pat. No. 8,777,956, filed Aug. 16, 2012, Chondral Defect Repair.
U.S. Appl. No. 11/740,035, filed Apr. 25, 2007, Method for Treating Cartilage Defects.
U.S. Appl. No. 11/739,768 U.S. Pat. No. 8,137,354, filed Apr. 25, 2007, Localized Cartilage Defect Therapy.
U.S. Appl. No. 13/350,985 U.S. Pat. No. 9,198,673, filed Jan. 16, 2012, Localized Cartilage Defect Therapy.
U.S. Appl. No. 14/923,506, filed Oct. 27, 2015, Localized Cartilage Defect Therapy.
U.S. Appl. No. 13/111,564 U.S. Pat. No. 8,574,235, filed May 19, 2011, Method for Trochanteric Reattachment.
U.S. Appl. No. 14/071,295 U.S. Pat. No. 9,005,287, filed Nov. 4, 2013, Method for Bone Reattachment.
U.S. Appl. No. 13/288,459 U.S. Pat. No. 9,468,433, filed Nov. 3, 2011, Method and Apparatus for Forming a Self-Locking Adjustable Loop.
U.S. Appl. No. 15/294,994 U.S. Pat. No. 10,517,587, filed Oct. 17, 2016, Method and Apparatus for Forming a Self-Locking Adjustable Loop.
U.S. Appl. No. 16/443,391 U.S. Pat. No. 11,317,907, filed Jun. 17, 2019, Method and Apparatus for Forming a Self-Locking Adjustable Loop.
U.S. Appl. No. 13/288,463 U.S. Pat. No. 8,936,621, filed Nov. 3, 2011, Method and Apparatus for Forming a Self-Locking Adjustable Loop.
U.S. Appl. No. 14/599,909 U.S. Pat. No. 9,993,241, filed Jan. 19, 2015, Method and Apparatus for Forming a Self-Locking Adjustable Loop.
U.S. Appl. No. 15/917,143 U.S. Pat. No. 11,039,826, filed Mar. 9, 2018, Method and Apparatus for Forming a Self-Locking Adjustable Loop.
U.S. Appl. No. 17/232,672, filed Apr. 16, 2021, Method and Apparatus for Forming a Self-Locking Adjustable Loop.
U.S. Appl. No. 13/720,648 U.S. Pat. No. 9,357,991, filed Dec. 19, 2012, Method and Apparatus for Stitching Tendons.
U.S. Appl. No. 15/166,480 U.S. Pat. No. 10,265,159, filed May 27, 2016, Method and Apparatus for Stitching Tendons.
U.S. Appl. No. 16/160,559 U.S. Pat. No. 11,241,305, filed Oct. 15, 2018, Method and Apparatus for Stitching Tendons.
U.S. Appl. No. 14/095,639 U.S. Pat. No. 9,918,827, filed Dec. 3, 2013, Scaffold for Spring Ligament Repair.
U.S. Appl. No. 14/095,614 U.S. Pat. No. 9,918,826, filed Dec. 3, 2013, Scaffold for Spring Ligament Repair.
U.S. Appl. No. 15/722,002 U.S. Pat. No. 10,758,221, filed Oct. 2, 2017, Scaffold for Spring Ligament Repair.
U.S. Appl. No. 13/098,897 U.S. Pat. No. 8,562,645, filed May 2, 2011, Method and Apparatus for Forming a Self-Locking Adjustable Loop.
U.S. Appl. No. 14/055,191 U.S. Pat. No. 9,539,003, filed Oct. 16, 2013, Method and Apparatus for Forming a Self-Locking Adjustable Loop.
U.S. Appl. No. 15/401,768 U.S. Pat. No. 10,610,217, filed Jan. 9, 2017, Method and Apparatus for Forming a Self-Locking Adjustable Loop.
U.S. Appl. No. 15/972,646 U.S. Pat. No. 11,096,684, filed May 7, 2018, Method and Apparatus for Forming a Self-Locking Adjustable Loop.
U.S. Appl. No. 13/098,927 U.S. Pat. No. 8,652,171, filed May 2, 2011, Method and Apparatus for Soft Tissue Fixation.
U.S. Appl. No. 14/182,038 U.S. Pat. No. 9,763,656, filed Feb. 17, 2014, Method and Apparatus for Soft Tissue Fixation.
U.S. Appl. No. 15/682,187 U.S. Pat. No. 10,729,421, filed Aug. 21, 2017, Method and Apparatus for Soft Tissue Fixation.
U.S. Appl. No. 16/895,246 U.S. Pat. No. 11,723,648, filed Jun. 8, 2020, Method and Apparatus for Soft Tissue Fixation.
U.S. Appl. No. 18/093,114, filed Jan. 4, 2023, Method and Apparatus for Soft Tissue Fixation.
U.S. Appl. No. 18/134,897, filed Apr. 14, 2023, Method and Apparatus for Soft Tissue Fixation.
U.S. Appl. No. 18/497,342, filed Oct. 30, 2023, Method and Apparatus for Soft Tissue Fixation.
U.S. Appl. No. 12/788,978 U.S. Pat. No. 8,801,783, filed May 27, 2010, Prosthetic Ligament System for Knee Joint.
U.S. Appl. No. 14/456,286 U.S. Pat. No. 9,681,940, filed Aug. 11, 2014, Ligament System for Knee Joint.
U.S. Appl. No. 15/626,384 U.S. Pat. No. 10,517,714, filed Jun. 19, 2017, Ligament System for Knee Joint.
U.S. Appl. No. 16/690,671 U.S. Pat. No. 11,376,115, filed Nov. 21, 2019, Prosthetic Ligament System for Knee Joint.
U.S. Appl. No. 11/386,071 U.S. Pat. No. 8,034,090, filed Mar. 21, 2006, Bone Fixation Device.
U.S. Appl. No. 13/293,825 U.S. Pat. No. 9,149,267, filed Nov. 10, 2011, Method and Apparatus for Coupling Soft Tissue to a Bone.
U.S. Appl. No. 14/854,308 U.S. Pat. No. 10,022,118, filed Sep. 15, 2015, Method and Apparatus for Coupling Soft Tissue to a Bone.
U.S. Appl. No. 13/071,563 U.S. Pat. No. 8,926,613, filed Mar. 25, 2011, Method and Apparatus for Forming a Bone Hole.
U.S. Appl. No. 14/589,101, filed Jan. 5, 2015, Method and Apparatus for Forming a Bone Hole.
U.S. Appl. No. 13/311,936 U.S. Pat. No. 9,408,599, filed Dec. 6, 2011, Method and Apparatus for Coupling Soft Tissue to a Bone.
U.S. Appl. No. 15/231,074, filed Aug. 8, 2016, Method and Apparatus for Coupling Soft Tissue to a Bone.
U.S. Appl. No. 13/757,003 U.S. Pat. No. 9,357,992, filed Feb. 1, 2013, Method for Coupling Soft Tissue to a Bone.
U.S. Appl. No. 13/295,126 U.S. Pat. No. 9,271,713, filed Nov. 14, 2011, Method and Apparatus for Tensioning a Suture.
U.S. Appl. No. 13/281,009 U.S. Pat. No. 9,538,998, filed Oct. 25, 2011, Method and Apparatus for Fracture Fixation.
U.S. Appl. No. 13/269,097 U.S. Pat. No. 8,672,969, filed Oct. 7, 2011, Fracture Fixation Device.
U.S. Appl. No. 14/215,550 U.S. Pat. No. 9,788,876, filed Mar. 17, 2014, Fracture Fixation Device.
U.S. Appl. No. 15/715,731 U.S. Pat. No. 10,743,925, filed Sep. 26, 2017, Fracture Fixation Device.
U.S. Appl. No. 13/757,019 U.S. Pat. No. 9,314,241, filed Feb. 1, 2013, Apparatus for Coupling Soft Tissue to a Bone.
U.S. Appl. No. 15/131,663 U.S. Pat. No. 10,368,856, filed Apr. 18, 2016, Apparatus for Coupling Soft Tissue to a Bone.
U.S. Appl. No. 13/790,982 U.S. Pat. No. 9,370,350, filed Mar. 8, 2013, Apparatus for Coupling Soft Tissue to a Bone.
U.S. Appl. No. 13/790,997 U.S. Pat. No. 9,381,013, filed Mar. 8, 2013, Method for Coupling Soft Tissue to a Bone.
U.S. Appl. No. 15/200,546 U.S. Pat. No. 10,363,028, filed Jul. 1, 2016, Method for Coupling Soft Tissue to a Bone.
U.S. Appl. No. 16/428,277 U.S. Pat. No. 11,534,157, filed May 31, 2019, Method for Coupling Soft Tisuse to a Bone.
U.S. Appl. No. 17/991,832, filed Nov. 21, 2022, Method for Coupling Soft Tissue to a Bone.
U.S. Appl. No. 12/788,973 U.S. Pat. No. 8,500,818, filed May 27, 2010, Knee Prosthesis Assembly With Ligament Link.
U.S. Appl. No. 13/959,145 U.S. Pat. No. 9,414,925, filed Aug. 5, 2013, Method of Implanting a Knee Prosthesis Assembly With a Ligament Link.
U.S. Appl. No. 13/109,672 U.S. Pat. No. 8,968,364, filed May 17, 2011, Method and Apparatus for Fixation of an ACL Graft.
U.S. Appl. No. 14/635,055 U.S. Pat. No. 10,004,588, filed Mar. 2, 2015, Method and Apparatus for Fixation of an ACL Graft.
U.S. Appl. No. 15/956,444 U.S. Pat. No. 11,065,103, filed Apr. 18, 2018, Method and Apparatus for Fixation of an ACL Graft.
U.S. Appl. No. 13/109,667 U.S. Pat. No. 8,771,352, filed May 17, 2011, Method and Apparatus for Tibial Fixation of an ACL Graft.
U.S. Appl. No. 13/889,851 U.S. Pat. No. 9,216,078, filed May 8, 2013, Method and Apparatus for Tibial Fixation of an ACL Graft.
U.S. Appl. No. 14/974,516, filed Dec. 18, 2015, Method and Apparatus for Tibial Fixation of an ACL Graft.
U.S. Appl. No. 13/177,153 U.S. Pat. No. 8,652,172, filed Jul. 6, 2011, Flexible Anchors for Tissue Fixation.

(56) References Cited

OTHER PUBLICATIONS

U.S. Appl. No. 14/182,046 U.S. Pat. No. 9,603,591, filed Feb. 17, 2014, Flexible Anchors for Tissue Fixation.
U.S. Appl. No. 12/107,437, filed Apr. 22, 2008, Method and Apparatus for Attaching Soft Tissue to Bone.
U.S. Appl. No. 12/398,548 U.S. Pat. No. 8,118,868, filed Mar. 5, 2009, Method and Apparatus for Attaching Soft Tissue to Bone.
"Applicant U.S. Appl. No. 17/516,664, Response filed Sep. 18, 2024 to Non Final Office Action mailed Jun. 20, 2024", 10 pgs.
"U.S. Appl. No. 17/232,672, Notice of Allowance mailed Apr. 16, 2024", 11 pgs.
"U.S. Appl. No. 17/232,672, Preliminary Amendment filed Apr. 19, 2021", 5 pgs.
"U.S. Appl. No. 17/232,672, Response filed Feb. 29, 2024 to Restriction Requirement mailed Feb. 26, 2024", 6 pgs.
"U.S. Appl. No. 17/232,672, Restriction Requirement mailed Feb. 26, 2024", 6 pgs.
"U.S. Appl. No. 17/392,971, Examiner Interview Summary mailed Oct. 7, 2024", 2 pgs.
"U.S. Appl. No. 17/392,971, Examiner Interview Summary mailed Oct. 11, 2024", 3 pgs.
"U.S. Appl. No. 17/392,971, Non Final Action with Restriction Requirement mailed Apr. 18, 2024", 8 pgs.
"U.S. Appl. No. 17/392,971, Non Final Office Action mailed Apr. 18, 2024", 8 pgs.
"U.S. Appl. No. 17/392,971, Notice of Allowance mailed Sep. 18, 2024", 8 pgs.
"U.S. Appl. No. 17/392,971, Response filed Jul. 17, 2024 to Non Final Office Action mailed Apr. 18, 2024", 9 pgs.
"U.S. Appl. No. 17/392,971, Response filed Jul. 17, 2024 to Non Final Office Action mailed Apr. 18, 2024", 10 pgs.
"U.S. Appl. No. 17/392,971, Supplemental Preliminary Amendment filed Jan. 12, 2024", 7 pgs.
"U.S. Appl. No. 17/516,664, Non Final Office Action mailed Jun. 20, 2024", 16 pgs.
"U.S. Appl. No. 17/516,664, Notice of Allowance mailed Jan. 31, 2025", 8 pgs.
"U.S. Appl. No. 17/550,074, Notice of Allowance mailed Jun. 3, 2024", 9 pgs.
"U.S. Appl. No. 17/577,188, Supplemental Preliminary Amendment filed Dec. 21, 2023", 5 pgs.
"U.S. Appl. No. 17/940,022, Notice of Allowance mailed Feb. 7, 2024", 8 pgs.
"U.S. Appl. No. 18/093,114, Notice of Allowance mailed May 8, 2025", 10 pgs.
"U.S. Appl. No. 18/093,114, PTO Response to Rule 312 Communication mailed May 19, 2025", 2 pgs.
"U.S. Appl. No. 18/093,114, PTO Response to Rule 312 Communication mailed May 20, 2025", 2 pgs.
"U.S. Appl. No. 18/093,114, Response filed Apr. 7, 2025 to Restriction Requirement mailed Mar. 31, 2025", 7 pgs.
"U.S. Appl. No. 18/093,114, Restriction Requirement mailed Mar. 31, 2025", 6 pgs.
"U.S. Appl. No. 18/101,490, Non Final Office Action mailed Jun. 12, 2024", 20 pgs.
"U.S. Appl. No. 18/101,490, Notice of Allowance mailed Nov. 14, 2024", 10 pgs.
"U.S. Appl. No. 18/101,490, Response filed Sep. 12, 2024 to Non Final Office Action mailed Jun. 12, 2024", 10 pgs.
"U.S. Appl. No. 18/102,518, Corrected Notice of Allowability mailed Aug. 27, 2024", 2 pgs.
"U.S. Appl. No. 18/102,518, Notice of Allowance mailed Apr. 18, 2024", 11 pgs.
"U.S. Appl. No. 18/126,022, Notice of Allowance mailed Jul. 29, 2025", 12 pgs.
"U.S. Appl. No. 18/126,022, Response filed Jun. 5, 2025 to Restriction Requirement mailed Apr. 30, 2025", 6 pgs.
"U.S. Appl. No. 18/126,022, Restriction Requirement mailed Apr. 30, 2025", 8 pgs.
"U.S. Appl. No. 18/134,897, Notice of Allowance mailed May 15, 2025", 11 pgs.
"U.S. Appl. No. 18/134,897, Response filed Apr. 9, 2025 to Restriction Requirement mailed Apr. 2, 2025", 9 pgs.
"U.S. Appl. No. 18/134,897, Restriction Requirement mailed Apr. 2, 2025", 6 pgs.
"U.S. Appl. No. 18/235,540, Advisory Action mailed Apr. 4, 2025", 3 pgs.
"U.S. Appl. No. 18/235,540, Final Office Action mailed Feb. 28, 2025", 19 pgs.
"U.S. Appl. No. 18/235,540, Non Final Office Action mailed Nov. 14, 2024", 17 pgs.
"U.S. Appl. No. 18/235,540, Notice of Allowance mailed Jun. 4, 2025", 12 pgs.
"U.S. Appl. No. 18/235,540, Response filed Mar. 27, 2025 to Final Office Action malled Feb. 28, 2025", 8 pgs.
"U.S. Appl. No. 18/235,540, Response filed Dec. 13, 2024 to Non Final Office Action mailed Nov. 14, 2024", 11 pgs.
"U.S. Appl. No. 18/471,089, Response filed Jul. 18, 2025 to Restriction Requirement mailed Jun. 5, 2025", 8 pgs.
"U.S. Appl. No. 18/471,089, Restriction Requirement mailed Jun. 5, 2025", 6 pgs.
"U.S. Appl. No. 18/497,342, Restriction Requirement mailed Jul. 28, 2025", 6 pgs.
"U.S. Appl. No. 18/531,362, Supplemental Preliminary Amendment filed Dec. 21, 2023", 6 pgs.
"U.S. Appl. No. 18/531,396, Supplemental Amendment filed Jan. 18, 2024", 10 pgs.
"U.S. Appl. No. 18/531,431, Supplemental Preliminary Amendment filed Jan. 19, 2024", 5 pgs.
"U.S. Appl. No. 18/583,499, Corrected Notice of Allowability mailed Dec. 4, 2024", 2 pgs.
"U.S. Appl. No. 18/583,499, Notice of Allowance mailed Nov. 21, 2024", 9 pgs.
"U.S. Appl. No. 18/583,499, Preliminary Amendment filed Feb. 26, 2024", 6 pgs.

* cited by examiner

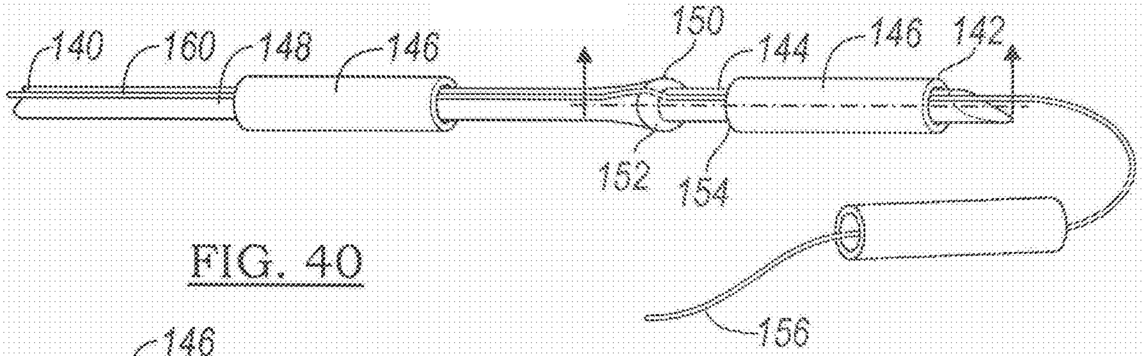
FIG. 40
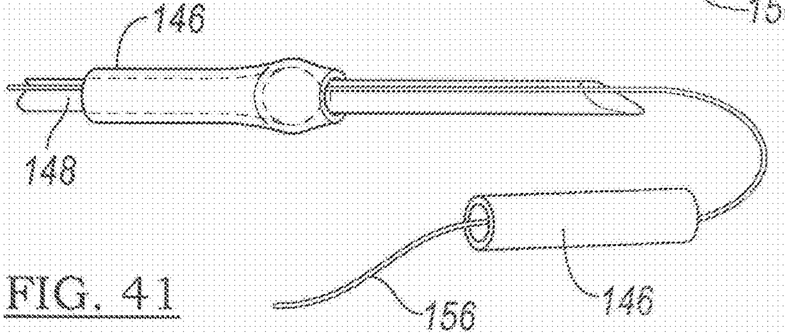
FIG. 41
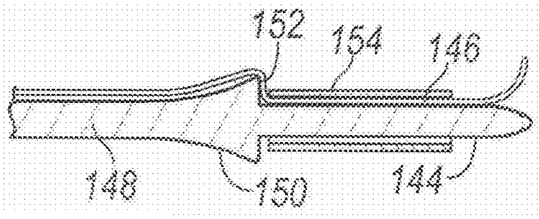
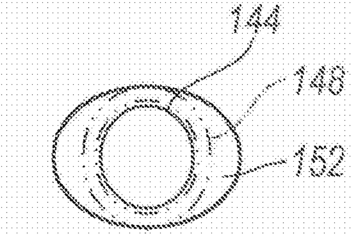
FIG. 43
FIG. 42
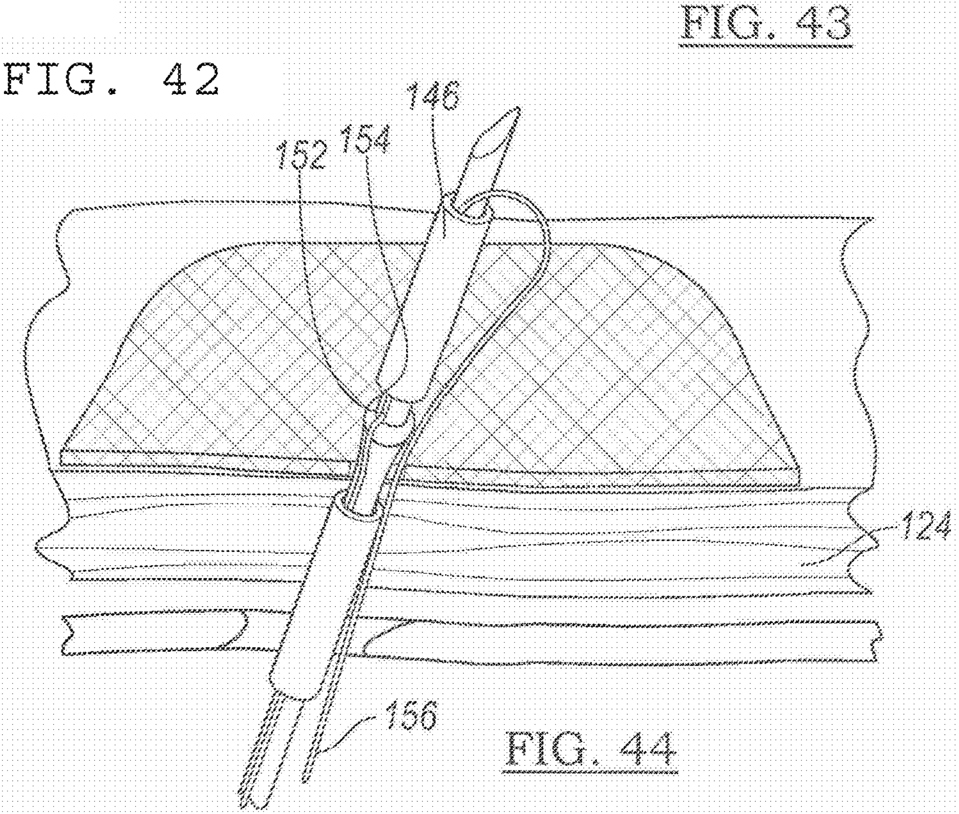
FIG. 44

METHOD AND APPARATUS FOR COUPLING SOFT TISSUE TO A BONE

CROSS-REFERENCE TO RELATED APPLICATIONS

This application is a continuation of U.S. patent application Ser. No. 17/190,686 filed Mar. 3, 2021, now U.S. Pat. No. 11,896,210 issued on Feb. 13, 2024, which is a continuation of U.S. patent application Ser. No. 15/941,481 filed Mar. 30, 2018, now U.S. Pat. No. 10,973,507 issued on Apr. 13, 2021, which is a continuation of U.S. patent application Ser. No. 14/983,747 filed Dec. 30, 2015, now U.S. Pat. No. 10,154,837 issued on Dec. 18, 2018, which is a continuation of U.S. patent application Ser. No. 13/751,846 filed Jan. 28, 2013, now U.S. Pat. No. 9,492,158 issued on Nov. 15, 2016, which is a divisional of U.S. patent application Ser. No. 12/489,168 filed Jun. 22, 2009, now U.S. Pat. No. 8,361,113 issued on Jan. 29, 2013.

The disclosures of the above applications are incorporated herein by reference.

FIELD

The present disclosure relates to method of coupling soft tissue to a bone and, more particularly, to a method of implanting an ACL within a femoral tunnel.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors may be made. For example, the procedure of tying knots may be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations may be significantly lower than the tensile strength of the suture material.

To improve on these uses, sutures having a single preformed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Relaxation of the system, however may allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

To overcome the aforementioned deficiencies, a method for configuring a braided tubular suture and a suture configuration are disclosed. The method includes passing a first end of the suture through a first aperture into a passage defined by the suture and out a second aperture defined by the suture so as to place the first end outside of the passage. A second end of the suture is passed through the second aperture into the passage and out the first aperture so as to place the second end outside of the passage.

A method of surgically implanting a suture construction in a femoral tunnel is disclosed. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. The first and second ends and the first and second loops are then passed through the femoral tunnel. Soft tissue is then passed through the first and second loops. Tension is applied onto the first and second ends to constrict the first and second loops to pull the soft tissue into the tunnel.

In another embodiment, a method of surgically implanting a suture is disclosed. The suture is passed through a bore defined by a first fastener. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. A second fastener is coupled to at least one of the first and second loops. After the fastener is coupled to the patient, tension is applied onto the first and second ends to constrict at least one of the first and second loops.

In another embodiment a method of surgically implanting a soft tissue replacement for attaching two bone members is disclosed. A first and second tunnel is formed in first and second bones. A locking member having a first profile which allows insertion of the locking member through the tunnel and a second profile which allows engagement with the positive locking surface upon rotation of the locking member is provided. The suture construction described above is coupled to the locking member. The first and second ends and the first and second loops of the construction and the locking member are threaded through the first and second tunnels. Soft tissue is threaded through the first and second loops so as to engage bearing surfaces on the first and second loops. The locking member is then engaged.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 40-45 represent an alternate suture construction.

DETAILED DESCRIPTION

Figure 1:
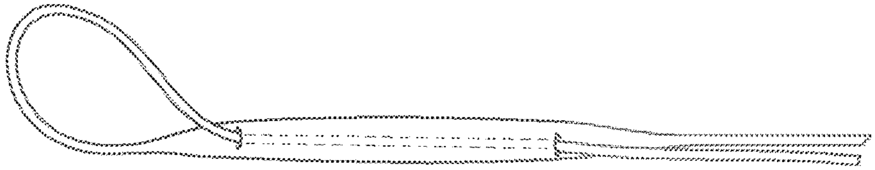
FIG. 1 (prior art)
FIG. 1 represents a prior art suture configuration.

The following description is merely exemplary in nature and is not intended to limit the present disclosure, application, or uses. It should be understood that throughout the drawings, corresponding reference numerals indicate like or corresponding parts and features.

Figure 2A:
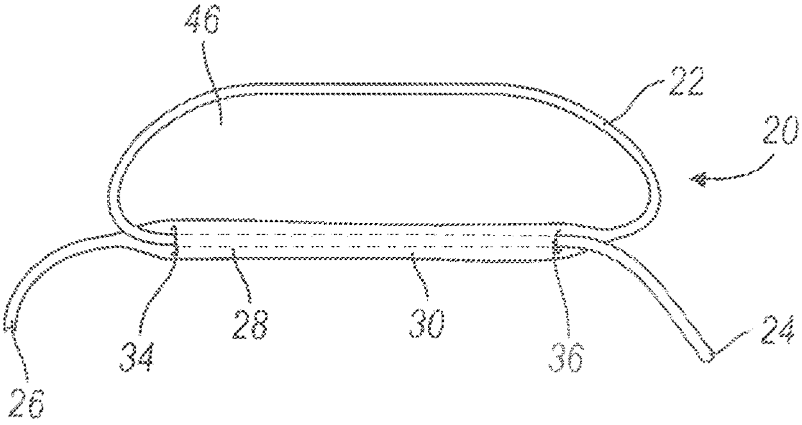
FIGS. 2A and 2B represent suture constructions according to the teachings.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Figure 2B:
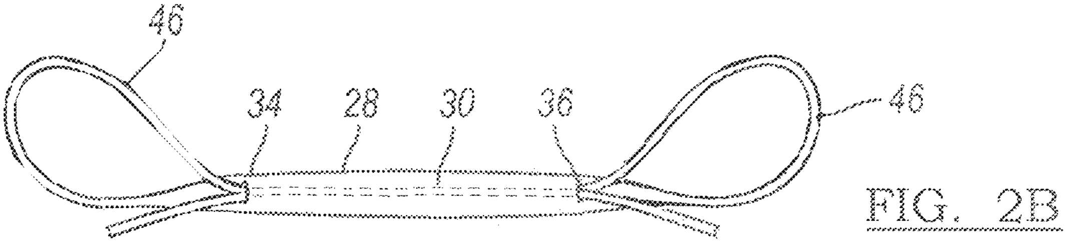
Figure 3:
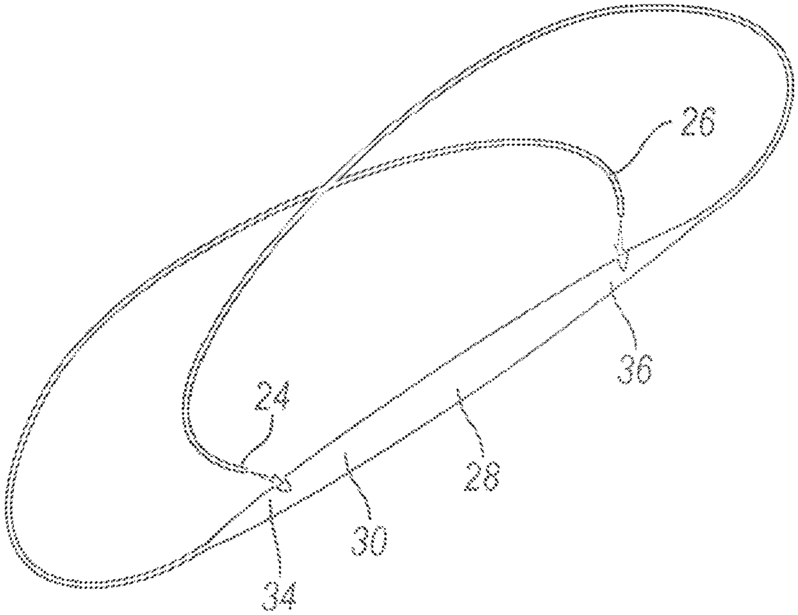
FIG. 3 represents the formation of the suture configuration shown in FIG. 4A.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two loops 46 and 46'. As seen in FIG. 2B, the relationship of the first and second apertures 32 and 34 with respect to the first and second ends 24 and 26 can be modified so as to allow a bow-tie suture construction 36. As described below, the longitudinal and parallel placement of first and second suture portions 38 and 40 of the suture 22 within the longitudinal passage 30 resists the reverse relative movement of the first and second portions 38 and 40 of the suture once it is tightened.

The first and second apertures are formed during the braiding process as loose portions between pairs of fibers defining the suture. As further described below, the first and second ends 24 and 26 can be passed through the longitudinal passage 30 multiple times. It is envisioned that either a single or multiple apertures can be formed at the ends of the longitudinally formed passage.

Figure 4A:
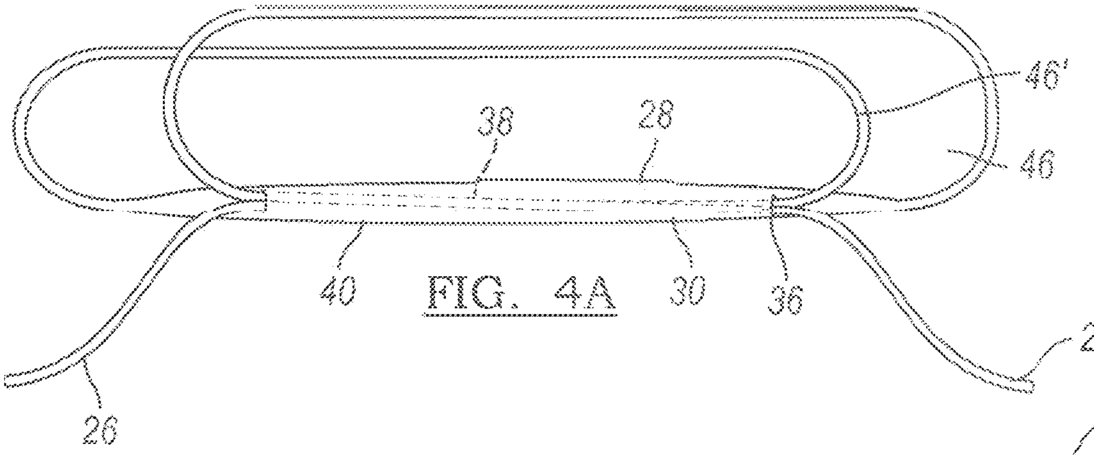
FIGS. 4A and 4B represent alternate suture configurations.
Figure 4B:
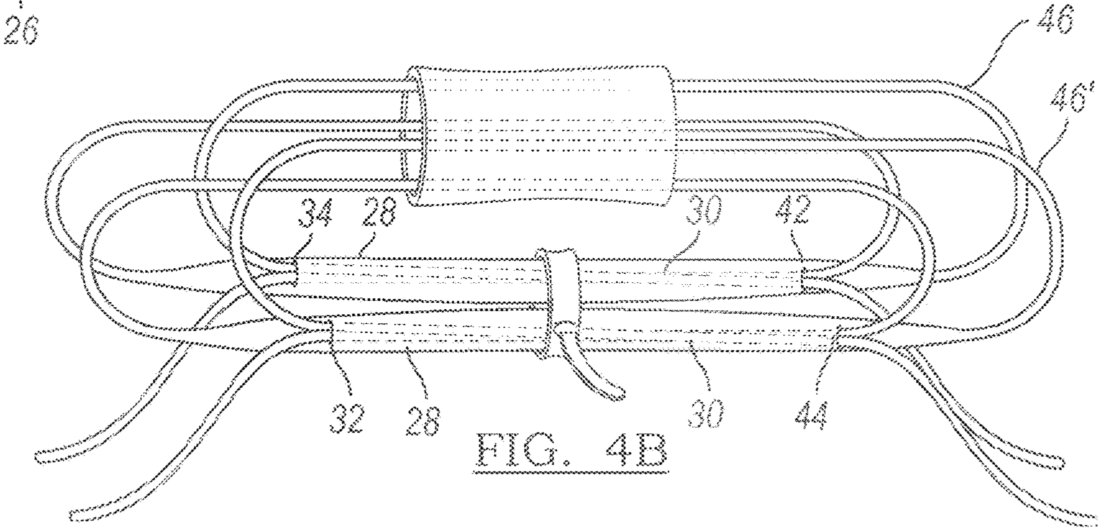

As best seen in FIGS. 4A and 4B, a portion of the braided body 28 of the suture defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 5:
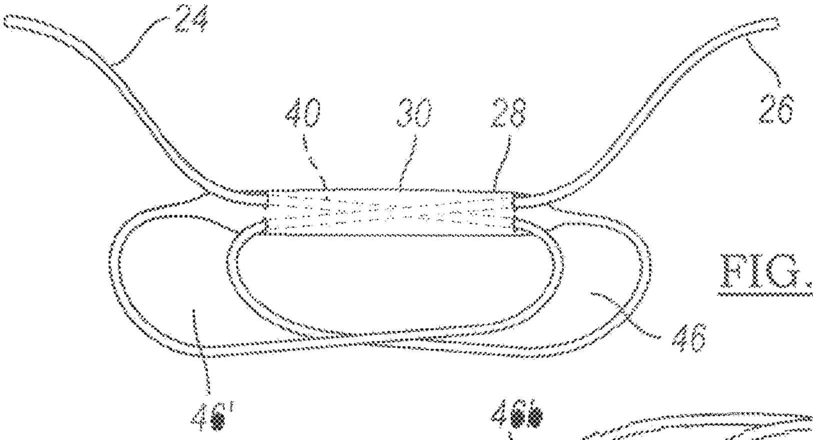
FIGS. 5-7 represent further alternate suture configurations.
Figure 6:
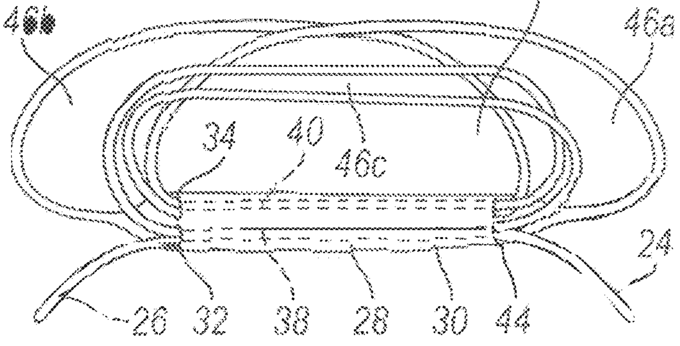
Figure 7:
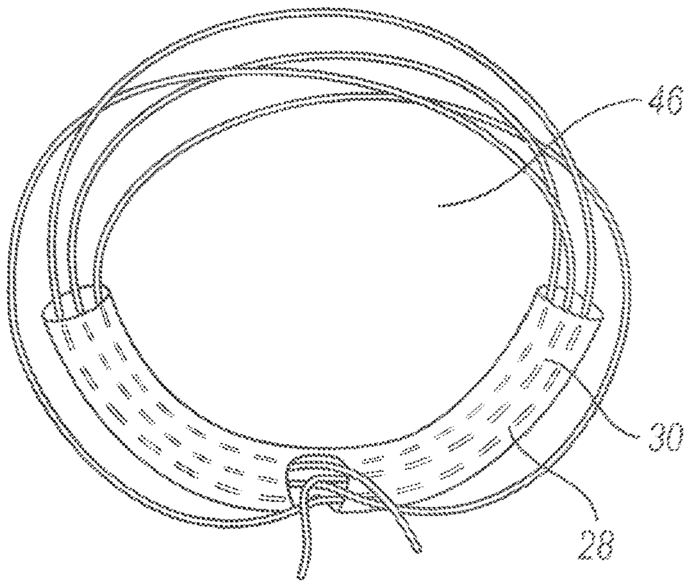
Figure 8:
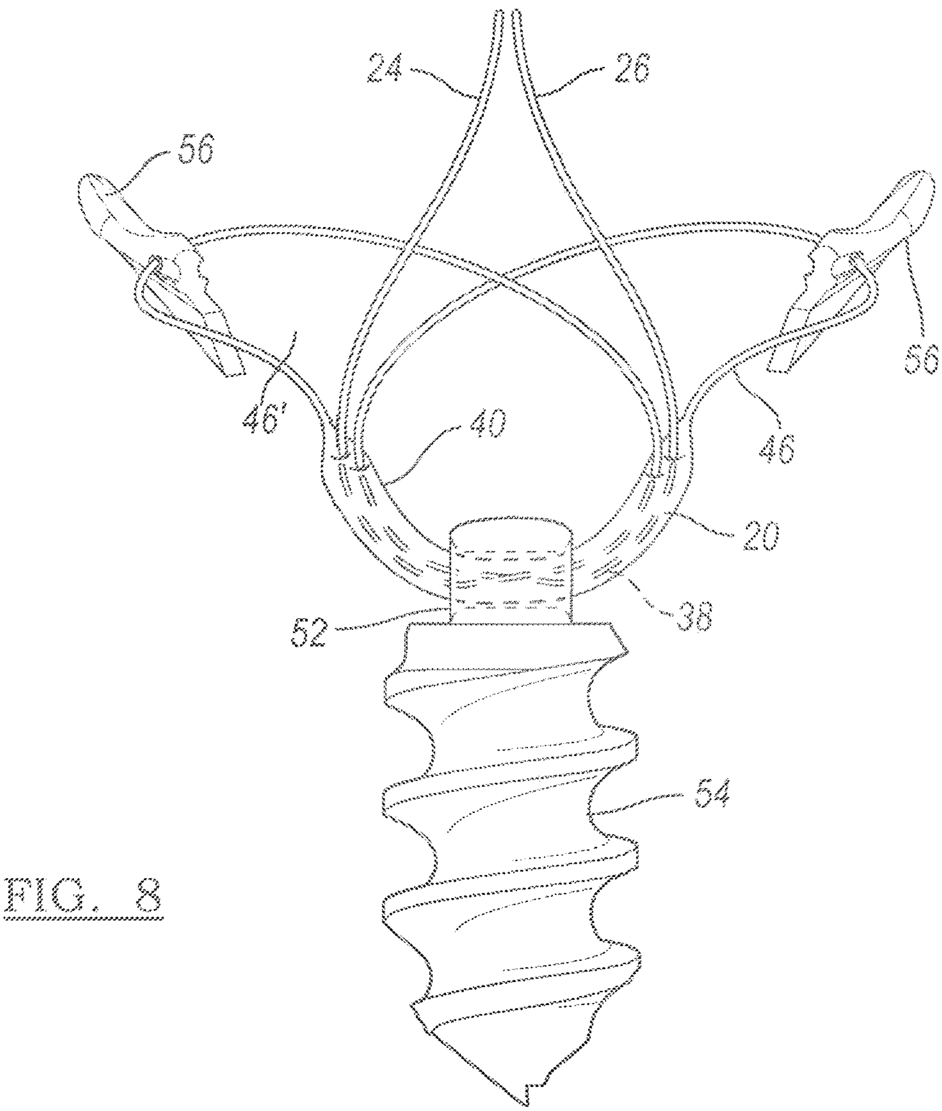
FIG. 8 represents the suture construction according to FIG. 5 coupled to a bone engaging fastener.
Figure 9:
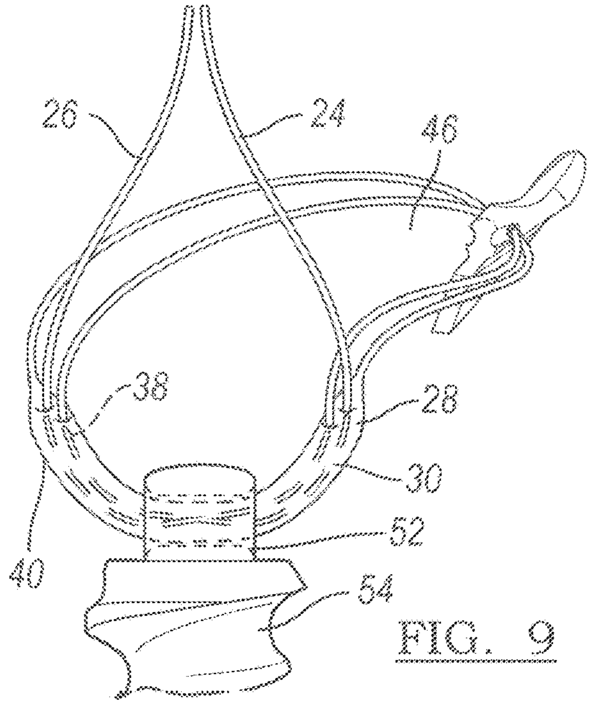
FIGS. 9-11B represent the coupling of the suture construction according to FIG. 5 to a bone screw.
Figure 10:
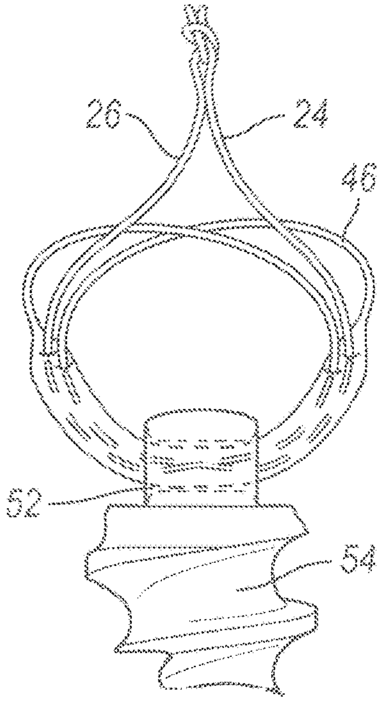

FIGS. 5-7 represent alternate constructions wherein a plurality of loops 46*a-d* are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture with respect to each other.

Upon applying tension to the first and second ends 24 and 26 of the suture 22, the size of the loops 46*a-d* is reduced to a desired size or load. At this point, additional tension causes the body of the suture defining the longitudinal passage 30 to constrict about the parallel portions of the suture within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
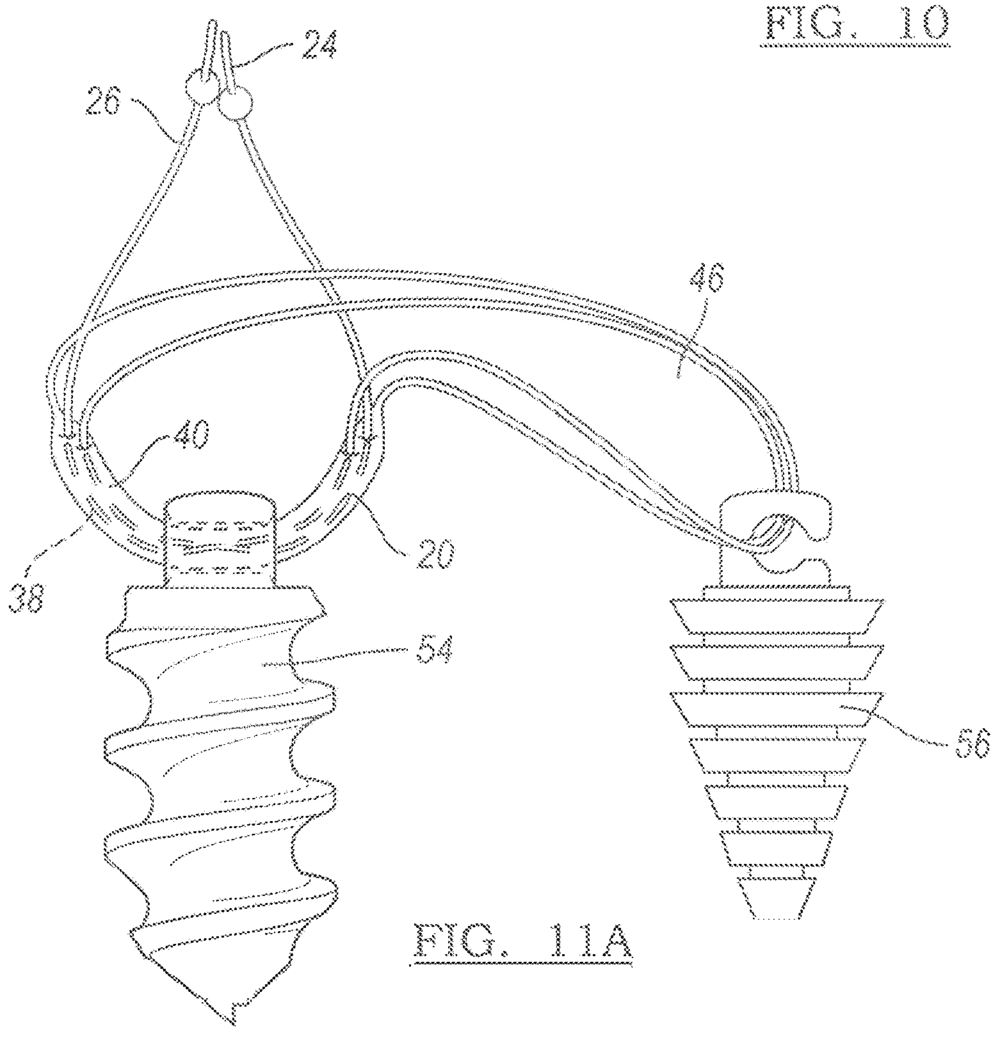
Figure 11B:
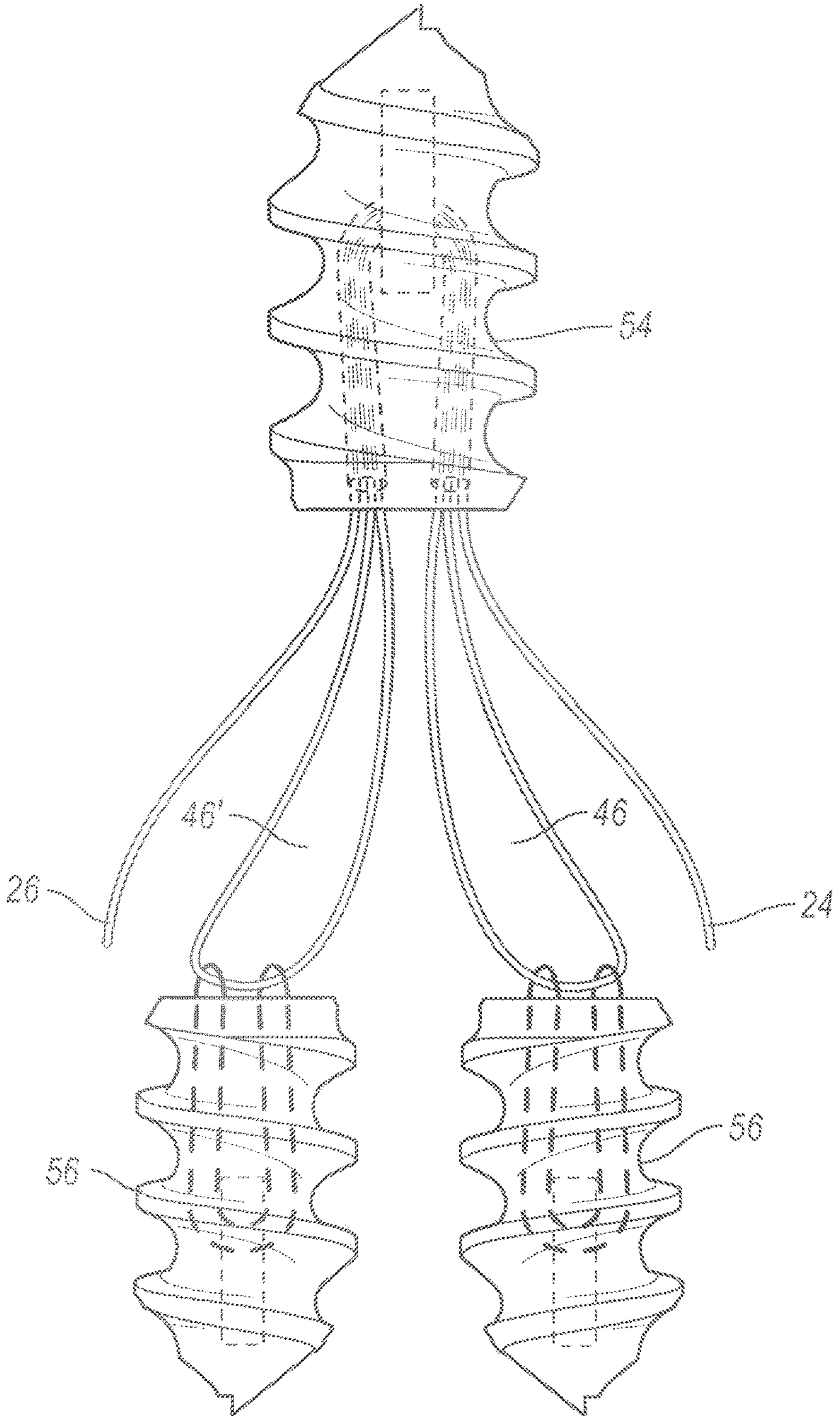

FIG. 11B represents the coupling of the suture construction according to FIG. 2B with a bone fastening member. Coupled to a pair of loops 46 and 46' is tissue fastening members 56. The application of tension to either the first or second end 24 or 26 will tighten the loops 46 or 46' separately.

Figure 12A:
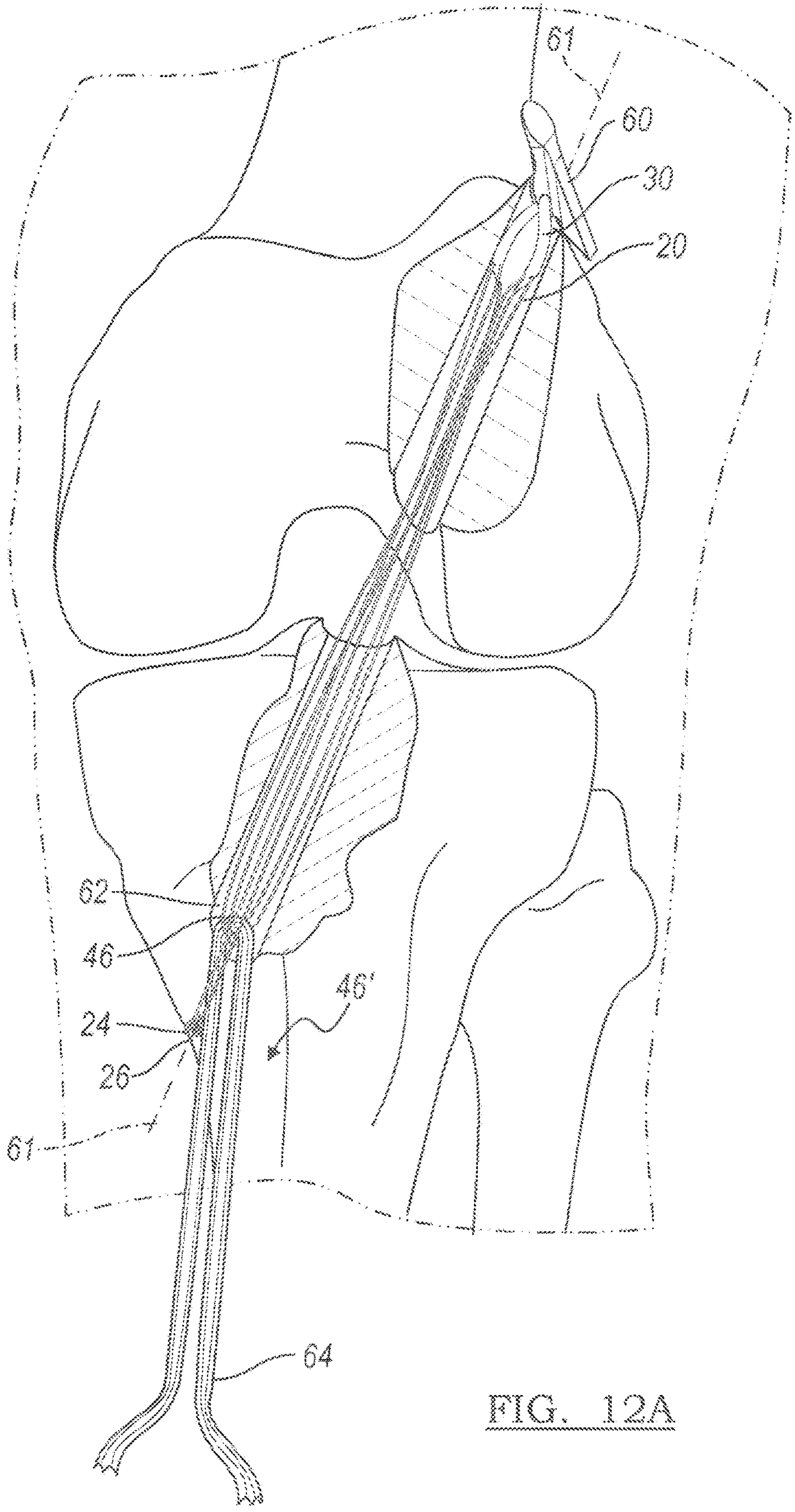
FIGS. 12A-12E represent the coupling of a soft tissue to an ACL replacement in a femoral/humeral reconstruction.
Figure 12B:
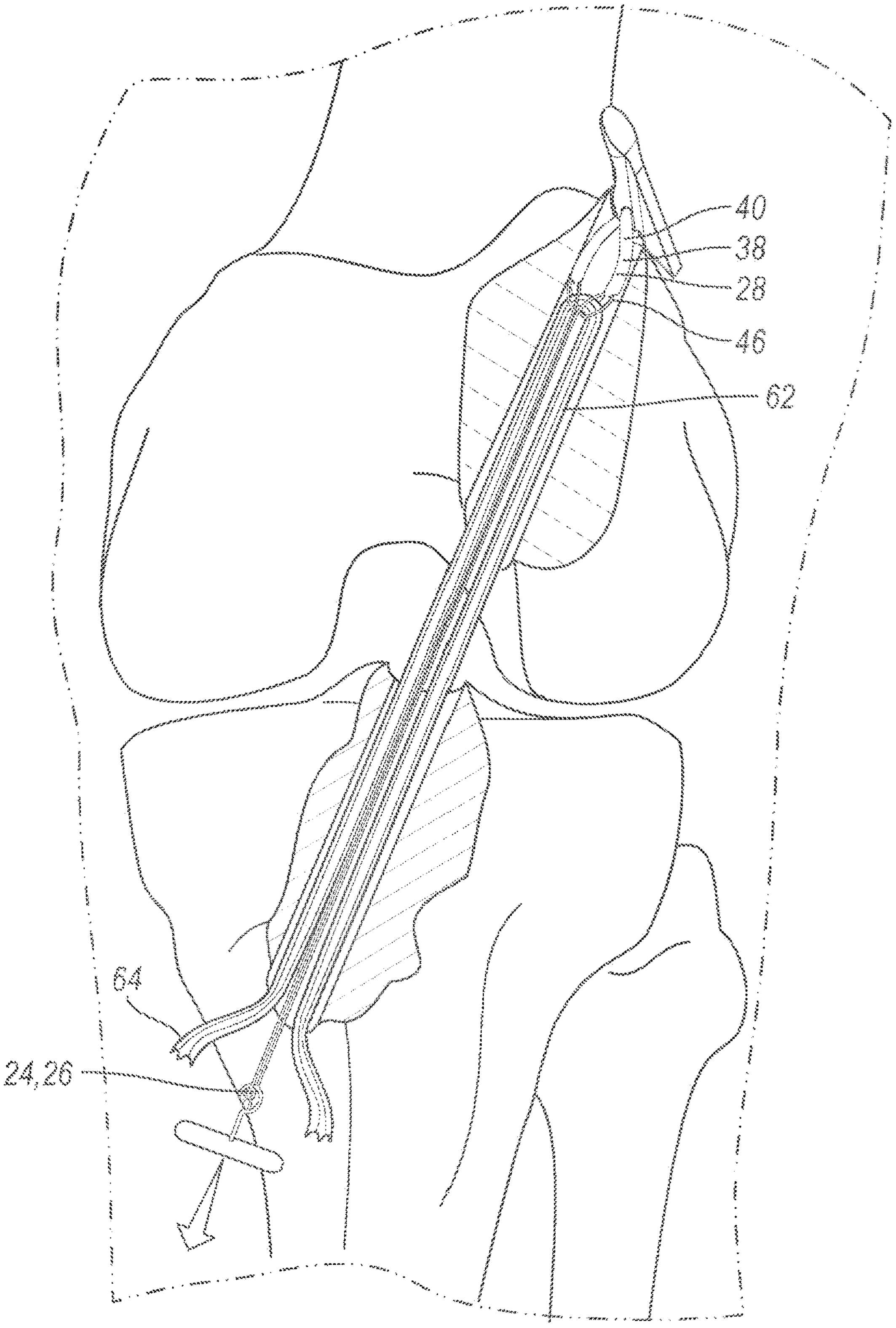

FIGS. 12A-12E represent potential uses of the suture constructions 20 in FIGS. 2A-7 in an ACL repair. As can be seen in FIG. 12A, the longitudinal passage portion 30 of suture construction 20 can be first coupled to a fixation member 60. The member 60 can have a first profile which allows insertion of the member 60 through the tunnel and a second profile which allows engagement with a positive locking surface upon rotation. The longitudinal passage portion 30 of the suture construction 20, member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the orientation of the longitudinal passage portion 30, the loops 46, and ends 24, 26 allow for tension to be applied to the construction 20 without applying non-seating forces to the fixation member 60. As an example, should the loops 24, 26 be positioned at the member 60, application of forces to the ends 24, 26 may reduce the seating force applied by the member 60 onto the bone.

Figure 12C:
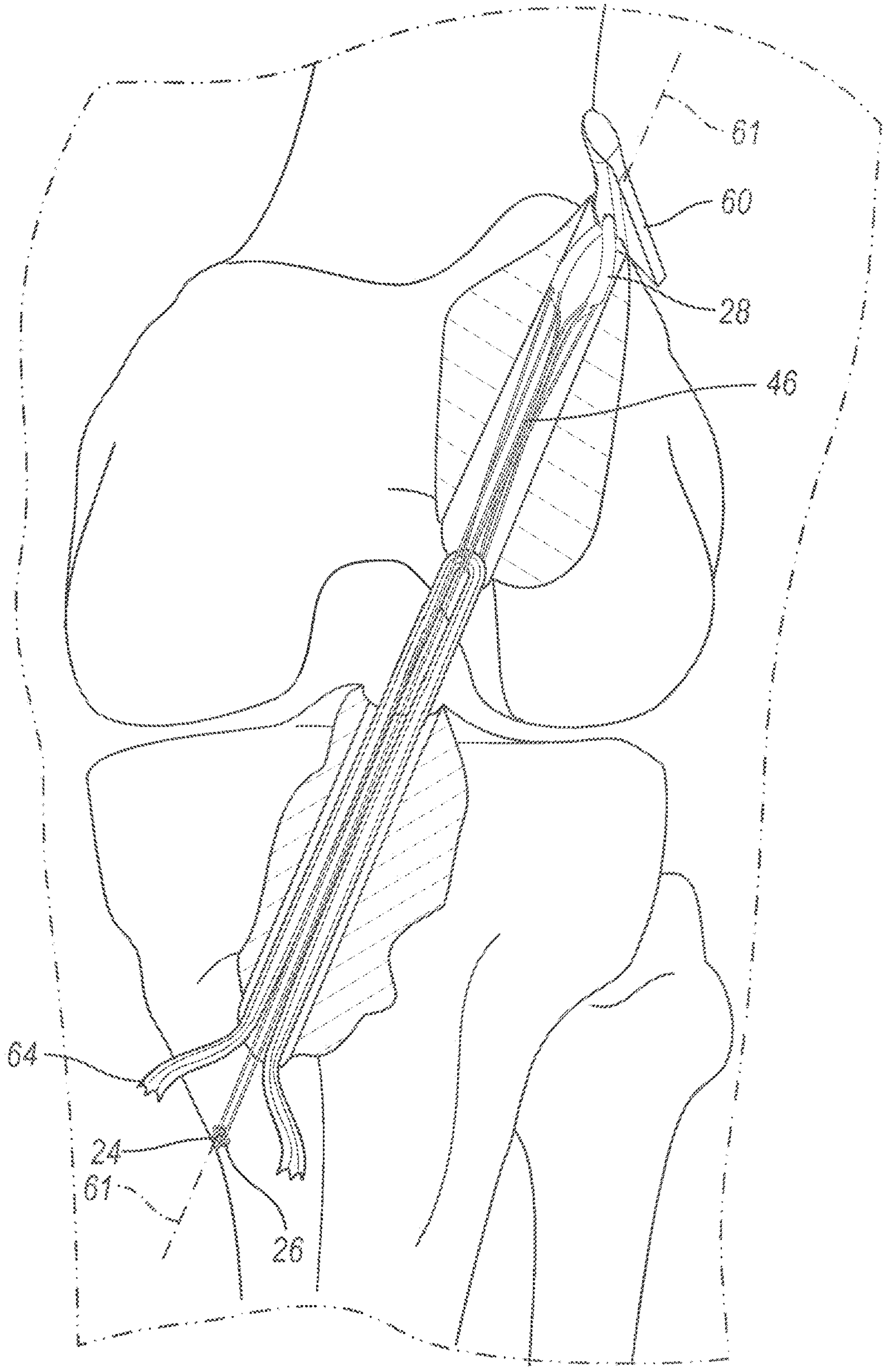
Figure 12D:
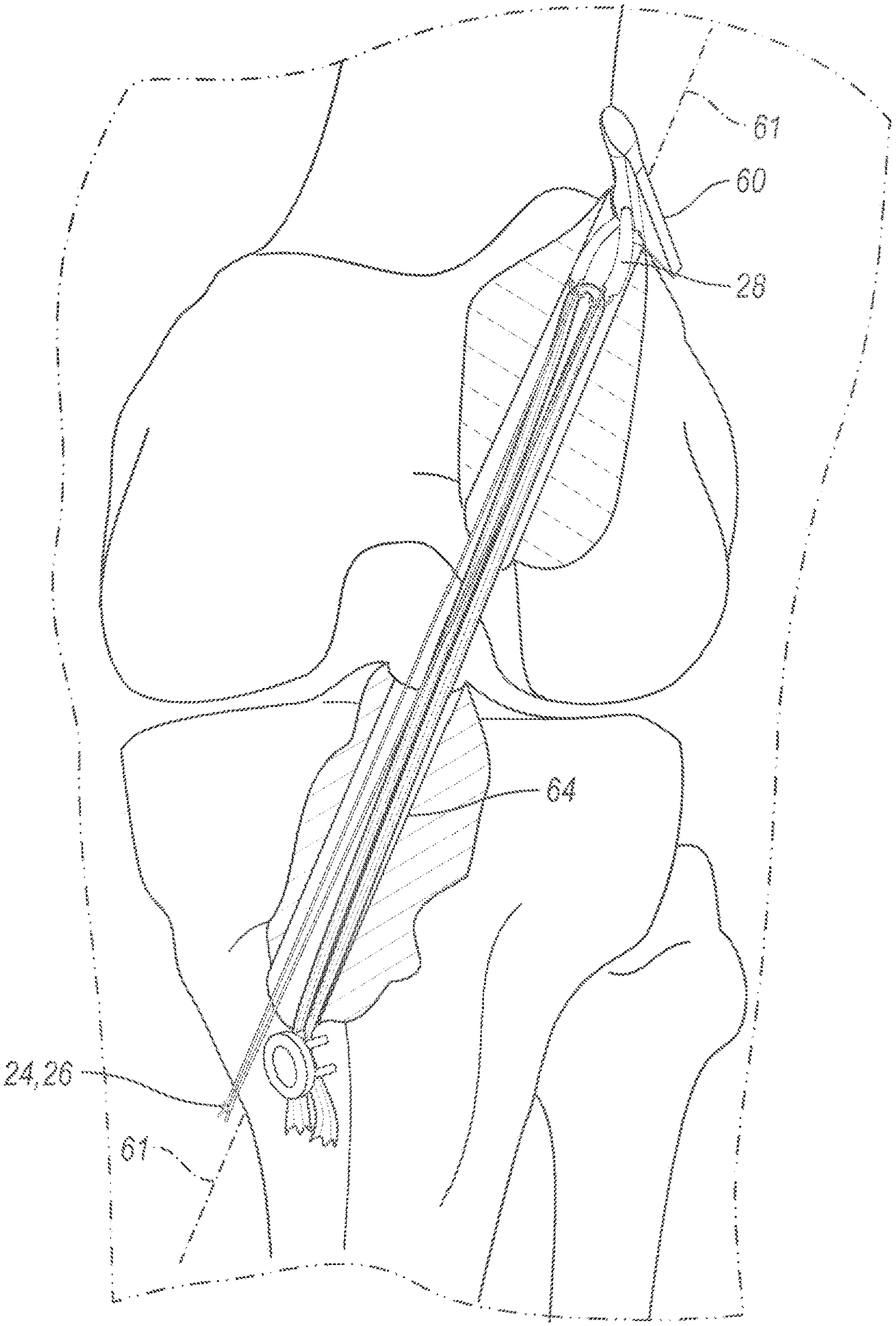

As best seen in FIG. 12C, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known. The suture construction has loops 46 and 46' with a first length which allows rotation of the fixation member 60. Application of tension onto the ends 24, 26 of the sutures pulls the fixation member 60 into position and the loops 46 and 46' into a second length. In this position, rotation of the locking member in inhibited.

Figure 12E:
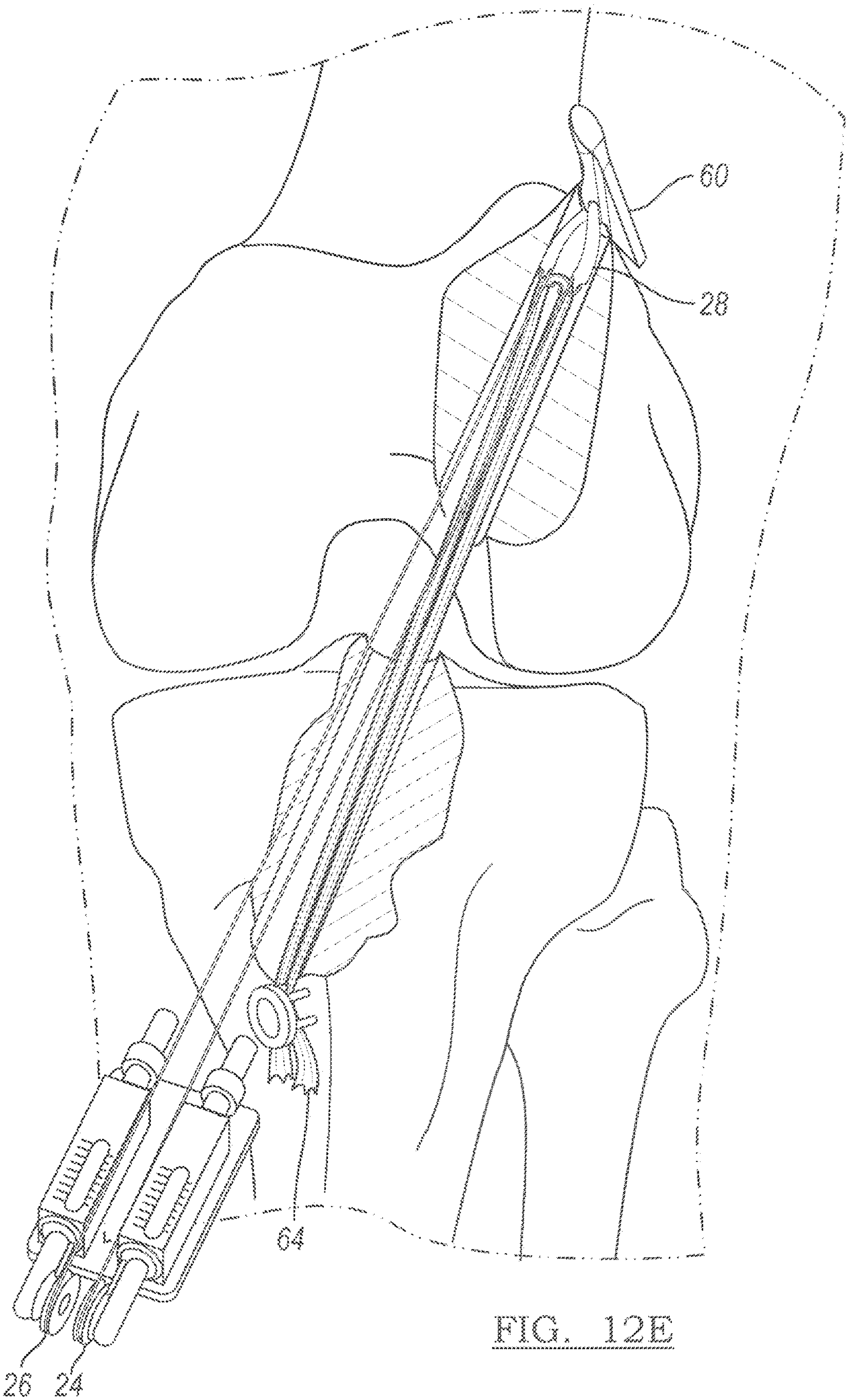
Figure 13A:
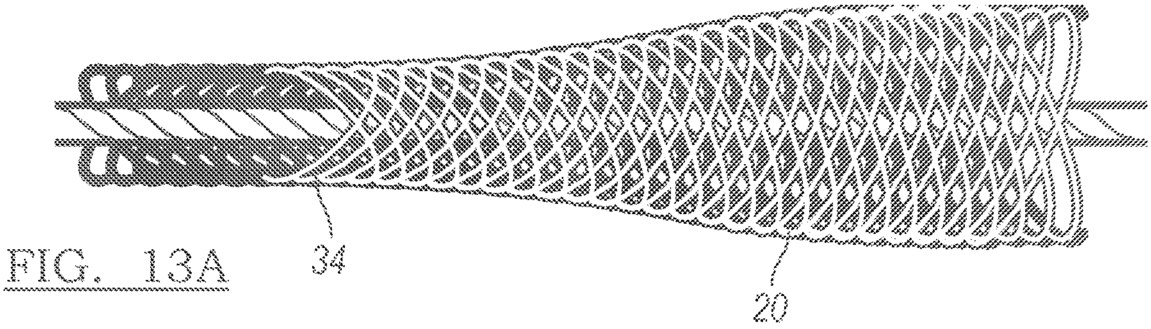
FIGS. 13A-13D represent a close-up view of the suture shown in FIGS. 1-11C.
Figure 13B:
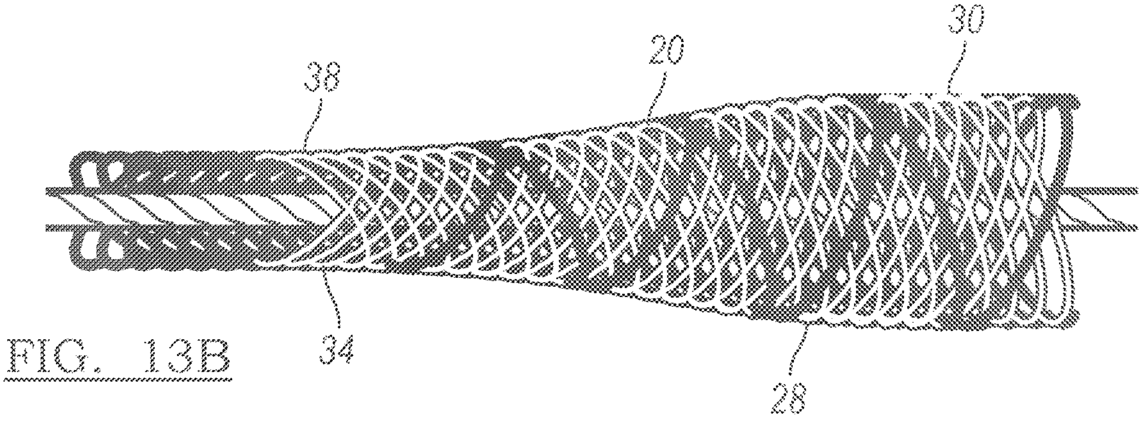
Figure 13C:
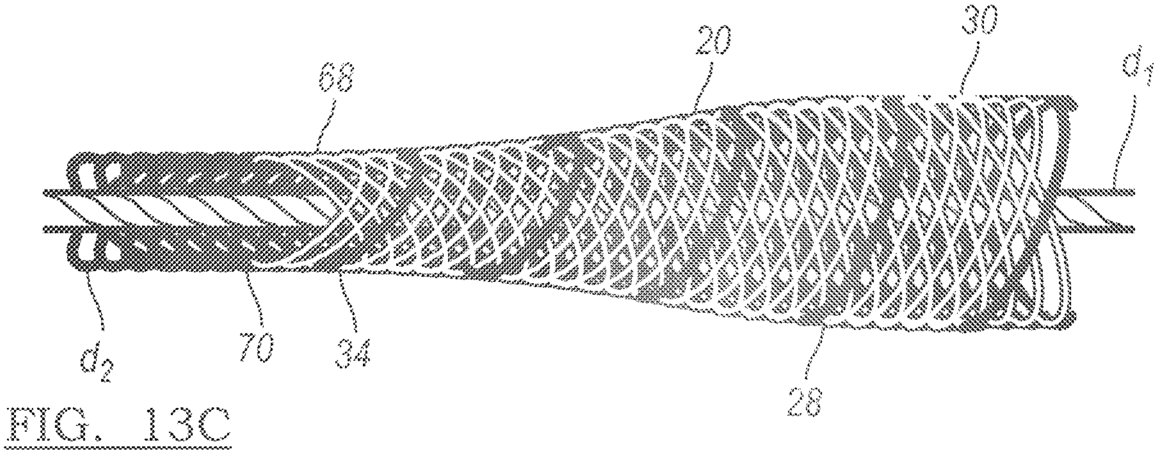
Figure 13D:
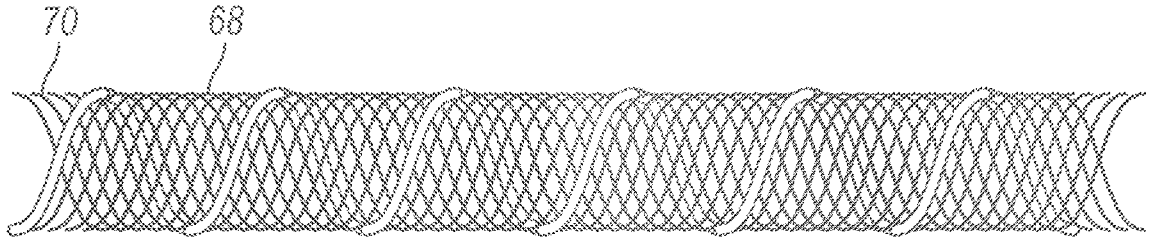

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL. This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter $d_1$ which is larger than the diameter $d_2$ of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

Figure 14:
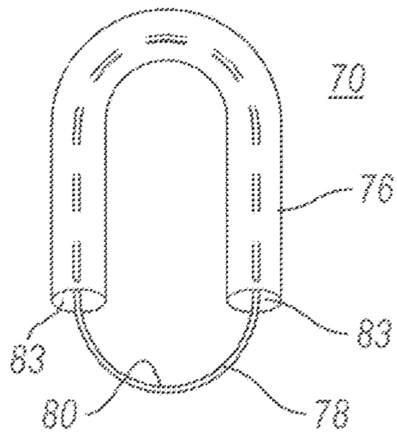
FIGS. 14-16 represent fixed length textile anchors.
Figure 15:
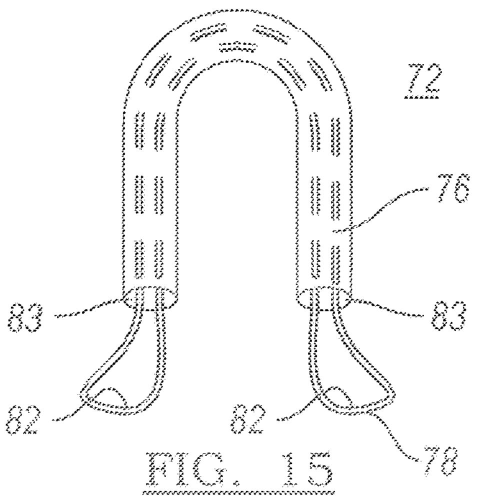
Figure 16:
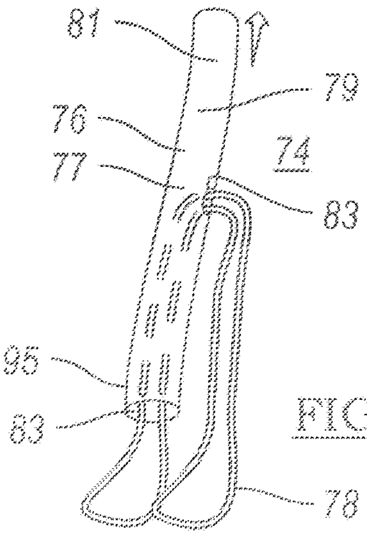

FIGS. 14-16 represent collapsible anchors 70, 72, 74 according to the present teachings. The anchors are deformable from a first cross section to a second engaging cross section. The anchors 70, 72, 74 are biocompatible materials for example polymer or a knit or woven textile such as a braided nylon material. Disposed within a collapsible tube 76 is a closed loop of suture material 78 which may form a portion of the collapsible tube 76. Optionally, this collapsible tube 76 can be slidable with respect to the closed loop of suture material 78. The collapsible tube 76 is further collapsible to form a fabric mass 110 (see for example FIG. 29B).

The suture material 78 can be passed through a pair of openings 83 in the collapsible tube 76 a single time to form a single soft tissue bearing surface 80. Additionally, (see FIG. 15), the closed loop of the suture material 78 can be looped over itself and passed through the collapsible flexible tube 76 to form a pair of soft tissue bearing surface portions 82. In each of the embodiments shown, the collapsible tube 76 defines at least one tube bearing surface.

FIG. 16 represents a closed loop of suture 78 passed through an aperture 77 defined in a body 79 of the collapsible tube 76. In this regard, the suture 78 is passed through a first open end 95 of the tube 78 and through the aperture 77 leaving a portion 81 of the collapsible tube 76 which can be used to assist in the insertion of a graft to a patient (see FIG. 32A).

Figure 17:
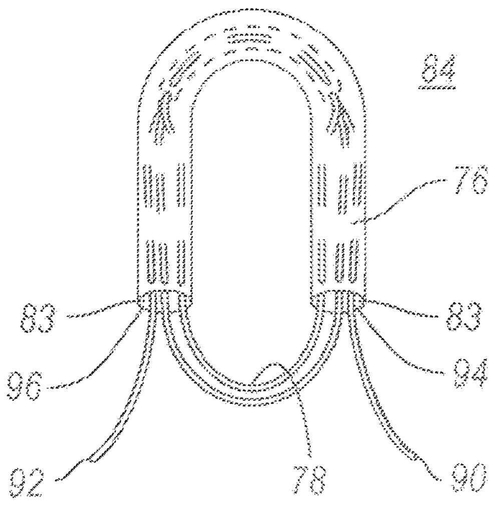
FIGS. 17-21 represent adjustable length textile anchors according to the teachings herein.
Figure 18:
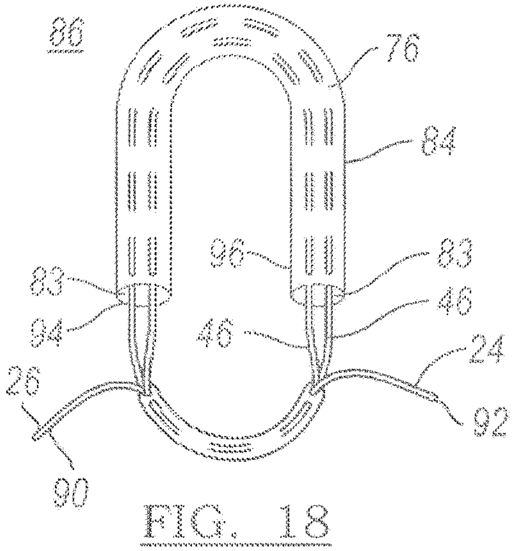
Figure 19:
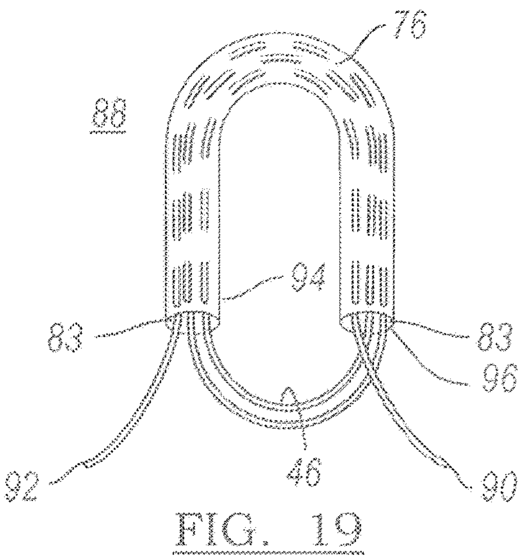

FIGS. 17-19 represent adjustable sized loops of suture material 78 disposed within the collapsible tube 76 so as to form a suture anchor assembly 84, 86, 88. FIG. 17 shows the suture material 78 passed several times through the collapsible tube 76. By applying tension to the ends 90 and 92 of the suture material 78, the loops of the suture material constrict. If placed adjacent to a bearing surface (not shown), the end 94 and 96 of the collapsible tube 76 are brought together, thus collapsing the tube to form a collapsed material or fabric mass 110. It is envisioned a portion of the suture material 78 can be passed through the collapsible tube 76 to help maintain the position of the suture with respect to the collapsible tube 76.

FIGS. 18 and 19 show the loops of the suture construction of FIG. **4*a* within a collapsible tube 76. The tubular portion of the construction of FIG. 4*a* can be disposed either within or outside of the collapsible tube 76. As with the embodiment shown in FIGS. 14-16, translation of the tube 76 with respect to the suture material 78 can cause the ends 94 of the tube 76 to be brought together to compress the loops into a fabric mass 110**.

Figure 20:
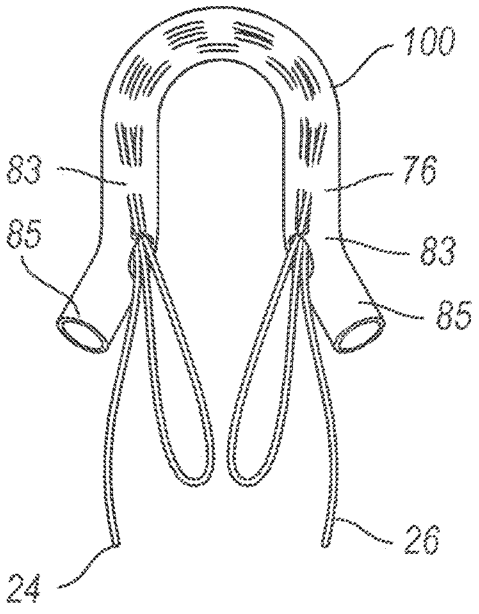
Figure 21:
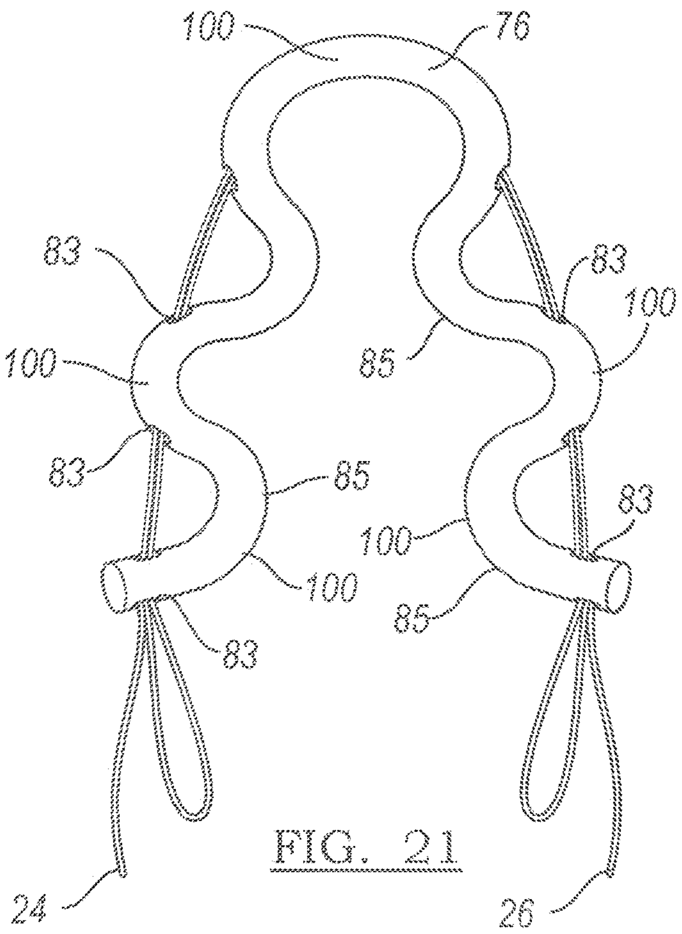

FIGS. 20 and 21 show the loops of FIG. 2B, 4A or 5 disposed within the collapsible tube 76. Shown are the ends and loops disposed at least partially through a portion 100 of the tube 76. Tensioning of the ends 24, 26 causes the portions 100 of the tube 76 to collapse to form a mass 110, while leaving other portions 85 uncollapsed. The outer uncollapsed portion 85 can function as a bearing surface to assist in the collapse of portion 100 when portion 100 is subjected to compressive loads.

Figure 22:
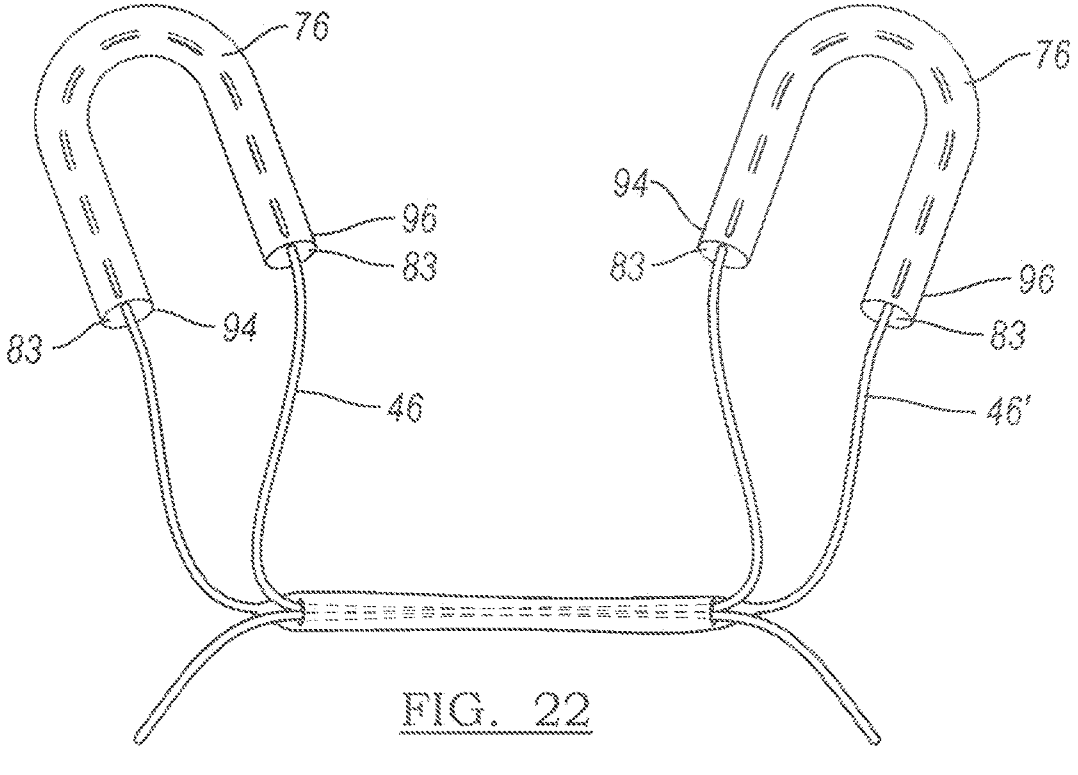
FIGS. 22-24 represent alternate adjustable length textile anchors.

FIG. 21 shows an embodiment where suture loops are passed through the sidewalls of the collapsible tube 76. Optionally, the loops 46 and 47 as well as the ends 24 and 26 can be passed through together. This construction can be used in situations where a large collapsed mass 110 is needed FIG. 22 shows the loop of FIG. 2B having a pair of collapsible tubes 76. The collapsible tubes 76 are disposed about the loops 46 and 46' and will collapse upon application of tension to the ends of the suture construction in a manner which places compressive loads onto the ends of the tube 76. It is envisioned that these collapsible tubes 76 can be collapsed simultaneously or staggered in time as needed by a treating physician. It is also envisioned that the loop construction can be used to pull adjacent portions of a patient's anatomy together.

Figure 23:
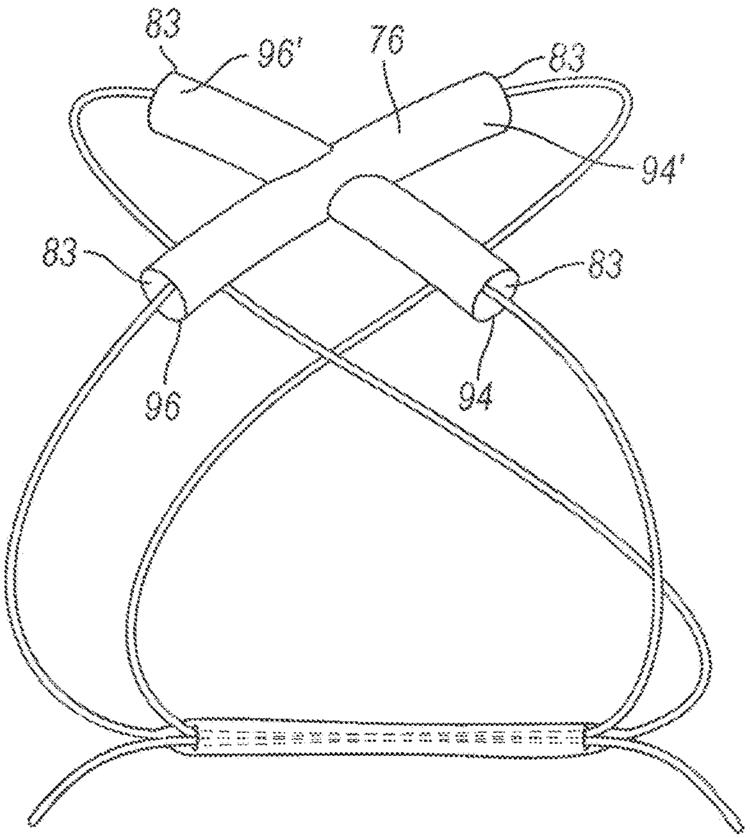

FIG. 23 depicts the loop construction shown in FIG. 2A having its loops disposed through a pair of co-joined crossed collapsible tubes 76. If placed adjacent to a bearing surface, the ends of the co-joined tubes come together, thus increasing in cross-section. This forms the fabric mass 110. This construction can be used in situations where a large collapsed mass is needed.

Figure 24:
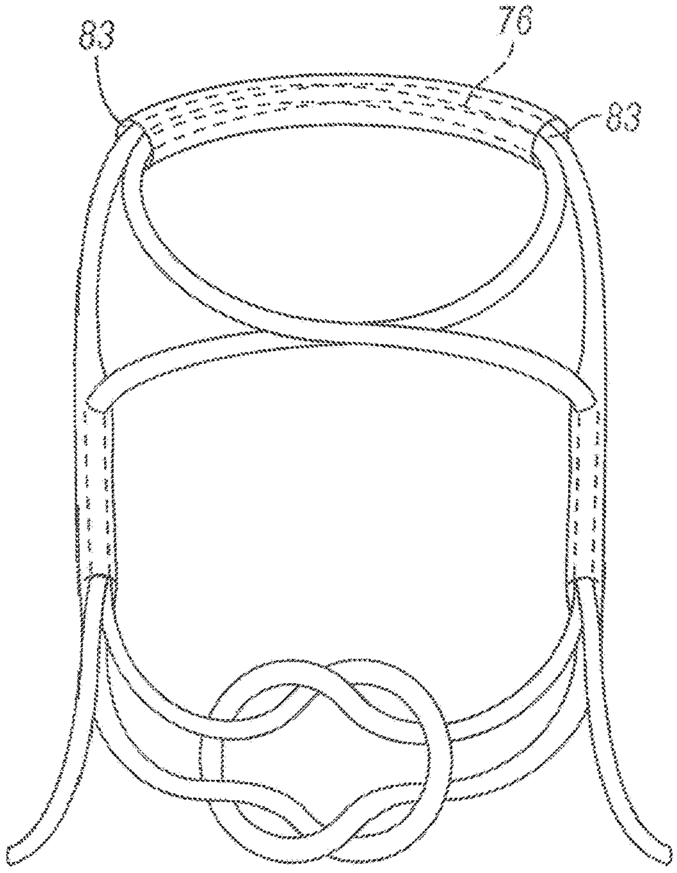

FIG. 24 shows the complex suture construction which embodies a pair of suture constructions of FIG. 2A coupled together using a collapsible tube 76. The ends of the suture 22 can be passed though a pair of passages 30 and 30' formed in the suture material 22. Portions of the suture 22 are looped through each other to form a pair of locked loops 112. This construction can be used to provide a static seat for a graft bearing surface.

Figure 25:
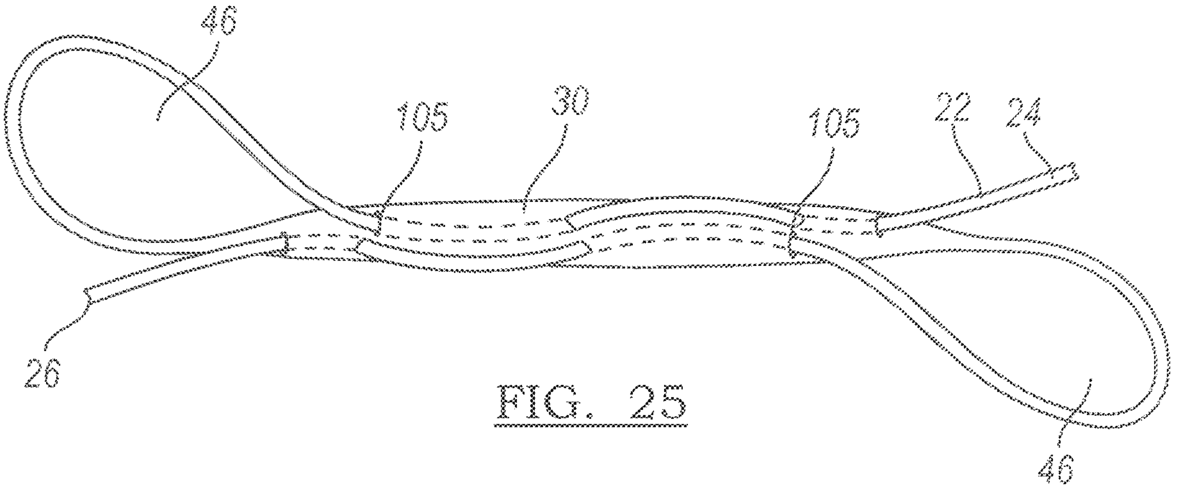
FIGS. 25-27 represent alternate suture configurations.
Figure 26:
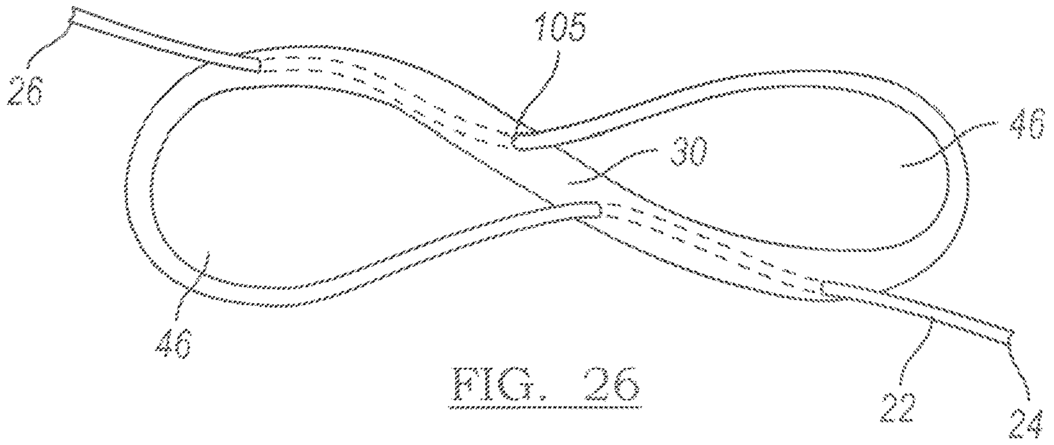
Figure 27:
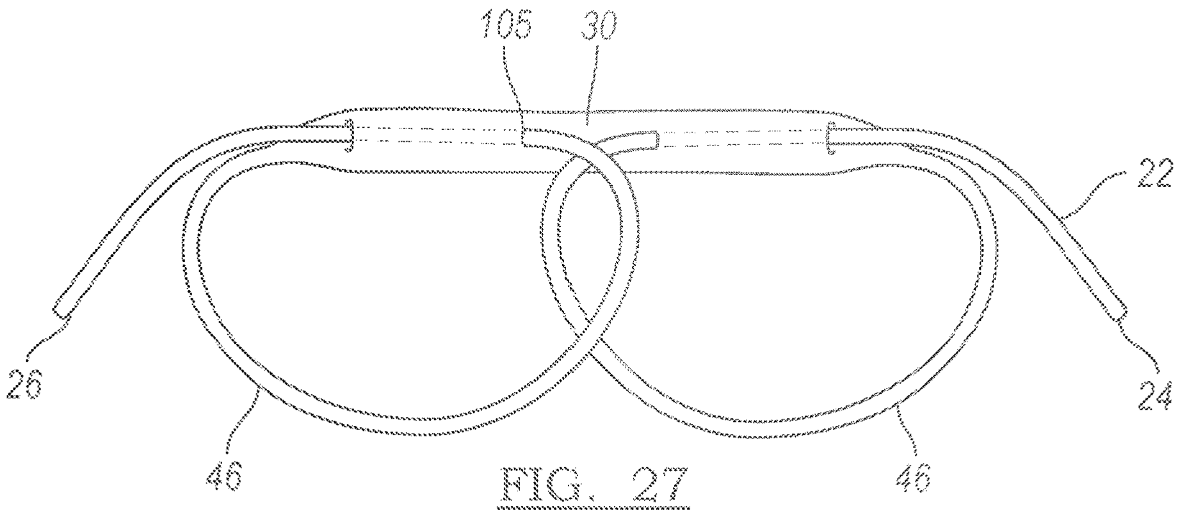

FIGS. 25-27 represent alternate suture constructions where the ends of the sutures 22 are fed multiple times through holes 105 defined within longitudinal passage 30 of the suture to form adjustable loops 46. In situations where relaxation of a tightened construction is to be minimized, the ends can be passed in and out of the passage 30 several times. In this regard, the first and second ends are positioned so as to be parallel and adjacent to each other in the passage 30.

FIGS. 26 and 27 represent constructions where the first and second ends 24 and 26 a passed through the same passage 30, but do not overlap and are not adjacent. This construction may be useful for joining pairs of members. This construction would be useful to bind pairs of appendages such as fingers.

Figure 28:
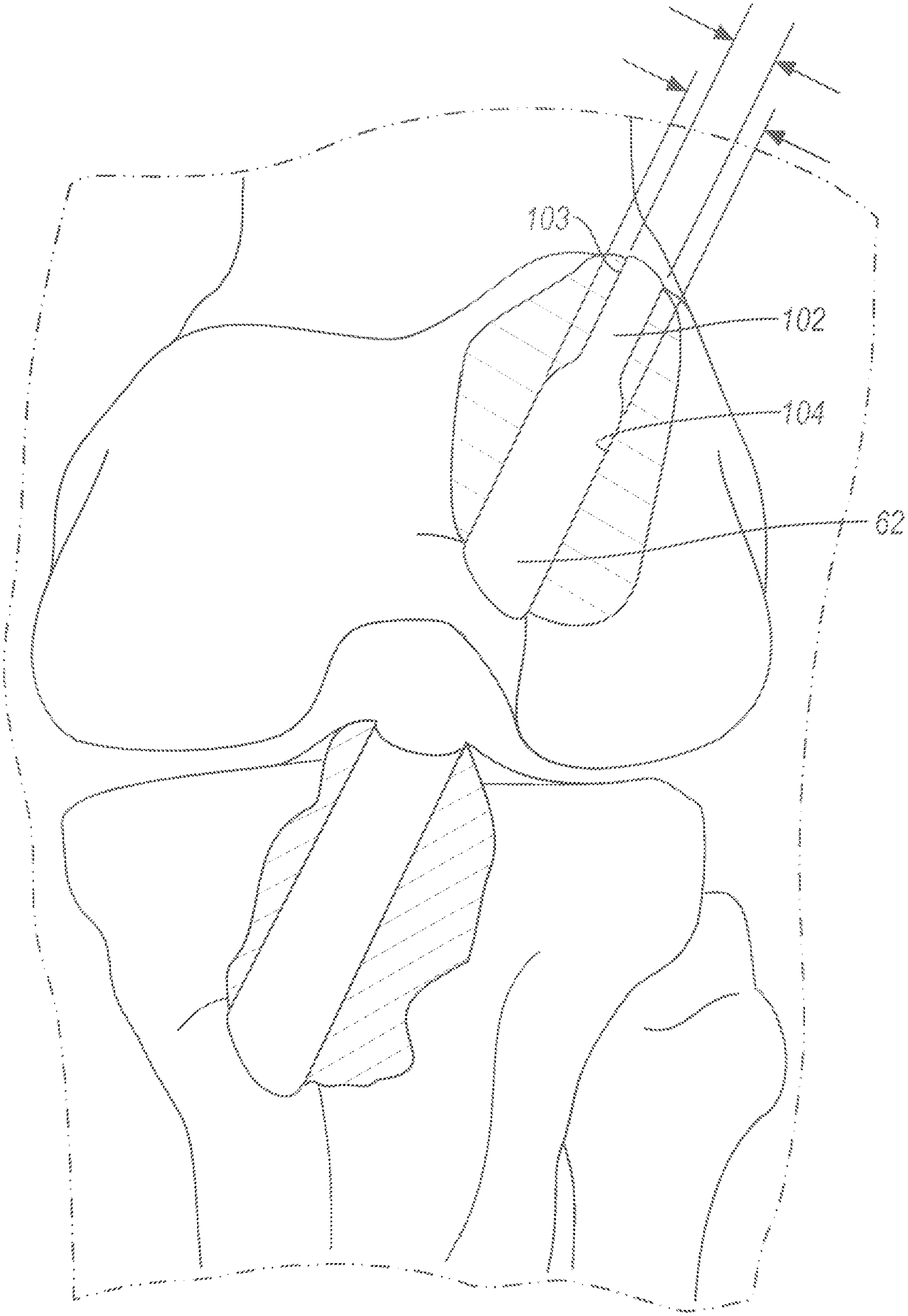
FIG. 28 represents the preparation of the tibia and femur to accept the anchors disclosed in FIGS. 14-24.

FIG. 28 represents the formation of a femoral tunnel shown as a tunnel 62 having a varying diameter. Disposed within either the femoral or tibial tunnel 62 are a first portion 102 having a first diameter and a second portion 104 having a second diameter larger than the first diameter. Defined on an exterior surface of either the tibia or femur is a bearing surface 103, which is configured to interface with the fabric mass 110 of compressed textile material to prevent the relative motion of the fabric mass 110, and thus the suture construction with respect to the bone. This bearing surface can be machined or natural.

Figure 29A:
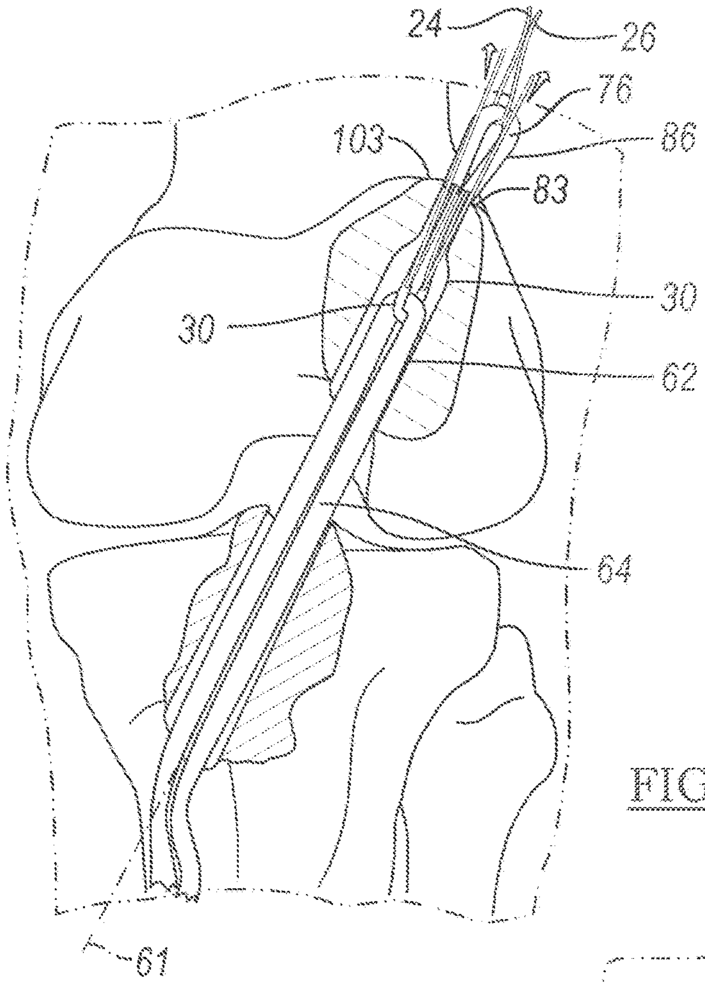
FIGS. 29A and 29B represent the coupling of an ACL replacement in a femoral/tibial reconstruction using the textile anchor of FIG. 18.
Figure 29B:
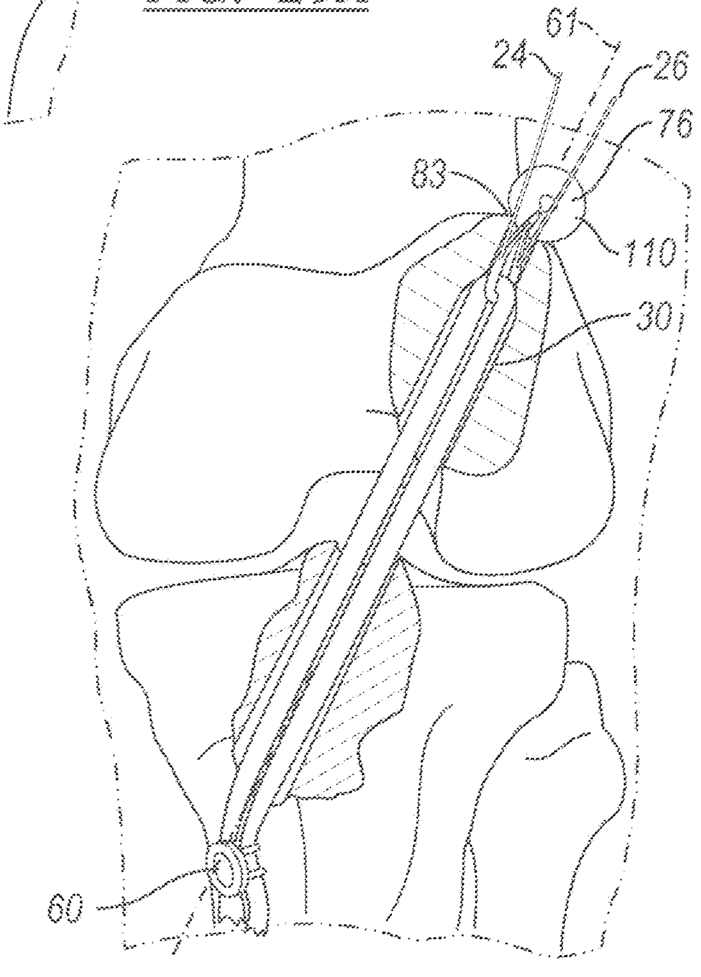

FIGS. 29A and 29B represent potential uses of the suture construction 86 in FIG. 18 in an ACL repair. As can be seen in FIG. 29A, the longitudinal passage portion 30 of suture construction 86 can be first coupled to a collapsible tube 76. The tube 76 can have a first profile which allows insertion of the tube 76 through the tunnel 62 and a second cross-sectional profile which allows engagement with a positive locking surface 103 upon collapse of the collapsible tube 76 into the fabric mass 110. The longitudinal passage portion 30 of the suture construction 84, tube 76, loops 46 and ends 24, 26 can then be pulled through a femoral and tibial tunnel 62. The tube 76 is positioned or coupled to the femur. At this point, a natural or artificial ACL 64 can be passed through a loop or loops 46 formed in the suture construction 20 or can be supported by the passage portion 30. Tensioning of the first and second ends 24 and 26 applies tension to the loops 46 and 47, thus pulling the ACL 64 into the tunnel. In this regard, the first and second ends are pulled through the femoral and tibial tunnel 62, thus constricting the loops 46 about the ACL 64.

After feeding the ACL 64 through the loops 46, tensioning of the ends allows engagement of the ACL with bearing surfaces defined on the loops. The tensioning pulls the ACL 64 through a femoral and tibial tunnel and collapses the tube 76 to form a locking fabric mass 110 outside the bone or tunnel 62. The ACL 64 could be further coupled to the femur or tibia using a transverse pin or plug. As shown in FIG. 29B, once the ACL is fastened to the tibia, further tensioning can be applied to the first and second ends 24, 26 placing a desired predetermined load on the ACL. As described above, this tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62. The longitudinal passage 30 resists relaxation or reverse movement of the suture.

As best seen in FIG. 29B, the body portion 28 and parallel portions 38, 40 of the suture construction 86 remain disposed within the femoral tunnel 62. Further tension of the first ends draws the ACL 64 up through the tibial component into the femoral component. In this way, suture ends can be used to apply appropriate tension onto the ACL 64 component. The ACL 64 would be fixed to the tibial component using a plug or screw either before or after the application of the tension to the suture 22. Additionally, tension can be set on the ACL 64 after the collapsible tube 76 has been compressed.

Figure 30A:
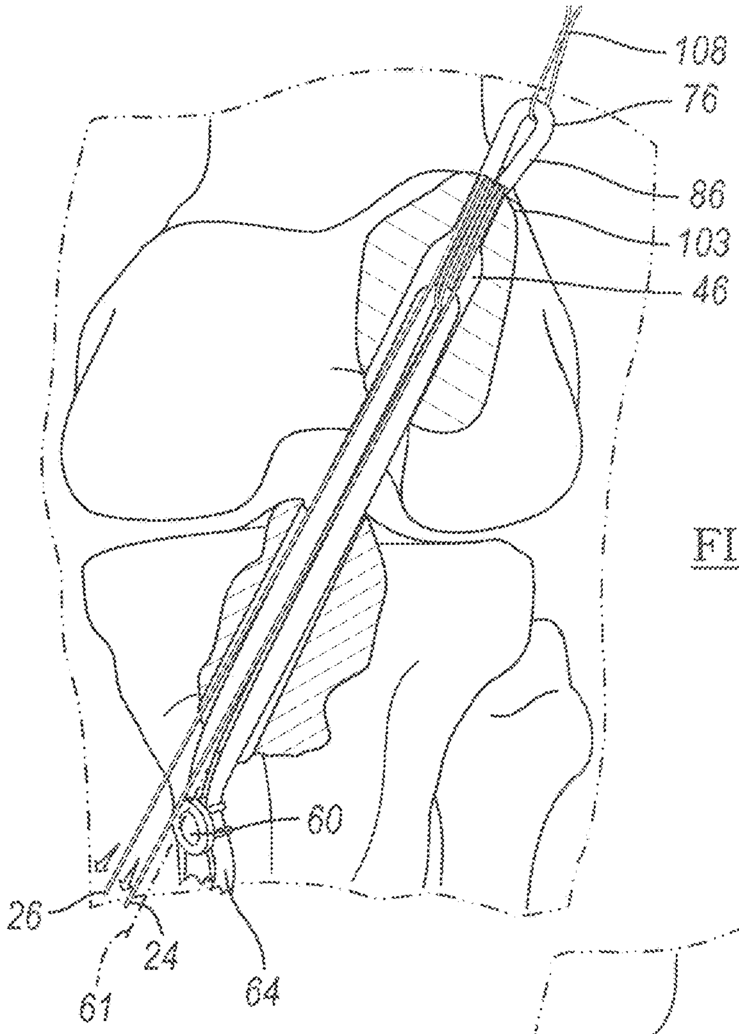
FIGS. 30A and 30B represent the coupling of an ACL replacement in a femoral/tibial reconstruction using the textile anchor of FIG. 17.
Figure 30B:
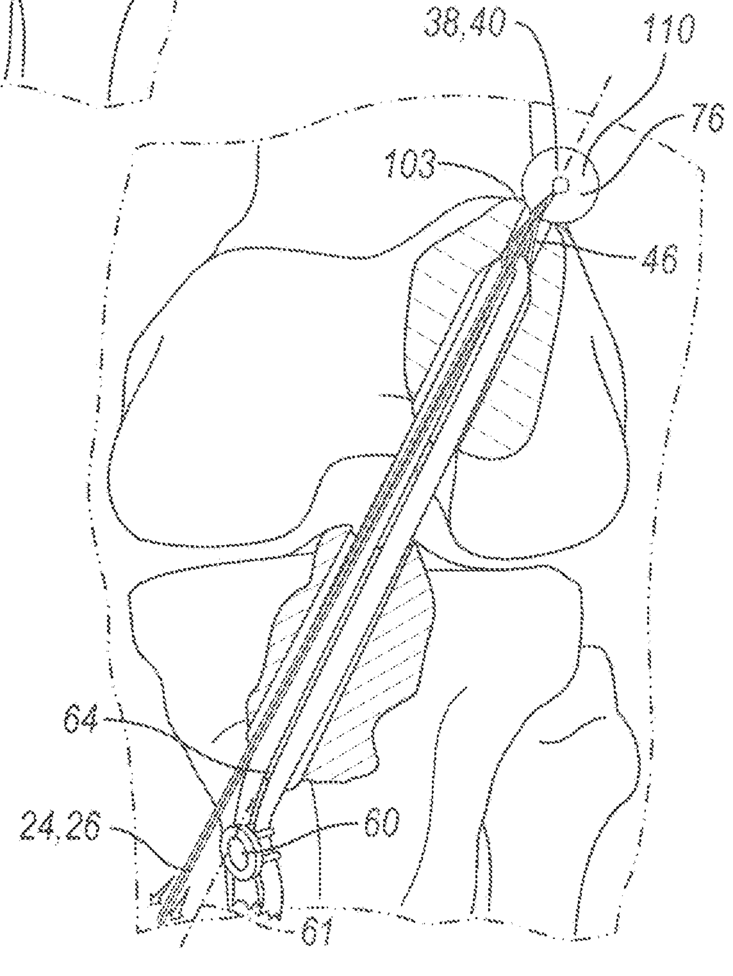

FIGS. 30A and 30B represent potential uses of the suture constructions 84 in FIG. 17 in an ACL repair. As can be seen in FIG. 30A, the longitudinal passage portion 30 of suture construction 86 can be first disposed within the tube 76. The tube 76 has a first profile which allows insertion of the tube 76 through the tunnel and a second collapsed profile which allows engagement with a positive locking surface 103. The collapsible tube 76 of the suture construction 84, member 60, and loops 46, 47 can then be passed through a femoral and tibial tunnel 62 using a suture 108. The tube 76 is positioned or coupled to the femur. At this point, a natural or artificial ACL 64 can be passed through a loop or loops 46, 47 formed in the suture construction 84. Tensioning of the first and second ends 24 and 26 applies tension to the loops 46, 47 thus pulling the ACL 64 into the tunnel. In this regard, the first and second ends 26 and 24 are pulled through the femoral and tibial tunnel, thus constricting the loops 46 about the ACL 64 (see FIG. 30B) and collapsing the tube 76 to form the anchoring mass 110. Force applied to graft 64 along axis 61 in the distal direction will seat tube 76 and form anchoring mass 110.

As shown, by holding the suture construction in place 108, the suture construction 84 allows for the application of force along an axis 61 defining the femoral tunnel 62. Specifically, the orientation of the suture construction 84 and, more specifically, the orientation of the longitudinal passage portion 30, the loops 46, and ends 24, 26 allow for tension to be applied to the construction 86 without applying non-seating forces to the tube 76. As an example, should the loops 24, 26 be positioned at the tube 76, application of forces to the ends 24, 26 may reduce the seating force applied by the tube 76 onto the bone.

As best seen in FIG. 30B, the loop portions 46, 47 of the suture construction 84 remain disposed within to the tunnel 62. Further tension of the first ends draws the ACL 64 up through the tibial component into the femoral component. In this way, suture ends can be used to apply appropriate tension onto the ACL 64 component. The ACL 64 would be fixed to the tibial component using a plug or screw 60 adjacent the suture construction 84, as is known.

Alternatively, as shown in FIG. 30B, once the ACL is fastened to the tibia, further tensioning can be applied to the first and second ends 24, 26 placing a desired predetermined load on the ACL. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

Figure 31A:
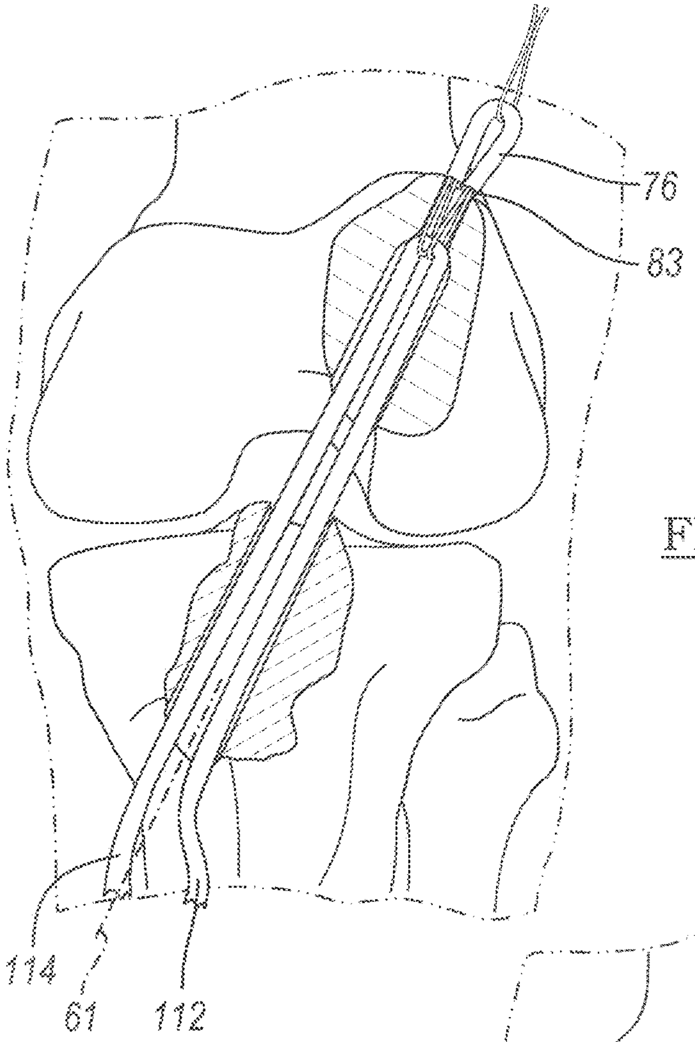
FIGS. 31A and 31B represent the coupling of an ACL replacement in the femoral/tibial reconstruction using the textile anchor of FIG. 15.
Figure 31B:
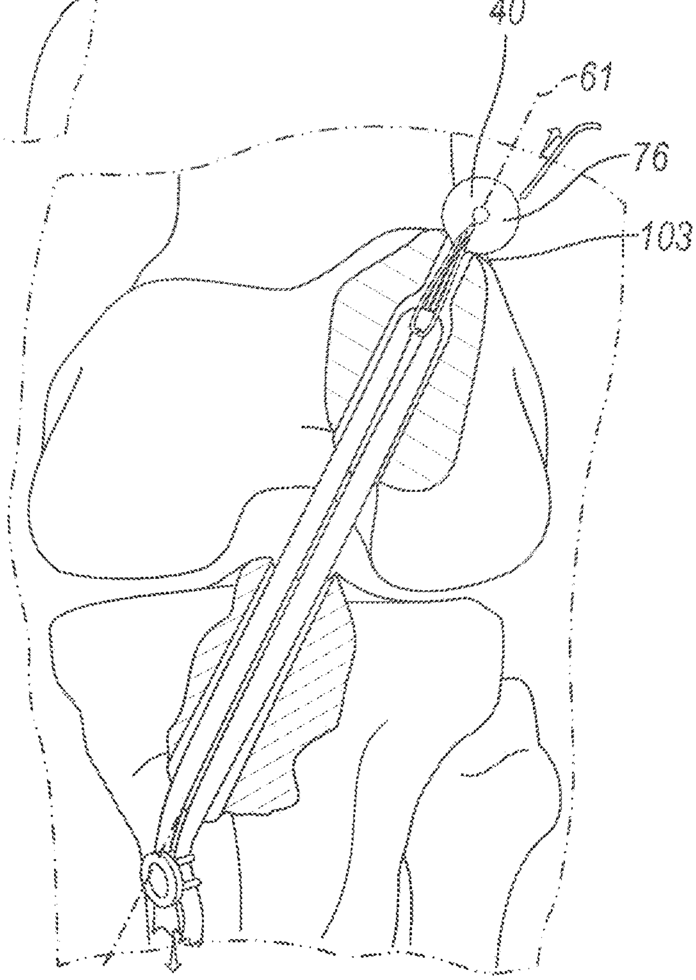

FIGS. 31A and 31B represent potential uses of the suture construction 70 in FIG. 14 in an ACL repair. The suture material 78 of suture construction 70 can be first coupled to a collapsible tube 76. The collapsible tube 76 can have a first profile which allows insertion of the construction 70 through the tunnel and a second profile which allows engagement with a positive locking surface 103 upon its compression. Prior to attachment to the femur, a natural or artificial ACL 64 can be passed through a loop or loops 46 formed in the suture material 78. Suture construction 70 can then be passed through a femoral and tibial tunnel 62. The tube 76 is positioned or coupled to the femur. Tensioning of the first and second ends 112 and 114 of the soft tissue applies tension to the loop 76, thus collapsing the tube 76 to form the fabric mass 110. Tension can be applied to the soft tissue which can then be fastened to the tibia using a fastener 60.

Figure 32A:
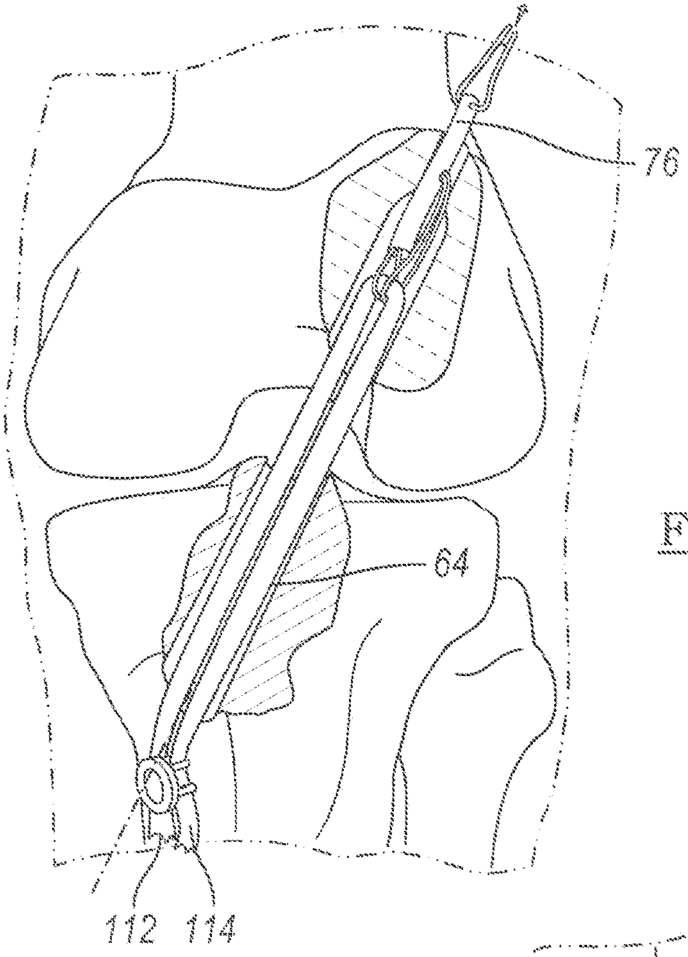
FIGS. 32A and 32B represent the coupling of an ACL replacement in a femoral/humeral reconstruction using the textile anchor of FIG. 16.
Figure 32B:
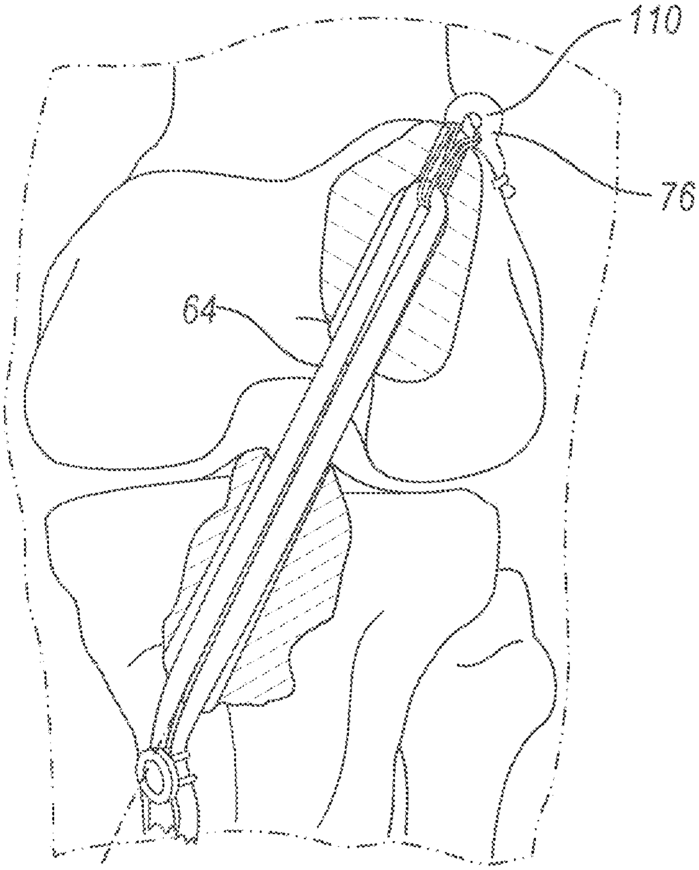

FIGS. 32A and 32B represent potential uses of the suture constructions 74 in FIG. 16 in an ACL repair. The loop of suture 78 is coupled to a collapsible tube 76. The construction 74 can have a first profile which allows insertion of the tube 76 through the tunnel and a second profile which allows engagement with a positive locking surface upon compression. The suture portion 78 of the suture construction 74, tube 76, and soft tissue 64 can then be passed through a femoral and tibial tunnel 62. The tube 76 is positioned or coupled to the femur 103 and collapsed by the application of tension to the soft tissue 64.

As best seen in FIG. 32B, the anchoring mass 110 of the suture construction 72 remains disposed outside the femoral tunnel. Tension is applied to the ends of the ACL 64 up through the tibial component into the femoral component. In this way, ends of the ACL 112, 114 can be used to apply appropriate tension onto the ACL 64 component. The ACL 64 would be fixed to the tibial component using a plug or screw as is known.

Figure 33:
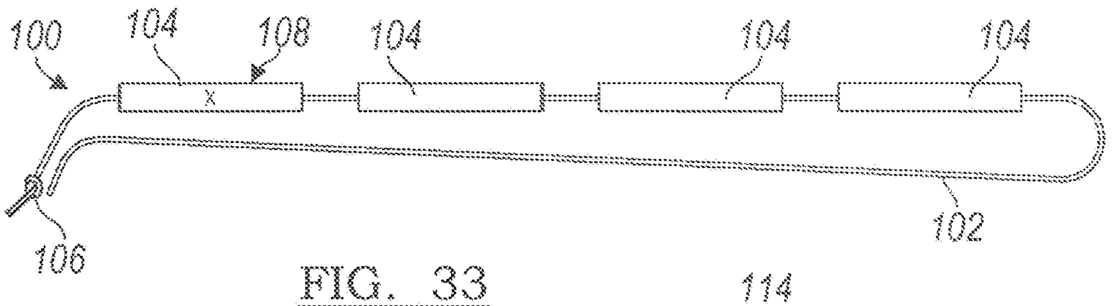
FIG. 33 represents a suture construction having a plurality of collapsible tubes.

FIG. 33 represents a suture construction 100 according to the present teachings. The suture construction 100 is formed of a suture 102 having a plurality of collapsible tubes 104 disposed thereon. The collapsible tubes 104 can be knit suture material or a polymer tube. Formed on one or both ends of the suture 102 can be a knot 106. Optionally, the collapsible tube 104 can be coupled to the suture 102 using a stitch 108, to prevent translation of the collapsible tube 104 with respect to the suture 102.

Figure 34A:
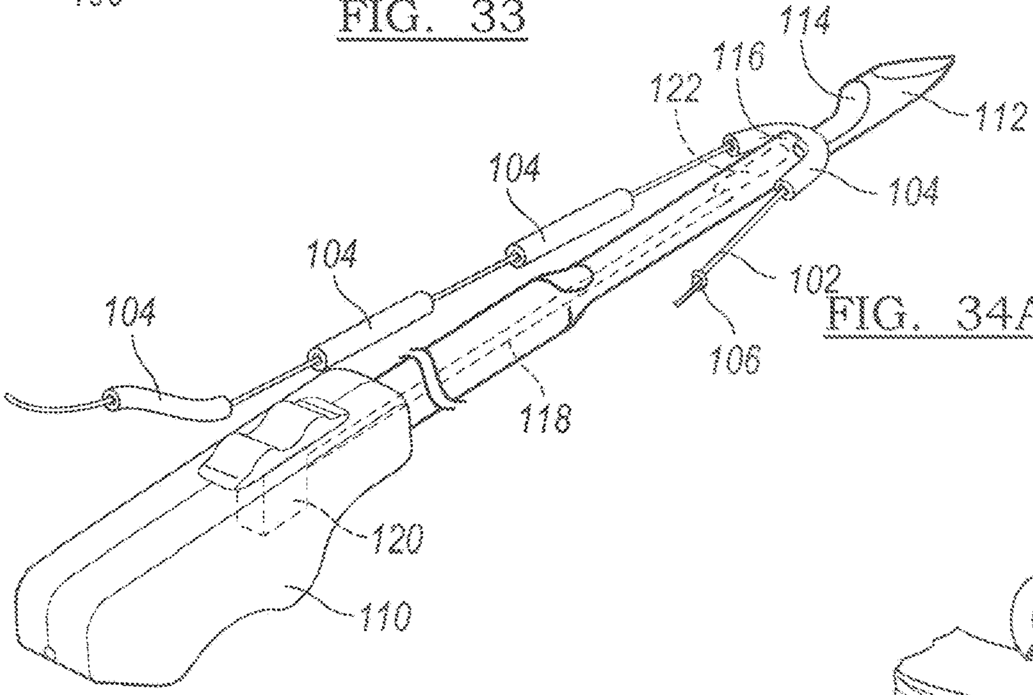
FIGS. 34A-34C represent a tool used to surgically implant the suture construction shown in FIG. 33.
Figure 34C:
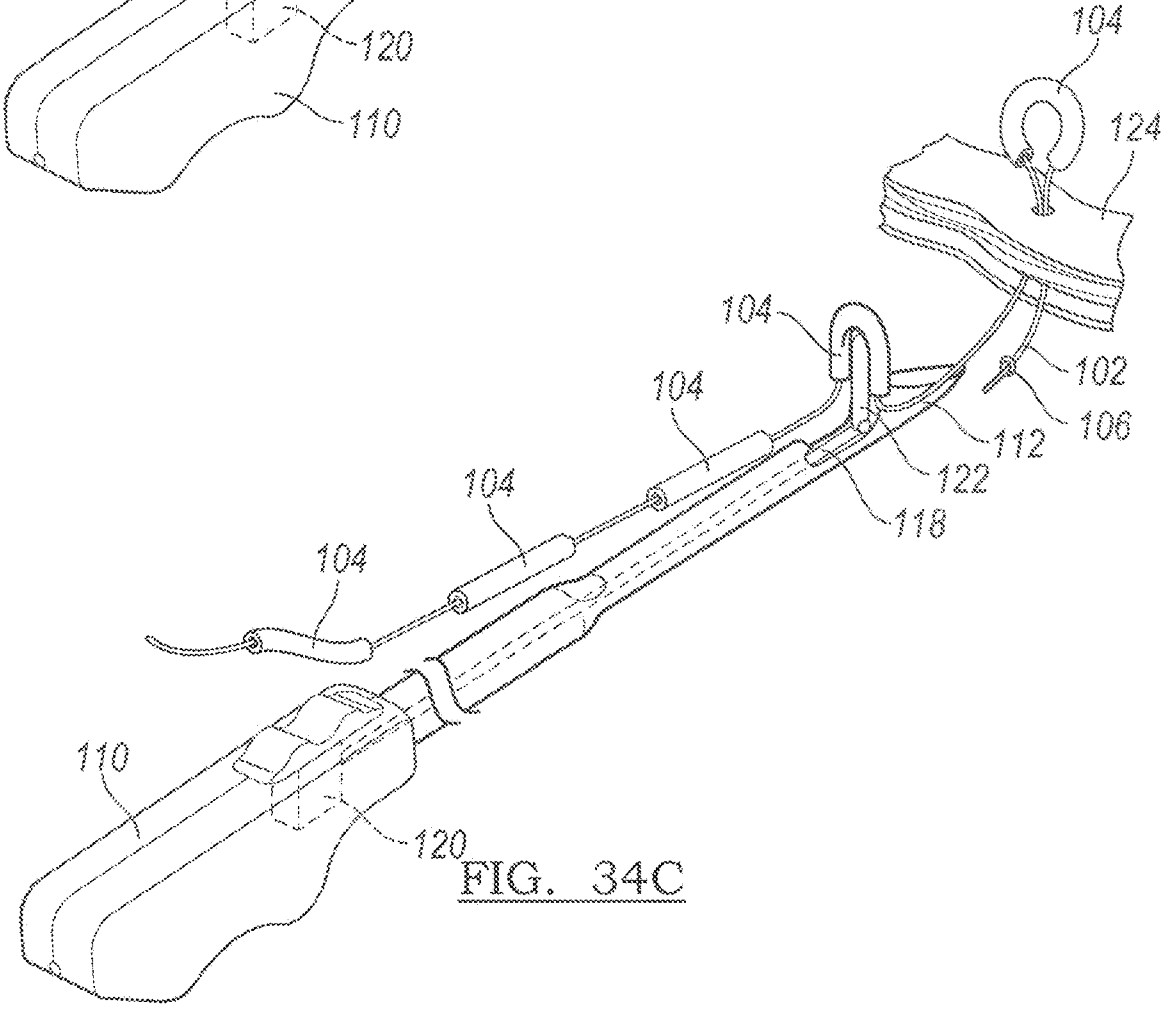
Figure 34B:
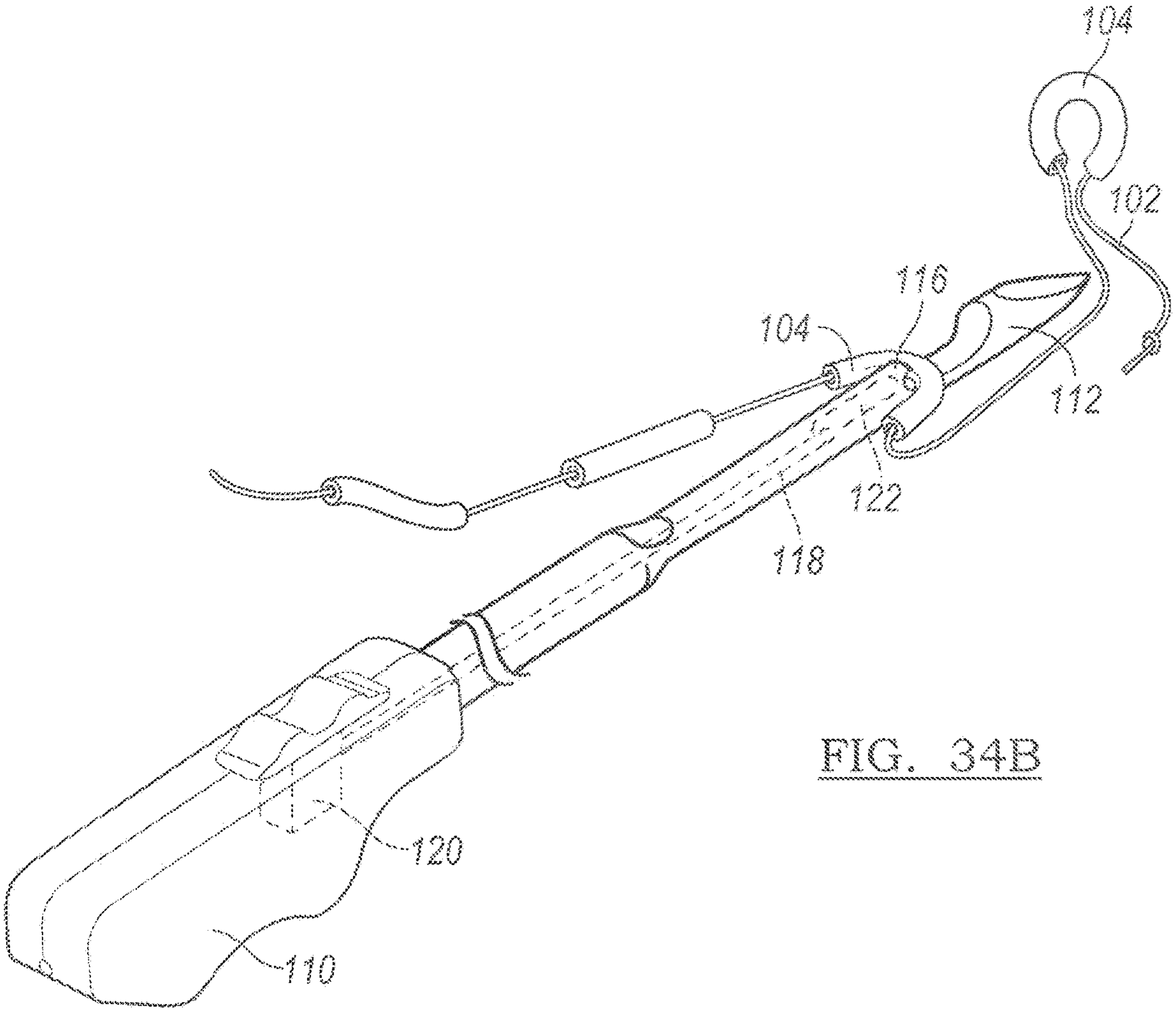

FIGS. 34A-34C represent a tool 110 used to couple the suture construction 100 with soft tissue. In this regard, the tool 110 has a sharpened end 112 configured to pierce soft tissue 124. Disposed adjacent the sharpened end 112 is a recess 114 configured to support a collapsible tube 104. Disposed within the recess 114 is a collapsible tube holding member 116. This member 116 can be a flange or a retractable member which selectively engages the collapsible tube 104 to hold the collapsible tube within the recess 114. Disposed within the tool 100 is an actuatable member 118. The actuatable member 118 functions to deploy or deliver the collapsible tube 104 from the holding member 116 of the recess 114. This generally occurs after the collapsible tube 104 has been pressed through the soft tissue 124.

As shown in FIG. 34C, the sharpened end 112 can be pressed through soft tissue 124, thus positioning the collapsible tube 104 on an obverse side of the soft tissue 124. Application of force by the drive member 120 onto the actuatable member 118 causes an engagable member 122 to deliver the collapsible tube 104 from the recessed portion 114 of the tool 110, the engagable member 122 can be formed of Nitonol or can be pivotably coupled to the actuatable member 118. At this point, the sharpened end can be removed from the soft tissue 124, leaving the compressible tube and its associated suture 102 therethrough.

Figure 35A:
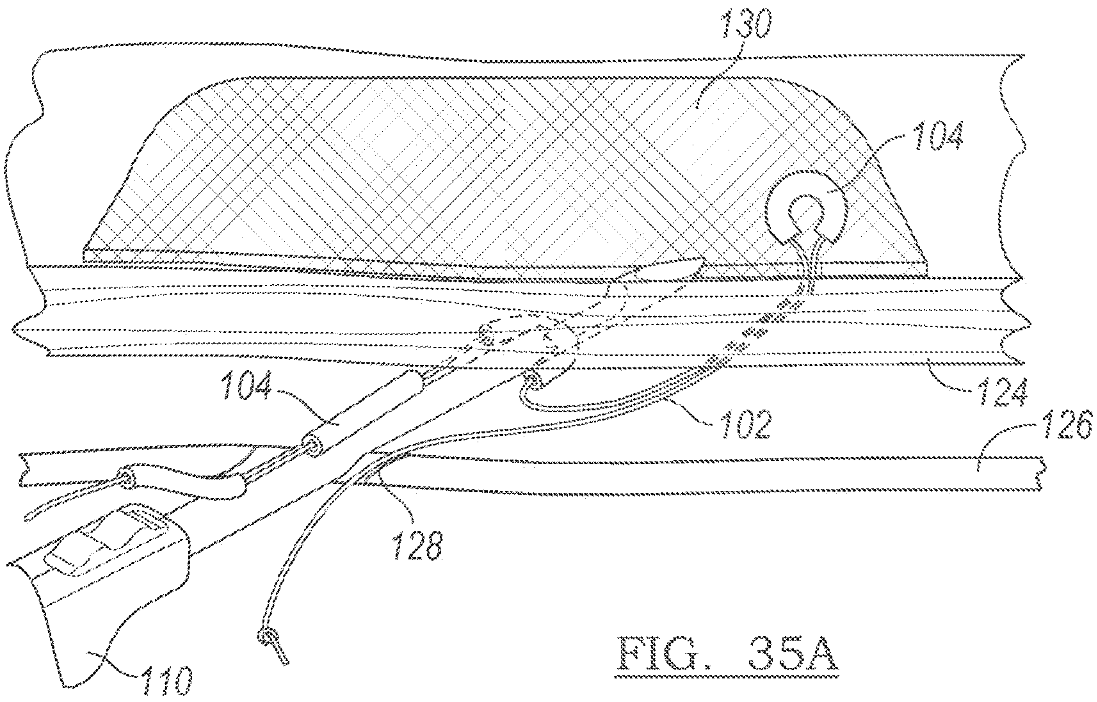
FIGS. 35A-35C show the suture construction of FIG. 33 coupled to an orthopedic mesh.
Figure 35B:
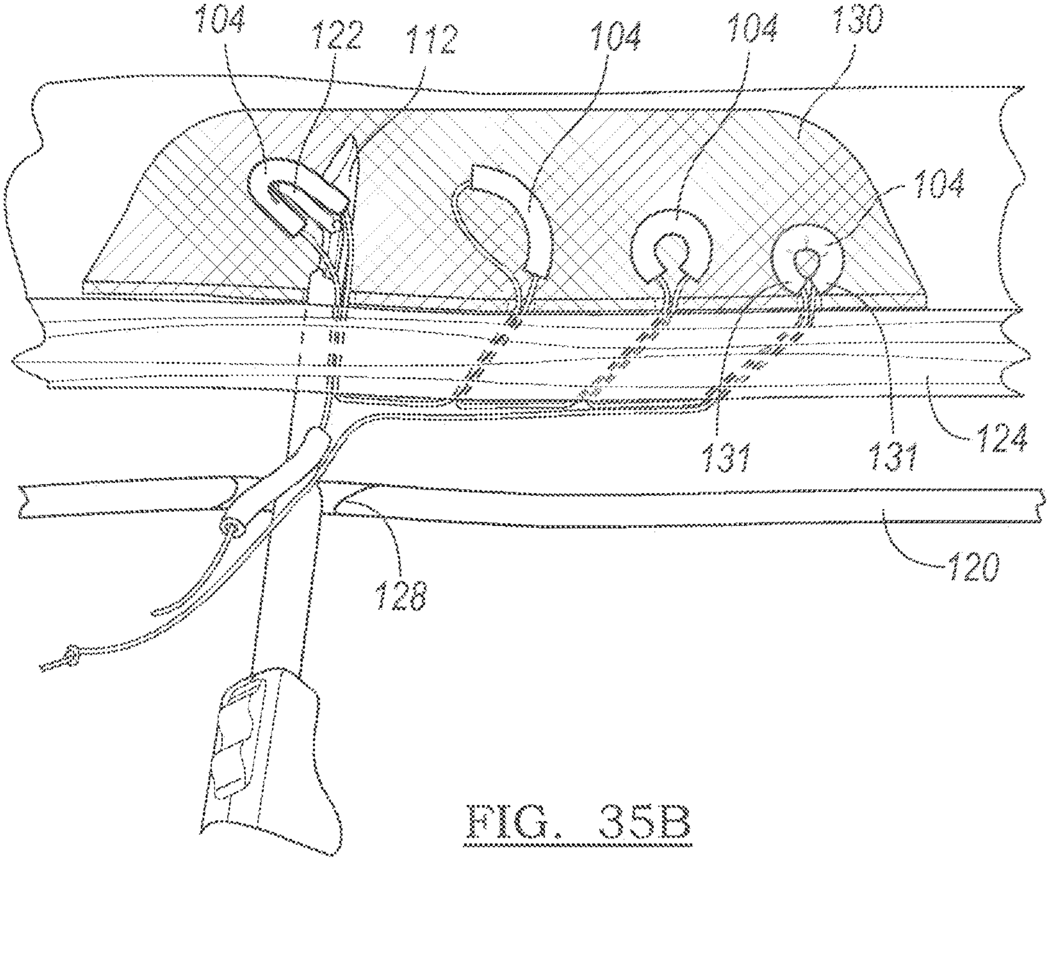
Figure 35C:
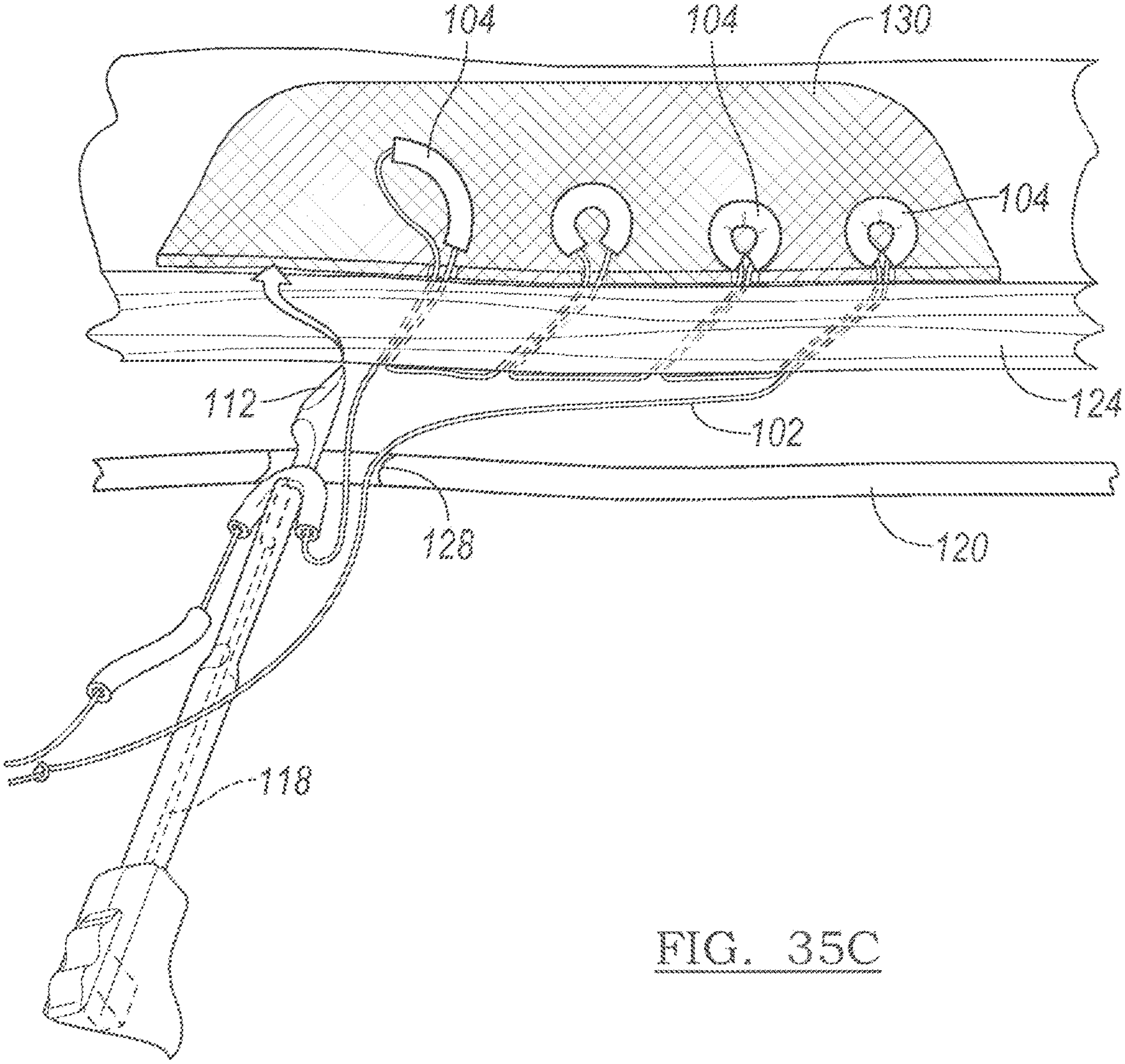

As shown in FIGS. 35A-35C, multiple collapsible tubes 104 on the suture 102 can be inserted through multiple apertures formed within the soft tissue 124. Additionally shown is an implantable orthopedic mesh 130. As best seen in FIG. 35B, the sharp end 112 of the tool 110 can be fed through a single aperture 128 formed in a layer of soft tissue 120 such as skin. The sharp end 112 is pressed through several apertures within the soft tissue 124 and through apertures within the implantable orthopedic mesh 130. The application of tensional force onto the suture 102 allows the ends 131 of the collapsible tubes 104 to engage the orthopedic mesh 130. This allows the collapsible tube 104 to form a loop structure locking the suture to the mesh 130. Further, the mesh is coupled to the soft tissue 124, bone, skin, tendon, xenograft, allograft and autograft.

As best seen in FIG. 35C, once the collapsible tube 104 has been positioned through the orthopedic mesh 130, the needle is withdrawn to allow the engagement of the next collapsible tube 104 within the recess 114 of the tool 110. The tool 110 is moved to position the sharp end 112 in a desired location on the soft tissue 124. Pressure is then applied to the tool 110 forming a hole within the soft tissue 124.

As described above, once the recess portion 114 is passed through the soft tissue 124 or the orthopedic sports mesh 130, the actuator 118 can be used to decouple the collapsible tube 104 from the recessed portion 114. The sports mesh can be one sold by Biomet Sports Medicine as Sport Mesh™. This allows the removal of the tool 110 while leaving collapsible tube 104 and associated suture 102 on the obverse side of the soft tissue 124 and the orthopedic mesh 130. The orthopedic mesh can be formed of resorbable materials.

Figure 36A:
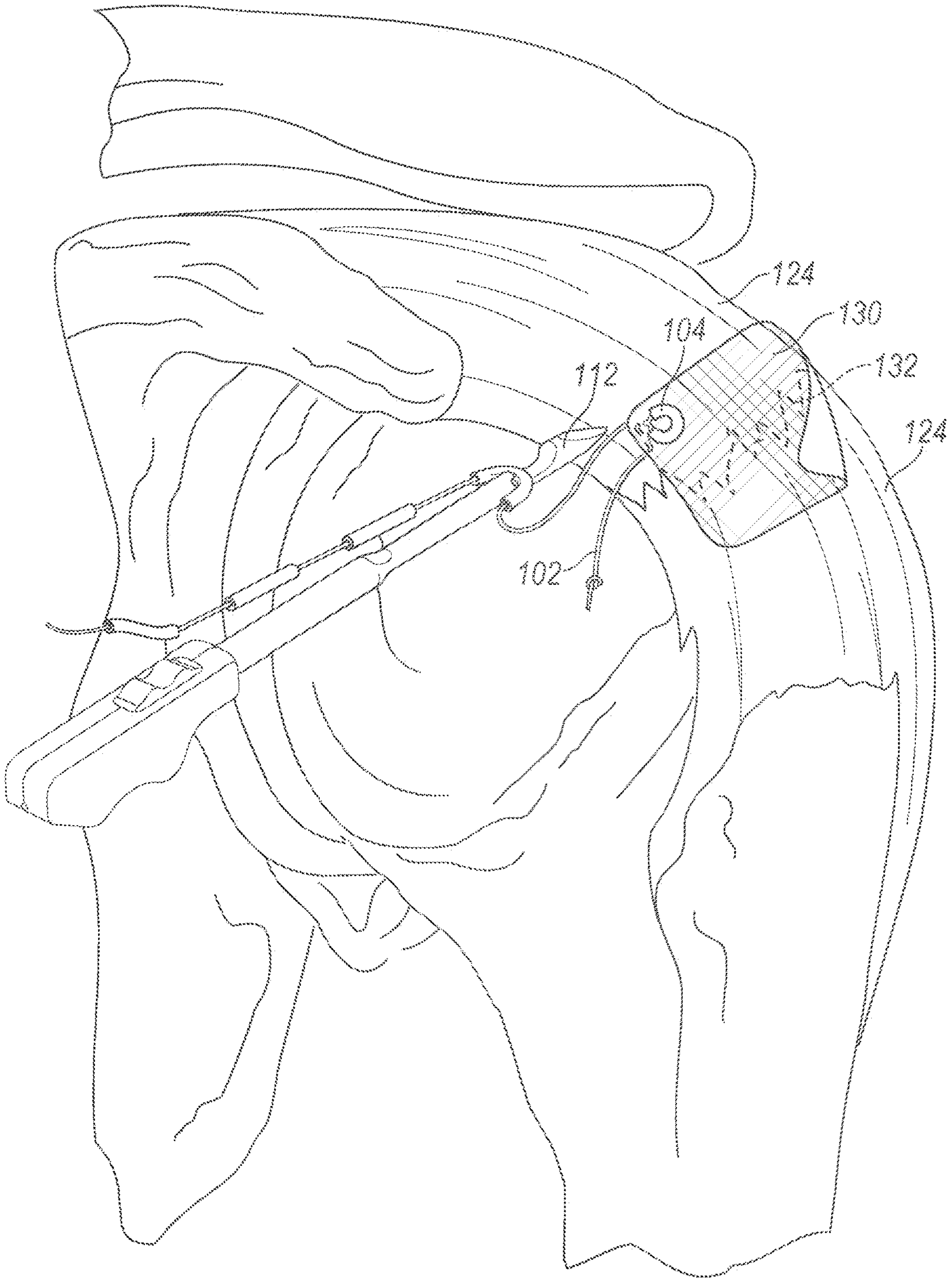
FIGS. 36A-36C represent the use of an orthopedic mesh to repair a soft tissue tear.
Figure 36B:
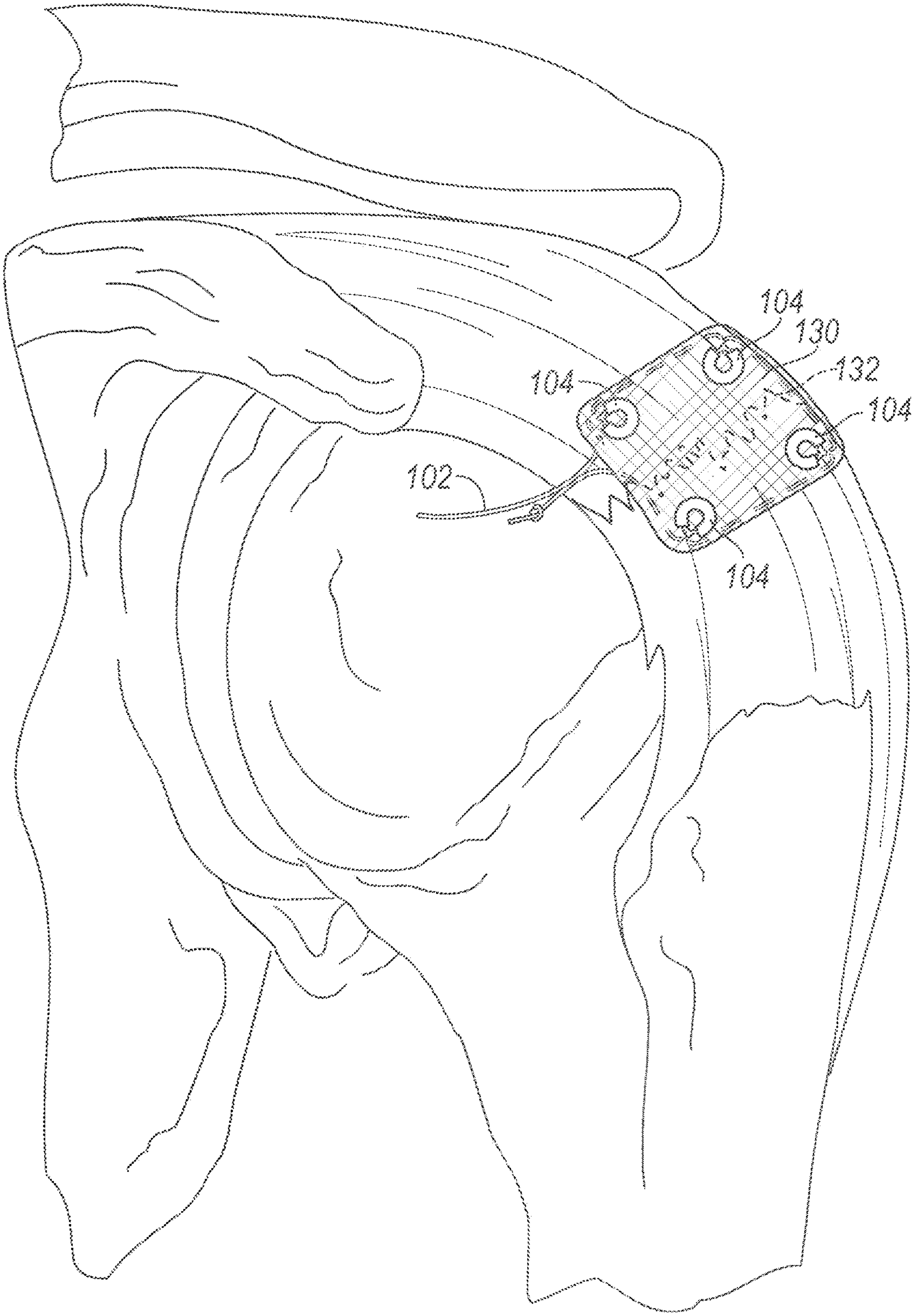
Figure 36C:
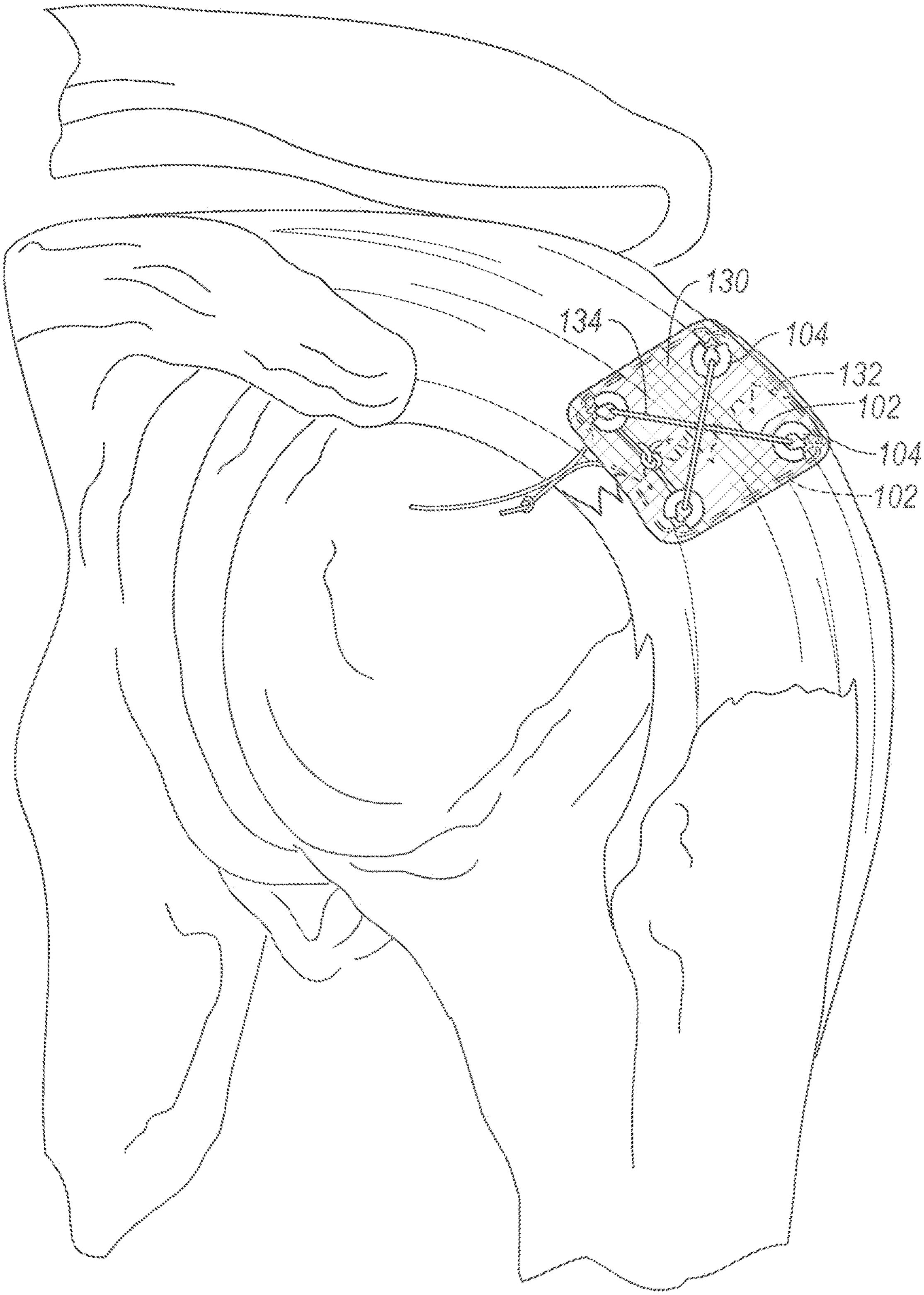

As shown in FIGS. 36A-36C, the construction in FIGS. 35A-35C and, particularly, the orthopedic mesh 130 can be used to repair torn soft tissue 124. In this regard, it is envisioned the mesh 130 can be placed over a muscle tear 132. A series of collapsible tubes 104 are disposed over a suture 102 and can be coupled to the soft tissue by pushing the collapsible tubes 104 through the soft tissue 124 and the mesh 130. Tension can be applied to the suture 102 to collapse the collapsible tube 104, thus coupling the sports mesh 130 to the two portions of soft tissue 124 which are being repaired.

As best seen in FIGS. 36B and 36C, several different stitching techniques can be used to couple multiple collapsible tubes 104 along the periphery of the orthopedic mesh 130 on either side of a tear 132. The orthopedic mesh 130 functions to distribute loads along the muscle 124, thus allowing the torn muscle 132 to heal properly.

As seen in FIG. 36C, sutures 134 can be added between the loops of collapsible tubes 104. It is envisioned that this functions to transfer loads from one portion of the muscle to a second, thus allowing the muscle tear 132 to heal more rapidly and compress the tear 132.

Figure 37A:
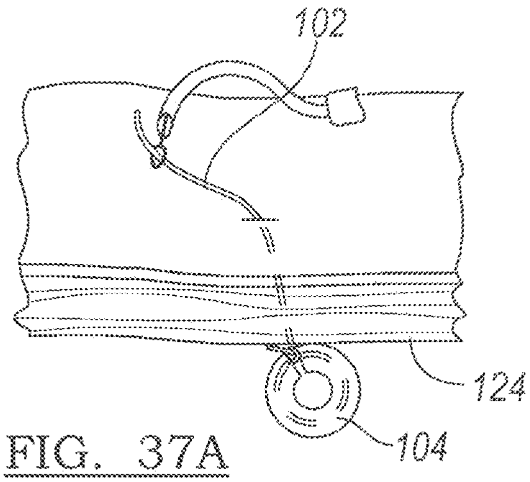
FIGS. 37A-39D represent various methodologies of coupling the suture constructions of FIG. 33 to soft tissue.
Figure 37B:
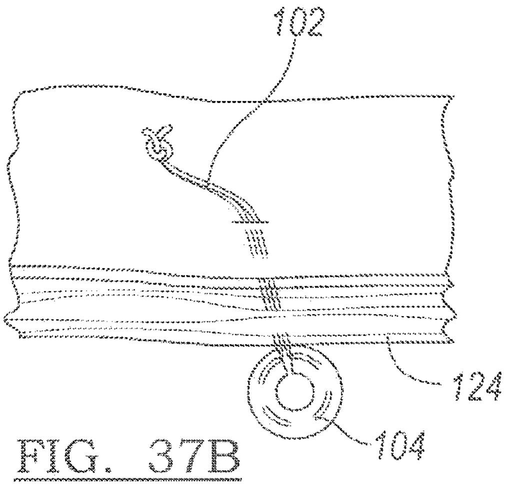

FIGS. 37A-39D represent various methods of inserting the suture constructions shown above into soft tissue. FIGS. 37A and 37B represent a collapsible tube having a single and double suture and constructions. These constructions are being threaded through a soft tissue 124, using a speed pass suture retriever from Biomet Sports Medicine. A passage is formed within a soft tissue 124 using the speed pass suture retriever has a deployable portion which can grab a suture and pull it through the passage. At this point, the suture construction having a suture 102 and collapsible tube is positioned within the speed pass and pulled through the aperture formed within the soft tissue 124. Tension is applied to the suture 102, thus collapsing the collapsible tube 104.

Figure 38A:
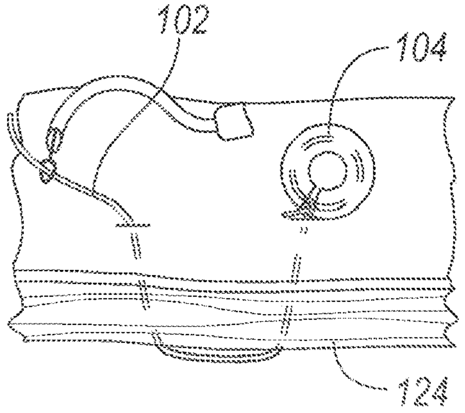
Figure 38B:
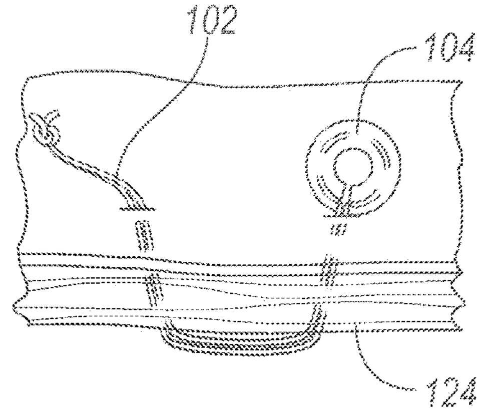
Figure 39A:
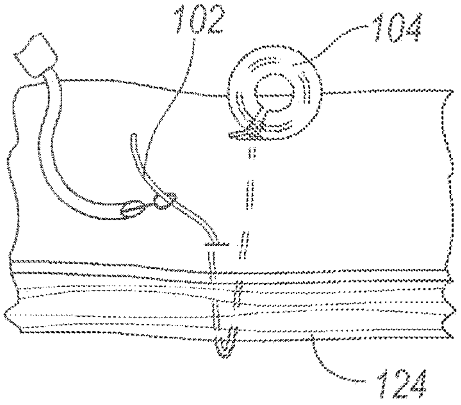
Figure 39B:
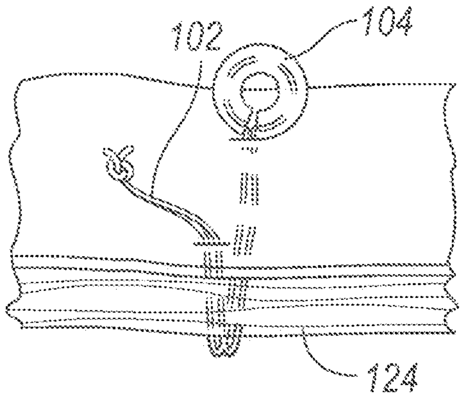
Figure 37C:
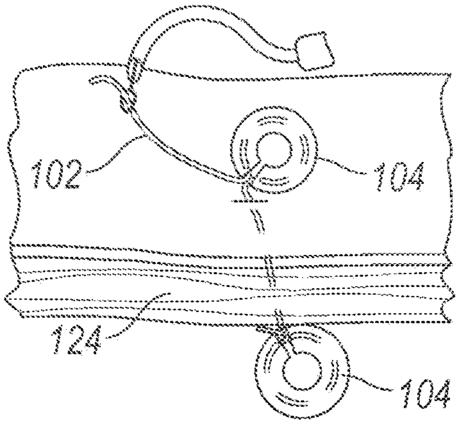
Figure 37D:
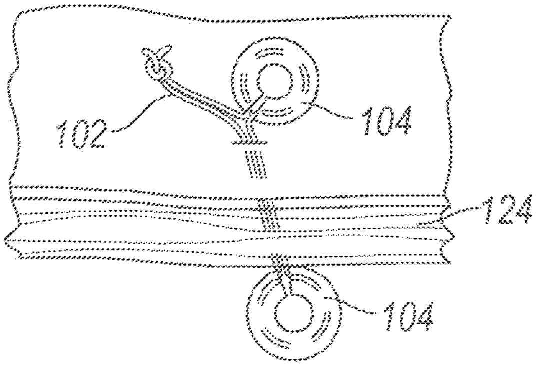
Figure 38C:
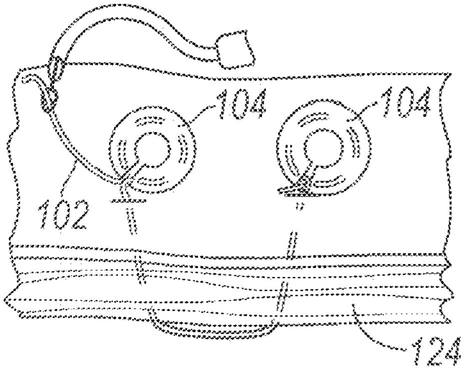
Figure 38D:
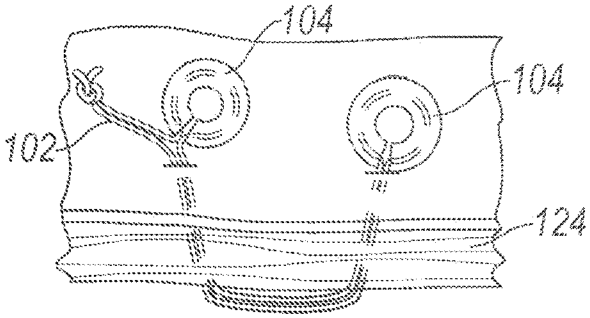
Figure 39C:
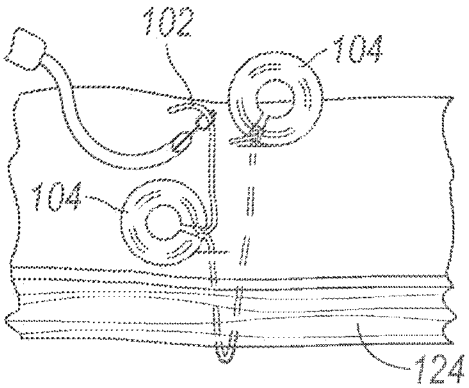
Figure 39D:
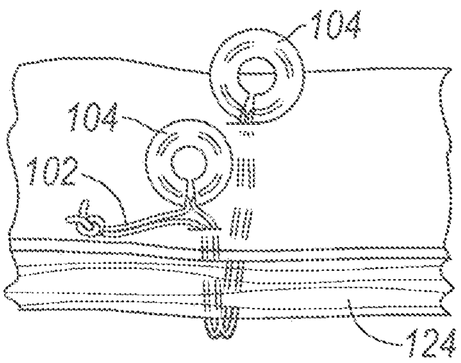

As seen in FIGS. 38A and 38B, by using a curved speed pass instrument, a pair of apertures can be formed within the soft tissue. The speed pass instrument is then used to pull the suture construction through the two apertures formed in the soft tissue 124. Alternatively, the suture construction may be pressed within the speed pass 125 and released (pushed out) after the speed pass 125 has pierced the soft tissue.

As seen in FIGS. 38A and 38B, the speed pass having a corkscrew shape can be used to form a pair of apertures in soft tissues which are generally perpendicular to the tool threading direction. In each of these conditions, tension is applied to the sutures 102 to compress the tubes 104. It is envisioned the speed pass can be used to feed the suture constructions through the orthopedic mesh as described above.

FIGS. 40-45 represent a tool 140 used to couple the suture construction 100 with soft tissue. In this regard, the tool 140 has a sharpened end 142 configured to pierce soft tissue 124. Disposed adjacent to the sharpened end 142 is a first portion 144 configured to support a collapsible tube anchor 146. Adjacent to the first portion 144 is a second portion 148 which can support a plurality of collapsible tube anchors 146. Disposed between the first 144 and second portions 148 is a generally conical portion 150. As shown in FIG. 41, the conical portion 150 facilitates movement of the collapsible tubes 146 from the second portion 148 to the first portion 144. Defined between the conical portion 150 and the first portion 144 is a generally flat or planar support surface 152. The flat surface 152 is configured to support and apply axial forces to an end 154 of the collapsible tube anchor 146.

As best seen in FIG. 43, the conical portion 150 can have an oblong cross-section. This cross-section can help facilitate the passing of the suture through the soft tissue. The sharpened end 142 can be passed through soft tissue 124, thus placing the collapsible tube 146 on an obverse side of the soft tissue 124. At this point, the sharpened end 142 can be passed through another soft tissue layer, a shorts mesh, or skin.

Figure 45:
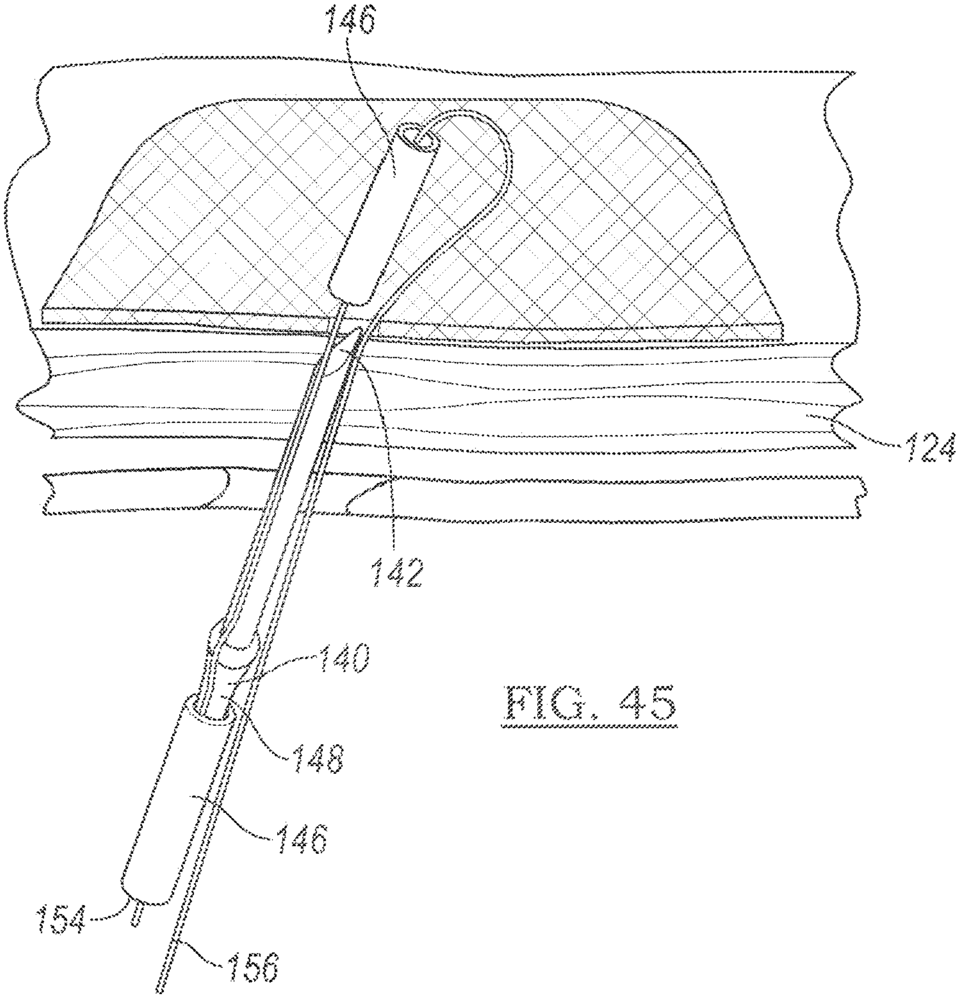

As shown in FIG. 45, the tool 140 can be withdrawn leaving the collapsible tube 146 on the obverse side of the soft tissue. Force can then be applied to the suture 156, as described above, to collapse the collapsible tube 146.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices e.g. humeral, femoral or tibial stems. Such variations are not to be regarded as a departure from the spirit and scope of the invention.

What is claimed is:

1. A method of repairing a rotator cuff, comprising:

locating a first collapsible anchor along a top surface of the rotator cuff;

locating a second collapsible anchor along a bottom surface of the rotator cuff between the rotator cuff and underlying bone; and pulling on a first free end of a tensioning strand, the tensioning strand extending through the rotator cuff to couple the first collapsible anchor to the second collapsible anchor.

2. The method of claim 1, wherein said pulling causes at least one of the first collapsible tube and the second collapsible tube to change shape from a first shape to a second shape.

3. The method of claim 1 further comprising locating a resorbable material along the rotator cuff between the first collapsible anchor and the second collapsible anchor with the tensioning strand also extending through the resorbable material.

4. The method of claim 3, wherein the resorbable material extends over a tear in the rotator cuff.

5. The method of claim 3, wherein the resorbable material comprises a sheet material.

6. The method of claim 3, wherein the resorbable material comprises a mesh material.

7. The method of claim 1, wherein a knot is formed in the tensioning strand along the top surface of the rotator cuff.

8. The method of claim 1, wherein a knot is formed in the tensioning strand along the bottom surface of the rotator cuff.

9. The method of claim 1, wherein at least one of the first collapsible anchor and the second collapsible anchor comprises a collapsible tube.

10. The method of claim 9, wherein the collapsible tube includes a longitudinal bore, and wherein the tensioning strand passes longitudinally through at least part of the longitudinal bore of the collapsible tube.

11. The method of claim 1, wherein the tensioning strand forms part of a suture loop construct.

12. The method of claim 11, wherein at least part of a loop portion of the suture loop construct extends through the rotator cuff.

13. The method of claim 12, wherein the loop portion of the suture loop construct extends fully through the rotator cuff from a first location along the bottom surface of the rotator cuff to a second location along the top surface of the rotator cuff.

14. The method of claim 11, wherein the suture loop construct comprises an adjustable loop portion.

15. The method of claim 14, wherein the first free end of the tensioning strand passes longitudinally through a longitudinal passage in the tensioning strand to form the adjustable loop portion.

16. The method of claim 1, wherein the tensioning strand is made to extend through the rotator cuff using a suture passer.

17. The method of claim 1, wherein at least one of the first collapsible anchor and the second collapsible anchor is slidable along the tensioning strand.

18. The method of claim 1, wherein at least one of the first collapsible anchor and the second collapsible anchor is fixed along the tensioning strand.

* * * * *